US006468749B1

(12) United States Patent
Ulanovsky et al.

(10) Patent No.: US 6,468,749 B1
(45) Date of Patent: Oct. 22, 2002

(54) SEQUENCE-DEPENDENT GENE SORTING TECHNIQUES

(75) Inventors: Levy Ulanovsky, Palo Alto, CA (US); Raja C. Mugasimangalam, Bangalore (IN); Paz Einat, Ness-Ziona (IL); Dina Zezin-Sonkin, Rehovot (IL); Shlomit Gilad, Gedera (IL)

(73) Assignee: Quark Biotech, Inc., Cleveland, OH (US)

(*) Notice: Subject to any disclaimer, the term of this patent is extended or adjusted under 35 U.S.C. 154(b) by 0 days.

(21) Appl. No.: 09/538,709

(22) Filed: Mar. 30, 2000

(51) Int. Cl.[7] ........................... C12Q 1/68; C12P 19/34; C07H 21/04
(52) U.S. Cl. .................. 435/6; 435/91.1; 435/91.2; 536/23.1; 536/24.1; 536/24.2; 536/24.3; 536/24.33; 536/25.4
(58) Field of Search .................. 435/6, 91.1, 91.2, 435/91.5; 536/24.3, 24.33

(56) References Cited

U.S. PATENT DOCUMENTS

| | | | |
|---|---|---|---|
| 5,407,813 A | 4/1995 | Gold | 435/91.2 |
| 5,413,909 A | 5/1995 | Bassam et al. | 435/6 |
| 5,487,985 A | 1/1996 | McClelland et al. | 435/91.2 |
| 5,508,169 A | 4/1996 | Deugau et al. | 435/6 |
| 5,556,773 A | 9/1996 | Yourno | 435/91.2 |
| 5,580,726 A | 12/1996 | Villeponteau et al. | 435/6 |
| 5,629,179 A | 5/1997 | Mierendorf et al. | 435/91.2 |
| 5,650,274 A | 7/1997 | Kambara et al. | 435/6 |
| 5,695,937 A | 12/1997 | Kinzler et al. | 435/6 |
| 5,700,644 A | 12/1997 | Gould et al. | 435/6 |
| 5,707,807 A | 1/1998 | Kato | 435/6 |
| 5,710,000 A | 1/1998 | Sapolsky et al. | 435/6 |
| 5,728,524 A | 3/1998 | Sibson | 435/6 |
| 5,763,239 A | 6/1998 | Short et al. | 435/172.1 |
| 5,804,382 A | 9/1998 | Sytkowski et al. | 435/6 |
| 5,814,445 A | 9/1998 | Belyavsky et al. | 435/6 |
| 5,837,468 A | 11/1998 | Wang et al. | 435/6 |
| 5,858,656 A | 1/1999 | Deugau et al. | 435/6 |
| 5,863,722 A | 1/1999 | Brenner | 435/6 |
| 5,866,330 A | 2/1999 | Kinzler et al. | 435/6 |
| 5,871,697 A | 2/1999 | Rothberg et al. | 422/68.1 |
| 5,994,068 A * | 11/1999 | Guilfoyle et al. | 435/6 |
| 6,060,271 A * | 5/2000 | Walewski et al. | 435/69.1 |

FOREIGN PATENT DOCUMENTS

| | | |
|---|---|---|
| WO | WO 93/18176 | 9/1993 |
| WO | WO 94/01582 | 1/1994 |
| WO | WO 98/51789 | 11/1998 |
| WO | WO 99/60164 | 11/1999 |

OTHER PUBLICATIONS

Belavsky et al., Nucleic Acids Research, vol. 17, No. 8, pp. 2919–2932, 1989.
Calvet, Pediatric Nephrology, vol. 5, pp. 751–757, 1991.
Cooke et al., The Plant Journal, vol. 9, No. 1, pp. 101–124, 1996.
Domec et al., Analytical Biochemistry, vol. 188, pp. 422–426, 1990.
Haymerle et al., Nucleic Acids Research, vol. 14, No. 21, pp. 8615–8624.
Kato et al., Gene, vol. 150, pp. 243–250, 1994.
Kohchi et al., The Plant Journal, vol. 8, No. 5, pp. 771–776.
Patanjali et al., Proc. Natl. Acad. Sci., USA, vol. 88, pp. 1943–1947, Mar. 1991.
Podhajska et al., Methods in Enzymology, vol. 216, pp. 303–309, 1992.
Szybalski et al., Gene, vol. 100, pp. 13–26, 1991.
Edwards et al., Nucleic Acids Research, vol. 19, No. 19, pp. 5227–5232, 1991.
Hoog, Nucleic Acids Research, vol. 19, No. 22, pp. 6123–6127, 1991.
Kato, Nucleic Acids Research, vol. 25, No. 22, pp. 4694–4696, 1997.
Mutchler et al., PCR Methods and Applications, vol. 1, pp. 195–198, 1992.
Sokolov et al., Nucleic Acids Research, vol. 22, No. 19, pp. 4009–4015, 1994.
Schmidt et al., Nucleic Acids Research, vol. 24, No. 9, pp. 1789–1791, 1996.
Prashar et al., Proc. Natl. Acad. Sci. USA, vol. 93, pp. 659–663, Jan. 1996.
Ko, Nucleic Acids Research, vol. 18, No. 19, pp. 5705–5711, 1990.
Unrau et al., Gene, vol. 145, pp. 163–169, 1994.
Guilfoyle et al., Nucleic Acids Research, vol. 25, No. 9, pp. 1854–1858, 1997.
Mahadeva et al., J. Mol. Biol., vol. 284, pp. 1391–1398, 1998.
Troutt et al., Proc. Natl. Acad. Sci. USA, vol. 89, pp. 9823–9825, Oct. 1992.
Ivanova et al., Nucleic Acids Research, vol. 23, No. 15, pp. 2954–2958, 1995.
Smith, PCR Methods and Applications, vol. 2, pp. 21–27, 1992.
Gubler et al, Gene, vol. 25, pp. 263–269, 1983.
Kato, Nucleic Acids Research, vol. 23, No. 18, pp. 3685–3690, 1995.
Liu et al., "A Bridging PCR Assay for DNA Discontinuities", Manuscript dated Jul. 8, 1996.

* cited by examiner

*Primary Examiner*—Kenneth R. Horlick
*Assistant Examiner*—Alexander H. Spiegler
(74) *Attorney, Agent, or Firm*—Frommer Lawrence & Haug, LLP; Edgar H. Haug; Thomas J. Kowalski

(57) ABSTRACT

This invention provides a method of sorting genes comprising: (1) preparing ds cDNA molecules from mRNA molecules (2) digesting the ds cDNA molecules (3) ligating to the digested cDNA molecules a set of dsDNA oligonucleotide adaptors; (4) amplifying the ligated cDNA molecules; and (5) sorting the amplified cDNA molecules into nonoverlapping groups. This invention also provides two additional methods of sorting genes. This invention further provides a method of making sub-libraries of ligation sets.

40 Claims, 23 Drawing Sheets mRNA

5' CCCTGCCTCTACTGGCGCTGCC--578bp--GCTCAACCAAAAAAAAA 3'

Double Stranded cDNA

↓

5'     CCCTGCCTCTACTGGCGCTGCC--578BP--GCTCAACCAAAAAAAAA 3'
3'     GGGACGGAGATGACCGCGACGG----------CGAGTTGGT(T)₁₈CCGCGCGGACATGCTCAGC----5'
                Bbvl

Bbvl digestion product

↓

|  END PRIMER                   |
5' GCCTCTACTGGCGCTGCC---578bp--GCTCAACCA(A)₁₈GGCGCGCCTGTACGAGTCG 3'
3'         GATGACCGCGACGG-----------CGAGTTGGT(T)₁₈CCGCGCGGACATGCTCAGC---5'

Ligation of TAIL adaptor

↓

↓ mismatched nucleotide
    5'---helper --GCCTCTACTGGCGCTGCC---578bp--------GCTCAACCA(A)₁₈--END-- 3'
    3'-specific- -constant-NGGAGATGACCGCGCGG-----------------CGAGTTGGT(T)₁₈--END-- 5'
    |_____|
       TAIL adaptor

Tail-End Amplification

↓

TAIL-GGA→

5' ---helper – GCCTCTACTGGCGCTGCC-----------578bp--GCTCAACCA(A)₁₈--END--3'
3' –specific- -constant--NGGAGATGACCGCGACGG-------------------CGAGTTGGT(T)₁₈--END-- 5'

←END-1

First Nesting

↓

1ˢᵗ nest-CTAC→

5'---helper—GCCTCTACTGGCGCTGCC---578bp-------GCTCAACCA(A)₁₈--END-- 3'
3'-constant-NGGAGATGACCGCGACGG------------------CGAGTTGGT(T)₁₈--END-- 5'

|___|                                                  ←END-2
   Nested nucleotide

Second Nesting

↓

2ⁿᵈ nest-TG→

5'---helper—GCCTCTACTGGCGCTGCC---578bp---------GCTCAACCA(A)₁₈--END-- 3'
3'-constant-NGGAGATGACCGCGACGG-------------------CGAGTTGGT(T)₁₈--END-- 5'

|_|                                                   ←END-3
   Nested  nucleotides

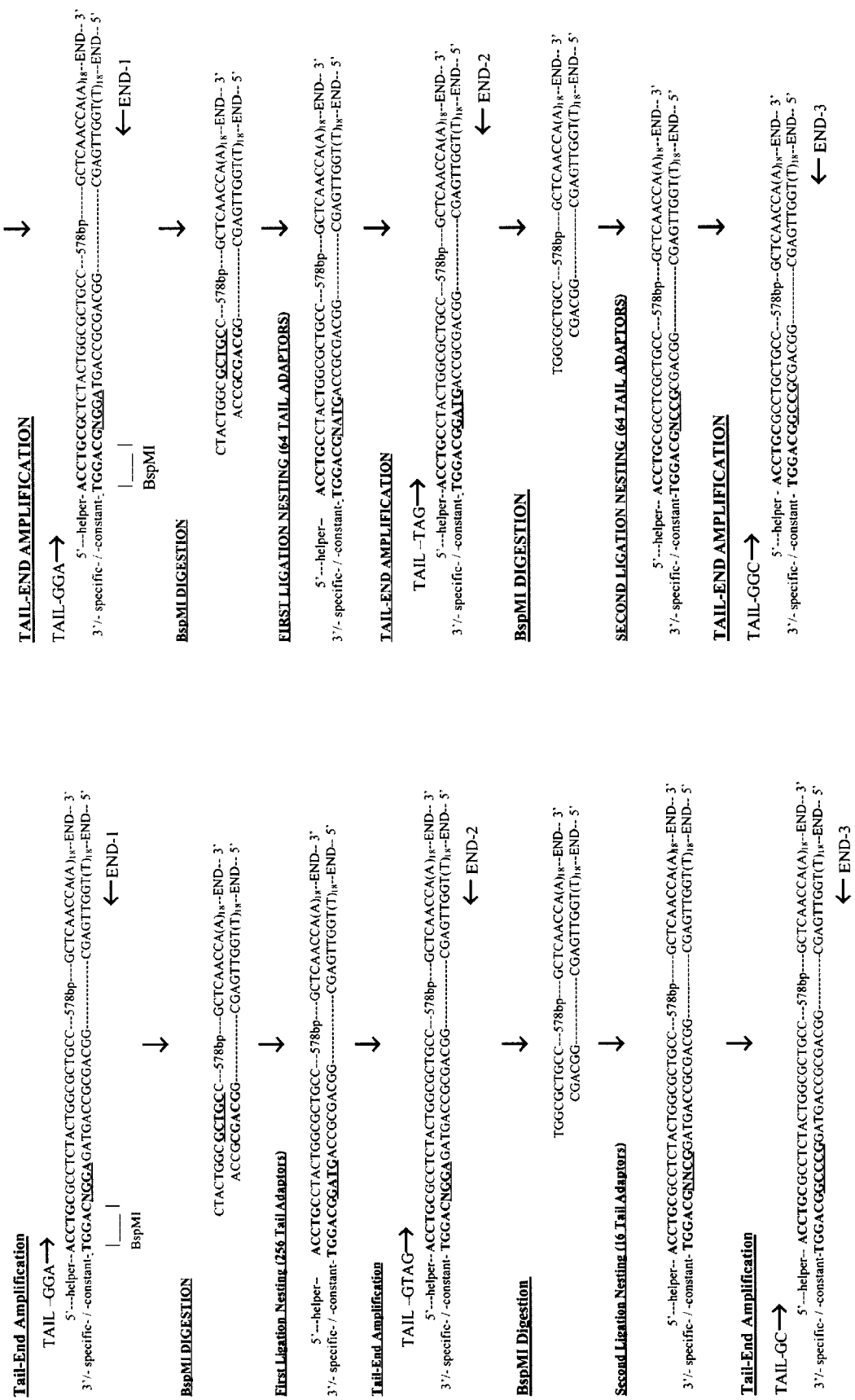

A. Standard Ligation Conditions
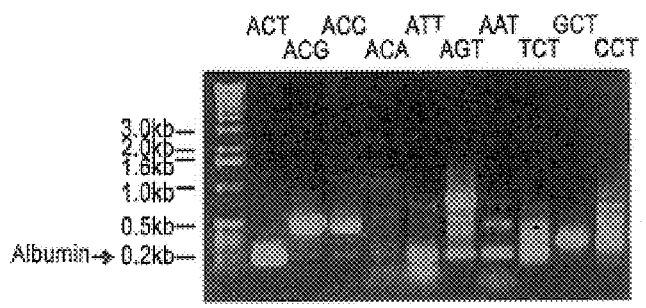
B. QBI's Specific Ligation Conditions
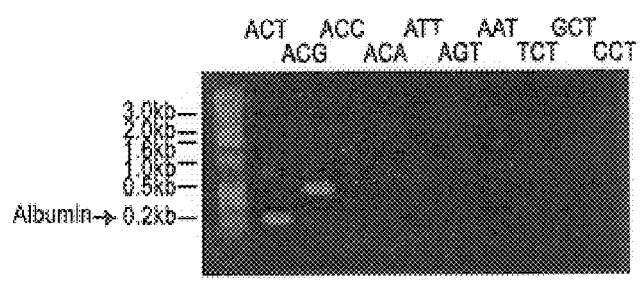
FIG. 4
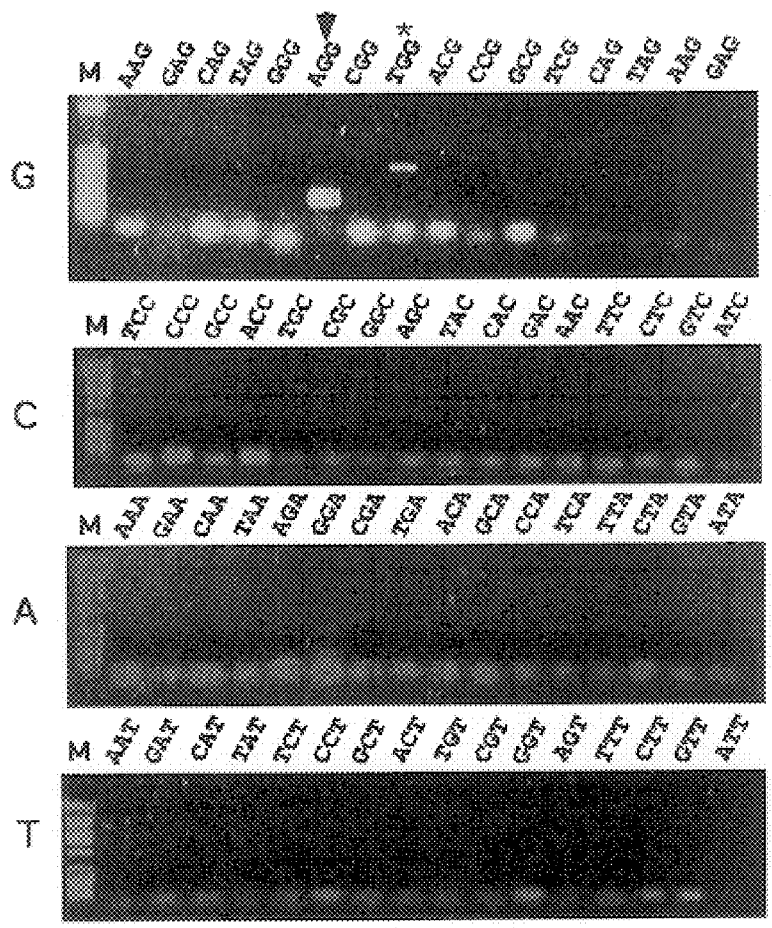
FIG. 5

```
5' XXXN GCAGGT ACGTCGTACC GCGGCCGC-x-x-x-x-x-x-x-x-3'

Bases    4    BspMI(6)constant(10)  NOTI(8)    Tail (20)

primer set J2
5' TTTNGCAGGTACGTCGTCGTACC  GTGAGCTTGAGTGCGTGGA     5' CTTNGCAGGTACGTCGTCGTACC  GCGGCCGC  CTACTCGCGAGAGAGGGCTATG
5' TTGNGCAGGTACGTCGTCGTACC  CCAAGTCGCGAGTTAGTCAG    5' CTGNGCAGGTACGTCGTCGTACC  GCGGCCGC  CTTGATCCGTAGTCGAGACGG
5' TTCNGCAGGTACGTCGTCGTACC  AGGTAGACGCGTATGTTCGTA   5' CTCNGCAGGTACGTCGTCGTACC  GCGGCCGC  GTACAGACGTAGCGATCGAC
5' TTANGCAGGTACGTCGTCGTACC  CGTGTCGTAGAGTCGCGTGTT   5' CTANGCAGGTACGTCGTCGTACC  GCGGCCGC  gTGACTAACGAGGTCGTAAGCTa
5' TGTNGCAGGTACGTCGTCGTACC  CGACAGTACCGCGACAGCTA    5' CGTNGCAGGTACGTCGTCGTACC  GCGGCCGC  GTCTgAGAGTCGACTgCGCTAAG
5' TGGNGCAGGTACGTCGTCGTACC  GCACTTAACTACGCCGACGAAG  5' CGGNGCAGGTACGTCGTCGTACC  GCGGCCGC  CTcAGTAAGCCGGAGTCTAGCTAg
5' TGCNGCAGGTACGTCGTCGTACC  gTACTAGCCTAACCGAGGCGTA  5' CGCNGCAGGTACGTCGTCGTACC  GCGGCCGC  CGCCCTAAACGGATCGAGCGA
5' TGANGCAGGTACGTCGTCGTACC  TCGGATCACGTACACGTGCT    5' CGANGCAGGTACGTCGTCGTACC  GCGGCCGC  CGTACAGGCTAGGGGTTAGTCG 5' TCTNGCAGGTACGTCGTCGTACC  GTACGTCGCCTAGTCGACCTG   5' CCTNGCAGGTACGTCGTCGTACC  GCGGCCGC  CGATGCTCTAGTGCCTACG
5' TCGNGCAGGTACGTCGTCGTACC  CTCTCCTAACGGACGACTAAC   5' CCGNGCAGGTACGTCGTCGTACC  GCGGCCGC  gACTGCGATTCGTGACACTAGT
5' TCCNGCAGGTACGTCGTCGTACC  CGTTCCGATCTAGCGGTATCTT  5' CCCNGCAGGTACGTCGTCGTACC  GCGGCCGC  TGCGTAATAGCGACTGTACCCt 5' TCANGCAGGTACGTCGTCGTACC  gcACCCGTACaGGATGCGAG    5' CCANGCAGGTACGTCGTCGTACC  GCGGCCGC  cTAGGTCATCCCTCCGGTAC
5' TATNGCAGGTACGTCGTCGTACC  GCAACGCGCTATGCTCGTag    5' CATNGCAGGTACGTCGTCGTACC  GCGGCCGC  gATCGGACTAATCCGCTACGT
5' TAGNGCAGGTACGTCGTCGTACC  GACTgTGGAACTACGACGATCg  5' CAGNGCAGGTACGTCGTCGTACC  GCGGCCGC  GACTACCGACTAGTCGTGCGAC
5' TACNGCAGGTACGTCGTCGTACC  aGCaGACCGAACCCTAGTCG    5' CACNGCAGGTACGTCGTCGTACC  GCGGCCGC  TAGGGCCCTAACGTAGCTCG
5' TAANGCAGGTACGTCGTCGTACC  cATACGTCGTAgggTTCGCGA   5' CAANGCAGGTACGTCGTCGTACC  GCGGCCGC  TACCTAGCCCTAACGGGTCG 5' GTTNGCAGGTACGTCGTCGTACC  cTCTCATACGCGTCTGCGCGT   5' ATTNGCAGGTACGTCGTCGTACC  GCGGCCGC  TAGTGCGGTACTACCGACT
5' GTGNGCAGGTACGTCGTCGTACC  gAGTgTGCCTTACGTCGAGttc  5' ATGNGCAGGTACGTCGTCGTACC  GCGGCCGC  AGaCGGTATGCGTCGGa
5' GTCNGCAGGTACGTCGTCGTACC  GTcACGTtGCGGCCTTAGTC    5' ATCNGCAGGTACGTCGTCGTACC  GCGGCCGC  ACCTACGAACACGCGTAACTCg
5' GTANGCAGGTACGTCGTCGTACC  GagGTAGCAgACTTGACACACG  5' ATANGCAGGTACGTCGTCGTACC  GCGGCCGC  AgcTACGTGGGTGGCAGAC
5' GGTNGCAGGTACGTCGTCGTACC  GACcAGttGCCTAACGACaCACT 5' AGTNGCAGGTACGTCGTCGTACC  GCGGCCGC  TACCGATACGGTCGACCATC
5' GGGNGCAGGTACGTCGTCGTACC  GCAACTAGTTCTCGACCTCGA   5' AGGNGCAGGTACGTCGTCGTACC  GCGGCCGC  GTACGCTAGGTaggAACTAAGCG
5' GGCNGCAGGTACGTCGTCGTACC  GTACCTCGACGACCGTACTGTg  5' AGCNGCAGGTACGTCGTCGTACC  GCGGCCGC  CGGACGACTAGTTGCTAGCGTC
5' GGANGCAGGTACGTCGTCGTACC  ACGCGTGATATAGTACGGAGTCG 5' AGANGCAGGTACGTCGTCGTACC  GCGGCCGC  GTGAACCTACGCGTTGACGC 5' GCTNGCAGGTACGTCGTCGTACC  CACTAGAGCGGCGTCAGTCTA   5' ACTNGCAGGTACGTCGTCGTACC  GCGGCCGC  GTGTCTCGGGCTAGGCGTAGA
5' GCGNGCAGGTACGTCGTCGTACC  GCACAGCGCTAGCACAGGA     5' ACGNGCAGGTACGTCGTCGTACC  GCGGCCGC  TCCGTGTGTCCATGGAG
5' GCCNGCAGGTACGTCGTCGTACC  TACCGACAGTCCTCGCGTGC    5' ACCNGCAGGTACGTCGTCGTACC  GCGGCCGC  CTACGCGTAACGCTAGCAGGT
5' GCANGCAGGTACGTCGTCGTACC  CTACGCTACGTTGCGAAGAAGTA 5' ACANGCAGGTACGTCGTCGTACC  GCGGCCGC  gAAGAGCCGTAAGGTACGGCT
5' GATNGCAGGTACGTCGTCGTACC  GTCTGTCGTACCTGTCAGTGACTg 5' AATNGCAGGTACGTCGTCGTACC GCGGCCGC  gTACGTCAGCGTACGCTAAGTC
5' GAGNGCAGGTACGTCGTCGTACC  ATCGAACCGTGCTCCTTGG     5' AAGNGCAGGTACGTCGTCGTACC  GCGGCCGC  TCTAGTTCCGTTGTAGCGCT
5' GACNGCAGGTACGTCGTCGTACC  AGGTTGAGGTGTACGCGATAGC  5' AACNGCAGGTACGTCGTCGTACC  GCGGCCGC  AGCAACGAGACGACACGAC
5' GAANGCAGGTACGTCGTCGTACC  GACTTCAACCCCTGACGTACACa 5' AAANGCAGGTACGTCGTCGTACC  GCGGCCGC  GTCTAGAACCCACGCACGGTA
```

FIG. 10

| Name | Sequence | | Name | Sequence | |
|---|---|---|---|---|---|
| Tail-TTT | 5' | TCCACGCGACTCAAGCTCAC | Tail-CTT | 5' | CATAGCCCTCTCGCGAGTAG |
| Tail-TTG | 5' | CTGACTAACTCGCGACGTTGG | Tail-CTG | 5' | CCGTCTCGACTACGCGATCAAG |
| Tail-TTC | 5' | TACGAACATACCGCGTCTACCT | Tail-CTC | 5' | CTGCGATCGCTACGTCTGTAC |
| Tail-TTA | 5' | AACACGCGACTCTAGCACCG | Tail-CTA | 5' | TAGCTTACAGACCTCGTTAGTCAC |
| Tail-TGT | 5' | TAGCTGTCGCGGTACTGTCG | Tail-CGT | 5' | CTTAGCGCAGTCGACTCTCAGAC |
| Tail-TGG | 5' | CTTCGTCGGCGTAGTTAAGTGC | Tail-CGG | 5' | CTAGCTAGACTCCGGCTTACTGAG |
| Tail-TGC | 5' | TACGCCTCGTTAGGCTAGTAC | Tail-CGC | 5' | TCGCTCGATCCCGTTAGGGCG |
| Tail-TGA | 5' | AGCACGTGTACGTGATCCGA | Tail-CGA | 5' | CGACTAACCCCTAGCCTGTACG |
| Tail-TCT | 5' | CAGGTCGACTAGGCGACGTAC | Tail-CCT | 5' | CGTAGGCACTAGAGCGATCG |
| Tail-TCG | 5' | GTTAGTCGGTCCGTTAGGAGAG | Tail-CCG | 5' | ACTAGTGTCACGAATCGCAGTC |
| Tail-TCC | 5' | AAGATACCGCTAGAATCGGAACG | Tail-CCC | 5' | AGGGTACAGTGCTATTACGCA |
| Tail-TCA | 5' | CTCACATCCTGTACGGGTGC | Tail-CCA | 5' | GTACCGGAGGGATGACCTAG |
| Tail-TAT | 5' | CTACGAGCATAGCGCGTTGC | Tail-CAT | 5' | ACGTAGGCGATTAGTCCGATC |
| Tail-TAG | 5' | CGATCGTCGTAGTTCCACAGTC | Tail-CAG | 5' | GTCGCACGACTAGTCGGTAGTC |
| Tail-TAC | 5' | GCGACTAGGGTTCGGTCTGCT | Tail-CAC | 5' | CGAGCTACGTTAGGGCCCTA |
| Tail-TAA | 5' | TCGCGAACCCTACGACGTATG | Tail-CAA | 5' | CGACCCGTTAGGGCTAGGTA |
| Tail-GTT | 5' | ACGCGCAGAGCGCGTATGAGAG | Tail-ATT | 5' | AGTCGGTAGTACCGGCACTA |
| Tail-GTG | 5' | GAACTCGACGTAAGGCACACTC | Tail-ATG | 5' | TCCCGACGCATAGCCGTCT |
| Tail-GTC | 5' | GACTAAGGCCGCAACGTGAC | Tail-ATC | 5' | CGAGTTACGCGTGTTCGTAGGT |
| Tail-GTA | 5' | CGTGTGTCAAGTCTCGTACCTC | Tail-ATA | 5' | GTCTGCCACCCACGTAGCT |
| Tail-GGT | 5' | AGTGTCCGTTAGGCAACTGGTC | Tail-AGT | 5' | GATGGTCGACCGTATCGGTA |
| Tail-GGG | 5' | TCGCAGGTCGAGACTAGTTGC | Tail-AGG | 5' | CGCTTAGTTCCTACCTAGCGTAC |
| Tail-GGC | 5' | CACAGTACGGTCGTCGAGGTAC | Tail-AGC | 5' | GACGCTAGCAACTAGTCGTCCG |
| Tail-GGA | 5' | CGACTCCGTACTATCACGCGT | Tail-AGA | 5' | GCGTCAACGCGTAGGTTCAC |
| Tail-GCT | 5' | TAGACTGACGCGCCGCTTAGTG | Tail-ACT | 5' | TCTACGCCTAGCCCGAGACAC |
| Tail-GCG | 5' | TCCTGTGCTAGCGCTGTGC | Tail-ACG | 5' | CTCCCATGACGACACCACGGA |
| Tail-GCC | 5' | GCACGCAGAGGACTGTCGGTA | Tail-ACC | 5' | ACCTGCTAGCGTTACGCGTAG |
| Tail-GCA | 5' | TACCTTCTTCGCAACGTAGCGTAG | Tail-ACA | 5' | AGCCGTACCTTACGGCTCTTC |
| Tail-GAT | 5' | CAGTCACTGACAGTACGACAGAC | Tail-AAT | 5' | GACTTAGGTACGCTGACGTAC |
| Tail-GAG | 5' | CCAAGGAGCACGTTCGAT | Tail-AAG | 5' | AGCGCTACAACGGAACCTAGA |
| Tail-GAC | 5' | GCTATCGCGTACACCTCAACCT | Tail-AAC | 5' | GTCGTGTCGTCGTTGCT |
| Tail-GAA | 5' | TGTGTACGTCAGGGGTTGAAGTC | Tail-AAA | 5' | TACCGTGCGTGGGTTCTAGAC |

FIG. 11

| | | | | | |
|---|---|---|---|---|---|
| TnewTTT | 5' AACGACGCTCGCGGTACCAG | TnewCTT | 5' ACGTCTGTACCCGTCTCGACTAC | TnewATT | 5' TCGTCGAGGTACTTCGCAGGT |
| TnewTTG | 5' GGGCTCTAGAACTGACTCCAGAC | TnewCTG | 5' GGATCAAGCATAGCCCGTCTC | TnewATG | 5' CGAGACTAGTTGCAGTTCCGT |
| TnewTTC | 5' GTAGTAGCGGCGACTAGTACC | TnewCTC | 5' TCGCGAGTAGTGTACGTCAG | TnewATC | 5' TAGGCaaCTAGTCCGTGTGTC |
| TnewTTA | 5' GGCAGGGATCGACCTAGGGTAC | TnewCTA | 5' GGGTTAAGTCGCTATCGCGTAC | TnewATA | 5' AAGTTCGTACCtCGACTAAGC |
| TnewTGT | 5' AGTCGCTATTACGCACCTAGTG | TnewCGT | 5' ACCTCAACCTCCAAGGAGCAC | TnewAGT | 5' GCCGCGACGTAACGaaCTCGA |
| TnewTGG | 5' TCACGAATCGCAATCCCGTAGG | TnewCGG | 5' GGCGTTCGATAGTCACTGACAG | TnewAGG | 5' CGTAAGGCATACTACGCGCAG |
| TnewTGC | 5' CACTAGAGCGACGTACCGTGC | TnewCGC | 5' GTACGACAGACTACCTTCTTCG | TnewAGC | 5' ACGCGTATGAGAaGTCGCGAAC |
| TnewTGA | 5' GTGGGTTCTAGACCGGTCGT | TnewCGA | 5' CAACGTAGCGTAGCGTCACGCAG | TnewAGA | 5' cCTACGACGTATCGCGACTAG |
| | | | | | |
| TnewTCT | 5' GTCGATCTTTGCTAGCGCTAC | TnewCAT | 5' AGGACTGTCGGTATCCCTTGTGC | TnewACT | 5' GGTTCGGTCGCtCGATCGTCG |
| TnewTCG | 5' AACGGAACCTAGAGAGACTTAGC | TnewCAG | 5' TAGGCTCGTGCTAGACTGACG | TnewACG | 5' TAGTTCCAAGTCGCGACGAGC |
| TnewTCC | 5' .GTACGCTGACGTATAGCCGTAC | TnewCAC | 5' CCGCTCTAGTGCGACTCCGT | TnewACC | 5' .ATAGCGCGTTGCCCTCACATC |
| TnewTCA | 5' CTTACGGCTCTTACCGTGCTAG | TnewCAA | 5' ACTATCACGCGTACAGTACGG | TnewACA | 5' CtGTACGGGTgCAAGATACCG |
| TnewTAT | 5' CGTTACGCGTAGACTCCCATG | | | TnewAAT | 5' CTAGATCGGAACGGTTAGTCG |
| TnewTAG | 5' GACACCACGGGATCTACGCCT | | | TnewAAG | 5' GTCCGTTAGGAGAGACAGGTCGA |
| TnewTAC | 5' AGCCCGAGACACAGCGTCAAC | | | TnewAAC | 5' CTAGGCGACGTACCAGCACGT |
| TnewTAA | 5' GCGTAGGTTCACGACGCTAGC | | | TnewAAA | 5' GTACGTGATCCGATACGCCTC |
| | | | | | |
| TnewGTT | 5' AACTAGTCGTCGCGCTTAGT | | | | |
| TnewGTG | 5' TTACCTAGCGTACGGATGGTC | | | | |
| TnewGTC | 5' GACCGTATCGGTAGTCTGCCA | | | | |
| TnewGTA | 5' CCGCACGTAAACGTGAGTTACG | | | | |
| TnewGGT | 5' CGTGTTCGTAGGTCCGGCGAC | | | | |
| TnewGGG | 5' GCATAGGCCGCCTAGTCGGTAG | | | | |
| TnewGGC | 5' TACCGCGCACTAGCGACCCGT | | | | |
| TnewGGA | 5' TAGGGCTAGGTACGAGCTACG | | | | |
| | | | | | |
| TnewGCT | 5' TTAGGGCCCTAGTCGCACGAC | | | | |
| TnewGCG | 5' TAGTCGGTAGTCACCCGTAGC | | | | |
| TnewGCC | 5' GGATTAGTCCGATGCGACTAACC | | | | |
| TnewGCA | 5' CCTAGCCTGTACGTCGCTCGATCC | | | | |
| TnewGAT | 5' CGTTTAGGGCGTAGCTAGACTCC | | | | |
| TnewGAG | 5' GGCTTACTAGCTTAGCGAGTC | | | | |
| TnewGAC | 5' GACTCTAGACAGCTTACAGACC | | | | |
| TnewGAA | 5' TCGTTAGTCACtGCGATCGCT | | | | |

| | |
|---|---|
| tailTTTT | 5'AACGCAGTGTTCGTTCGACGA |
| tailTTTG | 5'TGCAGAGCGGAACGAGaCGTA |
| tailTTTC | 5'AGCGCACGTCGTCTAGCGAAG |
| tailTTTA | 5'TCTGAGACGGaGTACGAGCGA |
| tailTTGT | 5'ACAGTGACCGTTTTCGCGCAT |
| tailTTGG | 5'AcTCTGGGACGACGAAAAGCG |
| tailTTGC | 5'TGACCGAACCGGGTTTACCAG |
| tailTTGA | 5'ACGAGACGTCTCGGACTATCG |
| tailTTCT | 5'CAACAACGTGCCGTTCGATAG |
| tailTTCG | 5'GTACCACCCGAACGGTCGTAG |
| tailTTCC | 5'GCACAACCGTCGACCGTACGA |
| tailTTCA | 5'AAGCCGAGACGAGGTCTAACG |
| tailTTAT | 5'ATCGCTGCGATCGGACGTTAG |
| tailTTAG | 5'ACCGCAGACGTTCCGATACCG |
| tailTTAC | 5'TCTACGTACGACGGTTCGGTA |
| tailTTAA | 5'TACACCACGTGAATCCGCTAG |
| tailTGTT | 5'ATCCTGGACAGAGTCGTCGAC |
| tailTGTG | 5'TCGTGAGTCAAGAACCGTCGA |
| tailTGTC | 5'ACAGCACACGTGATCcTTACG |
| tailTGTA | 5'TGGTACACGCTCGATCCGTAAG |
| tailTGGT | 5'CTCACTCGGGTCGTTGCGTATG |
| tailTGGG | 5'gGaTTACACACGCAAgGATACG |
| tailTGGC | 5'TGGCATCGTGCTTCTTCCGAT |
| tailTGGA | 5'GACGTCCTCGCGAGAAATCGG |
| tailTGCT | 5'AGTATCCAGCAGTGGGATGCG |
| tailTGCG | 5'ACGAAGAGCGACCGAACCGTA |
| tailTGCC | 5'GCAACTGCGGTTCGACGAATG |
| tailTGCA | 5'ACGTTCGCGAGTCGAAATTCG |
| tailTGAT | 5'AACGTGTCACTGCGTCGCGTT |
| tailTGAG | 5'GTCTAGACGGAGAAGCAAAGC |
| tailTGAC | 5'CGTTAGCGCTCGACGTTACGT |
| tailTGAA | 5'GATCACTCCGCACGTCACGTA |
| tailTCTT | 5'ACTAGTTACCGAGCGTCTACG |
| tailTCTG | 5'CTATGCGAGAGACGCTCGTAG |
| tailTCTC | 5'ACACGAACGGATGCGTTTCGC |
| tailTCTA | 5'TACTAGCAGCAACGAAGCGAA |
| tailTCGT | 5'CTAGACTCCGGTGTCGATCGT |
| tailTCGG | 5'CGACTACGTCCCGACAACGAT |
| tailTCGC | 5'AACTCGGAAGACGATGGTCGT |
| tailTCGA | 5'AAGTATGGACGCATCGACGAC |
| tailTCCT | 5'TGAAGGTCGACACGTTCGGTT |
| tailTCCG | 5'AATACCGCGCAAACGTAACCA |
| tailTCCC | 5'TAGACACAGGACCAGGGTTCG |
| tailTCCA | 5'AGTACTTCGTGACGAGCGAAC |
| tailTCAT | 5'AACTAGAAGCTGCGGTTTGCG |
| tailTCAG | 5'ACTAGCTGCGAACGGTCGCAA |
| tailTCAC | 5'AGCATACGCTTACCTGCGACT |
| tailTCAA | 5'ACGTGGAGCCTACGATAGTCG |
| tailTATT | 5'CCTAACCTCGAATCGCTCGAT |
| tailTATG | 5'ACCACGGCGCTACGGTATCGA |
| tailTATC | 5'ATGCCGTCGAGAGAGTTCGGT |

| | |
|---|---|
| tailTATA | 5'TCAACCACGAGTGACGATCGA |
| tailTAGT | 5'ACTATCCTCGTCGTCAGTCGC |
| tailTAGG | 5'AGGTTATCCGTCTGCCACGAC |
| tailTAGC | 5'TCCACGACTGACGAACCGCAT |
| tailTAGA | 5'GAGCTAGACGGAATCGATACG |
| tailTACT | 5'AACGGAGCCGTCGATCTTCGT |
| tailTACG | 5'CAGTACGTGGTCTTCGTTCGA |
| tailTACC | 5'CGATCACCGCCGAAGTCAGCA |
| tailTACA | 5'GTCAGACTCGCGTCTACGAAC |
| tailTAAT | 5'CCATTCGAGTAAACGCGATTG |
| tailTAAG | 5'ATAGTCGCTCGTTCCGAATCG |
| tailTAAC | 5'GCCTTAGAGCCAGGAAGAACG |
| tailTAAA | 5'GGTTCACGCACGTTAGCGTTC |
| tailGTTT | 5'CCAATTCCTTCCCTGGCTCATC |
| tailGTTG | 5'TCTCGGTCGCCTCGTCTAATC |
| tailGTTC | 5'AGACTCCTCAGCTGACCTAGTC |
| tailGTTA | 5'AGTCAGCTCGCCACTCGTAGT |
| tailGTGT | 5'AGAGTACTCGAGTCAGTAGGC |
| tailGTGG | 5'ACAGAGGAGTCGGGAACAACG |
| tailGTGC | 5'CTTGGGTACCTGTGTCCGTTG |
| tailGTGA | 5'ACAGTACGAAGCAATCTGTGA |
| tailGTCT | 5'AGCTCGGAGAGCATAAGGACG |
| tailGTCG | 5'TCTCGGGCATTACTGGATAGG |
| tailGTCC | 5'CCTTAACCtGATCTGTCcCATG |
| tailGTCA | 5'GTGCGAGTCCAGTTTGACTGA |
| tailGTAT | 5'GGTGGCCAACCACAGCCTTC |
| tailGTAG | 5'TGAGATGAGGTGTACGACTGC |
| tailGTAC | 5'TGTCAATGCGCCAGTTGTCTA |
| tailGTAA | 5'GCACCAACACCTAGTGGCATC |
| tailGGTT | 5'GATCTGTAGAGCGGGAGGTCT |
| tailGGTG | 5'TGGCTAAGGGTGCTGCCACGC |
| tailGGTC | 5'ATGAGACTCCAGCCGAAACCT |
| tailGGTA | 5'AGTGTAGGGACGACCTGCAGA |
| tailGGGT | 5'GGCAACGGCATAGCTGATACA |
| tailGGGG | 5'GATGCTGAGGTATGAGGCAACG |
| tailGGGC | 5'ACGTCATTTGGCCTGTCTGCT |
| tailGGGA | 5'GACTCACGTGCTCGAACTGCT |
| tailGGCT | 5'AGTCGGCaTGTgGCAcAtcTc |
| tailGGCG | 5'ACTCGGTAGACAGCCGCTAAC |
| tailGGCC | 5'CTGGGACACGGTCACTATTCAC |
| tailGGCA | 5'ACCCTTGGAACGCTGTACACA |
| tailGGAT | 5'TCĊGGACACGTAGTGAGACGT |
| tailGGAG | 5'TGCCTTGCACTCTTACCTAGC |
| tailGGAC | 5'TAGCCAGTATCGTGCACTTGG |
| tailGGAA | 5'AAGCTTACCACCCTACACGAA |
| tailGCTT | 5'AgGATGaTGACaTGGgTCGAa |
| tailGCTG | 5'AACCTCCATGACAAGTCCTCC |
| tailGCTC | 5'AACACCGTGGGACAGACATCT |
| tailGCTA | 5'CCACGGAACATACAGGGCATT |
| tailGCGT | 5'CATGAGCGTGGAGCTAAGCAT |
| tailGCGG | 5'CATCTGTCACAAGGTACGAGG |
| tailGCGC | 5'AgGaGATgGAaCGCTCGcACA |
| tailGCGA | 5'TCTGTGTCCTCGACCAGCATC |
| tailGCCT | 5'AACTCCAGGTGGAAGCTGGTT |

| | | | |
|---|---|---|---|
| tailGCCG | 5'CAGACTCACATCGAACGTCAC | tailCGAa | 5'CTACGGTCAGTACGACGTGGA |
| tailGCCC | 5'TGTAACTCCGAATGGGACACC | tailCCTT | 5'AAATTATTCGCTGGAGCGCTG |
| tailGCCA | 5'GTTGATGCTCTCCCTCACCTG | tailCCTg | 5'CAGCTGCGGTGTAGCATACAG |
| tailGCAT | 5'GAGTCTGCCAACAAGGTCGAG | tailCCTc | 5'ACTCGTAATCGTTCCAGACGC |
| tailGCAG | 5'GTTGTGAGGAACCGCAATGCA | tailCCTa | 5'ATACGTGTTATGGCCGGAAAG |
| tailGCAC | 5'ACCTCAGTGAACAGCTCTCAG | tailCcgT | 5'GCTCCGAAGTTAGGTTGGGAA |
| tailGCAA | 5'GATCCAGGTCGCTATCCACTG | tailCcgg | 5'GTTCACCCTTGCAACGATAGC |
| tailGATT | 5'CcACATGCGaTCTCAAaTCCa | tailCcgc | 5'AGGGAGACTCCCTACTCGGAT |
| tailGATG | 5'TTGTCGTGACGACCTAGACGC | tailCcga | 5'GAGTTGCCAGACATGTACCAG |
| tailGATC | 5'TTGAGGCGTCTAATCATCGGG | tailCcCt | 5'GCCAGTTTCTTCCCACAAGCA |
| tailGATA | 5'CGCTCAGCAATCGCCACTATC | tailCcCg | 5'GTGAACGAGTATGCGACCCAG |
| tailGAGT | 5'CATTATCACACATGAGCCGCC | tailCcCc | 5'TTGCCTGTATTGCAACGCCTA |
| tailGAGG | 5'GAGGGGCAAGAGAAAACCACC | tailCcCa | 5'TGAGCTGCTGGAAGATCAGGA |
| tailGAGC | 5'AAGTCCAGCGAGCTGTCTTCC | tailCcAt | 5'AGTAGGGGAATACGCAACATGA |
| tailGAGA | 5'AgGCCgctTCTCAGtAAGGTC | tailCcAg | 5'GATCCACTTCGAGGAGTGACC |
| tailGACT | 5'GTGTACGCAGAGAACCCCACA | tailCcAc | 5'GTACCACATTCGCTCGACACG |
| tailGACG | 5'GGTCTCCTGGACAACAGTTCC | tailCcAa | 5'CATTTCCCTCTCGAATTGGCA |
| tailGACC | 5'CaGttGCATCACtCtggCATC | tailCaTT | 5'TCCGATGTATCGCCGAGATGT |
| tailGACA | 5'AAGACCGAATCGCGAAATGAG | tailCaTg | 5'ACCAACTGAGAAGGAAGGTCA |
| tailGAAT | 5'GTTCAGACCACCCGGTTCACA | tailCaTc | 5'CGAATCCTAGTCACCAGTACTC |
| tailGAAG | 5'TGCTACAGCAGGATCCTCTGG | tailCaTa | 5'GGAAGGATGCACTCCTACCGA |
| tailGAAC | 5'GATACCTAGACCGGCAGCAAC | tailCagT | 5'AATAGCTCCCTCCCTCACCAC |
| tailGAAA | 5'CACTGAGAGCTAGGAAACCCAC | tailCagg | 5'GAGGACCATCTGCTACATCTC |
| tailCTTT | 5'GGGATAAATCCTGATGCCGTC | tailCagc | 5'ATTACTTCGCGGGTCCTAATC |
| tailCTTg | 5'CAGTCTCAACCCTTGCCTGTC | tailCaga | 5'CAGCGACAACAAAAGGCTATG |
| tailCTTc | 5'TCACGGAGCTCACCTAAGCAC | tailCaCT | 5'GCGTTGACACCTCATCACTAG |
| tailCTTa | 5'GATTTGGAGCTGACCTGATGC | tailCaCg | 5'TCTACCACTCACCGTCCGAAC |
| tailCTGT | 5'GATGTATCTATGAAATCGAGT | tailCaCc | 5'AGCATGCTTCTGAGGAAGTGC |
| tailCTGg | 5'CAACCCCGTAACTCCGTTCAG | tailCaCa | 5'AGTCATCGTGGCTTGTGTTACA |
| tailCTGc | 5'CGTCGACTTGTGCGACCTTCG | tailCaAT | 5'GACACTTGGCTATGGGTCCCA |
| tailCTGa | 5'AACACGCACAACCAGGTCATG | tailCaAg | 5'CACAGTACGTGAGAGCTCCAA |
| tailCTCT | 5'TCGTCTCCAGCTACTGGACTC | tailCaAc | 5'GAAGCAACCCAACAGGACCAG |
| tailCTCg | 5'TACGCTCAACACTTACAGACG | tailCaAa | 5'AGAGACTCACCAGGAAGCAGCA |
| tailCTCc | 5'GGGCAACAGCACCTACTATAC | tailATTT | 5'TGTGGTACAGCAGAAGGCTGA |
| tailCTCa | 5'CGTCTGACCAGTCTTCCACTC | tailATTG | 5'TCCAAGTTCGCCAAAGCAGGA |
| tailCTAT | 5'GGGAGAGGTGTTTTCCAGTCG | tailATTC | 5'CGTGCGATTCTGGAATGCTTC |
| tailCTAg | 5'GACCCAAGTAGTCGTCGCGAA | tailATTA | 5'ACTCGGAATGGTGGGAGAGGA |
| tailCTAc | 5'CACCATGGTGAATCAGGCTCC | tailATGT | 5'AGCAGATTCTCGAGGAAACCA |
| tailCTAa | 5'ACCTGAGTGTGGGAAGGTCGA | tailATGG | 5'ACCTCTCTGGTCTGGTCAGCA |
| tailCGTT | 5'TGCGAAACTGTCTGTCGGAAG | tailATGC | 5'TGACAAGTGGATGAGTGAGCAG |
| tailCGTg | 5'GCTTTGGCAATCCTCAAGCAG | tailATGA | 5'GGATTTTTCGACCGTGGTACA |
| tailCGTc | 5'TCGCTCCTGACTCATCGAACA | tailATCT | 5'GCCTGAGAGCTTTACTCACCA |
| tailCGTa | 5'CAGAGTCGGTACCATCTCGAC | tailATCG | 5'GCTTAGCTTCTGCGATGGCAC |
| tailCGGT | 5'GCGGACAAAGGATATGTTGATC | tailATCC | 5'CAGCAGTGTCAGGTAGCCTCA |
| tailCGGg | 5'CACTAGGACCTTTTGTCGGAAG | tailATCA | 5'AGACAAGAGGTTCTGGCACCA |
| tailCGGc | 5'TAAGAGCGGTGCTAGCGTGAG | tailATAT | 5'TGGTGGGTCTATCAAGTCGCA |
| tailCGGa | 5'GGAGCCTCGAGATTCGTTGGT | tailATAG | 5'TGTCGTAGCCACTGATGCTAC |
| tailCGCT | 5'GCCTGGTCTTTCAGCATGGAC | tailATAC | 5'TCATCCCTGGCATCGATGCTC |
| tailCGCg | 5'CTTGTCAGCCGAACGTCTGTC | tailATAA | 5'GAGGTGCCTTCCCAGACAGAG |
| tailCGCc | 5'ACGCTGCAAGGCGGATAACAG | tailAGTT | 5'CGTCTCTGGAGTCGTCCTCTC |
| tailCGCa | 5'CAGCACATAGACAGGTGCCTCA | tailAGTG | 5'TGGAGTCACGGTCTATGGATG |
| tailCGAT | 5'ATCATCACGTTGCACCAAGGG | tailAGTC | 5'AGTCTCCTGGAATGACGTGGAC |
| tailCGAg | 5'TCCAGAGGAACGTACGACCCT | tailAGTA | 5'CCAGTGTCCTCACCTAGATCG |
| tailCGAc | 5'GAACAGGAGACAGAGCGAGCA | tailAGGT | 5'AGCCTACGCCAGTTGTCCTTC |

FIG. 13C

| | |
|---|---|
| FIG. 13 | FIG. 13A |
| | FIG. 13B |
| | FIG. 13C |

```
tailAGGG    5'CCTTGTAGAGGATACGAACGAC
tailAGGC    5'AGGTAGCACAGCCAGGAACTC
tailAGGA    5'TCGTACACGATCCATCAGCAG
tailAGCT    5'GAACCCTCTGCCTTCGAACAC
tailAGCG    5'CTCAACCTAGACCCCTTAAACC
tailAGCC    5'CTTAGCAACGTCCCAGAGGAG
tailAGCA    5'AGGAGATCACTGCGTCTGCTG
tailAGAT    5'CCAGCTGCTCACTTCATGCTC
tailAGAG    5'ACCAGTCTCTACTGAGGCCAG
tailAGAC    5'CTATTGCACTAGTGCCTGCCA
tailAGAA    5'TGCGGACACGACAGGATGTAG
tailACTT    5'CCAGTGCTACCTCAGATCCGT
tailACTG    5'GAATCGAGCTGAGGCTTCTCA
tailACTC    5'CAGGCGAATTAACCTCAAACG
tailACTA    5'GCTCGGGTATTTGCAGTAGCA
tailACGT    5'TGAGGAGTTACGTGCAGACGA
tailACGG    5'TGACAGTCGCTTGAACCATCC
tailACGC    5'ACAGACCACCAGCTGAGAGTG
tailACGA    5'GTCCATTCCCATCAACCAAGC
tailACCT    5'GTACGTCTAGTCTTGCTTGCAG
tailACCG    5'GACACTTGGGAGCTTCATGGA
tailACCC    5'CCTGCGTTTAACCAATGTGCA
tailACCA    5'ATCTACCTGCAATGATCTGCA
tailACAT    5'AGACCGTCTTCCAGTCGTGCT
tailACAG    5'ACCACCGATGATGTTCATGCT
tailACAC    5'TCCACCACAGTCCAGACTCCA
tailACAA    5'GACGAGTCGACGAGGTGTAAG
tailAATT    5'GACCTACGGAAGCTTAGCCCT
tailAATG    5'ACACCACCGCAACTAGCCAAC
tailAATC    5'CGTTGTGCCTAAGACCTGCGA
tailAATA    5'GGAACCAGAATCGGACCTGAC
tailAAGT    5'TGGAGTTGATGGGTCGAGCTG
tailAAGG    5'GACAGCTATGTTGCCGGTAGC
tailAAGC    5'TCAGAGTGGCACATACTGAGGA
tailAAGA    5'GATGGCACGTAGGCAAGCAAC
tailAACT    5'CTCTGTGCTTCGGGCCTAGTC
tailAACG    5'CGTATCACCTGTGTCCAGCAA
tailAACC    5'CTAACAACGGTGGCGTTCCA
tailAACA    5'TGCAACCTCGATCCCATACG
tailAAAT    5'GTGAGGAGCTGATGAGACTGA
tailAAAG    5'CGAACGGTTACGTCACCAAGG
tailAAAC    5'ACTTCAGTTCCTAGGCTCGTC
tailAAAA    5'AGGTCTCCATCACGACTCCAC
```

FIG. 17

```
5' GGTACGACGTTCAGCTNGGGIIIAA
5' GGTACGACGTTCAGCTNGGGIIIAC
5' GGTACGACGTTCAGCTNGGGIIIAG
5' GGTACGACGTTCAGCTNGGGIIIAT
5' GGTACGACGTTCAGCTNGGGIIICA
5' GGTACGACGTTCAGCTNGGGIIICC
5' GGTACGACGTTCAGCTNGGGIIICG
5' GGTACGACGTTCAGCTNGGGIIICT

5' GGTACGACGTTCAGCTNGGGIIIGA
5' GGTACGACGTTCAGCTNGGGIIIGC
5' GGTACGACGTTCAGCTNGGGIIIGG
5' GGTACGACGTTCAGCTNGGGIIIGT
5' GGTACGACGTTCAGCTNGGGIIITA
5' GGTACGACGTTCAGCTNGGGIIITC
5' GGTACGACGTTCAGCTNGGGIIITG
5' GGTACGACGTTCAGCTNGGGIIITT
```

```
5' GGTACGACGTTCAGCTNIIIAAAA    5' GGTACGACGTTCAGCTNIIIAGTA    5' GGTACGACGTTCAGCTNIIICCAA
5' GGTACGACGTTCAGCTNIIIAAAC    5' GGTACGACGTTCAGCTNIIIAGTC    5' GGTACGACGTTCAGCTNIIICCAC
5' GGTACGACGTTCAGCTNIIIAAAG    5' GGTACGACGTTCAGCTNIIIAGTG    5' GGTACGACGTTCAGCTNIIICCAG
5' GGTACGACGTTCAGCTNIIIAAAT    5' GGTACGACGTTCAGCTNIIIAGTT    5' GGTACGACGTTCAGCTNIIICCAT
5' GGTACGACGTTCAGCTNIIIAACA                                   5' GGTACGACGTTCAGCTNIIICCCA
5' GGTACGACGTTCAGCTNIIIAACC    5' GGTACGACGTTCAGCTNIIIATAA    5' GGTACGACGTTCAGCTNIIICCCC
5' GGTACGACGTTCAGCTNIIIAACG    5' GGTACGACGTTCAGCTNIIIATAC    5' GGTACGACGTTCAGCTNIIICCCG
5' GGTACGACGTTCAGCTNIIIAACT    5' GGTACGACGTTCAGCTNIIIATAG    5' GGTACGACGTTCAGCTNIIICCCT
                              5' GGTACGACGTTCAGCTNIIIATAT
5' GGTACGACGTTCAGCTNIIIAAGA    5' GGTACGACGTTCAGCTNIIIATCA    5' GGTACGACGTTCAGCTNIIICCGA
5' GGTACGACGTTCAGCTNIIIAAGC    5' GGTACGACGTTCAGCTNIIIATCC    5' GGTACGACGTTCAGCTNIIICCGC
5' GGTACGACGTTCAGCTNIIIAAGG    5' GGTACGACGTTCAGCTNIIIATCG    5' GGTACGACGTTCAGCTNIIICCGG
5' GGTACGACGTTCAGCTNIIIAAGT    5' GGTACGACGTTCAGCTNIIIATCT    5' GGTACGACGTTCAGCTNIIICCGT
5' GGTACGACGTTCAGCTNIIIAATA                                   5' GGTACGACGTTCAGCTNIIICCTA
5' GGTACGACGTTCAGCTNIIIAATC    5' GGTACGACGTTCAGCTNIIIATGA    5' GGTACGACGTTCAGCTNIIICCTC
5' GGTACGACGTTCAGCTNIIIAATG    5' GGTACGACGTTCAGCTNIIIATGC    5' GGTACGACGTTCAGCTNIIICCTG
5' GGTACGACGTTCAGCTNIIIAATT    5' GGTACGACGTTCAGCTNIIIATGG    5' GGTACGACGTTCAGCTNIIICCTT
                              5' GGTACGACGTTCAGCTNIIIATGT
5' GGTACGACGTTCAGCTNIIIACAA    5' GGTACGACGTTCAGCTNIIICAAA    5' GGTACGACGTTCAGCTNIIICGAA
5' GGTACGACGTTCAGCTNIIIACAC    5' GGTACGACGTTCAGCTNIIICAAC    5' GGTACGACGTTCAGCTNIIICGAC
5' GGTACGACGTTCAGCTNIIIACAG    5' GGTACGACGTTCAGCTNIIICAAG    5' GGTACGACGTTCAGCTNIIICGAG
5' GGTACGACGTTCAGCTNIIIACAT                                   5' GGTACGACGTTCAGCTNIIICGAT
5' GGTACGACGTTCAGCTNIIIACCA    5' GGTACGACGTTCAGCTNIIICACA    5' GGTACGACGTTCAGCTNIIICGCA
5' GGTACGACGTTCAGCTNIIIACCC    5' GGTACGACGTTCAGCTNIIICACC    5' GGTACGACGTTCAGCTNIIICGCC
5' GGTACGACGTTCAGCTNIIIACCG    5' GGTACGACGTTCAGCTNIIICACG    5' GGTACGACGTTCAGCTNIIICGCG
5' GGTACGACGTTCAGCTNIIIACCT    5' GGTACGACGTTCAGCTNIIICACT    5' GGTACGACGTTCAGCTNIIICGCT

5' GGTACGACGTTCAGCTNIIIACGA    5' GGTACGACGTTCAGCTNIIICAGA    5' GGTACGACGTTCAGCTNIIICGGA
5' GGTACGACGTTCAGCTNIIIACGC    5' GGTACGACGTTCAGCTNIIICAGC    5' GGTACGACGTTCAGCTNIIICGGC
5' GGTACGACGTTCAGCTNIIIACGG    5' GGTACGACGTTCAGCTNIIICAGG    5' GGTACGACGTTCAGCTNIIICGGG
5' GGTACGACGTTCAGCTNIIIACGT                                   5' GGTACGACGTTCAGCTNIIICGGT
5' GGTACGACGTTCAGCTNIIIACTA    5' GGTACGACGTTCAGCTNIIICAGT    5' GGTACGACGTTCAGCTNIIICGTA
5' GGTACGACGTTCAGCTNIIIACTC    5' GGTACGACGTTCAGCTNIIICATA    5' GGTACGACGTTCAGCTNIIICGTC
5' GGTACGACGTTCAGCTNIIIACTG    5' GGTACGACGTTCAGCTNIIICATC    5' GGTACGACGTTCAGCTNIIICGTG
5' GGTACGACGTTCAGCTNIIIACTT    5' GGTACGACGTTCAGCTNIIICATG    5' GGTACGACGTTCAGCTNIIICGTT
                              5' GGTACGACGTTCAGCTNIIICATT
5' GGTACGACGTTCAGCTNIIIAGAA                                   5' GGTACGACGTTCAGCTNIIICTAA
5' GGTACGACGTTCAGCTNIIIAGAC                                   5' GGTACGACGTTCAGCTNIIICTAC
5' GGTACGACGTTCAGCTNIIIAGAG                                   5' GGTACGACGTTCAGCTNIIICTAG
5' GGTACGACGTTCAGCTNIIIAGAT                                   5' GGTACGACGTTCAGCTNIIICTAT
5' GGTACGACGTTCAGCTNIIIAGCA                                   5' GGTACGACGTTCAGCTNIIICTCA
5' GGTACGACGTTCAGCTNIIIAGCC                                   5' GGTACGACGTTCAGCTNIIICTCC
5' GGTACGACGTTCAGCTNIIIAGCG                                   5' GGTACGACGTTCAGCTNIIICTCG
5' GGTACGACGTTCAGCTNIIIAGCT                                   5' GGTACGACGTTCAGCTNIIICTCT

5' GGTACGACGTTCAGCTNIIIAGGA
5' GGTACGACGTTCAGCTNIIIAGGC
5' GGTACGACGTTCAGCTNIIIAGGG
5' GGTACGACGTTCAGCTNIIIAGGT
```

5' GGTACGACGTTCAGCTNIIICTGA 5' GGTACGACGTTCAGCTNIIIGAAA 5' GGTACGACGTTCAGCTNIIITAAA
5' GGTACGACGTTCAGCTNIIICTGC 5' GGTACGACGTTCAGCTNIIIGAAC 5' GGTACGACGTTCAGCTNIIITAAC
5' GGTACGACGTTCAGCTNIIICTGG 5' GGTACGACGTTCAGCTNIIIGAAG 5' GGTACGACGTTCAGCTNIIITAAG
5' GGTACGACGTTCAGCTNIIICTGT 5' GGTACGACGTTCAGCTNIIIGAAT 5' GGTACGACGTTCAGCTNIIITAAT
5' GGTACGACGTTCAGCTNIIICTTA 5' GGTACGACGTTCAGCTNIIIGACA 5' GGTACGACGTTCAGCTNIIITACA
5' GGTACGACGTTCAGCTNIIICTTC 5' GGTACGACGTTCAGCTNIIIGACC 5' GGTACGACGTTCAGCTNIIITACC
5' GGTACGACGTTCAGCTNIIICTTG 5' GGTACGACGTTCAGCTNIIIGACG 5' GGTACGACGTTCAGCTNIIITACG
5' GGTACGACGTTCAGCTNIIICTTT 5' GGTACGACGTTCAGCTNIIIGACT 5' GGTACGACGTTCAGCTNIIITACT

5' GGTACGACGTTCAGCTNIIIGAGA 5' GGTACGACGTTCAGCTNIIIGGGA 5' GGTACGACGTTCAGCTNIIITAGA
5' GGTACGACGTTCAGCTNIIIGAGC 5' GGTACGACGTTCAGCTNIIIGGGC 5' GGTACGACGTTCAGCTNIIITAGC
5' GGTACGACGTTCAGCTNIIIGAGG 5' GGTACGACGTTCAGCTNIIIGGGG 5' GGTACGACGTTCAGCTNIIITAGG
5' GGTACGACGTTCAGCTNIIIGAGT 5' GGTACGACGTTCAGCTNIIIGGGT 5' GGTACGACGTTCAGCTNIIITAGT
5' GGTACGACGTTCAGCTNIIIGATA 5' GGTACGACGTTCAGCTNIIIGGTA 5' GGTACGACGTTCAGCTNIIITATA
5' GGTACGACGTTCAGCTNIIIGATC 5' GGTACGACGTTCAGCTNIIIGGTC 5' GGTACGACGTTCAGCTNIIITATC
5' GGTACGACGTTCAGCTNIIIGATG 5' GGTACGACGTTCAGCTNIIIGGTG 5' GGTACGACGTTCAGCTNIIITATG
5' GGTACGACGTTCAGCTNIIIGATT 5' GGTACGACGTTCAGCTNIIIGGTT 5' GGTACGACGTTCAGCTNIIITATT

5' GGTACGACGTTCAGCTNIIIGTAA 5' GGTACGACGTTCAGCTNIIITCAA
                              5' GGTACGACGTTCAGCTNIIIGTAC 5' GGTACGACGTTCAGCTNIIITCAC
                              5' GGTACGACGTTCAGCTNIIIGTAG 5' GGTACGACGTTCAGCTNIIITCAT
                              5' GGTACGACGTTCAGCTNIIIGTAT 5' GGTACGACGTTCAGCTNIIITCCA
                              5' GGTACGACGTTCAGCTNIIIGTCA 5' GGTACGACGTTCAGCTNIIITCCC
                              5' GGTACGACGTTCAGCTNIIIGTCC 5' GGTACGACGTTCAGCTNIIITCCG
                              5' GGTACGACGTTCAGCTNIIIGTCG 5' GGTACGACGTTCAGCTNIIITCCT
                              5' GGTACGACGTTCAGCTNIIIGTCT

5' GGTACGACGTTCAGCTNIIIGCAA 5' GGTACGACGTTCAGCTNIIIGTGA 5' GGTACGACGTTCAGCTNIIITCGA
5' GGTACGACGTTCAGCTNIIIGCAC 5' GGTACGACGTTCAGCTNIIIGTGC 5' GGTACGACGTTCAGCTNIIITCGC
5' GGTACGACGTTCAGCTNIIIGCAG 5' GGTACGACGTTCAGCTNIIIGTGG 5' GGTACGACGTTCAGCTNIIITCGG
5' GGTACGACGTTCAGCTNIIIGCAT 5' GGTACGACGTTCAGCTNIIIGTGT 5' GGTACGACGTTCAGCTNIIITCGT
5' GGTACGACGTTCAGCTNIIIGCCA 5' GGTACGACGTTCAGCTNIIIGTTA 5' GGTACGACGTTCAGCTNIIITCTA
5' GGTACGACGTTCAGCTNIIIGCCC 5' GGTACGACGTTCAGCTNIIIGTTC 5' GGTACGACGTTCAGCTNIIITCTC
5' GGTACGACGTTCAGCTNIIIGCCG 5' GGTACGACGTTCAGCTNIIIGTTG 5' GGTACGACGTTCAGCTNIIITCTG
5' GGTACGACGTTCAGCTNIIIGCCT 5' GGTACGACGTTCAGCTNIIIGTTT 5' GGTACGACGTTCAGCTNIIITCTT

5' GGTACGACGTTCAGCTNIIIGCGA
5' GGTACGACGTTCAGCTNIIIGCGC
5' GGTACGACGTTCAGCTNIIIGCGG
5' GGTACGACGTTCAGCTNIIIGCGT
5' GGTACGACGTTCAGCTNIIIGCTA
5' GGTACGACGTTCAGCTNIIIGCTC
5' GGTACGACGTTCAGCTNIIIGCTG
5' GGTACGACGTTCAGCTNIIIGCTT

FIG. 14B

| FIG. 14 | FIG. 14A |
|         | FIG. 14B |

5' GGTACGACGTTCAGCTNIIIAAA
5' GGTACGACGTTCAGCTNIIIAAC
5' GGTACGACGTTCAGCTNIIIAAG
5' GGTACGACGTTCAGCTNIIIAAT
5' GGTACGACGTTCAGCTNIIIACA
5' GGTACGACGTTCAGCTNIIIACC
5' GGTACGACGTTCAGCTNIIIACG
5' GGTACGACGTTCAGCTNIIIACT

5' GGTACGACGTTCAGCTNIIIAGA
5' GGTACGACGTTCAGCTNIIIAGC
5' GGTACGACGTTCAGCTNIIIAGG
5' GGTACGACGTTCAGCTNIIIAGT
5' GGTACGACGTTCAGCTNIIIATA
5' GGTACGACGTTCAGCTNIIIATC
5' GGTACGACGTTCAGCTNIIIATG
5' GGTACGACGTTCAGCTNIIIATT

5' GGTACGACGTTCAGCTNIIICAA
5' GGTACGACGTTCAGCTNIIICAC
5' GGTACGACGTTCAGCTNIIICAG
5' GGTACGACGTTCAGCTNIIICAT
5' GGTACGACGTTCAGCTNIIICCA
5' GGTACGACGTTCAGCTNIIICCC
5' GGTACGACGTTCAGCTNIIICCG
5' GGTACGACGTTCAGCTNIIICCT

5' GGTACGACGTTCAGCTNIIICGA
5' GGTACGACGTTCAGCTNIIICGC
5' GGTACGACGTTCAGCTNIIICGG
5' GGTACGACGTTCAGCTNIIICGT
5' GGTACGACGTTCAGCTNIIICTA
5' GGTACGACGTTCAGCTNIIICTC
5' GGTACGACGTTCAGCTNIIICTG
5' GGTACGACGTTCAGCTNIIICTT

5' GGTACGACGTTCAGCTNIIIGAA
5' GGTACGACGTTCAGCTNIIIGAC
5' GGTACGACGTTCAGCTNIIIGAG
5' GGTACGACGTTCAGCTNIIIGAT
5' GGTACGACGTTCAGCTNIIIGCA
5' GGTACGACGTTCAGCTNIIIGCC
5' GGTACGACGTTCAGCTNIIIGCG
5' GGTACGACGTTCAGCTNIIIGCT

5' GGTACGACGTTCAGCTNIIIGGA
5' GGTACGACGTTCAGCTNIIIGGC
5' GGTACGACGTTCAGCTNIIIGGG
5' GGTACGACGTTCAGCTNIIIGGT

5' GGTACGACGTTCAGCTNIIIGTA
5' GGTACGACGTTCAGCTNIIICTC
5' GGTACGACGTTCAGCTNIIIGTG
5' GGTACGACGTTCAGCTNIIIGTT

5' GGTACGACGTTCAGCTNIIITAA
5' GGTACGACGTTCAGCTNIIITAC
5' GGTACGACGTTCAGCTNIIITAG
5' GGTACGACGTTCAGCTNIIITAT
5' GGTACGACGTTCAGCTNIIITCA
5' GGTACGACGTTCAGCTNIIITCC
5' GGTACGACGTTCAGCTNIIITCG
5' GGTACGACGTTCAGCTNIIITCT

5' GGTACGACGTTCAGCTNIIITGA
5' GGTACGACGTTCAGCTNIIITGC
5' GGTACGACGTTCAGCTNIIITGG
5' GGTACGACGTTCAGCTNIIITGT
5' GGTACGACGTTCAGCTNIIITTA
5' GGTACGACGTTCAGCTNIIITTC
5' GGTACGACGTTCAGCTNIIITTG
5' GGTACGACGTTCAGCTNIIITTT

FIG. 15

```
5' GGTACGACGTTCAGCTNGGGIIIAAA
5' GGTACGACGTTCAGCTNGGGIIIAAC
5' GGTACGACGTTCAGCTNGGGIIIAAG
5' GGTACGACGTTCAGCTNGGGIIIAAT
5' GGTACGACGTTCAGCTNGGGIIIACA
5' GGTACGACGTTCAGCTNGGGIIIACC
5' GGTACGACGTTCAGCTNGGGIIIACG
5' GGTACGACGTTCAGCTNGGGIIIACT

5' GGTACGACGTTCAGCTNGGGIIIAGA
5' GGTACGACGTTCAGCTNGGGIIIAGC
5' GGTACGACGTTCAGCTNGGGIIIAGG
5' GGTACGACGTTCAGCTNGGGIIIAGT
5' GGTACGACGTTCAGCTNGGGIIIATA
5' GGTACGACGTTCAGCTNGGGIIIATC
5' GGTACGACGTTCAGCTNGGGIIIATG
5' GGTACGACGTTCAGCTNGGGIIIATT

5' GGTACGACGTTCAGCTNGGGIIICAA
5' GGTACGACGTTCAGCTNGGGIIICAC
5' GGTACGACGTTCAGCTNGGGIIICAG
5' GGTACGACGTTCAGCTNGGGIIICAT
5' GGTACGACGTTCAGCTNGGGIIICCA
5' GGTACGACGTTCAGCTNGGGIIICCC
5' GGTACGACGTTCAGCTNGGGIIICCG
5' GGTACGACGTTCAGCTNGGGIIICCT

5' GGTACGACGTTCAGCTNGGGIIICGA
5' GGTACGACGTTCAGCTNGGGIIICGC
5' GGTACGACGTTCAGCTNGGGIIICGG
5' GGTACGACGTTCAGCTNGGGIIICGT
5' GGTACGACGTTCAGCTNGGGIIICTA
5' GGTACGACGTTCAGCTNGGGIIICTC
5' GGTACGACGTTCAGCTNGGGIIICTG
5' GGTACGACGTTCAGCTNGGGIIICTT

5' GGTACGACGTTCAGCTNGGGIIIGAA
5' GGTACGACGTTCAGCTNGGGIIIGAC
5' GGTACGACGTTCAGCTNGGGIIIGAG
5' GGTACGACGTTCAGCTNGGGIIIGAT
5' GGTACGACGTTCAGCTNGGGIIIGCA
5' GGTACGACGTTCAGCTNGGGIIIGCC
5' GGTACGACGTTCAGCTNGGGIIIGCG
5' GGTACGACGTTCAGCTNGGGIIIGCT

5' GGTACGACGTTCAGCTNGGGIIIGGA
5' GGTACGACGTTCAGCTNGGGIIIGGC
5' GGTACGACGTTCAGCTNGGGIIIGGG
5' GGTACGACGTTCAGCTNGGGIIIGGT

5' GGTACGACGTTCAGCTNGGGIIIGTA
5' GGTACGACGTTCAGCTNGGGIIICTC
5' GGTACGACGTTCAGCTNGGGIIIGTG
5' GGTACGACGTTCAGCTNGGGIIIGTT

5' GGTACGACGTTCAGCTNGGGIIITAA
5' GGTACGACGTTCAGCTNGGGIIITAC
5' GGTACGACGTTCAGCTNGGGIIITAG
5' GGTACGACGTTCAGCTNGGGIIITAT
5' GGTACGACGTTCAGCTNGGGIIITCA
5' GGTACGACGTTCAGCTNGGGIIITCC
5' GGTACGACGTTCAGCTNGGGIIITCG
5' GGTACGACGTTCAGCTNGGGIIITCT

5' GGTACGACGTTCAGCTNGGGIIITGA
5' GGTACGACGTTCAGCTNGGGIIITGC
5' GGTACGACGTTCAGCTNGGGIIITGG
5' GGTACGACGTTCAGCTNGGGIIITGT
5' GGTACGACGTTCAGCTNGGGIIITTA
5' GGTACGACGTTCAGCTNGGGIIITTC
5' GGTACGACGTTCAGCTNGGGIIITTG
5' GGTACGACGTTCAGCTNGGGIIITTT
```

```
AdaTTTT  5' TTTTGCAGGTACGTCGTACCGCGGCCGCTCGTCGAACGAACACTGCGTT
AdaTTTG  5' TTTGGCAGGTACGTCGTACCGCGGCCGCTACGTCTCGTTCCGCTCTGCA
AdaTTTC  5' TTTCGCAGGTACGTCGTACCGCGGCCGCCTTCGCTAGACGACGTGCGCT
AdaTTTA  5' TTTAGCAGGTACGTCGTACCGCGGCCGCTCGCTCGTACTCCGTCTCAGA
AdaTTGT  5' TTGTGCAGGTACGTCGTACCGCGGCCGCATGCGCGAAAACGGTCACTGT
AdaTTGG  5' TTGGGCAGGTACGTCGTACCGCGGCCGCCGCTTTTCGTCGTCCCAGAGT
AdaTTGC  5' TTGCGCAGGTACGTCGTACCGCGGCCGCCTGGTAAACCCGGTTCGGTCA
AdaTTGA  5' TTGAGCAGGTACGTCGTACCGCGGCCGCCGATAGTCCGAGACGTCTCGT

AdaTTCT  5' TTCTGCAGGTACGTCGTACCGCGGCCGCCTATCGAACGGCACGTTGTTG
AdaTTCG  5' TTCGGCAGGTACGTCGTACCGCGGCCGCCTACGACCGTTCGGGTGGTAC
AdaTTCC  5' TTCCGCAGGTACGTCGTACCGCGGCCGCTCGTACGGTCGACGGTTGTGC
AdaTTCA  5' TTCAGCAGGTACGTCGTACCGCGGCCGCCGTTAGACCTCGTCTCGGCTT
AdaTTAT  5' TTATGCAGGTACGTCGTACCGCGGCCGCCTAACGTCCGATCGCAGCGAT
AdaTTAG  5' TTAGGCAGGTACGTCGTACCGCGGCCGCCGGTATCGGAACGTCTGCGGT
AdaTTAC  5' TTACGCAGGTACGTCGTACCGCGGCCGCTACCGAACCGTCGTACGTAGA
AdaTTAA  5' TTAAGCAGGTACGTCGTACCGCGGCCGCCTAGCGGATTCACGTGGTGTA

AdaTGTT  5' TGTTGCAGGTACGTCGTACCGCGGCCGCGTCGACGACTCTGTCCAGGAT
AdaTGTG  5' TGTGGCAGGTACGTCGTACCGCGGCCGCTCGACGGTTCTTGACTCACGA
AdaTGTC  5' TGTCGCAGGTACGTCGTACCGCGGCCGCCGTAAGGATCACGTGTGCTGT
AdaTGTA  5' TGTAGCAGGTACGTCGTACCGCGGCCGCCTTACGGATCGAGCGTGTACCA
AdaTGGT  5' TGGTGCAGGTACGTCGTACCGCGGCCGCCATACGCAACGACCCGAGTGAG
AdaTGGG  5' TGGGGCAGGTACGTCGTACCGCGGCCGCCGTATCCTTGCGTGTGTAATCC
AdaTGGC  5' TGGCGCAGGTACGTCGTACCGCGGCCGCATCGGAAGAAGCACGATGCCA
AdaTGGA  5' TGGAGCAGGTACGTCGTACCGCGGCCGCCCGATTTCTCGCGAGGACGTC

AdaTGCT  5' TGCTGCAGGTACGTCGTACCGCGGCCGCCGCATCCCACTGCTGGATACT
AdaTGCG  5' TGCGGCAGGTACGTCGTACCGCGGCCGCTACGGTTCGGTCGCTCTTCGT
AdaTGCC  5' TGCCGCAGGTACGTCGTACCGCGGCCGCCATTCGTCGAACCGCAGTTGC
AdaTGCA  5' TGCAGCAGGTACGTCGTACCGCGGCCGCCGAATTTCGACTCGCGAACGT
AdaTGAT  5' TGATGCAGGTACGTCGTACCGCGGCCGCAACGCGACGCAGTGACACGTT
AdaTGAG  5' TGAGGCAGGTACGTCGTACCGCGGCCGCGCTTTGCTTCTCCGTCTAGAC
AdaTGAC  5' TGACGCAGGTACGTCGTACCGCGGCCGCACGTAACGTCGAGCGCTAACG
AdaTGAA  5' TGAAGCAGGTACGTCGTACCGCGGCCGCTACGTGACGTGCGGAGTGATC

AdaTCTT  5' TCTTGCAGGTACGTCGTACCGCGGCCGCCGTAGACGCTCGGTAACTAGT
AdaTCTG  5' TCTGGCAGGTACGTCGTACCGCGGCCGCTACGAGCGTCTCTCGCATAG
AdaTCTC  5' TCTCGCAGGTACGTCGTACCGCGGCCGCGCGAAACGCATCCGTTCGTGT
AdaTCTA  5' TCTAGCAGGTACGTCGTACCGCGGCCGCTTCGCTTCGTTGCTGCTAGTA
AdaTCGT  5' TCGTGCAGGTACGTCGTACCGCGGCCGCACGATCGACACCGGAGTCTAG
AdaTCGG  5' TCGGGCAGGTACGTCGTACCGCGGCCGCATCGTTGTCGGGACGTAGTCG
AdaTCGC  5' TCGCGCAGGTACGTCGTACCGCGGCCGCACGACCATCGTCTTCCGAGTT
AdaTCGA  5' TCGAGCAGGTACGTCGTACCGCGGCCGCGTCGTCGATGCGTCCATACTT

AdaTCCT  5' TCCTGCAGGTACGTCGTACCGCGGCCGCAACCGAACGTGTCGACCTTCA
AdaTCCG  5' TCCGGCAGGTACGTCGTACCGCGGCCGCTGGTTACGTTTGCGCGGTATT
AdaTCCC  5' TCCCGCAGGTACGTCGTACCGCGGCCGCCGAACCCTGGTCCTGTGTCTA
AdaTCCA  5' TCCAGCAGGTACGTCGTACCGCGGCCGCGTTCGCTCGTCACGAAGTACT
AdaTCAT  5' TCATGCAGGTACGTCGTACCGCGGCCGCCGCAAACCGCAGCTTCTAGTT
AdaTCAG  5' TCAGGCAGGTACGTCGTACCGCGGCCGCTTGCGACCGTTCGCAGCTAGT

AdaTCAC  5' TCACGCAGGTACGTCGTACCGCGGCCGCAGTCGCAGGTAAGCGTATGCT
AdaTCAA  5' TCAAGCAGGTACGTCGTACCGCGGCCGCCGACTATCGTAGGCTCCACGT

AdaTATT  5' TATTGCAGGTACGTCGTACCGCGGCCGCATCGAGCGATTCGAGGTTAGG
AdaTATG  5' TATGGCAGGTACGTCGTACCGCGGCCGCTCGATACCGTAGCGCCGTGGT
AdaTATC  5' TATCGCAGGTACGTCGTACCGCGGCCGCACCGAACTCTCTCGACGGCAT
AdaTATA  5' TATAGCAGGTACGTCGTACCGCGGCCGCTCGATCGTCACTCGTGGTTGA
AdaTAGT  5' TAGTGCAGGTACGTCGTACCGCGGCCGCGCGACTGACGACGAGGATAGT
AdaTAGG  5' TAGGGCAGGTACGTCGTACCGCGGCCGCGTCGTGGCAGACGGATAACCT
AdaTAGC  5' TAGCGCAGGTACGTCGTACCGCGGCCGCATGCGGTTCGTCAGTCGTGGA
AdaTAGA  5' TAGAGCAGGTACGTCGTACCGCGGCCGCCGTATCGATTCCGTCTAGCTC
```

FIG. 18B

| | | |
|---|---|---|
| AdaTACT | 5' | TACTGCAGGTACGTCGTACCGCGGCCGCACGAAGATCGACGGCTCCGTT |
| AdaTACG | 5' | TACGGCAGGTACGTCGTACCGCGGCCGCTCGAACGAAGACCACGTACTG |
| AdaTACC | 5' | TACCGCAGGTACGTCGTACCGCGGCCGCTGCTGACTTCGGCGGTGATCG |
| AdaTACA | 5' | TACAGCAGGTACGTCGTACCGCGGCCGCGTTCGTAGACGCGAGTCTGAC |
| AdaTAAT | 5' | TAATGCAGGTACGTCGTACCGCGGCCGCCAATCGCGTTTACTCGAATGG |
| AdaTAAG | 5' | TAAGGCAGGTACGTCGTACCGCGGCCGCCGATTCGGAACGAGCGACTAT |
| AdaTAAC | 5' | TAACGCAGGTACGTCGTACCGCGGCCGCCGTTCTTCCTGGCTCTAAGGC |
| AdaTAAA | 5' | TAAAGCAGGTACGTCGTACCGCGGCCGCGAACGCTAACGTGCGTGAACC |
| AdaGTTT | 5' | GTTTGCAGGTACGTCGTACCGCGGCCGCGATGAGCCAGGGAAGGAATTGG |
| AdaGTTG | 5' | GTTGGCAGGTACGTCGTACCGCGGCCGCGATTAGACGAGGCGACCGAGA |
| AdaGTTC | 5' | GTTCGCAGGTACGTCGTACCGCGGCCGCGACTAGGTCAGCTGAGGAGTCT |
| AdaGTTA | 5' | GTTAGCAGGTACGTCGTACCGCGGCCGCACTACGAGTGGCGAGCTGACT |
| AdaGTGT | 5' | GTGTGCAGGTACGTCGTACCGCGGCCGCGCCTACTGACTCGAGTACTCT |
| AdaGTGG | 5' | GTGGGCAGGTACGTCGTACCGCGGCCGCCGTTGTTCCCGACTCCTCTGT |
| AdaGTGC | 5' | GTGCGCAGGTACGTCGTACCGCGGCCGCCAACGGACACAGGTACCCAAG |
| AdaGTGA | 5' | GTGAGCAGGTACGTCGTACCGCGGCCGCTCACAGATTGCTTCGTACTGT |
| AdaGTCT | 5' | GTCTGCAGGTACGTCGTACCGCGGCCGCCGTCCTTATGCTCTCCGAGCT |
| AdaGTCG | 5' | GTCGGCAGGTACGTCGTACCGCGGCCGCCCTATCCAGTAATGCCCGAGA |
| AdaGTCC | 5' | GTCCGCAGGTACGTCGTACCGCGGCCGCCATGGGACAGATCAGGTTAAGG |
| AdaGTCA | 5' | GTCAGCAGGTACGTCGTACCGCGGCCGCTCAGTCAAACTGGACTCGCAC |
| AdaGTAT | 5' | GTATGCAGGTACGTCGTACCGCGGCCGCGAAGGCTGTGGTTGGCCACC |
| AdaGTAG | 5' | GTAGGCAGGTACGTCGTACCGCGGCCGCGCAGTCGTACACCTCATCTCA |
| AdaGTAC | 5' | GTACGCAGGTACGTCGTACCGCGGCCGCTAGACAACTGGCGCATTGACA |
| AdaGTAA | 5' | GTAAGCAGGTACGTCGTACCGCGGCCGCGATGCCACTAGGTGTTGGTGC |
| AdaGGTT | 5' | GGTTGCAGGTACGTCGTACCGCGGCCGCAGACCTCCCGCTCTACAGATC |
| AdaGGTG | 5' | GGTGGCAGGTACGTCGTACCGCGGCCGCGCGTGGCAGCACCCTTAGCCA |
| AdaGGTC | 5' | GGTCGCAGGTACGTCGTACCGCGGCCGCAGGTTTCGGCTGGAGTCTCAT |
| AdaGGTA | 5' | GGTAGCAGGTACGTCGTACCGCGGCCGCTCTGCAGGTCGTCCCTACACT |
| AdaGGGT | 5' | GGGTGCAGGTACGTCGTACCGCGGCCGCTGTATCAGCTATGCCGTTGCC |
| AdaGGGG | 5' | GGGGGCAGGTACGTCGTACCGCGGCCGCCGTTGCCTCATACCTCAGCATC |
| AdaGGGC | 5' | GGGCGCAGGTACGTCGTACCGCGGCCGCAGCAGACAGGCCAAATGACGT |
| AdaGGGA | 5' | GGGAGCAGGTACGTCGTACCGCGGCCGCAGCAGTTCGAGCACGTGAGTC |
| AdaGGCT | 5' | GGCTGCAGGTACGTCGTACCGCGGCCGCGAGATGTGCCACATGCCGACT |
| AdaGGCG | 5' | GGCGGCAGGTACGTCGTACCGCGGCCGCGTTAGCGGCTGTCTACCGAGT |
| AdaGGCC | 5' | GGCCGCAGGTACGTCGTACCGCGGCCGCGTGAATAGTGACCGTGTCCCAG |
| AdaGGCA | 5' | GGCAGCAGGTACGTCGTACCGCGGCCGCTGTGTACAGCGTTCCAAGGGT |
| AdaGGAT | 5' | GGATGCAGGTACGTCGTACCGCGGCCGCACGTCTCACTACGTGTCCGGA |
| AdaGGAG | 5' | GGAGGCAGGTACGTCGTACCGCGGCCGCGCTAGGTAAGAGTGCAAGGCA |
| AdaGGAC | 5' | GGACGCAGGTACGTCGTACCGCGGCCGCCCAAGTGCACGATACTGGCTA |
| AdaGGAA | 5' | GGAAGCAGGTACGTCGTACCGCGGCCGCTTCGTGTAGGGTGGTAAGCTT |
| AdaGCTT | 5' | GCTTGCAGGTACGTCGTACCGCGGCCGCTTCGACCCATGTCATCATCCT |
| AdaGCTG | 5' | GCTGGCAGGTACGTCGTACCGCGGCCGCGGAGGACTTGTCATGGAGGTT |
| AdaGCTC | 5' | GCTCGCAGGTACGTCGTACCGCGGCCGCAGATGTCTGTCCCACGGTGTT |
| AdaGCTA | 5' | GCTAGCAGGTACGTCGTACCGCGGCCGCAATGCCCTGTATGTTCCGTGG |
| AdaGCGT | 5' | GCGTGCAGGTACGTCGTACCGCGGCCGCATGCTTAGCTCCACGCTCATG |
| AdaGCGG | 5' | GCGGGCAGGTACGTCGTACCGCGGCCGCCCTCGTACCTTGTGACAGATG |
| AdaGCGC | 5' | GCGCGCAGGTACGTCGTACCGCGGCCGCTGTGCGAGCGTTCCATCTCCT |
| AdaGCGA | 5' | GCGAGCAGGTACGTCGTACCGCGGCCGCGATGCTGGTCGAGGACACAGA |
| AdaGCCT | 5' | GCCTGCAGGTACGTCGTACCGCGGCCGCAACCAGCTTCCACCTGGAGTT |
| AdaGCCG | 5' | GCCGGCAGGTACGTCGTACCGCGGCCGCGTGACGTTCGATGTGAGTCTG |
| AdaGCCC | 5' | GCCCGCAGGTACGTCGTACCGCGGCCGCGGTGTCCCATTCGGAGTTACA |
| AdaGCCA | 5' | GCCAGCAGGTACGTCGTACCGCGGCCGCCAGGTGAGGGAGAGCATCAAC |
| AdaGCAT | 5' | GCATGCAGGTACGTCGTACCGCGGCCGCTCGACCTTGTTGGCAGACTC |
| AdaGCAG | 5' | GCAGGCAGGTACGTCGTACCGCGGCCGCTGCATTGCGGTTCCTCACAAC |
| AdaGCAC | 5' | GCACGCAGGTACGTCGTACCGCGGCCGCCTGAGAGCTGTTCACTGAGGT |
| AdaGCAA | 5' | GCAAGCAGGTACGTCGTACCGCGGCCGCCAGTGGATAGCGACCTGGATC |

```
AdaGATT  5' GATTGCAGGTACGTCGTACCGCGGCCGCTGGATTTGAGATCGCATGTGG
AdaGATG  5' GATGGCAGGTACGTCGTACCGCGGCCGCGCGTCTAGGTCGTCACGACAA
AdaGATC  5' GATCGCAGGTACGTCGTACCGCGGCCGCCCCGATGATTAGACGCCTCAA
AdaGATA  5' GATAGCAGGTACGTCGTACCGCGGCCGCGATAGTGGCGATTGCTGAGCG
AdaGAGT  5' GAGTGCAGGTACGTCGTACCGCGGCCGCGGCGGCTCATGTGTGATAATG
AdaGAGG  5' GAGGGCAGGTACGTCGTACCGCGGCCGCGGTGGTTTTCTCTTGCCCCTC
AdaGAGC  5' GAGCGCAGGTACGTCGTACCGCGGCCGCGGAAGACAGCTCGCTGGACTT
AdaGAGA  5' GAGAGCAGGTACGTCGTACCGCGGCCGCGACCTTACTGAGAAGCGGCCT

AdaGACT  5' GACTGCAGGTACGTCGTACCGCGGCCGCTGTGGGGTTCTCTGCGTACAC
AdaGACG  5' GACGGCAGGTACGTCGTACCGCGGCCGCGGAACTGTTGTCCAGGAGACC
AdaGACC  5' GACCGCAGGTACGTCGTACCGCGGCCGCGATGCCAGAGTGATGCAACTG
AdaGACA  5' GACAGCAGGTACGTCGTACCGCGGCCGCCTCATTTCGCGATTCGGTCTT
AdaGAAT  5' GAATGCAGGTACGTCGTACCGCGGCCGCTGTGAACCGGGTGGTCTGAAC
AdaGAAG  5' GAAGGCAGGTACGTCGTACCGCGGCCGCCCAGAGGATCCTGCTGTAGCA
AdaGAAC  5' GAACGCAGGTACGTCGTACCGCGGCCGCGTTGCTGCCGGTCTAGGTATC
AdaGAAA  5' GAAAGCAGGTACGTCGTACCGCGGCCGCGTGGGTTTCCTAGCTCTCAGTG

AdaCTTT  5' CTTTGCAGGTACGTCGTACCGCGGCCGCGACGGCATCAGGATTTATCCC
AdaCTTg  5' CTTgGCAGGTACGTCGTACCGCGGCCGCGACAGGCAAGGGTTGAGACTG
AdaCTTc  5' CTTcGCAGGTACGTCGTACCGCGGCCGCGTGCTTAGGTGAGCTCCGTGA
AdaCTTa  5' CTTaGCAGGTACGTCGTACCGCGGCCGCGCATCAGGTCAGCTCCAAATC
AdaCTGT  5' CTGTGCAGGTACGTCGTACCGCGGCCGCACTCGATTTCATAGATACATC
AdaCTGg  5' CTGgGCAGGTACGTCGTACCGCGGCCGCCTGAACGGAGTTACGGGGTTG
AdaCTGc  5' CTGcGCAGGTACGTCGTACCGCGGCCGCCGAAGGTCGCACAAGTCGACG
AdaCTGa  5' CTGaGCAGGTACGTCGTACCGCGGCCGCCATGACCTGGTTGTGCGTGTT

AdaCTCT  5' CTCTGCAGGTACGTCGTACCGCGGCCGCGAGTCCAGTAGCTGGAGACGA
AdaCTCg  5' CTCgGCAGGTACGTCGTACCGCGGCCGCCGTCTGTAAGTGTTGAGCGTA
AdaCTCc  5' CTCcGCAGGTACGTCGTACCGCGGCCGCGTATAGTAGGTGCTGTTGCCC
AdaCTCa  5' CTCaGCAGGTACGTCGTACCGCGGCCGCGAGTGGAAGACTGGTCAGACG
AdaCTAT  5' CTATGCAGGTACGTCGTACCGCGGCCGCCGACTGGAAAACACCTCTCCC
AdaCTAg  5' CTAgGCAGGTACGTCGTACCGCGGCCGCTTCGCGACGACTACTTGGGTC
AdaCTAc  5' CTAcGCAGGTACGTCGTACCGCGGCCGCGGAGCCTGATTCACCATGGTG
AdaCTAa  5' CTAaGCAGGTACGTCGTACCGCGGCCGCTCGACCTTCCCACACTCAGGT

AdaCGTT  5' CGTTGCAGGTACGTCGTACCGCGGCCGCCTTCCGACAGACAGTTTCGCA
AdaCGTg  5' CGTgGCAGGTACGTCGTACCGCGGCCGCCTGCTTGAGGATTGCCAAAGC
AdaCGTc  5' CGTcGCAGGTACGTCGTACCGCGGCCGCTGTTCGATGAGTCAGGAGCGA
AdaCGTa  5' CGTaGCAGGTACGTCGTACCGCGGCCGCGTCGAGATGGTACCGACTCTG
AdaCGGT  5' CGGTGCAGGTACGTCGTACCGCGGCCGCGATCAACATATCCTTTGTCCGC
AdaCGGg  5' CGGgGCAGGTACGTCGTACCGCGGCCGCCTTCCGACAAAAGGTCCTAGTG
AdaCGGc  5' CGGcGCAGGTACGTCGTACCGCGGCCGCCTCACGCTAGCACCGCTCTTA
AdaCGGa  5' CGGaGCAGGTACGTCGTACCGCGGCCGCACCAACGAATCTCGAGGCTCC

AdaCGCT  5' CGCTGCAGGTACGTCGTACCGCGGCCGCGTCCATGCTGAAAGACCAGGC
AdaCGCg  5' CGCgGCAGGTACGTCGTACCGCGGCCGCGACAGACGTTCGGCTGACAAG
AdaCGCc  5' CGCcGCAGGTACGTCGTACCGCGGCCGCCTGTTATCCGCCTTGCAGCGT
AdaCGCa  5' CGCaGCAGGTACGTCGTACCGCGGCCGCTGAGGCACCTGTCTATGTGCTG
AdaCGAT  5' CGATGCAGGTACGTCGTACCGCGGCCGCCCCTTGGTGCAACGTGATGAT
AdaCGAg  5' CGAgGCAGGTACGTCGTACCGCGGCCGCAGGGTCGTACGTTCCTCTGGA
AdaCGAc  5' CGAcGCAGGTACGTCGTACCGCGGCCGCTGCTCGCTCTGTCTCCTGTTC
AdaCGAa* 5' CGAaGCAGGTACGTCGTACCGCGGCCGCTCCACGTCGTACTGACCGTAG

AdaCCTT  5' CCTTGCAGGTACGTCGTACCGCGGCCGCCAGCGCTCCAGCGAATAATTT
AdaCCTg  5' CCTgGCAGGTACGTCGTACCGCGGCCGCCTGTATGCTACACCGCAGCTG
AdaCCTc  5' CCTcGCAGGTACGTCGTACCGCGGCCGCGCGTCTGGAACGATTACGAGT
AdaCCTa  5' CCTaGCAGGTACGTCGTACCGCGGCCGCCTTTCCGGCCATAACACGTAT
AdaCcgT  5' CcgTGCAGGTACGTCGTACCGCGGCCGCTTCCCAACCTAACTTCGGAGC
AdaCcgg  5' CcggGCAGGTACGTCGTACCGCGGCCGCGCTATCGTTGCAAGGGTGAAC
AdaCcgc  5' CcgcGCAGGTACGTCGTACCGCGGCCGCATCCGAGTAGGGAGTCTCCCT
AdaCcga  5' CcgaGCAGGTACGTCGTACCGCGGCCGCCTGGTACATGTCTGGCAACTC
```

```
AdaAGCT    5' AGCTGCAGGTACGTCGTACCGCGGCCGCGTGTTCGAAGGCAGAGGGTTC
AdaAGCG    5' AGCGGCAGGTACGTCGTACCGCGGCCGCGGTTTAAGGGGTCTAGGTTGAG
AdaAGCC    5' AGCCGCAGGTACGTCGTACCGCGGCCGCCTCCTCTGGGACGTTGCTAAG
AdaAGCA    5' AGCAGCAGGTACGTCGTACCGCGGCCGCCAGCAGACGCAGTGATCTCCT
AdaAGAT    5' AGATGCAGGTACGTCGTACCGCGGCCGCGAGCATGAAGTGAGCAGCTGG
AdaAGAG    5' AGAGGCAGGTACGTCGTACCGCGGCCGCCTGGCCTCAGTAGAGACTGGT
AdaAGAC    5' AGACGCAGGTACGTCGTACCGCGGCCGCTGGCAGGCACTAGTGCAATAG
AdaAGAA    5' AGAAGCAGGTACGTCGTACCGCGGCCGCCTACATCCTGTCGTGTCCGCA

AdaACTT    5' ACTTGCAGGTACGTCGTACCGCGGCCGCACGGATCTGAGGTAGCACTGG
AdaACTG    5' ACTGGCAGGTACGTCGTACCGCGGCCGCTGAGAAGCCTCAGCTCGATTC
AdaACTC    5' ACTCGCAGGTACGTCGTACCGCGGCCGCCGTTTGAGGTTAATTCGCCTG
AdaACTA    5' ACTAGCAGGTACGTCGTACCGCGGCCGCTGCTACTGCAAATACCCGAGC
AdaACGT    5' ACGTGCAGGTACGTCGTACCGCGGCCGCTCGTCTGCACGTAACTCCTCA
AdaACGG    5' ACGGGCAGGTACGTCGTACCGCGGCCGCGGATGGTTCAAGCGACTGTCA
AdaACGC    5' ACGCGCAGGTACGTCGTACCGCGGCCGCCACTCTCAGCTGGTGGTCTGT
AdaACGA    5' ACGAGCAGGTACGTCGTACCGCGGCCGCGCTTGGTTGATGGGAATGGAC

AdaACCT    5' ACCTGCAGGTACGTCGTACCGCGGCCGCCTGCAAGCAAGACTAGACGTAC
AdaACCG    5' ACCGGCAGGTACGTCGTACCGCGGCCGCTCCATGAAGCTCCCAAGTGTC
AdaACCC    5' ACCCGCAGGTACGTCGTACCGCGGCCGCTGCACATTGGTTAAACGCAGG
AdaACCA    5' ACCAGCAGGTACGTCGTACCGCGGCCGCTGCAGATCATTGCAGGTAGAT
AdaACAT    5' ACATGCAGGTACGTCGTACCGCGGCCGCAGCACGACTGGAAGACGGTCT
AdaACAG    5' ACAGGCAGGTACGTCGTACCGCGGCCGCAGCATGAACATCATCGGTGGT
AdaACAC    5' ACACGCAGGTACGTCGTACCGCGGCCGCTGGAGTCTGGACTGTGGTGGA
AdaACAA    5' ACAAGCAGGTACGTCGTACCGCGGCCGCCTTACACCTCGTCGACTCGTC

AdaAATT    5' AATTGCAGGTACGTCGTACCGCGGCCGCAGGGCTAAGCTTCCGTAGGTC
AdaAATG    5' AATGGCAGGTACGTCGTACCGCGGCCGCGTTGGCTAGTTGCGGTGGTGT
AdaAATC    5' AATCGCAGGTACGTCGTACCGCGGCCGCTCGCAGGTCTTAGGCACAACG
AdaAATA    5' AATAGCAGGTACGTCGTACCGCGGCCGCGTCAGGTCCGATTCTGGTTCC
AdaAAGT    5' AAGTGCAGGTACGTCGTACCGCGGCCGCCAGCTCGACCCATCAACTCCA
AdaAAGG    5' AAGGGCAGGTACGTCGTACCGCGGCCGCGCTACCGGCAACATAGCTGTC
AdaAAGC    5' AAGCGCAGGTACGTCGTACCGCGGCCGCTCCTCAGTATGTGCCACTCTGA
AdaAAGA    5' AAGAGCAGGTACGTCGTACCGCGGCCGCGTTGCTTGCCTACGTGCCATC

AdaAACT    5' AACTGCAGGTACGTCGTACCGCGGCCGCGACTAGGCCCGAAGCACAGAG
AdaAACG    5' AACGGCAGGTACGTCGTACCGCGGCCGCTTGCTGGACACAGGTGATACG
AdaAACC    5' AACCGCAGGTACGTCGTACCGCGGCCGCTGGAACGCCACCGTTGTTAG
AdaAACA    5' AACAGCAGGTACGTCGTACCGCGGCCGCCGTATGGATCGAGGTTGCA
AdaAAAT    5' AAATGCAGGTACGTCGTACCGCGGCCGCTCAGTCTCATCAGCTCCTCAC
AdaAAAG    5' AAAGGCAGGTACGTCGTACCGCGGCCGCCCTTGGTGACGTAACCGTTCG
AdaAAAC    5' AAACGCAGGTACGTCGTACCGCGGCCGCGACGAGCCTAGGAACTGAAGT
AdaAAAA    5' AAAAGCAGGTACGTCGTACCGCGGCCGCGTGGAGTCGTGATGGAGACCT
```

FIG. 18E

| | FIG. 18A |
|---|---|
| | FIG. 18B |
| FIG. 18 | FIG. 18C |
| | FIG. 18D |
| | FIG. 18E |

```
AdaCcCt    5' CcCtGCAGGTACGTCGTACCGCGGCCGCTGCTTGTGGGAAGAAACTGGC
AdaCcCg    5' CcCgGCAGGTACGTCGTACCGCGGCCGCCTGGGTCGCATACTCGTTCAC
AdaCcCc    5' CcCcGCAGGTACGTCGTACCGCGGCCGCTAGGCGTTGCAATACAGGCAA
AdaCcCa    5' CcCaGCAGGTACGTCGTACCGCGGCCGCTCCTGATCTTCCAGCAGCTCA
AdaCcAt    5' CcAtGCAGGTACGTCGTACCGCGGCCGCTCATGTTGCGTATTCCCCTACT
AdaCcAg    5' CcAgGCAGGTACGTCGTACCGCGGCCGCGGTCACTCCTCGAAGTGGATC
AdaCcAc    5' CcAcGCAGGTACGTCGTACCGCGGCCGCCGTGTCGAGCGAATGTGGTAC
AdaCcAa    5' CcAaGCAGGTACGTCGTACCGCGGCCGCTGCCAATTCGAGAGGGAAATG

AdaCaTT    5' CaTTGCAGGTACGTCGTACCGCGGCCGCACATCTCGGCGATACATCGGA
AdaCaTg    5' CaTgGCAGGTACGTCGTACCGCGGCCGCTGACCTTCCTTCTCAGTTGGT
AdaCaTc    5' CaTcGCAGGTACGTCGTACCGCGGCCGCGAGTACTGGTGACTAGGATTCG
AdaCaTa    5' CaTaGCAGGTACGTCGTACCGCGGCCGCTCGGTAGGAGTGCATCCTTCC
AdaCagT    5' CagTGCAGGTACGTCGTACCGCGGCCGCGTGGTGAGGGAGGGAGCTATT
AdaCagg    5' CaggGCAGGTACGTCGTACCGCGGCCGCGAGATGTAGCAGATGGTCCTC
AdaCagc    5' CagcGCAGGTACGTCGTACCGCGGCCGCGATTAGGACCCGCGAAGTAAT
AdaCaga    5' CagaGCAGGTACGTCGTACCGCGGCCGCCATAGCCTTTTGTTGTCGCTG AdaCaCT    5' CaCTGCAGGTACGTCGTACCGCGGCCGCCTAGTGATGAGGTGTCAACGC
AdaCaCg    5' CaCgGCAGGTACGTCGTACCGCGGCCGCGTTCGGACGGTGAGTGGTAGA
AdaCaCc    5' CaCcGCAGGTACGTCGTACCGCGGCCGCGCACTTCCTCAGAAGCATGCT
AdaCaCa    5' CaCaGCAGGTACGTCGTACCGCGGCCGCTGTAACACAAGCCACGATGACT
AdaCaAT    5' CaATGCAGGTACGTCGTACCGCGGCCGCTGGGACCCATAGCCAAGTGTC
AdaCaAg    5' CaAgGCAGGTACGTCGTACCGCGGCCGCTTGGAGCTCTCACGTACTGTG
AdaCaAc    5' CaAcGCAGGTACGTCGTACCGCGGCCGCCTGGTCCTGTTGGGTTGCTTC
AdaCaAa    5' CaAaGCAGGTACGTCGTACCGCGGCCGCTGCTGCTTCCTGGTGAGTCTCT AdaATTT    5' ATTTGCAGGTACGTCGTACCGCGGCCGCTCAGCCTTCTGCTGTACCACA
AdaATTG    5' ATTGGCAGGTACGTCGTACCGCGGCCGCTCCTGCTTTGGCGAACTTGGA
AdaATTC    5' ATTCGCAGGTACGTCGTACCGCGGCCGCGAAGCATTCCAGAATCGCACG
AdaATTA    5' ATTAGCAGGTACGTCGTACCGCGGCCGCTCCTCTCCCACCATTCCGAGT
AdaATGT    5' ATGTGCAGGTACGTCGTACCGCGGCCGCTGGTTTCCTCGAGAATCTGCT
AdaATGG    5' ATGGGCAGGTACGTCGTACCGCGGCCGCTGCTGACCAGACCAGAGAGGT
AdaATGC    5' ATGCGCAGGTACGTCGTACCGCGGCCGCCTGCTCACTCATCCACTTGTCA
AdaATGA    5' ATGAGCAGGTACGTCGTACCGCGGCCGCTGTACCACGGTCGAAAATCC AdaATCT    5' ATCTGCAGGTACGTCGTACCGCGGCCGCTGGTGAGTAAAGCTCTCAGGC
AdaATCG    5' ATCGGCAGGTACGTCGTACCGCGGCCGCGTGCCATCGCAGAAGCTAAGC
AdaATCC    5' ATCCGCAGGTACGTCGTACCGCGGCCGCTGAGGCTACCTGACACTGCTG
AdaATCA    5' ATCAGCAGGTACGTCGTACCGCGGCCGCTGGTGCCAGAACCTCTTGTCT
AdaATAT    5' ATATGCAGGTACGTCGTACCGCGGCCGCTGCGACTTGATAGACCCACCA
AdaATAG    5' ATAGGCAGGTACGTCGTACCGCGGCCGCGTAGCATCAGTGGCTACGACA
AdaATAC    5' ATACGCAGGTACGTCGTACCGCGGCCGCGAGCATCGATGCCAGGGATGA
AdaATAA    5' ATAAGCAGGTACGTCGTACCGCGGCCGCCTCTGTCTGGGAAGGCACCTC AdaAGTT    5' AGTTGCAGGTACGTCGTACCGCGGCCGCGAGAGGACGACTCCAGAGACG
AdaAGTG    5' AGTGGCAGGTACGTCGTACCGCGGCCGCCATCCATAGACCGTGACTCCA
AdaAGTC    5' AGTCGCAGGTACGTCGTACCGCGGCCGCGTCCACGTCATTCCAGGAGACT
AdaAGTA    5' AGTAGCAGGTACGTCGTACCGCGGCCGCCGATCTAGGTGAGGACACTGG
AdaAGGT    5' AGGTGCAGGTACGTCGTACCGCGGCCGCGAAGGACAACTGGCGTAGGCT
AdaAGGG    5' AGGGGCAGGTACGTCGTACCGCGGCCGCGTCGTTCGTATCCTCTACAAGG
AdaAGGC    5' AGGCGCAGGTACGTCGTACCGCGGCCGCGAGTTCCTGGCTGTGCTACCT
AdaAGGA    5' AGGAGCAGGTACGTCGTACCGCGGCCGCCTGCTGATGGATCGTGTACGA
```

```
            |----constant----|------specific------|
AdaTTT  5'-Ph-TTTNAGCTGAACGTCGTACC CGTCG AACGA ACACG GGCGT
AdaTTG  5'-Ph-TTGNAGCTGAACGTCGTACC TACGC TCGTT CCGCT CTGCG
AdaTTC  5'-Ph-TTCNAGCTGAACGTCGTACC CGCGA GACGA CGTGC GCGCC
AdaTTA  5'-Ph-TTANAGCTGAACGTCGTACC TCGCG TCGTC CCCGT CGCAG
AdaTGT  5'-Ph-TGTNAGCTGAACGTCGTACC ACGCG CGAAA ACGGG CACCG
AdaTGG  5'-Ph-TGGNAGCTGAACGTCGTACC CGCGT TTTCG CCGTC CGAGA
AdaTGC  5'-Ph-TGCNAGCTGAACGTCGTACC CGTAC CGGAC GCCGA CGCCA
AdaTGA  5'-Ph-TGANAGCTGAACGTCGTACC CGATA GTCCG AGACG TCTCG AdaTCT  5'-Ph-TCTNAGCTGAACGTCGTACC TATCG CACGT TGGCG
AdaTCG  5'-Ph-TCGNAGCTGAACGTCGTACC TACGA CCGTT GGTAC
AdaTCC  5'-Ph-TCCNAGCTGAACGTCGTACC TCGTA CGGTC GACGG CCGTG
AdaTCA  5'-Ph-TCANAGCTGAACGTCGTACC CGTTA GACCG CGTCT CGGCT
AdaTAT  5'-Ph-TATNAGCTGAACGTCGTACC TAACG TCCGA TCGGG CAGCG
AdaTAG  5'-Ph-TAGNAGCTGAACGTCGTACC CGGTA TCGGA ACGGC GCCGC
AdaTAC  5'-Ph-TACNAGCTGAACGTCGTACC TACCG ATCGC TCGGC CGGAG
AdaTAA  5'-Ph-TAANAGCTGAACGTCGTACC TAGCG CGGCG TCACG CGGTG AdaGTT  5'-Ph-GTTNAGCTGAACGTCGTACC GTCGA CCCGA CACGG
AdaGTG  5'-Ph-GTGNAGCTGAACGTCGTACC TCGAC CGTGA CTCCG
AdaGTC  5'-Ph-GTCNAGCTGAACGTCGTACC CGTAA CGATC ACGTG CGCTG
AdaGTA  5'-Ph-GTANAGCTGAACGTCGTACC TTACG GATCG AGCGG CAGCC
AdaGGT  5'-Ph-GGTNAGCTGAACGTCGTACC ATACG CAACG ACCCG AGCCG
AdaGGG  5'-Ph-GGGNAGCTGAACGTCGTACC CGTAT CGTGT GTAAC
AdaGGC  5'-Ph-GGCNAGCTGAACGTCGTACC ATCGG CCGAA GCACG GCGCC
AdaGGA  5'-Ph-GGANAGCTGAACGTCGTACC CCGAT TTCGG GCGAG GGCGC AdaGCT  5'-Ph-GCTNAGCTGAACGTCGTACC CCGTA CGGAC TGCGG GATAC
AdaGCG  5'-Ph-GCGNAGCTGAACGTCGTACC TACGG GTCGG TCGCT CCTCG
AdaGCC  5'-Ph-GCCNAGCTGAACGTCGTACC ATTCG TCGAA CCGCA GTTAC
AdaGCA  5'-Ph-GCANAGCTGAACGTCGTACC CGAAT TTCGA CCGGA GCCCG
AdaGAT  5'-Ph-GATNAGCTGAACGTCGTACC CGAGC AACGC AGCGA CACGG
AdaGAG  5'-Ph-GAGNAGCTGAACGTCGTACC AACGC GCGTT TCCGC TAGAC
AdaGAC  5'-Ph-GACNAGCTGAACGTCGTACC ACGTA GCGTC GAGCG CTAAC
AdaGAA  5'-Ph-GAANAGCTGAACGTCGTACC TACGT GACGT GCGGA GTATC AdaCTT  5'-Ph-CTTNAGCTGAACGTCGTACC CGTAG AGCGT CGGCA ACTAG
AdaCTG  5'-Ph-CTGNAGCTGAACGTCGTACC CTACG AGCGT CGCTC GCATA
AdaCTA  5'-Ph-CTANAGCTGAACGTCGTACC GCGAA ACGCA TCCGG GCGTG
AdaCTC  5'-Ph-CTCNAGCTGAACGTCGTACC TTCGC TGCGT TGCCG CTAGT
AdaCGT  5'-Ph-CGTNAGCTGAACGTCGTACC ACGAT CGACA CCGAA GTCTA
AdaCGG  5'-Ph-CGGNAGCTGAACGTCGTACC ATCGT TGTCG GGACG TAGTG
AdaCGC  5'-Ph-CGCNAGCTGAACGTCGTACC ACGAC CATCG TCGCC CGAGG
AdaCGA  5'-Ph-CGANAGCTGAACGTCGTACC GTCGT CGATG CGTCC ATACC AdaCCT  5'-Ph-CCTNAGCTGAACGTCGTACC AACCG AACGT GGCGA CCGGC
AdaCCG  5'-Ph-CCGNAGCTGAACGTCGTACC CGGTT ACGTT TGCGC GGTAT
AdaCCC  5'-Ph-CCCNAGCTGAACGTCGTACC CGAAC CCGCG TCGTG GCCGG
AdaCCA  5'-Ph-CCANAGCTGAACGTCGTACC GTTCG CGCGG CACGA AGTAC
AdaCAT  5'-Ph-CATNAGCTGAACGTCGTACC CGCAA ACCGG CGCTT CTAGC AdaCAG  5'-Ph-CAGNAGCTGAACGTCGTACC TTGCG ACCGG GCGCA GCTAG
AdaCAC  5'-Ph-CACNAGCTGAACGTCGTACC AGTCG CCGGT AAGCG TATGC
AdaCAA  5'-Ph-CAANAGCTGAACGTCGTACC CGACT ATCGC GCGCT CCACG AdaATT  5'-Ph-ATTNAGCTGAACGTCGTACC ATCGA GCGAT TCGAG GTTAG
AdaATG  5'-Ph-ATGNAGCTGAACGTCGTACC TCGAT ACGGT AGCGC GTGG
AdaATC  5'-Ph-ATCNAGCTGAACGTCGTACC ACCGA ACGGT CTCGA CGGCC
AdaATA  5'-Ph-ATANAGCTGAACGTCGTACC TCGGT CGTCA CTCGT GGTTA
AdaAGT  5'-Ph-AGTNAGCTGAACGTCGTACC GCGAC TGACG ACGAG GATAG
AdaAGG  5'-Ph-AGGNAGCTGAACGTCGTACC GTCGC CGCCG ACGGA TAACC
AdaAGC  5'-Ph-AGCNAGCTGAACGTCGTACC ATGCG GTCCG TCCGT CGGGA
AdaAGA  5'-Ph-AGANAGCTGAACGTCGTACC CGCAT CGCGC GCCGT CTATC AdaACT  5'-Ph-ACTNAGCTGAACGTCGTACC ACGAA GCGCG ACGGC TCCCG
AdaACG  5'-Ph-ACGNAGCTGAACGTCGTACC TGCAA CGAAG ACCGC GTACT
AdaACC  5'-Ph-ACCNAGCTGAACGTCGTACC TGCGA CTTCG GCGGT GGCCG
AdaACA  5'-Ph-ACANAGCTGAACGTCGTACC TTCGT AAACG CGAGT CTAAC
AdaAAT  5'-Ph-AATNAGCTGAACGTCGTACC AATCG CGTTT ACTCG GGCGG
AdaAAG  5'-Ph-AAGNAGCTGAACGTCGTACC CGATT CGGAA CGAGC GACTA
AdaAAC  5'-Ph-AACNAGCTGAACGTCGTACC CGTTC TTCCG GTCCG CGGGC
AdaAAA  5'-Ph-AAANAGCTGAACGTCGTACC GAACG CGCAC GTGCG TAACC Helper Oligonucleotides UniL1  5'  GGTACGACGTTCAGCT
UniL2  5'  GGTACGACGTTCAGCA
UniL3  5'  GGTACGACGTTCAGAT
```

| | | |
|---|---|---|
| 5' Ph-TTTNCAGGTACGTCGTACC | GCGGCCGC | GTGAGCTTGAGTCGCGTGGA |
| 5' Ph-TTGNCAGGTACGTCGTACC | GCGGCCGC | CCAACGTCGCGAGTTAGTCAG |
| 5' Ph-TTCNCAGGTACGTCGTACC | GCGGCCGC | AGGTAGACGCGGTATGTTCGTA |
| 5' Ph-TTANCAGGTACGTCGTACC | GCGGCCGC | CGGTGCTAGAGTCGCGTGTT |
| 5' Ph-TGTNCAGGTACGTCGTACC | GCGGCCGC | CGACAGTACCGCGACAGCTA |
| 5' Ph-TGGNCAGGTACGTCGTACC | GCGGCCGC | GCACTTAACTACGCCGACGAAG |
| 5' Ph-TGCNCAGGTACGTCGTACC | GCGGCCGC | gTACTAGCCTAACCGAGGCGTA |
| 5' Ph-TGANCAGGTACGTCGTACC | GCGGCCGC | TCGGATCACGTACACGTGCT |
| | | |
| 5' Ph-TCTNCAGGTACGTCGTACC | GCGGCCGC | GTACGTCGCCTAGTCGACCTG |
| 5' Ph-TCGNCAGGTACGTCGTACC | GCGGCCGC | cTCTCCTAACGGACCGACTAAC |
| 5' Ph-TCCNCAGGTACGTCGTACC | GCGGCCGC | CGTTCCGATCTAGCGGTATCTT |
| 5' Ph-TCANCAGGTACGTCGTACC | GCGGCCGC | gcACCCGTACaGGATGTGAG |
| 5' Ph-TATNCAGGTACGTCGTACC | GCGGCCGC | GCAACGCGCTATGCTCGTag |
| 5' Ph-TAGNCAGGTACGTCGTACC | GCGGCCGC | GACTgTGGAACTACGACGATCg |
| 5' Ph-TACNCAGGTACGTCGTACC | GCGGCCGC | aGCaGACCGAACCCTAGTCGC |
| 5' Ph-TAANCAGGTACGTCGTACC | GCGGCCGC | cATACGTCGTAgggTTCGCGA |
| | | |
| 5' Ph-GTTNCAGGTACGTCGTACC | GCGGCCGC | ctCTCATACGCGTCTGCGCGT |
| 5' Ph-GTGNCAGGTACGTCGTACC | GCGGCCGC | gAGTgTGCCTTACGTCGAGttc |
| 5' Ph-GTCNCAGGTACGTCGTACC | GCGGCCGC | GTcACGTtGCGGCCTTAGTC |
| 5' Ph-GTANCAGGTACGTCGTACC | GCGGCCGC | GagGTACGAgACTTGACACACG |
| 5' Ph-GGTNCAGGTACGTCGTACC | GCGGCCGC | GACcAGttGCCTAACGGAcACT |
| 5' Ph-GGGNCAGGTACGTCGTACC | GCGGCCGC | GCAACTAGTCTCGACCTGCGA |
| 5' Ph-GGCNCAGGTACGTCGTACC | GCGGCCGC | GTACCTCGACGACCGTACTGTg |
| 5' Ph-GGANCAGGTACGTCGTACC | GCGGCCGC | ACGCGTGATAGTACGGAGTCG |
| | | |
| 5' Ph-GCTNCAGGTACGTCGTACC | GCGGCCGC | CACTAGAGCGGCGTCAGTCTA |
| 5' Ph-GCGNCAGGTACGTCGTACC | GCGGCCGC | GCACAGCGCTAGCACAGGA |
| 5' Ph-GCCNCAGGTACGTCGTACC | GCGGCCGC | TACCGACAGTCCTCTGCGTGC |
| 5' Ph-GCANCAGGTACGTCGTACC | GCGGCCGC | CTACGCTACGTTGCGAAGAAGGTA |
| 5' Ph-GATNCAGGTACGTCGTACC | GCGGCCGC | GTCTGTCGTACCTGTCAGTGACTg |
| 5' Ph-GAGNCAGGTACGTCGTACC | GCGGCCGC | ATCGAACCGTGCTCCTTGG |
| 5' Ph-GACNCAGGTACGTCGTACC | GCGGCCGC | AGGTTGAGGTGTACGCGATAGC |
| 5' Ph-GAANCAGGTACGTCGTACC | GCGGCCGC | GACTTcAACCCCTGACGTACACa |
| | | |
| 5' Ph-CTTNCAGGTACGTCGTACC | GCGGCCGC | CTACTCGCGAGAGAGGGCTATG |
| 5' Ph-CTGNCAGGTACGTCGTACC | GCGGCCGC | CTTGATCCGTAGTCGAGACGG |
| 5' Ph-CTCNCAGGTACGTCGTACC | GCGGCCGC | GTACAGACGTAGCGATCGCaG |
| 5' Ph-CTANCAGGTACGTCGTACC | GCGGCCGC | gTGACTAACGAGGTCTGTAAGCTa |
| 5' Ph-CGTNCAGGTACGTCGTACC | GCGGCCGC | GTCTgAGAGTCGACTgCGCTAAG |
| 5' Ph-CGGNCAGGTACGTCGTACC | GCGGCCGC | CTcAGTAAGCCGGAGTCTAGCTAg |
| 5' Ph-CGCNCAGGTACGTCGTACC | GCGGCCGC | CGCCCTAAACGGGATCGAGCGA |
| 5' Ph-CGANCAGGTACGTCGTACC | GCGGCCGC | CGTACAGGCTAGGGGTTAGTCG |

5' Ph-CATNGCAGGTACGTCGTACC GCGGCCGC gATCGGACTAATCCGCTACGT
5' Ph-CAGNGCAGGTACGTCGTACC GCGGCCGC GACTACCGACTAGTCGTGCGAC
5' Ph-CACNGCAGGTACGTCGTACC GCGGCCGC TAGGGCCCTAACGTAGCTCG
5' Ph-CAANGCAGGTACGTCGTACC GCGGCCGC TACCTAGCCCTAACGGGTCG
5' Ph-CCTNGCAGGTACGTCGTACC GCGGCCGC CGATCGCTCTAGTGCCTACG
5' Ph-CCGNGCAGGTACGTCGTACC GCGGCCGC gAcTGCGATTCGTGACACTAGT
5' Ph-CCCNGCAGGTACGTCGTACC GCGGCCGC TGCGTAATAGCGACTGTACCCt
5' Ph-CCANGCAGGTACGTCGTACC GCGGCCGC cTAGGTCATCCCTCCGGTAC

5' Ph-ATTNGCAGGTACGTCGTACC GCGGCCGC TAGTGCGCGGTACTACCGACT
5' Ph-ATGNGCAGGTACGTCGTACC GCGGCCGC AGaCGGCTATGCGTCGGGa
5' Ph-ATCNGCAGGTACGTCGTACC GCGGCCGC ACCTACGAACACGCGTAACTCg
5' Ph-ATANGCAGGTACGTCGTACC GCGGCCGC AgcTACGTGGGTGGCAGAC
5' Ph-AGTNGCAGGTACGTCGTACC GCGGCCGC TACCGATACGGTCGACCATC
5' Ph-AGGNGCAGGTACGTCGTACC GCGGCCGC GTACGCTAGGTaggAACTAAGCG
5' Ph-AGCNGCAGGTACGTCGTACC GCGGCCGC CGGACGACTAGTTGCTAGCGTC
5' Ph-AGANGCAGGTACGTCGTACC GCGGCCGC GTGAACCTACGCGTTGACGC 5' Ph-ACTNGCAGGTACGTCGTACC GCGGCCGC GTGTCTCGGGCTAGGCGTAGA
5' Ph-ACGNGCAGGTACGTCGTACC GCGGCCGC TCCGTGGTGTCCATGGGAG
5' Ph-ACCNGCAGGTACGTCGTACC GCGGCCGC CTACGCGTAACGCTAGCAGGT
5' Ph-ACANGCAGGTACGTCGTACC GCGGCCGC gAAGAGCCGTAAGGTACGGCT
5' Ph-AATNGCAGGTACGTCGTACC GCGGCCGC gTACGTCAGCGTACGCTAAGTC
5' Ph-AAGNGCAGGTACGTCGTACC GCGGCCGC TCTAGGTTCCGTTGTAGCGCT
5' Ph-AACNGCAGGTACGTCGTACC GCGGCCGC AGCAACGAGACGACACGAC
5' Ph-AAANGCAGGTACGTCGTACC GCGGCCGC GTCTAGAACCCACGCACGGTA

Helper Oligonucleotides

HOLL1  5' GGTACGACGTACCTGA 3'
       [mismatch at the first most 3' base]

HOLL2  5' GGTACGACGTACCTGC 3'
       [perfect match to the constant]

HOLL3  5' GGTACGACGTACCTAC 3'
       [mismatch at the second most 3' base]

SEQUENCE-DEPENDENT GENE SORTING TECHNIQUES

CROSS-REFERENCES

Throughout this application, various references are cited author and publication date. Full citation of these references may be found at the end of the specification, immediately preceding the claims. Each of these publications and each of the documents cited in each of these publications, and each document referenced or cited in the publication cited documents are hereby incorporated herein by reference.

FIELD OF THE INVENTION

The present invention discloses techniques for simply and efficiently sorting expressed genes into nonredundant groups of cDNA molecules reverse-transcribed from any source of eukaryotic RNA. These groups of cDNA molecules can themselves be used for genetic analyses according to methods in the art, or they can be further sorted according to the techniques of the present invention. By applying these techniques one can obtain a collection of nonredundant subgroups of cDNA molecules, with every expressed-gene transcript from the original mRNA sample uniquely represented in its own subgroup. The method further allows to reach a stage in which each expressed-gene transcript is found in one tube, i.e. "one gene per well." Uses of the present invention include the isolation, identification and analysis of genes, the analysis and diagnosis of disease states, the study of cellular differentiation, and gene therapy.

BACKGROUND OF THE INVENTION

The production of cDNA or gene libraries has involved cloning by the use of cloning vectors placed in host organisms such as bacteria or yeast. These libraries suffer from redundancy: they contain either multiple copies of particular cDNA sequences, or multiple cDNA fragments from each expressed gene, or both. This redundancy persists in all of the current normalization procedures. The presence in a collection of cDNAs of multiple copies of particular cDNA sequences, and/or multiple cDNA fragments from each expressed gene, can result in pointless duplication of research efforts and other significant inefficiencies.

U.S. Pat. No. 5,707,807, Molecular Indexing For Expressed Gene Analysis, concerns the creation of subgroups of DNA by repeated digestions with a number of restriction enzymes, followed by ligation with adaptors having a common primer template, PCR amplification and, finally, comparison of patterns of PCR products separated by polyacrylamide-gel electrophoresis. The method of this patent creates groups of DNA molecules. However, because each PCR step indiscriminately amplifies all ligated DNA molecules in each sample, the method has a limited capacity to sort DNA into nonredundant groups.

P. Unrau and K. V. Deugau, Non-cloning amplification of specific DNA fragments from whole genomic DNA digests using DNA 'indexers', Gene 145:163–169 (1994) concerns characterizing fragments of digested DNA by the sequences of their cohesive ends and their lengths, optionally aided by PCR. However, each PCR step indiscriminately amplifies all ligated DNA molecules in each sample, and amplifies numerous DNA fragments per gene. The method does not yield nonredundant groups of genes.

U.S. Pat. No. 5,728,524, Process For Categorizing Nucleotide Sequence Populations, concerns obtaining groups of DNA molecules by using pools of adaptors ligated to digested DNA, followed by PCR. Each PCR step amplifies numerous DNA fragments per gene. The method fails to produce nonredundant groups of genes.

D. R. Smith, Ligation-mediated PCR of Restriction Fragments from Large DNA Molecules, concerns a general method for PCR amplification of type IIs restriction fragments by ligation of adaptors with degenerate end sequences complementary to cohesive ends of digested DNA fragments. Each PCR step amplifies numerous DNA fragments per gene. The method fails to produce nonredundant groups of genes.

U.S. Pat. No. 5,871,697, Method And Apparatus For Identifying, Classifying, Or Quantifying DNA Sequences In A Sample Without Sequencing, concerns classifying DNA sequences by making extensive use of comparative databases and fragment-length and restriction-digest information. The patent concerns DNA digestion and ligation of adaptors with priming sequences specific for a particular restriction enzyme. The method in this patent does not aim at the production of nonredundant groups of genes.

OBJECTS AND SUMMARY OF THE INVENTION

The present invention provides novel techniques for producing a cDNA or gene library without redundancy. These techniques sort DNA on a sequence-dependent basis into nonredundant groups. At the same time, however, these techniques eliminate the need to determine any of the DNA sequences prior to sorting and identifying genes.

One object of the present invention is providing a method of sorting cDNA or genes into nonredundant groups, which can then be analyzed by various techniques known in the art. One of many such techniques is the cDNA microarray method in which the cDNA clones derived from the present invention are used to produce the array that is then examined by hybridization to determine differential gene expression. Another technique is differential display of gel-electrophoresis patterns involving mRNA sources to analyze biological models such as disease states or cellular differentiation. In application to this technique the groups derived from the present invention can be used for differential display of gel-electrophoresis patterns.

Another object of the present invention is providing a method of obtaining a collection of nonredundant subgroups of cDNA molecules, with every expressed-gene transcript from an original mRNA sample uniquely represented in its own subgroup, i.e. "one gene per well." Such isolated genes have a wide variety of uses, notably including gene therapy and analysis of the human genome.

The present invention provides a method of sorting genes and/or gene fragments comprising the following steps (herein called "Method I"):

(1) preparing ds cDNA molecules from mRNA molecules by reverse transcription, using a poly-T primer optionally having a general primer-template sequence upstream from the poly-T sequence, yielding ds cDNA molecules having the poly-T sequence, optionally having the general primer-template sequence;

(2) digesting the ds cDNA molecules with a restriction enzyme that produces digested cDNA molecules with cohesive ends having overhanging ssDNA sequences of a constant number of arbitrary nucleotides;

(3) ligating to the digested cDNA molecules a set of dsDNA oligonucleotide adaptors, each of which adaptors has at one of its ends a cohesive-end ssDNA adaptor sequence complementary to one of the possible overhanging ssDNA sequences of the digested cDNA, at the opposite end a specific primer-template sequence specific for the ssDNA adaptor complementary sequence, and in between the ends a constant sequence that is the same for all of the different adaptors of the set;

(4) amplifying by separate polymerase chain reactions the ligated cDNA molecules, utilizing for each separate polymerase chain reaction a primer that anneals to the cDNA poly-T sequence optionally having the cDNA general primer-template, and a primer from a set of different specific primers that anneal to the cDNA specific primer-template sequences; and (5) sorting the amplified cDNA molecules into nonoverlapping groups by collecting the amplification products after each separate polymerase chain reaction, each group of amplified cDNA molecules determined by the specific primer that annealed to the specific primer-template sequence and primed the polymerase chain reaction.

One embodiment of the present invention according to the principles of Method I, comprises a complete set of oligonucleotide adaptors and specific primers, containing an oligonucleotide adaptor and a specific primer complementary to each of the possible overhanging ssDNA sequences of the digested cDNA.

Another embodiment of the present invention according to the principles of Method I further comprises:

(6) amplifying the sorted nonredundant groups of cDNA molecules by nesting polymerase chain reaction, each amplification utilizing a primer that anneals to the cDNA poly-T sequence optionally having the cDNA general primer-template sequence, as well as one of a set of nesting primers with the following general formula 5'-|sequence complementary to the constant sequence of the oligonucleotide adaptors|-$NI_x$-|1–5 nucleotides complementary to one of the possible sequences of 1–5 nucleotides immediately upstream from the overhanging ssDNA sequence on the cDNA|-3' where N is an arbitrary nucleotide; I is inosine; and x=1,2,3 or 4, being one fewer than the constant number of nucleotides in the overhanging ssDNA sequences; and (7) sorting the amplified cDNA molecules into nonredundant subgroups by collecting the amplification products after each separate nesting polymerase chain reaction, each nonredundant subgroup of cDNA molecules determined by the particular nested primer that complemented the 1–5 nucleotides immediately upstream from the overhanging ssDNA sequence on the cDNA.

Another embodiment of the present invention according to the principles of Method I further comprises conducting further polymerase chain reactions with further nesting primers complementary to the next immediately upstream cDNA nucleotides, thereby sorting the amplified cDNA molecules further into nonredundant subgroups.

A preferred embodiment of the present invention according to the principles of Method I further comprises conducting further polymerase chain reactions with further nesting primers complementary to the next immediately upstream cDNA nucleotides until each nonredundant subgroup contains cDNA molecules all of essentially the same sequence, with every expressed-gene transcript in the mRNA sample uniquely represented in one of the nonredundant subgroups.

The present invention also concerns a method of sorting genes and/or gene fragments comprising the following steps (herein called "Method II"):

(1) preparing ds cDNA molecules from mRNA molecules by reverse transcription, using a poly-T primer optionally having a general primer-template sequence upstream from the poly-T sequence, yielding ds cDNA molecules having the poly-T sequence, optionally having the general primer-template sequence;

(2) digesting the ds cDNA molecules with a first restriction enzyme that produces digested cDNA molecules with cohesive ends having first overhanging ssDNA sequences of a constant number of arbitrary nucleotides;

(3) ligating to the digested cDNA molecules a set of dsDNA oligonucleotide adaptors, each of which adaptors has at one of its ends a cohesive-end ssDNA adaptor sequence complementary to one of the possible first overhanging ssDNA sequences of the digested cDNA, at the opposite end a specific primer-template sequence specific for the ssDNA adaptor complementary sequence, and in between the ends a constant sequence that is the same for all of the different adaptors of the set, and that contains a recognition site for a second restriction enzyme that can cleave the ligated cDNA molecules at a point further from the ligated oligonucleotide adaptor than the overhanging ssDNA sequences of the digested cDNA, and can create cohesive ends having second overhanging ssDNA sequences of a constant number of arbitrary nucleotides;

(4) amplifying by separate polymerase chain reactions the ligated cDNA molecules, utilizing for each separate polymerase chain reaction a primer that anneals to the cDNA poly-T sequence optionally having the cDNA general primer-template, and a primer from a set of different specific primers that anneal to the cDNA specific primer-template sequences; and (5) sorting the amplified cDNA molecules into nonoverlapping groups by collecting the amplification products after each separate polymerase chain reaction, each group of amplified cDNA molecules determined by the specific primer that annealed to the specific primer-template sequence and primed the polymerase chain reaction.

One embodiment of the present invention according to the principles of Method II comprises using a complete set of oligonucleotide adaptors and specific primers, containing an oligonucleotide adaptor and a specific primer complementary to each of the possible first overhanging ssDNA sequences of the digested cDNA.

Another embodiment of the present invention according to the principles of Method II further comprises (6) digesting the sorted nonredundant groups of cDNA molecules with the second restriction enzyme, cleaving the ligated cDNA molecules at a point further from the ligated oligonucleotide adaptor than the overhanging ssDNA sequences of the digested cDNA, and creating cohesive ends having second overhanging ssDNA sequences of a constant number of arbitrary nucleotides;

(7) ligating to the digested cDNA molecules a set of nesting dsDNA oligonucleotide adaptors, each of which adaptors has at one of its ends a cohesive-end ssDNA adaptor sequence complementary to one of the possible second overhanging ssDNA sequences of the digested cDNA, at the opposite end a specific primer-template sequence unique for the ssDNA adaptor complementary sequence, and in between the ends a constant sequence that is the same for all of the different adaptors of the set, and that contains the recognition site for the second restriction enzyme;

(8) amplifying by separate polymerase chain reactions the ligated cDNA molecules, utilizing for each separate polymerase chain reaction a primer that anneals to the cDNA poly-T sequence optionally having the cDNA general primer-template, and a primer from a set of different specific primers that anneal to the cDNA specific primer-template sequences; and (9) sorting the amplified cDNA molecules into nonredundant subgroups by collecting the amplification products after each separate polymerase chain reaction, each subgroup of amplified cDNA molecules determined by the specific primer that annealed to the specific primer-template sequence and primed the polymerase chain reaction.

One embodiment of the present invention according to the principles of Method II further comprises using a complete set of nesting dsDNA oligonucleotide adaptors, containing an oligonucleotide adaptor complementary to each of the possible second overhanging ssDNA sequences of the digested cDNA.

Another embodiment of the present invention according to the principles of Method II further comprises conducting further polymerase chain reactions using further nesting oligonucleotide adaptors, optionally with different restriction enzymes and recognition sites, thereby sorting the amplified cDNA molecules further into nonredundant subgroups.

A preferred embodiment of the present invention according to the principles of Method II further comprises conducting further ligations with further nesting oligonucleotide adaptors, optionally with different restriction enzymes and recognition sites, until each nonredundant subgroup contains cDNA molecules all of essentially the same sequence, with every expressed-gene transcript in the mRNA sample uniquely represented in one of the nonredundant subgroups.

The present invention also provides a method (Method III) of sorting genes and/or gene fragments comprising the steps of:

(1) preparing ds cDNA molecules from mRNA molecules by reverse transcription, using a poly-T primer having a general primer-template sequence upstream from the poly-T sequence that includes a recognition sequence for a restriction enzyme, yielding ds cDNA molecules having the poly-T sequence, having the general primer-template sequence;

(2) dividing the cDNA into N pools, wherein N is 1 to 25 digesting the ds cDNA molecules with different restriction enzymes that produce digested cDNA molecules with cohesive ends having overhanging ssDNA sequences of a constant number of arbitrary nucleotides;

(3) ligating to the digested cDNA molecules of each pool a set of dsDNA oligonucleotide adaptors, each of which adaptors has at one of its ends a cohesive-end ssDNA adaptor sequence complementary to one of the possible overhanging ssDNA sequences of the digested cDNA, at the opposite end a specific primer-template sequence specific for the ssDNA adaptor complementary sequence, and in between the ends a constant sequence that is the same for all of the different adaptors of the set;

(4) amplifying by separate polymerase chain reactions the ligated cDNA molecules of each pool, utilizing for each separate polymerase chain reaction a primer that anneals to the cDNA poly-T sequence optionally having the cDNA general primer-template, and a primer from a set of different specific primers that anneal to the cDNA specific primer-template sequences;

(5) sorting the amplified cDNA molecules from each pool into non-overlapping groups by collecting the amplification products after each separate polymerase chain reaction, each group of amplified cDNA molecules determined by the specific primer that annealed to the specific primer-template sequence and primed the polymerase chain reaction, wherein each of the restriction enzymes digests the N separate cDNA pools into 64 or 256 non-redundant sub-groups;

(6) digesting cDNA fragments in each non-redundant sub-group of the cDNA pools with different restriction enzymes and further purifying the digested cDNA fragments by removing the small end fragments produced by the cleavage;

This invention also provides a method of making sub-libraries of ligation sets by ligating restriction enzymes digested fragments generated by method III into a plasmid vector that have recognition sequence for said restriction enzymes and predigesting with these enzymes to make 64×N or 256×N sets of ligations, wherein N is 1 to 25.

This invention further provides a method of making sub-libraries of bacterial colonies, wherein the ligation sets, generated in the method of making sub-libraries of ligation sets, are transformed into bacteria and plated onto bacterial growth plates to produce bacteria colonies containing each of the 64×N or 256×N non-redundant subgroups of cDNA fragments, wherein N is 1 to 25.

In one embodiment of method III, N is two and the restriction enzymes in step (1) comprise AscI and another similar rare restriction enzyme.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which:

FIG. 1 schematically illustrates one embodiment of the principles of Method I.

FIG. 2 schematically illustrates one embodiment of the principles of Method II.

FIG. 3 schematically illustrates an alternative embodiment of the principles of Method II.

FIG. 4 shows ligation specificity permitting isolation of the rat albumin gene using the methods of the present invention.

FIG. 5 shows ligation specificity using human GAPDH gene with a particular set of ligation adaptors using the methods of the present invention.

FIG. 10 shows the general structure of the primer and the primer set J2.

FIG. 11 shows tail primers set J2.

FIG. 12 shows tail primers (set number 2).

FIG. 13 shows tail primers set 256.

FIG. 14 shows first nesting primers 256 for tail adaptor 64 set 1.

FIG. 15 shows first nesting primers 64 for tail adaptor 64 set 1.

FIG. 16 shows second nesting primers 64 for tail adaptor 64 set 1.

FIG. 17 shows second nesting primers 16 for tail adaptor 64 set 1.

FIG. 18 shows tail adaptors set 256.

FIG. 19 shows tail adaptors 64 (set number 1) and helper oligonucleotides.

FIG. 20 shows tail adaptors 64 (set number 2) and helper oligonucleotides.

Figure 6:
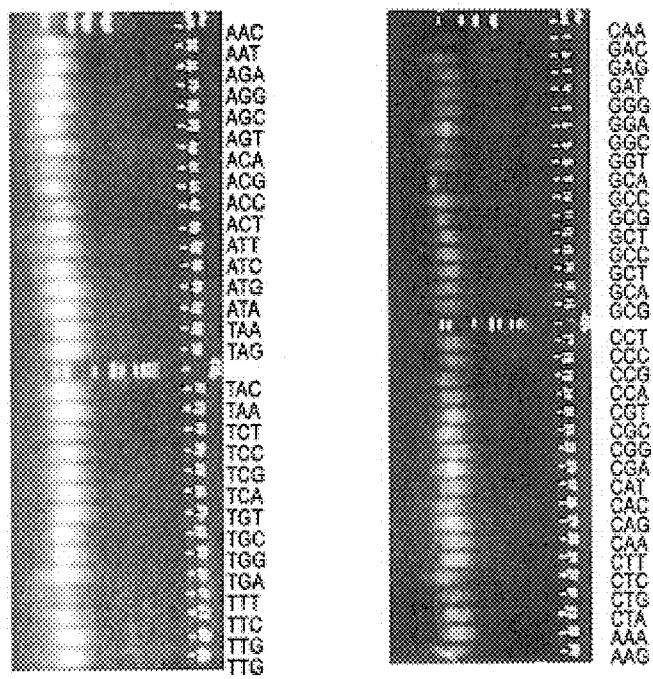
FIG. 6 shows PCR amplification products derived from Jurkat-cell mRNA using a particular set of ligation adaptors according to the methods of the present invention. "The double stranded cDNA (derived from Jurkat cells) that was ligated to the mix of all 64 "Tail adaptor set 1" adaptors was used as template. The cDNA group ligated to each adaptor was amplified separately using the specific Tail primer and the END primer. The figure shows the products of all 64 Tail-END amplification reactions. Amplification products were separated on a 1.5% agarose gel and ethidium bromide staining was used to visualize the DNA.

SEQ ID NOs: are assigned as follows:
SEQ ID NO: 33 refers to the upper counterpart of Fok I recognition sequence (SEQ ID NO: 7);
SEQ ID NO: 34 refers lower counterpart of SEQ ID NO:20;
SEQ ID NO: 35 refers to the upper sequence (helper) of the adaptor sequence (SEQ ID NO: 22);
SEQ ID NOs: 36–76 refer to the sequences depicted in FIG. 1;
SEQ ID NOs: 77–141 refer to the sequences depicted in FIG. 10;
SEQ ID NOs: 142–205 refer to the sequences depicted in FIG. 11;
SEQ ID NOs: 206–265 refer to the sequences depicted in FIG. 12;
SEQ ID NOs: 266–521 refer to the sequences depicted in FIG. 13;
SEQ ID NOs: 522–777 refer to the sequences depicted in FIG. 14;
SEQ ID NOs: 778–841 refer to the sequences depicted in FIG. 15;
SEQ ID NOs: 842–905 refer to the sequences depicted in FIG. 16;
SEQ ID NOs: 906–921 refer to the sequences depicted in FIG. 17;
SEQ ID NOs: 922–1177 refer to the sequences depicted in FIG. 18;
SEQ ID NOs: 1178–1244 refer to the sequences depicted in FIG. 19;
SEQ ID NOs: 1245–1311 refer to the sequences depicted in FIG. 20.

DETAILED DESCRIPTION OF THE INVENTION

The present invention provides techniques for obtaining groups of nonredundant cDNA molecules, including cDNA libraries containing "one gene per well" for every gene transcript present in an original mRNA source. These techniques sort DNA on a sequence-dependent basis into nonredundant groups, using PCR combined with (1) an initial step of "differential ligation" using a pool of dsDNA ligation adaptors, each of which has an arbitrary ssDNA end and a primer template specific for the ssDNA end, and optional further steps using (2) either nesting primers (in Method I) or nesting ligation adaptors (in Method II).

Method I broadly concerns a method of sorting genes and/or gene fragments comprising the following steps:

(1) preparing ds cDNA molecules from mRNA molecules by reverse transcription, using a poly-T primer optionally having a general primer-template sequence upstream from the poly-T sequence, yielding ds cDNA molecules having the poly-T sequence, optionally having the general primer-template sequence;

(2) digesting the ds cDNA molecules with a restriction enzyme that produces digested cDNA molecules with cohesive ends having overhanging ssDNA sequences of a constant number of arbitrary nucleotides;

(3) ligating to the digested cDNA molecules a set of dsDNA oligonucleotide adaptors, each of which adaptors has at one of its ends a cohesive-end ssDNA adaptor sequence complementary to one of the possible overhanging ssDNA sequences of the digested cDNA, at the opposite end a specific primer-template sequence specific for the ssDNA adaptor complementary sequence, and in between the ends a constant sequence that is the same for all of the different adaptors of the set;

(4) amplifying by separate polymerase chain reactions the ligated cDNA molecules, utilizing for each separate polymerase chain reaction a primer that anneals to the cDNA poly-T sequence optionally having the cDNA general primer-template, and a primer from a set of different specific primers that anneal to the cDNA specific primer-template sequences; and (5) sorting the amplified cDNA molecules into nonoverlapping groups by collecting the amplification products after each separate polymerase chain reaction, each group of amplified cDNA molecules determined by the specific primer that annealed to the specific primer-template sequence and primed the polymerase chain reaction.

The restriction enzyme can be any enzyme that produces digested cDNA molecules with cohesive ends having overhanging ssDNA sequences of a constant number of arbitrary nucleotides. Such restriction enzymes include type IIs restriction enzymes, including BbvI, BspMI, FokI, HgaI, MboI and SfaNI. Suitable type II restriction enzymes include BglI, BstXI and SfiI.

The groups of cDNA molecules produced by the techniques of Method I are nonredundant: only one DNA sequence will be present for each gene, since for each gene only the poly-T-containing fragment—possibly the entire gene—is primed and amplified. As used in this invention, all genes present as transcripts in a mRNA sample were obtained using complete sets of redundant adaptors. Thus, one embodiment of the present invention according to the principles of Method I comprises using a complete set of oligonucleotide adaptors and specific primers, containing an oligonucleotide adaptor and a specific primer complementary to each of the possible overhanging ssDNA sequences of the digested cDNA. If the constant number of arbitrary nucleotides in the overhanging ssDNA is 3, then a complete set of adaptors includes $4^3$ or 64 different oligonucleotide adaptors. If the constant number of arbitrary nucleotides is 4, then a complete set includes $4^4$ or 256 different adaptors.

Another embodiment of Method I utilizes adaptors with the 3'-most nucleotide of the ssDNA complementary sequence of the oligonucleotide adaptor an arbitrary nucleotide N, which pairs with the 5'-most nucleotide of each of the possible overhanging ssDNA sequences of the digested cDNA. A complete set of this kind of adaptors contains an oligonucleotide adaptor (for a specific primer) complementary to each of the possible overhanging ssDNA sequences of the digested cDNA excluding the 5'-most nucleotide that pairs with the arbitrary nucleotide N of the oligonucleotide adaptor.

One embodiment of the principles of Method I further comprises additional steps:

(6) amplifying the sorted nonredundant groups of cDNA molecules by nesting polymerase chain reaction, each amplification utilizing a primer that anneals to the cDNA poly-T sequence optionally having the cDNA general primer-template sequence, as well as one of a set of nesting primers with the following general formula 5'-|sequence complementary to the constant sequence of the oligonucleotide adaptors|-NI$_x$-|1–5 nucleotides complementary to one of the possible sequences of 1–5 nucleotides immediately upstream from the overhanging ssDNA sequence on the cDNA|-3' where N is an arbitrary nucleotide; I is inosine; and x=1,2,3 or 4, being one fewer than the constant number of nucleotides in the overhanging ssDNA sequences; and (7) sorting the amplified cDNA molecules into nonredundant subgroups by collecting the amplification products after each separate nesting polymerase chain reaction, each nonredundant subgroup of cDNA molecules determined by the particular nested primer that complemented the 1–5 nucleotides immediately upstream from the overhanging ssDNA sequence on the cDNA.

As before, a complete set of nesting primers can be used, which contains a nesting primer complementary to each of the possible sequences of 1–5 nucleotides immediately upstream from the overhanging ssDNA sequence on the cDNA.

The principles of Method I can be used to conduct further polymerase chain reactions with further nesting primers complementary to the next immediately upstream cDNA nucleotides, thereby sorting the amplified cDNA molecules further into nonredundant subgroups. A preferred embodiment involves conducting further polymerase chain reactions with further nesting primers complementary to the next immediately upstream cDNA nucleotides until each nonredundant subgroup contains cDNA molecules all of essentially the same sequence, with every expressed-gene transcript in the mRNA sample uniquely represented in one of the nonredundant subgroups, i.e. "one gene per well."

Method II broadly concerns a method of sorting genes and/or gene fragments comprising the following steps:

(1) preparing ds cDNA molecules from mRNA molecules by reverse transcription, using a poly-T primer optionally having a general primer-template sequence upstream from the poly-T sequence, yielding ds cDNA molecules having the poly-T sequence, optionally having the general primer-template sequence;

(2) digesting the ds cDNA molecules with a first restriction enzyme that produces digested cDNA molecules with cohesive ends having first overhanging ssDNA sequences of a constant number of arbitrary nucleotides;

(3) ligating to the digested cDNA molecules a set of dsDNA oligonucleotide adaptors, each of which adaptors has at one of its ends a cohesive-end ssDNA adaptor sequence complementary to one of the possible first overhanging ssDNA sequences of the digested cDNA, at the opposite end a specific primer-template sequence specific for the ssDNA adaptor complementary sequence, and in between the ends a constant sequence that is the same for all of the different adaptors of the set, and that contains a recognition site for a second restriction enzyme that can cleave the ligated cDNA molecules at a point further from the ligated oligonucleotide adaptor than the overhanging ssDNA sequences of the digested cDNA, and can create cohesive ends having second overhanging ssDNA sequences of a constant number of arbitrary nucleotides;

(4) amplifying by separate polymerase chain reactions the ligated cDNA molecules, utilizing for each separate polymerase chain reaction a primer that anneals to the cDNA poly-T sequence optionally having the cDNA general primer-template, and a primer from a set of different specific primers that anneal to the cDNA specific primer-template sequences; and (5) sorting the amplified cDNA molecules into nonoverlapping groups by collecting the amplification products after each separate polymerase chain reaction, each group of amplified cDNA molecules determined by the specific primer that annealed to the specific primer-template sequence and primed the polymerase chain reaction.

The first restriction enzyme can be any enzyme that produces digested cDNA molecules with cohesive ends having overhanging ssDNA sequences of a constant number of arbitrary nucleotides. Such restriction enzymes include type IIs restriction enzymes, including BbvI, BspMI, FokI, HgaI, MboI and SfaNI. Suitable type II restriction enzymes include BglI, BstXI and SfiI. The second restriction enzyme can be a type II restriction enzyme that cleaves the ligated cDNA molecules at a point further from the ligated oligonucleotide adaptor than the overhanging ssDNA sequences of the digested cDNA, and creates cohesive ends having second overhanging ssDNA sequences of a constant number of arbitrary nucleotides. Examples of suitable type IIs restriction enzymes include BspMI.

As in Method I, in Method II a complete set of oligonucleotide adaptors and specific primers contains an oligonucleotide adaptor and a specific primer complementary to each of the possible first overhanging ssDNA sequences of the digested cDNA. Where the 3'-most nucleotide of the ssDNA complementary sequence of the oligonucleotide adaptor is an arbitrary nucleotide N, which pairs with the 5'-most nucleotide of each of the possible first overhanging ssDNA sequences of the digested cDNA, a complete set of oligonucleotide adaptors and specific primers contains an oligonucleotide adaptor and a specific primer complementary to each of the possible first overhanging ssDNA sequences of the digested cDNA excluding the 5'-most nucleotide that pairs with the arbitrary nucleotide N of the oligonucleotide adaptor.

One embodiment of the principles of Method II further comprises additional steps:

(6) digesting the sorted nonredundant groups of cDNA molecules with the second restriction enzyme, cleaving the ligated cDNA molecules at a point further from the ligated oligonucleotide adaptor than the overhanging ssDNA sequences of the digested cDNA, and creating cohesive ends having second overhanging ssDNA sequences of a constant number of arbitrary nucleotides;

(7) ligating to the digested cDNA molecules a set of nesting dsDNA oligonucleotide adaptors, each of which adaptors has at one of its ends a cohesive-end ssDNA adaptor sequence complementary to one of the possible second overhanging ssDNA sequences of the digested cDNA, at the opposite end a specific primer-template sequence unique for the ssDNA adaptor complementary sequence, and in between the ends a constant sequence that is the same for all of the different adaptors of the set, and that contains the recognition site for the second restriction enzyme;

(8) amplifying by separate polymerase chain reactions the ligated cDNA molecules, utilizing for each separate polymerase chain reaction a primer that anneals to the cDNA poly-T sequence optionally having the cDNA general primer-template, and a primer from a set of different specific primers that anneal to the cDNA specific primer-template sequences; and (9) sorting the amplified cDNA molecules into nonredundant subgroups by collecting the amplification products after each separate polymerase chain reaction, each subgroup of amplified cDNA molecules determined by the specific primer that annealed to the specific primer-template sequence and primed the polymerase chain reaction.

A complete set of nesting dsDNA oligonucleotide adaptors contains an oligonucleotide adaptor complementary to each of the possible second overhanging ssDNA sequences of the digested cDNA.

An embodiment of Method II includes conducting further polymerase chain reactions using further nesting oligonucleotide adaptors, optionally with different restriction enzymes and recognition sites, thereby sorting the amplified cDNA molecules further into nonredundant subgroups. If different restriction enzymes are used, they must cleave the ligated cDNA molecules at a point further from the ligated oligonucleotide adaptor than the overhanging ssDNA sequences of the digested cDNA, and create cohesive ends having second overhanging ssDNA sequences of a constant number of arbitrary nucleotides.

A preferred embodiment of Method II comprises repeating nesting ligation and PCR until each nonredundant subgroup contains cDNA molecules all of essentially the same sequence, with every expressed gene transcript in the mRNA sample uniquely represented in one of the nonredundant subgroups, i.e. "one gene per well."

Method III utilizes the non-redundant groups of cDNA fragments collected in step (5) of Method I and II for the preparation of sets of non-redundant sub-libraries of cDNA. Such sub-libraries can be more economically used for the derivation of a complete cDNA library by selecting a group of clones from the sub-libraries. The principle of Method III is that cDNA fragments derived from a specific highly abundant mRNA will converge into one group. Thus, a few groups will contain a highly redundant cDNA population. These groups are identified by analysis of the cDNA content of the group by sequencing or other methods. All other groups will be devoid of cDNAs of highly redundant mRNAs and thus of low redundancy and are used, in combination, to derive a full cDNA library. Since the elimination of the groups that contain a highly redundant cDNA population also removes some cDNA fragments of low redundancy mRNAs an approach involving parallel processing of two cDNA pools, each digested with a type different IIs restriction enzyme, is used. This makes it highly improbable that a "rare" cDNA fragment will be found in a high-redundancy group in both digest pools.

Method III broadly concerns a method of sorting genes and/or gene fragments comprising the steps of:

(1) preparing ds cDNA molecules from mRNA molecules by reverse transcription, using a poly-T primer having a general primer-template sequence upstream from the poly-T sequence that includes a recognition sequence for a restriction enzyme, yielding ds cDNA molecules having the poly-T sequence, having the general primer-template sequence;

(2) dividing the cDNA into N pools, wherein N is 1 to 25 digesting the ds cDNA molecules with different restriction enzymes that produce digested cDNA molecules with cohesive ends having overhanging ssDNA sequences of a constant number of arbitrary nucleotides;

(3) ligating to the digested cDNA molecules of each pool a set of dsDNA oligonucleotide adaptors, each of which adaptors has at one of its ends a cohesive-end ssDNA adaptor sequence complementary to one of the possible overhanging ssDNA sequences of the digested cDNA, at the opposite end a specific primer-template sequence specific for the ssDNA adaptor complementary sequence, and in between the ends a constant sequence that is the same for all of the different adaptors of the set;

(4) amplifying by separate polymerase chain reactions the ligated cDNA molecules of each pool, utilizing for each separate polymerase chain reaction a primer that anneals to the cDNA poly-T sequence optionally having the cDNA general primer-template, and a primer from a set of different specific primers that anneal to the cDNA specific primer-template sequences;

(5) sorting the amplified cDNA molecules from each pool into non-overlapping groups by collecting the amplification products after each separate polymerase chain reaction, each group of amplified cDNA molecules determined by the specific primer that annealed to the specific primer-template sequence and primed the polymerase chain reaction, wherein each of the restriction enzymes digests the N separate cDNA pools into 64 or 256 non-redundant sub-groups; and (6) digesting cDNA fragments in each non-redundant sub-group of the cDNA pools with different restriction enzymes and further purifying the digested cDNA fragments by removing the small end fragments produced by the cleavage.

In one embodiment of the method of sorting genes and/or gene fragments, the method further comprises purifying the digested cDNA fragments by removing the small end fragments produced by the cleavage.

The reactions in Methods I, II and III eventually stop when the cDNAs are exhausted.

In another embodiment of the method of sorting genes and/or gene fragments, the method further comprises ligating the digested cDNA fragments into a plasmid vector that has recognition sequence for a restriction enzyme and is predigested with the enzyme.

In another embodiment of the method of sorting genes and/or gene fragments, the restriction enzyme is NotI or AscI.

In another embodiment of the method of sorting genes and/or gene fragments, the method further comprises ligating the digested cDNA fragments into a genetic vector.

In another embodiment of the method of sorting genes and/or gene fragments, the genetic vector is a viral vector, a bacterial vector, a protozoan vector, a retrotransposon, a transposon, a DNA vector, or a recombinant vector.

In another embodiment of the method of sorting genes and/or gene fragments, the method further comprises transforming the ligation products into bacteria and growing the bacteria in a suitable growth media.

In another embodiment of the method of sorting genes and/or gene fragments, the bacteria are grown on bacteria growth plates.

In another embodiment of the method of sorting genes and/or gene fragments, N is two and the restriction enzymes of step (2) are BbsI for one pool and BsaI for the second pool.

In another embodiment of the method of sorting genes and/or gene fragments, N is 2 to 20, preferably 2 to 15, more preferably 2 to 10 and most preferably 2 to 4.

In another embodiment of the method of sorting genes and/or gene fragments, N is two and the restriction enzymes in step (1) comprise AscI and another similar rare restriction enzyme In yet another embodiment of the method of sorting genes and/or gene fragments, N is two and the restriction enzymes in step (5) comprise BbsI and BsaI.

In a further embodiment of the method of sorting genes and/or gene fragments, N is two and the restriction enzymes in step (6) comprise NotI and AscI.

This invention also provides a method of making sub-libraries of ligation sets by ligating restriction enzyme digested fragments produced by the method of sorting genes and/or gene fragments, into plasmid vectors that have recognition sequences for said restriction enzymes and predigesting with these enzymes to make 64×N or 256×N sets of ligations, wherein N is 1 to 25.

In one embodiment of the method of making sub-libraries of expression system colonies, the expression system is a bacterium.

In another embodiment of the method of making sub-libraries of expression system colonies, the bacteria are grown under suitable conditions.

In a further embodiment of the method of making sub-libraries of expression system colonies, the bacteria are plated onto bacterial growth plates.

The practice of the present invention employs, unless indicated, conventional techniques of molecular biology (including recombinant techniques), microbiology, cell biology, biochemistry and immunology, which are within the skill of the art. Such techniques are explained fully in the literatures, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991). These technique are applicable to the production of the polynucleotides of the invention, and, as such, may be considered in making and practicing the invention. This invention can be applicable to the uses disclosed in PCT publications, such as WO 98/51789A2, WO 93/18176A1 and WO 99/60164 the contents of which are incorporated herein by reference.

Furthermore, reference is made to Gold P., U.S. Pat. No. 5,407,813, issued Apr. 18, 1995; Deugau et al., U.S. Pat. No. 5,508,169, issued Apr. 16, 1996; Deugau et al., U.S. Pat. No. 5,858,656, issued Jan. 12, 1999; R. A. Guilfoyle et al., "Ligation-mediated PCR amplification of specific fragments from a Class-II restriction endonuclease total digest" Nucleic Acids Research, 1997, Vol. 25(9):1854–1858; N. B. Ivanova and A. V. Belyavsky "Identification of differentially expressed genes by restriction endonuclease-based gene expression fingerprinting" Nucleic Acids Research, 1995, Vol. 23(15):2954–2958; H. Mahadeva et al. "A simple and efficient method for the isolation of differentially expressed genes" J. Mol. Biol., 1998, 284:1391–1398, A. B. Troutt et al., Proc. Natl. Acad. Sci. USA, Biochemistry, October 1992, 89:9823–9825; K. Kato, Nucleic Acids Research, 1995, 23(18):3685–3690; D. R. Sibson, U.S. Pat. No. 5,728,524, issued Mar. 17, 1998; R. J. Sapolsky et al, U.S. Pat. No. 5,710,000, issued Jan. 20, 1998; H. Kambara et al., U.S. Pat. No. 5,650,274, issued Jul. 22, 1997; Y. Prashar and S. M. Weissman, Proc. Natl. Acad. Sci. USA, 1996, 93:659–663; M. S. H. Ko, Nucleic Acids Research, Vol. 18(19):5705–5711; J. M. Rothberg, et al., U.S. Pat. No. 5,871,697, issued Feb. 16, 1999; J. B. D. M. Edward, Nucleic Acids Research, Vol. 19(19):5227–5232; C. Hoog, Nucleic Acids Research, Vol. 19(22):6123–6127; B. P. Sokolov et al., Nucleic Acids Research, 1994, Vol. 22(19):4009–4015; W. M. Schmidt and M. W. Mueller, Nucleic Acids Research, Vol. 24(9):1789–1791; A. Belyavsky et al. Nucleic Acids Research, 1989, Vol. 17(8):2919–2932; J. P. Calvet, Pediatric Nephrology, 1991, 5:751–757; R. Cooke et al., The Plant Journal, 1996, 9(1):101–124; Christine Domec et al., Analytical Biochemistry, 1990, 188:422–426; H. Haymerle et al., Nucleic Acids Research, 1986, Vol. 14(21):8615–8625; S. Kato et al., Gene, 1994, 150:243–250; T. Kohchi et al., The plant Journal, 1995, 8(5):771–776; S. R. Patanjali et al., Proc. Natl. Acad. Sci. USA, 1991, Vol. 88:1943–1947; A. J. Podhajska et al., Method in Enzymology, 1992, 216:303–309; W. Szybalski et al., Gene, 1991, 100:13–26; WO 94/01582, published Jan. 20, 1994; Gould et al., U.S. Pat. No. 5,700,644, issued Dec. 23, 1997; Short et al., U.S. Pat. No. 5,763,239, issued Jun. 9, 1998; Sytkowski et al., U.S. Pat. No. 5,804,382, issued Sep. 8, 1998; Belyavsky et al., U.S. Pat. No. 5,814,445, issued Sep. 29, 1998; Wang et al., U.S. Pat. No. 5,837,468, issued Nov. 17, 1998; Brenner, U.S. Pat. No. 5,863,722, issued Jan. 26, 1999; Kinzler et al., U.S. Pat. No. 5,866,330, issued Feb. 2, 1999; Kinzler et al., U.S. Pat. No. 5,695,937, issued Dec. 9, 1997; Bassam et al., U.S. Pat. No. 5,413,909, issued May 9, 1995; McClelland et al., U.S. Pat. No. 5,487,985, issued Jan. 30, 1996; Villeponteau et al., U.S. Pat. No. 5,580,726, issued Dec. 3, 1996; Mierendorf et al., U.S. Pat. No. 5,629,179, issued May 13, 1997; Yourno, U.S. Pat. No. 5,556,773, issued Sep. 17, 1996, and the documents cited therein and the documents of record in the prosecution of cited U.S. patent; all of which are incorporated herein by reference.

With respect to cDNAs for expression in a vector and documents providing such exogenous DNA, as well as with respect to the expression of transcription and/or translation factors for enhancing expression of nucleic acid molecule, reference is made to U.S. Pat. No. 5,990,091 issued Nov. 23, 1999, and WO 98/00166 and WO 99/60164, and the documents cited therein and the documents of record in the prosecution of that patent and those PCT applications; all of which are incorporated herein by reference. Thus, U.S. Pat. No. 5,990,091 and WO 98/00166 and WO 99/60164 and documents cited therein and documents or record in the prosecution of that patent and those PCT applications, and other documents cited herein or otherwise incorporated herein by reference, can be consulted in the practice of this invention; and, all exogenous nucleic acid molecules and vectors cited therein can be used in the practice of this invention. In this regard, mention is also made of U.S. Pat. Nos. 6,004,777, 5,997,878, 5,989,561, 5,976,552, 5,972,597, 5,858,368, 5,863,542, 5,833,975, 5,863,542, 5,843,456, 5,766,598, 5,766,597, 5,762,939, 5,756,102, 5,756,101, 5,494,807.

The expression systems are disclosed in U.S. Patent Nos. 5,830,692, 6,004,941, 5,641,663, and 5,538,885, the contents of which are hereby incorporated herein by reference.

As used herein, a genetic vector includes, but is not limited to a viral vector, a bacterial vector, a protozoan vector, a retrotransposon, a transposon, a DNA vector., or a recombinant vector thereof.

As used herein, "rare restriction enzymes" means restriction enzymes having a low chance of cleaving within the cDNA. Generally, enzymes that have recognition sequence of 8 or more base pairs are regarded as rare enzymes since they cleave, statistically, once every $4^8$ bp (~1 per 16,000 bp).

EXPERIMENTAL DETAILS

The following examples illustrate some embodiments of the present invention in more detail. However, the following examples should not be construed as limiting the scope of the present invention.

1. Preparation of cDNA

Conversion of mRNA into ds cDNA: For priming the synthesis of single stranded cDNA from polyA+mRNA an oligo(dT) primer was used. The primer was of the following structure, including a general primer-template sequence:
5'-TGCATGGCACAGTACTGAGTGGTATCGACTCGTA CAGGCGCGCCTTTTTTTTTTTT TTTTTTV-3'
(SEQ ID NO:1)
(V=C,G or A).
General primers for amplification from this sequence included:
1. GP1=5'-TGCATGGGACAGTACTGAGT-3' (SEQ ID NO:2)
2. GP2=5'-CACAGTACTGAGTGGTATCG-3' (SEQ ID NO:3)
3. GP3=5'-AGTGGTATCGACTCGTACAG-3' (SEQ ID NO:4)

As depicted here, the three general primers are nested relative to each other. Conventional methods were used for preparation of double stranded cDNA from polyA+mRNA. The double stranded cDNA were purified on a spin column (Qiagen—QIAquick PCR purification kit, catalogue No. 28106) to remove excess oligo(dT) primer and nucleotides.

ds cDNA digestion; restriction enzyme choice: The double stranded cDNA was digested with a type IIs restriction enzyme (RE) that produced a four base overhang structure and that cut at least 8 nucleotides away from the recognition sequence. Other enzymes, including type II restriction enzymes, that produce other overhangs or that cut closer to the recognition sequence can be used. REs used were:
BbvI (5'-GCAGCNNNNNNNNN-3' (SEQ ID NO:5)
3'-CGTCGNNNNNNNNNNNN-5') (SEQ ID NO:6)
and FokI (5'-GGATGNNNNNNNNN-3'
3'-CCTACNNNNNNNNNNNNN-5') (SEQ ID NO:7)

In the examples as shown in FIG. 4, double stranded cDNA derived from rat liver mRNA was digested with BbvI and ligated to Tail adaptor set 2. Helper oligo was HOLL2 for "FIG. 4A" and HOLL1 for "FIG. 4B". Ligation specificity was tested on the Albumin gene, which constitutes the most abundant mRNA in rat liver. Ligation specificity was tested with a Tail primer and Albumin reverse primer. The specific Tail adaptor that should ligate to the Albumin gene is Ada-ACT. All 9 Tail adaptors that have one base mismatch with the Albumin specific Tail adaptor were examined. Both "FIG. 4A" and "FIG. 4B" show separation of DNA on 1.5% agarose gel using and ethidium bromide staining was used to visualize the DNA.

In FIG. 4A, helper oligo HOLL2, that is a perfect match to the Tail adaptors, was used. Oligo concentration was 5 pmol/25 µl. The correct 200 bp band is observed in the specific ACT Tail primer. However, Tails ATT, AGT, ATT and TCT give a strong 200 bp-albumin band. Very weak 200 bp band is observed in Tail ACG, ACC and ACA. Thus, the ligation conditions used here allow frequent mis-ligations.

In FIG. 4B, helper oligo HOLL1, that has a mismatch to the first nucleotide of the constant region of the Tail adaptor, was used. Oligo concentration was 2.5 pmol/25 µl. The 200 bp Albumin specific band is observed only in the Tail-ACT amplification. None of the other Tails gave the Albumin band. The 500 bp band observed in the ACG lane (also seen in "A") is caused by Tail-Tail amplification of an undetermined gene. Thus, the ligation conditions used here give highly specific ligation and do not allow mis-ligations.

2. Differential Ligation

Adaptor design and sequence: The digested ds cDNA was ligated to a set of oligonucleotide adaptors. Two sets of adaptors were used: a set of 64 adaptors covering all 64 combinations of three of the four nucleotides of the overhang, and a set of 256 adaptors covering all 256 combinations of the four nucleotides of the overhang.

Each adaptor comprises two DNA strands: a "long" 49–51 bp strand that contains the sequence that fits into the overhang produced by the type IIs RE's, and a "short" 18-mer strand that complements the long strand up to the overhang. Three structural versions of the short strand were examined:
5'-XYZNGCAGGTACGTCGTACCGCGGCCGCGTGAG CTTGAGTCGCGTGGAT-3' long strand (SEQ ID NO:8)
3'-CGTCCATGCAGCATGGCG-5' short strand 1(SS1 ) (SEQ ID NO:9)
3'-AGTCCATGCAGCATGGCG-5' short strand 2(SS2 ) (SEQ ID NO:10)
3'-CATCCATGCACCATGGCG-5' short strand 3(SS3 ) (SEQ ID NO:11)

Note that SS2 has a mismatch to the 5th nucleotide of the long strand (just after the N) and that SS3 has a mismatch to the 6th nucleotide.

The general structure of the long strand of the adaptors is as follows for the set of 64:

5'P-XYZN - - - constant - - - | - - - Specific - - - | where each of X,Y and Z can be any of the nucleotides but are specific for each adaptor; N is a mix of all 4 nucleotides; P is a 5' phosphate; the constant region is a sequence which is common to all 64 adaptors while the specific region is specific to each of the 64 adaptors, each adaptor has a different specific sequence.

The general structure of the adaptors is as follows for the set of 256:

5'P-WXYZ - - - constant - - - | - - - Specific - - - | where each of W, X,Y and Z can be any of the nucleotides but are specific for each adaptor; P is a 5' phosphate; the constant region is a sequence which is common to all 256 adaptors while the specific region is specific to each of the 256 adaptors, each adaptor has a different specific sequence. For each adaptor from the set of 64 and set of 256 a specific primer, complementary to the specific region of the adaptor, has been synthesized. FIG. 18 shows tail adaptors set 256, which can be represented by such a general formula.

The sequences of the entire sets of 64 and 256 adaptors can be generated from the general structures for the set of 64 and the set of 256, respectively. The list of specific primers sets are appended to this application as FIGS. 10 to 13.

FIG. 10 shows the general structure of the primer and the primer set J2 having the general structure of the primers 5' XYZN GCAGGT ACGTCGTACC GCGGCCGC-x-x-x-x-x-x-x-x-x-x-x-3' (SEQ ID NO:12)
Bases 4 BspMI(6) constant(10) NOTI(8) Tail (20)
wherein X, Y and Z can be any of A, T, C or G.

FIG. 11 shows tail primers set J2 which can be represented by the general formula:

Tail-XYZ 5' TCCACGCGACTCAAGCTCAC (SEQ ID NO: 13)
wherein X, Y and Z in the primer name can be any of A, T, C or G. The sequence of the primer is different for each of the 64 different tail primers and each one of them is a complete reverse complement of the specific region of the tail adaptor that has the same X,Y,Z.

FIG. 12 shows tail primers (set number 2) which can be represented by the general formula:

TnewXYZ 5' AACGACGCGTCGCGGTACCAG (SEQ ID NO:14)
wherein X, Y and Z can be any of A, T, C or G.

FIG. 13 shows tail primers set 256 which can be represented by the general formula:

tailWXYZ 5'AACGCAGTGTTCGTTCGACGA (SEQ ID NO:15)
wherein each of W, X, Y and Z can be any of A, T, C or G.

Ligation procedure: For ligation, all 64 or 256 adaptors are mixed in equal molar concentrations. Initially ligation conditions followed conventional methods. This included the use of T4 DNA ligase at 16° C. and using the SS1 strand. These ligation conditions proved inadequate since ligation specificity was found to be low and many occasions of adaptors ligating to unmatched overhangs were noted (FIG. 4a). But the following conditions below were found to give very high ligation specificity:

100 ng of digested ds cDNA was placed in ligation buffer (50 mM Tris-HCl, pH=7.8; 10 mM $MgCl_2$; 10 mM dithiothreitol, 26 μM NAD+; 25 μg/ml bovine serum albumin). Adaptor concentration was 2.5 pmol/12 μl (long strand at 2.5 pmol/12 μl and the short strand at 10 pmol/12 μl). Importantly, short strand SS2 with one mismatch to the 5th nucleotide of the long strand (just after the N) was used. Other short strands always gave lower specificity.

At this point reaction volume was 10 μl. The reaction was heated to 65° C. for 5 minutes and then cooled to 8° C. 2 μl of E. coli DNA ligase (10 units/μl) were added.

Incubation was carried out for 12 hours. The reaction was stopped by heating to 65° C. for 15 minutes and stored at 4° C. Ligation products were purified on QIAquick spin columns to remove unligated adaptors.

Analysis of ligation specificity: Ligation specificity was tested on highly expressed genes. The following example details an experiment performed on mRNA from rat liver. The most abundant gene in this tissue is albumin and was selected (as well as other genes not shown here) to test ligation specificity. The type IIs RE used was BbvI. The 3'-most BbvI site in the rat albumin gene (genbank accession no. J00698) is at nucleotide 1740, 250 bp from the poly-A tail. A reverse oligonucleotide (5'-CACCAACAGAAGAGATGAGTCCTG-3' (SEQ ID NO:16)) matches nucleotides 1901 to 1881. The distance of this oligonucletide from the BbvI site is 160 bp.

The specific adaptor for ligation to this BbvI end of the rat albumin gene is Ada-ACT:
3'-AGATGCGGATCGGGCTCTGTGCGCCGGCGCCAT GCTGCATGGACGNTCA-5' (SEQ ID NO:17)

Amplification of the ligation product with specific-ACT (5'-TCTACGCCTAGCCCGAGACAC-3' (SEQ ID NO:18)) by PCR gave the correct fragment size of 209 bp on an agarose gel (FIG. 4 lane ACT). Had a different adaptor managed to ligate (i.e. misligate) to the end of albumin cDNA, then a different specific primer would have given a fragment of the same size. FIG. 4a shows the results of ligation done under non-specific conditions using a short strand with no mismatches. Lanes ATT, AGT, AAT, TCT show the presence of such a fragment after amplification with other tail primers indicating presence of misligation. However, when the conditions defined above were used, no misligations occurred (FIG. 4b).

Additional experiments performed on the GAPDH included testing ligation specificity on all 64 specific adaptors. Upon digestion with a type IIs restriction enzyme of a double-stranded cDNA derived from the mRNA of a specific gene, fragments with specific overhangs are produced. The example below describes the full human GAPDH cDNA sequence and the location of the recognition sites for the BbvI type IIs restriction enzyme. The "><" symbol marks the exact point were the enzyme cleaves the cDNA. The polyA addition signal (AATAAA), found 20 to 30 bases before the actual polyA addition site, is underlined. Also underlined, in the more upstream regions, are the BbvI recognition sequences. The example given here is in addition to the Rat albumin example given in the patent.

```
                                              (SEQ ID NO: 19)
GTTCGACAGT CAGCCGCATC TTCTTTTGCG TCGCCGCCG
    10         20         30

>< BbvI
AGCCACATCG CTCAGACACC ATGGGGAAGG TGAAGGTCGG
    50         60         70         80
```

```
                    -continued
AGTCAACGGA TTTGGTCGTA TTGGGCGCCT GGTCACCAGG
    90         100        110        120

GCTGCTTTTA ACTCTGGTAA AGTGGATATT GTTGCCATCA
   130         140        150

ATGACCCCTT CATTGACCTC AACTACATGG TTTACATGTT
   170         180        190        200

CCAATATGAT TCCACCCATG GCAAATTCCA TGGCACCGTC
   210         220        230        240

AAGGCTGAGA ACGGGAAGCT TGTCATCAAT GGAAATCCCA
   250         260        270        280

TCACCATCTT CCAGGAGCGA GATCCCTCCA AAATCAAGTG
   290         300        310        320

GGGCGATGCT GGCGCTGAGT ACGTCGTGGA GTCCACTGGC
   330         340        350        360

GTCTTCACCA CCATGGAGAA GGCTGGGGCT CATTTGCAGG
   370         380        390        400

GGGGAGCCAA AAGGGTCATC ATCTCTGCCC CCTCTGCTGA
   410         420        430        440

TGCCCCCATG TTCGTCATGG GTGTGAACCA TGAGAAGTAT
   450         460        470        480

GACAACAGCC TCAAGATCAT CAGCAATGCC TCCTGCACCA
   490         500        510        520

CCAACTGCTT AGCACCCCTG GCCAAGGTCA TCCATGACAA
   530         540        550        560

CTTTGGTATC GTGGAAGGAC TCATGACCAC AGTCCATGCC
   570         580        590        600

ATCACTGCCA CCCAGAAGAC TGTGGATGGC
   610         620        630

>< BbvI
CCCTCCGGGA AACTGTGGCG TGATGGCCGC GGGGCTCTCC
   640         650        660        670

AGAACATCAT CCCTGCCTCT ACTGGCGCTG CCAAGGCTGT
   680         690        700        710

GGGCAAGGTC ATCCCTGAGC TGAACGGGAA GCTCACTGGC
   720         730        740        750

ATGGCCTTCC GTGTCCCCAC TGCCAACGTG TCAGTGGTGG
```

```
                    -continued
    760        770        780        790

ACCTGACCTG CCGTCTAGAA AAACCTGCCA AATATGATGA
   800         810        820        830

CATCAAGAAG GTGGTGAAGC AGGCGTCGGA GGGCCCCCTC
   840         850        860        870

AAGGGCATCC TGGGCTACAC TGAGCACCAG GTGGTCTCCT
   880         890        900        910

CTGACTTCAA CAGCGACACC CACTCCTCCA CCTTTGACGC
   920         930        940        950

TGGGGCTGGC ATTGCCCTCA ACGACCACTT TGTCAAGCTC
   960         970        980        990

ATTTCCTGGT ATGACAACGA ATTTGGCTAC AGCAACAGGG
  1000        1010       1020       1030

TGGTGGACCT CATGGCCCAC ATGGCCTCCA AGGAGTAAGA
  1040        1050       1060       1070

CCCCTGGACC ACCAGCCCCA GCAAGAGCAC AAGAGGAAGA
  1080        1090       1100       1110

GAGAGACCCT CACTGCTGGG GAGTCCCTGC CACACTCAGT
  1120        1130       1140       1150

CCCCCACCAC ACTGAATCTC CCCTCCTCAC AGTTGCCATG
  1160        1170       1180       1190

TAGACCCCTT GAAGAGGGGA GGGGCCTAGG GAGCCGCACC
  1200        1210       1220       1230

TTGTCATGTA CCATCAATAA AGTACCCTGT GCTCAACC
  1240        1250       1260       1270
```

The expected end of the 3' fragment should be:

5'-AAGTGTTGCAAGGCTGCCGACAAGGATAAC - - - 3' (SEQ ID NO:20)
3'-CAACGTTCCGACGGCTGTTCCTATTG - - - 5'

The cDNA derived in the SDGI procedure has an extended polyA tail of a specific sequence. This is underlined in the sequence below. The sequence below describes the exact structure of the double stranded structure of the 3' most fragment of the human GAPDH cDNA. Note the structure of the 5' end. The BbvI recognition sequence is underlined.

```
                                                (SEQ ID NO:21)
                                                      ><BbvI
                                            GCCTCT ACTGGCGCTG
                                            GA TGACCGCGAC 640        650        660        670        680        690        700
         CCAAGGCTGT GGGCAAGGTC ATCCCTGAGC TGAACGGGAA GCTCACTGGC ATGGCCTTCC GTGTCCCCAC
         GGTTCCGACA CCCGTTCCAG TAGGGACTCG ACTTGCCCTT CGAGTGACCG TACCGGAAGG CACAGGGGTG 710        720        730        740        750        760        770
         TGCCAACGTG TCAGTGGTGG ACCTGACCTG CCGTCTAGAA AAACCTGCCA AATATGATGA CATCAAGAAG
         ACGGTTGCAC AGTCACCACC TGGACTGGAC GGCAGATCTT TTTGGACGGT TTATACTACT GTAGTTCTTC 780        790        800        810        820        830        840
         GTGGTGAAGC AGGCGTCGGA GGGCCCCCTC AAGGGCATCC TGGGCTACAC TGAGCACCAG GTGGTCTCCT
```

-continued

```
CACCACTTCG TCCGCAGCCT CCCGGGGGAG TTCCCGTAGG ACCCGATGTG ACTCGTGGTC CACCAGAGGA
    850        860        870        880        890        900        910

CTGACTTCAA CAGCGACACC CACTCCTCCA CCTTTGACGC TGGGGCTGGC ATTGCCCTCA ACGACCACTT

GACTGAAGTT GTCGCTGTGG GTGAGGAGGT GGAAACTGCG ACCCCGACCG TAACGGGAGT TGCTGGTGAA
    920        930        940        950        960        970        980

TGTCAAGCTC ATTTCCTGGT ATGACAACGA ATTTGGCTAC AGCAACAGGG TGGTGGACCT CATGGCCCAC

ACAGTTCGAG TAAAGGACCA TACTGTTGCT TAAACCGATG TCGTTGTCCC ACCACCTGGA GTACCGGGTG
    990       1000       1010       1020       1030       1040       1050

ATGGCCTCCA AGGAGTAAGA CCCCTGGACC ACCAGCCCCA GCAAGAGCAC AAGAGGAAGA GAGAGACCCT

TACCGGAGGT TCCTCATTCT GGGGACCTGG TGGTCGGGGT CGTTCTCGTG TTCTCCTTCT CTCTCTGGGA
   1060       1070       1080       1090       1100       1110       1120

CACTGCTGGG GAGTCCCTGC CACACTCAGT CCCCCACCAC ACTGAATCTC CCCTCCTCAC AGTTGCCATG

GTGACGACCC CTCAGGGACG GTGTGAGTCA GGGGGTGGTG TGACTTAGAG GGGAGGAGTG TCAACGGTAC
   1130       1140       1150       1160       1170       1180       1190

TAGACCCCTT GAAGAGGGGA GGGGCCTAGG GAGCCGCACC TTGTCATGTA CCATCAATAA AGTACCCTGT

ATCTGGGGAA CTTCTCCCCT CCCCGGATCC CTCGGCGTGG AACAGTACAT GGTAGTTATT TCATGGACA
   1200       1210       1220       1230       1240       1250       1260

GCTCAACCAAAAAAAAAAAAAAAAAAA

CGAGTTCCTTTTTTTTTTTTTTTTTT
```

The specific adaptor that will ligate to this overhang is: GGTACGACGTTCAGCA GCCTCTACTGGCGCTG - - -
Ada AGG 3' CCAATAGCAGCCGCCGCTGCCATGCT-GCAAGTCGANGGA GATGACCGCGAC - - - (SEQ ID NO:22)

Note the mismatch in the upper sequence (helper) of the adaptor, that marked by an underline. To the right of the adaptor the end of the human GAPDH sequence is shown to emphasize the match between the adaptor and the overhang. Ligation specificity is examined by the ability of the "TAIL" primer that matches the 3' (specific) part of the adaptor (Tail AGG 5' GGTTATCCGTCGGCGGCGAC 3') (SEQ ID NO: 23) to amplify, in combination with a GAPDH-specific reverse primer (underlined above—5' TACAGCAA-CAGGGTGGTGGA 3') (SEQ ID NO:24). This PCR amplification should result in a fragment of a specific size, 390 bp in the example of GAPDH (350+40 of the adaptor). A complete specificity is achieved when all of the other TAIL primers are unable to amplify the GAPDH sequence. This is what is shown in FIG. 5 whom all 64 TAIL plus GAPDH reverse PCR amplifications were performed and only the Ada-AGG TAIL was able to give the expected fragment of 390 bp.

Analysis of ligation efficiency: To examine the efficiency of ligation, the successful amplification of a set of rare mRNAs was tested. As in section 2.3, reverse primers for the specific genes are used in combination with the specific primers that were expected to ligate to the ends of these cDNAs. All reaction conditions were performed as described in section 2.3.

3. Amplification-division of the Different Groups (General-specific PCR)

Figure 7:
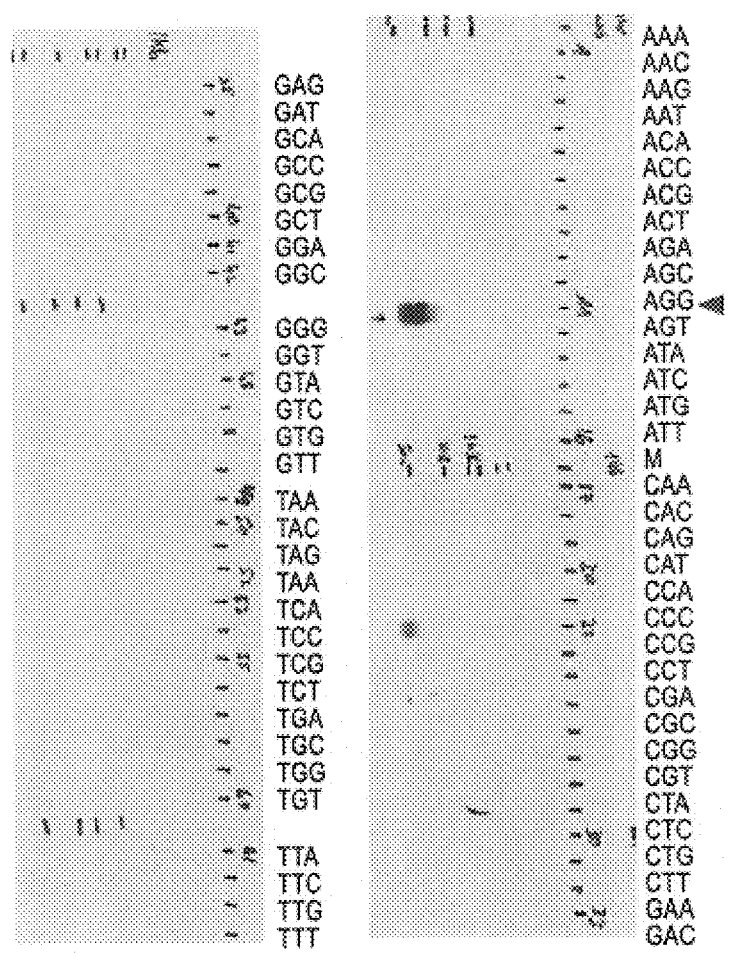
FIG. 7 is a Southern blot of PCR amplification products derived from Jurkat-cell mRNA showing ligation specificity according to the methods of the present invention. The agarose gel shown in FIG. 2 was blotted onto nylon membrane (Nytran, Schleicher & Schull). The membrane was then hybridized with a radioactive ($^{32}$P) probe specific to the human GAPDH gene. The specific signal was obtained in the correct "AGG" lane only. A weaker signal, observed in the "CCC" lane is not of the correct size and can be caused by spurious amplification of the abundant GAPDH cDNA by the "CCC" Tail primer alone.

The ligation could employ a mix of all 64 (or 256) adaptors. While the following details the protocol performed on the set of 64 adaptors, the same protocol applies to a set of 256 adaptors. To divide the ligated cDNA into 64 groups 64 PCR reactions were performed. Each reaction used a primer specific for one of the specific ligation adaptors, and the general primer. This resulted in a specific amplification of all cDNAs ligated with the specific adaptor. PCR conditions were 2 min. at 95° C. followed by 30 cycles of 1 min. at 95° C., 1 min. at 58° C. and 2 min. at 68° C. This was followed by incubation for 7 min. at 68° C. FIG. 6 shows the products of the 64 specific-general-primed PCR reaction. Southern blot analysis of the 64 reactions (FIG. 7) demonstrates the specificity of the procedure: after amplification with specific and general primers GAPDH mRNA was amplified only in the expected group (AGG).

The PCR products were purified over a QIAquick spin column to remove the unincorporated primers and nucleotides. In this step an mRNA source of 10,000 genes was divided into 64 groups each containing an average of 150 cDNA species (genes). If the source contains all 100,000 human genes each group will contain an average of 1500 cDNA species (genes).

4. Priming Nesting Procedure

First nesting: In this step each of the 64 groups from the previous step was further sorted into 256 subgroups. Of course, division into fewer groups was also possible. A set of nesting oligonucleotides—the 1st nesting set—was used. It should be noted that this set of 256 nesting primers could be used on all 64 general-specific primed groups (as well as on the 256 general-specific primed groups) since they prime from the "constant" region of the specific adaptor. The following is the overall structure of a 1st nesting primer:
5'-GCGGCCGCGGTACGACGTACCTGCNIIIWXYZ-3' (SEQ ID NO:25)

where I=inosine; N=any nucleotide; each of W,X,Y,Z=C, G, T or A.

The NIII nucleotides match the four nucleotides in the specific adaptor used to ligate to the overhang end of the cDNAs. The inosine nucleotides can match any of the regular nucleotides. The WXYZ nucleotides, covering all 256 possibilities of C, G, T or A allow nesting into the four nucleotides adjacent to the overhang. The first nesting oligonucleotide list is shown in FIGS. 14 and 15.

FIG. 14 shows first nesting primers 256 for tail adaptor 64 set 1, which can be represented by the general formula:

5' GGTACGACGTTCAGCTNIIIWXYZ (SEQ ID NO:26)

wherein W, X, Y and Z can be any of A, T, C or G.

FIG. 15 shows first nesting primers 64 for tail adaptor 64 set 1, which can be represented by the general formula:

5' GGTACGACGTTCAGCTNIIIXYZ (SEQ ID NO:27)

wherein X, Y and Z can be any of A, T, C or G.

An optional λ exonuclease reaction can be performed to eliminate carry-over of cDNA from the original cDNA reaction. This is possible since the oligo(dT) primer used to produce the cDNA in the reverse transcription reaction is phosphorylated and the general and specific primers used for general-specific primed amplifications are not phosphorylated. The following mixture was prepared: 2 µl of purified general-specific primed PCR product, 6 µl H2O, 1 µlλ exonuclease buffer and 1 µlλ exonuclease. The reaction mixture was then purified over a column.

For nesting, a 1:500 dilution of the general-specific PCR product was taken. PCR reaction constituents were standard (including anti-taq antibody). Cycling conditions were: 1 min. at 95° C., 1 min. at 59° C. and 2 min. at 70° C. 30 cycles were performed. After PCR, the unincorporated primers and nucleotides were removed using QIAquick spin columns.

Figure 8:
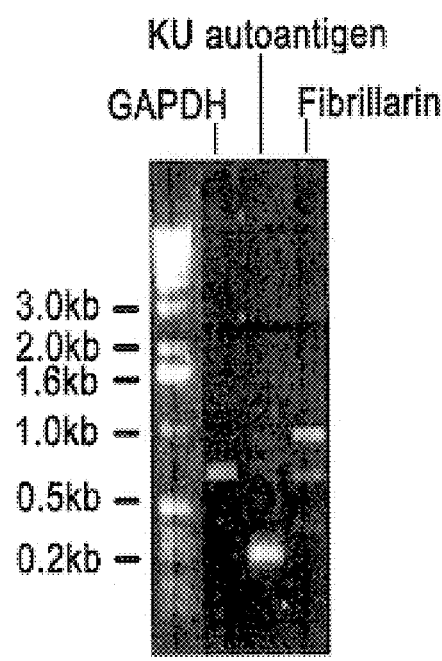
FIG. 8 shows isolation of three different genes obtained by using nesting PCR primers according to the methods of the present invention. The specific END-Tail groups, expected to contain the GAPDH, Ku antigen and fibrillarin cDNAs, were used as a template for nesting PCR. Nesting primers from the "$1^{st}$ Nest 256", expected to amplify these three genes were used. Amplification products were separated on a 1.5% agarose gel and ethidium bromide staining was used to visualize the DNA. For the GAPDH and Ku antigen cDNAs single bands of the correct size are observed. For fibrillarin cDNA three bands are observed, one of them, the middle 650bp band, is of the expected size.

The 1st nesting stage divides each of the 64 groups into 256 groups for a total of 16,384 groups. Thus, for an mRNA source of 10,000 genes, each of the 256 1st nesting tubes should contain an average of less than 1 cDNA species (gene). This means that most tubes (>100) will contain one cDNA species, some will be empty and a few will contain more then one cDNA species. FIG. 8 shows the results of a 1st nesting PCR done on 3 of the 64 groups. The object of the nesting PCR was to isolate three specific genes according to the sequences around the BbvI site closest to the 3' end.

For a source containing all 100,000 human genes, each of the 256 tubes will contain an average of 6 cDNA species (genes). Thus, a further nesting round would achieve one gene only per well.

Second nesting: In this stage each of the 256 1st nesting groups was further divided into 16 groups. As for the 1st nesting primers, this set of 16 2nd nesting primers can be used on all 1st-nesting primer reactions, since they prime from the "constant" region of the ligation adaptors.

The primers used for the 2nd nesting are of the following structure:

5'-GCGGCCGCGGTACGACGTACCTGCNGGGIIIINNXY-3' (SEQ ID NO:28)

where I=inosine; N=any nucleotide; each of W,X,Y and Z can be any of C, G, T or A. In places were inosine was present in the 1 st nesting primer a "G" is placed in the 2nd nesting primers (since a "C" is incorporated as a match to "I"). Lists detailing second nesting primers are shown in FIGS. 16 and 17.

FIG. 16 shows second nesting primers 64 for tail adaptor 64 set 1, which can be represented by the general formula:

5' GGTACGACGTTCAGCTNGGGIIIXYZ (SEQ ID NO:29)

wherein each of X, Y and Z can be any of A, T, C or G.

FIG. 17 shows second nesting primers 16 for tail adaptor 64 set 1, which can be represented by the general formula:

5' GGTACGACGTTCAGCTNGGGIIIXY (SEQ ID NO:30)

wherein each of X and Y can be any of A, T, C or G.

Figure 9:
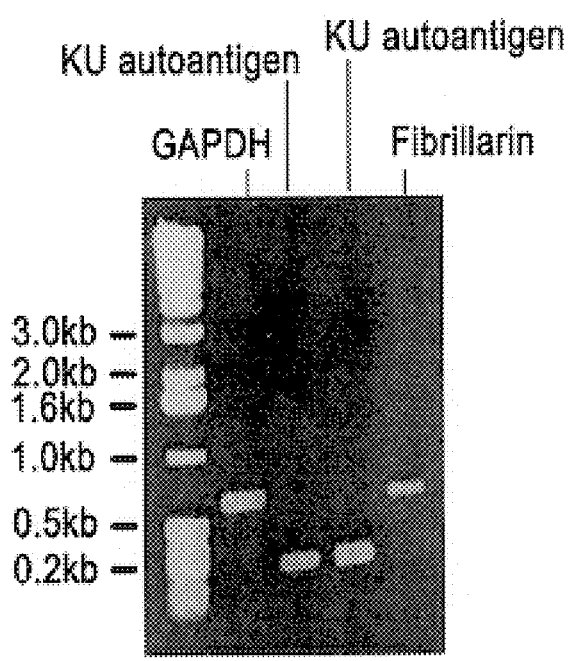
FIG. 9 shows isolation of three different genes obtained by using second nesting primers according to the methods of the present invention. Products of the $1^{st}$ nesting reactions were used as template for the second nesting. Primers from the "$2^{nd}$ nest 16" set were chosen that are expected to amplify the three cDNAs. As expected, single strong bands were obtained for GAPDH and KU antigen cDNAs. For fibrillarin, the second nesting step separated the three bands and only the correct 650 bp band was obtained.

A 1:500 proportion of the 1st nesting purified PCR products are used for a PCR reaction performed with exactly the same constituents and conditions as described above. FIG. 9 shows the results of 2nd nesting PCR on the three groups shown in FIG. 8. Highly pure DNA fragments were obtained.

The 2nd nesting stage divides each of the 16,384 1st nesting groups into sixteenths, for a total of 262,144 groups. Thus, about 100,000 of the groups should contain cDNA products and more than 95% of them should contain only one gene or gene fragment.

5. Ligation Nesting Procedure

Digestion of END-TAII PCR product: The QIAquick spin column purified PCR products of each of the 64 general-specific primed groups described above were digested with BspMI under standard manufacturer (New England BioLabs) conditions. The released. adaptors were removed by purifying the digestion products through a QIAquick spin column.

First nesting ligation (Adaptor set #2): 100 ng of each of the 64 digested products are ligated with a mix of 64 adaptors (nesting ligation adaptor set). Ligation conditions are identical to those detailed above in relation to differential ligation. The same tests of specificity and efficiency—detailed above—were successfully performed. Each ligation was purified over a QIAquick spin column to remove unligated adaptors. DNA was eluted from the column in a final volume of 100 µl. Adaptor set #2 is shown in FIG. 20. The tail adaptors 64 (set number 2) in FIG. 20 can be represented by the general formula:

|- - - specific - - - |-constant| - - - specific - - - |

5' Ph-XYZNGCAGGTACGTCGTACC GCGGCCGC GTGAGCTTGAGTCGCGTGGA (SEQ ID NO:31)

wherein X, Y and Z can be any of A, T, C or G.

Amplification of the first ligation products: Each of the 64 ligations was divided in this step into 64 tubes. The final number of tubes was thus 4096. From each ligation tube 1 µl was taken for each of the 64 amplifications. Each amplification was done by one of the 64 specific primers and the general primer. Amplification conditions were identical to those detailed in the "Amplification-division of the different groups (general-specific primed PCR)" section above. Each PCR reaction mixture was purified over a QIAquick spin column to remove unincorporated primers and nucleotides.

Digestion of END-TAII first ligation PCR product: The procedure detailed in the "Digestion of general-specific primed PCR product" above is exactly repeated.

Second nesting ligation: The procedure detailed for the 1st nesting ligation is exactly repeated with adaptor set #1 which is listed in FIG. 19. The tail adaptors 64 (set number 1) of FIG. 19 can be represented by the general formula:

|constant - - - | - - - specific - - - |

AdaXYZ 5'-Ph-TTTNAGCTGAACGTCGTACC CGTCG AACGA ACACG GGCGT SEQ ID NO:32)

wherein each of X, Y and Z can be any of A, T, C or G.

6. Gene Analysis (Agarose Gel and Sequencing)

PCR products obtained from the 2nd nesting reaction (either priming or ligation) are separated an agarose gel to examine the presence of PCR products and the number of fragments (FIG. 9). Sorted or isolated cDNAs are purified and sequenced using the constant region of the ligation adaptors as a primer.

7. Construction of cDNA Library from the Amplification Products Obtained from the Differential Ligation Step The double stranded cDNA, prepared as described in section 1, was divided into two pools. One pool was digested with BbsI and the second with BsaI. The following procedure was done in parallel for each pool.

Following the differential ligation, performed as described in section 2, using adaptor set J2 was used for ligation, the PCR amplification was performed as described with primer set J2. Amplified products were purified on QIAquick spin columns. The PCR products from each of the 64 groups were digested with NotI and AscI and were purified on QIAquick spin columns. A plasmid that contains NotI and AscI in its multiple cloning site is digested with NotI and AscI and the linearized fragment is purified using standard protocols. The purified NotI-AscI digested PCR products were ligated to the linearized plasmid using standard condition. Ligation products were transformed into bacteria using standard protocols. Transformed bacteria were plated onto growth plates and following standard incubation hundreds to thousands of colonies grow on each plate. For sequencing, each plasmid was purified from picked colonies and prepared for sequencing using standard protocols. Another option is to amplify the insert from the plasmid found in the picked colonies using primers flanking the insert. The amplified inserts are sequenced using standard protocols.

The double stranded cDNA which was prepared as described in section 1, was also divided into between 3 and 25 pools for digestion with restriction enzymes, for ligation and for expression. The expression of the separated genes can be in a bacterium.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

K. Kato, U.S. Pat. No. 5,707,807, issued Jan. 13, 1998, "Molecular Indexing For Expressed Gene Analysis";

P. Unrau and K. V. Deugau (1994) "Non-cloning amplification of specific DNA fragments from whole genomic DNA digests using DNA 'indexers'", Gene 145:163–169;

D. R. Sibson, et al., U.S. Pat. No. 5,728,524, issued Mar. 17, 1998 "Process For Categorizing Nucleotide Sequence Populations";

D. R. Smith, Ligation-mediated PCR of Restriction Fragments from Large DNA Molecules.

U.S. Pat. No. 5,871,697, Method And Apparatus For Identifying, Classifying, Or Quantifying DNA Sequences In A Sample Without Sequencing.

Gold P., U.S. Pat. No. 5,407,813, issued Apr. 18, 1995.

Deugau et al., U.S. Pat. No. 5,508,169, issued Apr. 16, 1996.

Deugau et al., U.S. Pat. No. 5,858,656, issued Jan. 12, 1999.

R. A. Guilfoyle et al., "Ligation-mediated PCR amplification of specific fragments from a Class-II restriction endonuclease total digest" Nucleic Acids Research, 1997, Vol. 25(9):1854–1858.

N. B. Ivanova and A. V. Belyavsky "Identification of differentially expressed genes by restriction endonuclease-based gene expression fingerprinting" Nucleic Acids Research, 1995, Vol. 23(15):2954–2958.

H. Mahadeva et al. "A simple and efficient method for the isolation of differentially expressed genes" J. Mol. Biol., 1998, 284:1391–1398.

A. B. Troutt et al. Proc. Natl. Acad. Sci. USA, Biochemistry, October 1992, 89:9823–9825.

K. Kato, Nucleic Acids Research, 1995, 23(18):3685–3690.

D. R. Sibson, U.S. Pat. No. 5,728,524, issued Mar. 17, 1998.

R. J. Sapolsky et al, U.S. Pat. No. 5,710,000, issued Jan. 20, 1998.

H. Kambara et al., U.S. Pat. No. 5,650,274, issued Jul. 22, 1997.

Y. Prashar and S. M. Weissman, Proc. Natl. Acad. Sci. USA, 1996, 93:659–663.

M. S. H. Ko, Nucleic Acids Research, Vol. 18(19):5705–5711.

J. M. Rothberg, et al., U.S. Pat. No. 5,871,697, issued Feb. 16, 1999.

J. B. D. M. Edward, Nucleic Acids Research, Vol. 19(19):5227–5232.

C. Hoog, Nucleic Acids Research, Vol. 19(22):6123–6127.

B. P. Sokolov et al., Nucleic Acids Research, 1994, Vol. 22(19):4009–4015.

W. M. Schmidt and M. W. Mueller, Nucleic Acids Research, Vol. 24(9):1789–1791.

A. Belyavsky et al. Nucleic Acids Research, 1989, Vol. 17(8):2919–2932.

J. P. Calvet, Pediatric Nephrology, 1991, 5:751–757.

R. Cooke et al., The Plant Journal, 1996, 9(1):101–124.

Christine Domec et al., Analytical Biochemistry, 1990, 188:422–426.

H. Haymerle et al., Nucleic Acids Research, 1986, Vol. 14(21):8615–8625.

S. Kato et al., Gene, 1994, 150:243–250.

T. Kohchi et al., The Plant Journal, 1995, 8(5):771–776.

S. R. Patanjali et al., Proc. Natl. Acad. Sci. USA, 1991, Vol. 88:1943–1947.

A. J. Podhajska et al., Method in Enzymology, 1992, 216:303–309.

W. Szybalski et al., Gene, 1991, 100:13–26.

WO 94/01582, published Jan. 20, 1994.

Gould et al., U.S. Pat. No. 5,700,644, issued Dec. 23, 1997.

Short et al., U.S. Pat. No. 5,763,239, issued June 9, 1998.

Sytkowski et al., U.S. Pat. No. 5,804,382, issued Sep. 8, 1998.

Belyavsky et al., U.S. Pat. No. 5,814,445, issued Sep. 29, 1998.

Wang et al., U.S. Pat. No. 5,837,468, issued Nov. 17, 1998.

Brenner, U.S. Pat. No. 5,863,722, issued Jan. 26, 1999.

Kinzler et al., U.S. Pat. No. 5,866,330, issued Feb. 2, 1999.

Kinzler et al., U.S. Pat. No. 5,695,937, issued Dec. 9, 1997.

Bassam et al., U.S. Pat. No. 5,413,909, issued May 9, 1995.

McClelland et al., U.S. Pat. No. 5,487,985, issued Jan. 30, 1996.

Villeponteau et al., U.S. Pat. No. 5,580,726, issued Dec. 3, 1996.

Mierendorf et al., U.S. Pat. No. 5,629,179, issued May 13, 1997.

Yourno, U.S. Pat. No. 5,556,773, issued Sep. 17, 1996.

Sambrook et al. (1989) Molecular Cloning: A Laboratory Manual, second edition.

M. J. Gait, ed. (1984) Oligonucleotide Synthesis.
R. I. Freshney, ed. (1987) Animal Cell Culture.
Methods in Enzymology, Academic Press, Inc.
D. M. Wei & C. C. Blackwell, eds., Handbook of Experimental Immunology.
J. M. Miller & M. P. Calos, eds. (1987) Gene Transfer Vectors for Mammalian Cells. F. M.
Ausubel et al., eds., (1987) Current Protocols in Molecular Biology.
Mullis et al., eds. (1994) PCR: The Polymerase Chain Reaction.
J. E. Coligan et al., eds. (1991) Current Protocols in Immunology.
P. R. Warthoe et al., WO 98/51789A2, published Nov. 19, 1998.
P. Liang et al., WO 93/18176A1., published Sep. 16, 1993.
P. Einat et al., WO 99/60164, published Nov. 25, 1999.

What is claimed is:

1. A method of sorting genes comprising:
   (1) preparing ds cDNA molecules from mRNA molecules by reverse transcription, using a poly-T primer optionally having a general primer-template sequence upstream from the poly-T sequence, yielding ds cDNA molecules having the poly-T sequence, optionally having the general primer-template sequence;
   (2) digesting the ds cDNA molecules with a restriction enzyme that produces digested cDNA molecules with cohesive ends having overhanging ssDNA sequences of a constant number of arbitrary nucleotides;
   (3) ligating to the digested cDNA molecules a set of dsDNA oligonucleotide adaptors, each of which adaptors has at one of its ends a cohesive-end ssDNA adaptor sequence complementary to one of the possible overhanging ssDNA sequences of the digested cDNA, at the opposite end a specific primer-template sequence specific for the ssDNA adaptor complementary sequence, and in between primer-template sequence specific for the ssDNA adaptor completmentary sequence, and in between the ends a constant sequence that is the same for all of the different adaptors of the set;
   (4) amplifying by separate polymerase chain reactions the ligated cDNA molecules, utilizing for each separate polymerase chain reaction a primer that anneals to the cDNA poly-T sequence optionally having the cDNA general primer-template, and a primer from a set of different specific primers that anneal to the cDNA specific primer-template sequences; and
   (5) sorting the amplified cDNA molecules into nonredundant groups by collecting the amplification products after each separate polymerase chain reaction, each group of amplified cDNA molecules determined by the specific primer that annealed to the specific primer-template sequence and primed the polymerase chain reaction.

2. The method of claim 1, wherein the restriction enzyme is selected from type IIs restriction enzymes.

3. The method of claim 2, wherein the type IIs restriction enzyme is BbvI, BspMI, FokI, HgaI, MboI, BbsI, BsaI, NspMI, BsmBI or SfaNI.

4. The method of claim 1, wherein the restriction enzyme is selected from type II restriction enzymes.

5. The method of claim 4, wherein the type II restriction enzyme is BglI BstXI or SfiI.

6. The method of claim 1, wherein a complete set of oligonucleotide adaptors and specific primers contains an oligonucleotide adaptor and a specific primer complementary to each of the possible overhanging ssDNA sequences of the digested cDNA.

7. The method of claim 1 wherein the 3'-most nucleotide of the ssDNA complementary sequence of the oligonucleotide adaptor is an arbitrary nucleotide N, which pairs with the 5'-most nucleotide of each of the possible overhanging ssDNA sequences of the digested cDNA.

8. The method of claim 7, comprising using a complete set of oligonucleotide adaptors and specific primers, containing an oligonucleotide adaptor and a specific primer complementary to each of the possible overhanging ssDNA sequences of the digested cDNA excluding the 5'-most nucleotide that pairs with the arbitrary nucleotide N of the oligonucleotide adaptor.

9. The method of claim 8, wherein a complete set of oligonucleotide adaptors have 4, 16, 64, 256, or 1024 oligonucleotide adaptors; wherein the constant number of arbitrary nucleotides is 1, 2,3,4,or 5.

10. The method of claim 1 further comprising:
   (1) amplifying the sorted nonredundant groups of cDNA molecules by nesting polymerase chain reaction, each amplification utilizing a primer that anneals to the cDNA poly-T sequence optionally having the cDNA general primer-template sequence, as well as one of a set of nesting primers with the following general formula 5'-|sequence complementary to the constant sequence of the oligonucleotide adaptors|-$NI_x$-|1–5 nucleotides complementary to one of the possible sequences of 1–5 nucleotides immediately upstream from the overhanging ssDNA sequence on the cDNA|-3' where N is an arbitrary nucleotide; I is inosine; and x=1,2,3 or 4, being one fewer than the constant number of nucleotides in the overhanging ssDNA sequences; and (2) sorting the amplified cDNA molecules into nonredundant subgroups by collecting the amplification products after each separate nesting polymerase chain reaction, each nonredundant subgroup of cDNA molecules determined by the particular nested primer that complemented the 1–5 nucleotides immediately upstream from the overhanging ssDNA sequence on the cDNA.

11. The method of claim 10 comprising using a complete set of nesting primers, containing a nesting primer complementary to each of the possible sequences of 1–5 nucleotides immediately upstream from the overhanging ssDNA sequence on the cDNA.

12. The method of claim 10, comprising conducting further polymerase chain reactions with further nesting primers complementary to the next immediately upstream cDNA nucleotides, thereby sorting the amplified cDNA molecules further into nonredundant subgroups.

13. The method of claim 12, further comprising repeating the steps of claim 10 until each nonredundant subgroup contains only one type of cDNA molecule, with every expressed-gene transcript in the mRNA sample uniquely represented in one of the nonredundant subgroups.

14. A method of sorting genes comprising:
  (1) preparing ds cDNA molecules from mRNA molecules by reverse transcription, using a poly-T primer optionally having a general primer-template sequence upstream from the poly-T sequence, yielding ds cDNA molecules having the poly-T sequence, optionally having the general primer-template sequence;
  (2) digesting the ds cDNA molecules with a first restriction enzyme that produces digested cDNA molecules with cohesive ends having first overhanging ssDNA sequences of a constant number of arbitrary nucleotides;
  (3) ligating to the digested cDNA molecules a set of dsDNA oligonucleotide adaptors, each of which adaptors has at one of its ends a cohesive-end ssDNA adaptor sequence complementary to one of the possible first overhanging ssDNA sequences of the digested cDNA, at the opposite end a specific primer-template sequence specific for the ssDNA adaptor complementary sequence, and in between the ends a constant sequence that is the same for all of the different adaptors of the set, and that contains a recognition site for a second restriction enzyme that can cleave the ligated cDNA molecules at a point further from the ligated oligonucleotide adaptor than the overhanging ssDNA sequences of the digested cDNA, and can create cohesive ends having second overhanging ssDNA sequences of a constant number of arbitrary nucleotides;
  (4) amplifying by separate polymerase chain reactions the ligated cDNA molecules, utilizing for each separate polymerase chain reaction a primer that anneals to the cDNA poly-T sequence optionally having the cDNA general primer-template, and a primer from a set of different specific primers that anneal to the cDNA specific primer-template sequences; and
  (5) sorting the amplified cDNA molecules into nonredundant groups by collecting the amplification products after each separate polymerase chain reaction, each group of amplified cDNA molecules determined by the specific primer that annealed to the specific primer-template sequence and primed the polymerase chain reaction.

15. The method of claim 14 wherein the first restriction enzyme is selected from type II and type IIs restriction enzymes.

16. The method of claim 14 wherein the second restriction enzyme is selected from type IIs restriction enzymes.

17. The method of claim 14 comprising using a complete set of oligonucleotide adaptors and specific primers, containing an oligonucleotide adaptor and a specific primer complementary to each of the possible first overhanging ssDNA sequences of the digested cDNA.

18. The method of claim 14 wherein the 3'-most nucleotide of the ssDNA complementary sequence of the oligonucleotide adaptor is an arbitrary nucleotide N, which pairs with the 5'-most nucleotide of each of the possible first overhanging ssDNA sequences of the digested cDNA.

19. The method of claim 18 comprising using a complete set of oligonucleotide adaptors and specific primers, containing an oligonucleotide adaptor and a specific primer complementary to each of the possible first overhanging ssDNA sequences of the digested cDNA excluding the 5'-most nucleotide that pairs with the arbitrary nucleotide N of the oligonucleotide adaptor.

20. The method of claim 14 further comprising:
  (1) digesting the sorted nonredundant groups of cDNA molecules with the second restriction enzyme, cleaving the ligated cDNA molecules at a point further from the ligated oligonucleotide adaptor than the overhanging ssDNA sequences of the digested cDNA, and creating cohesive ends having second overhanging ssDNA sequences of a constant number of arbitrary nucleotides;
  (2) ligating to the digested cDNA molecules a set of nesting dsDNA oligonucleotide adaptors, each of which adaptors has at one of its ends a cohesive-end ssDNA adaptor sequence complementary to one of the possible second overhanging ssDNA sequences of the digested cDNA, at the opposite end a specific primer-template sequence unique for the ssDNA adaptor complementary sequence, and in between the ends a constant sequence that is the same for all of the different adaptors of the set, and that contains the recognition site for the second restriction enzyme;
  (3) amplifying by separate polymerase chain reactions the ligated cDNA molecules, utilizing for each separate polymerase chain reaction a primer that anneals to the cDNA poly-T sequence optionally having the cDNA general primer-template, and a primer from a set of different specific primers that anneal to the cDNA specific primer-template sequences; and
  (4) sorting the amplified cDNA molecules into nonredundant subgroups by collecting the amplification products after each separate polymerase chain reaction, each subgroup of amplified cDNA molecules determined by the specific primer that annealed to the specific primer-template sequence and primed the polymerase chain reaction.

21. The method of claim 20 comprising using a complete set of nesting dsDNA oligonucleotide adaptors, containing an oligonucleotide adaptor complementary to each of the possible second overhanging ssDNA sequences of the digested cDNA.

22. The method of claim 20, further comprising conducting further polymerase chain reactions using further nesting oligonucleotide adaptors, optionally with different restriction enzymes and recognition sites, thereby sorting the amplified cDNA molecules further into nonredundant subgroups.

23. The method of claim 22, further comprising repeating the steps of claim 20 until each nonredundant subgroup contains only one type of cDNA molecule, with every expressed gene in the mRNA sample uniquely represented in one of the nonredundant subgroups.

24. A method of sorting genes and/or gene fragments comprising the steps of:
   (1) preparing ds cDNA molecules from mRNA molecules by reverse transcription, using a poly-T primer having a general primer-template sequence upstream from the poly-T sequence that includes a recognition sequence for a restriction enzyme, yielding ds cDNA molecules having the poly-T sequence, having the general primer-template sequence;
   (2) dividing the cDNA into N pools, wherein N is 1 to 25, by digesting the ds cDNA molecules with different restriction enzymes that produce digested cDNA molecules with cohesive ends having overhanging ssDNA sequences of a constant number of arbitrary nucleotides;
   (3) ligating to the digested cDNA molecules of each pool a set of dsDNA oligonucleotide adaptors, each of which adaptors has at one of its ends a cohesive-end ssDNA adaptor sequence complementary to one of the possible overhanging ssDNA sequences of the digested cDNA, at the opposite end a specific primer-template sequence specific for the ssDNA adaptor complementary sequence, and in between the ends a constant sequence that is the same for all of the different adaptors of the set;
   (4) amplifying by separate polymerase chain reactions the ligated cDNA molecules of each pool, utilizing for each separate polymerase chain reaction a primer that anneals to the cDNA poly-T sequence optionally having the cDNA general primer-template, and a primer from a set of different specific primers that anneal to the cDNA specific primer-template sequences;
   (5) sorting the amplified cDNA molecules from each pool into non-redundant groups by collecting the amplification products after each separate polymerase chain reaction, each group of amplified cDNA molecules determined by the specific primer that annealed to the specific primer-template sequence and primed the polymerase chain reaction, wherein each of the restriction enzymes digests the N separate cDNA pools into 64 or 256 non-redundant sub-groups;
   (6) digesting cDNA fragments in each non-redundant sub-group of the cDNA pools with different restriction enzymes.

25. The method of claim 24 further comprising purifying the digested cDNA fragments by removing the general primer-template sequence upstream from the poly-T sequence.

26. The method of claim 25 further comprising ligating the digested cDNA fragments into a plasmid vector that has a recognition sequence for a restriction enzyme and is predigested with the enzyme, thereby producing a set of ligations.

27. The method of claim 26, wherein the restriction enzyme is NotI or AscI.

28. The method of 26 further comprising transforming the ligation products into bacteria and growing the bacteria under suitable conditions.

29. The method of claim 30, wherein the bacteria are grown on bacteria growth plates.

30. The method of claim 25 further comprising ligating the digested cDNA fragments into a genetic vector.

31. The method of claim 30, wherein the genetic vector is a viral vector, a bacterial vector, a protozoan vector, a retrotransposon, a transposon, a DNA vector, or a recombinant vector.

32. The method of claim 24, wherein N is two and the restriction enzymes of step (2) are BbsI for one pool and BsaI for the second pool.

33. The method of claim 24, wherein N is two and the restriction enzyme in step (1) comprises AscI or another similar rare restriction enzyme.

34. The method of claim 24, wherein N is two and the restriction enzymes in step (5) comprise BbsI and BsaI.

35. The method of claim 24, wherein N is two and the restriction enzymes in step (6) comprise NotI and AscI.

36. A method of making sub-libraries of ligation sets by:
   (A) generating restriction enzyme digested fragments by a method of sorting genes and/or gene fragments comprising the steps of:
      (1) preparing ds cDNA molecules from mRNA molecules by reverse transcription, using a poly-T primer having a general primer-template sequence upstream from the poly-T sequence that includes a recognition sequence for a restriction enzyme, yielding ds cDNA molecules having the poly-T sequence, having the general primer-template sequence;
      (2) dividing the cDNA into N pools, wherein N is 1 to 25, by digesting the ds cDNA molecules with different restriction enzymes that produce digested cDNA molecules with cohesive ends having overhanging ssDNA sequences of a constant number of arbitrary nucleotides;
      (3) ligating to the digested cDNA molecules of each pool a set of dsDNA oligonucleotide adaptors, each of which adaptors has at one of its ends a cohesive-end ssDNA adaptor sequence. complementary to one of the possible overhanging ssDNA sequences of the digested cDNA, at the opposite end a specific primer-template sequence specific for the ssDNA adaptor complementary sequence, and in between the ends a constant sequence that is the same for all of the different adaptors of the set,
      (4) amplifying by separate polymerase chain reactions the ligated cDNA molecules of each pool, utilizing for each separate polymerase chain reaction a primer that anneals to the cDNA poly-T sequence optionally having the cDNA general primer-template, and a primer from a set of different specific primers that anneal to the cDNA specific primer-template sequences;
      (5) sorting the amplified cDNA molecules from each pool into non-redundant groups by collecting the amplification products after each separate polymerase chain reaction, each group of amplified cDNA molecules determined by the specific primer that annealed to the specific primer-template sequence and primed the polymerase chain reaction, wherein each of the restriction enzymes digests the N separate cDNA pools into 64 or 256 non-redundant sub-groups;
      (6) digesting cDNA fragments in each non-redundant sub-group of the cDNA pools with different restriction enzymes; and
   (B) ligating the restriction enzyme digested fragments into plasmid vectors that have recognition sequences for said restriction enzymes and predigesting with these enzymes to make 64×N or 256×N sets of ligations, wherein N is 1 to 25.

37. A method of making sub-libraries of bacterial colonies by:
   (A) generating restriction enzyme digested fragments by a method of sorting genes and/or gene fragments comprising the steps of:

(1) preparing ds cDNA molecules from mRNA molecules by reverse transcription, using a poly-T primer having a general primer-template sequence upstream from the poly-T sequence that includes a recognition sequence for a restriction enzyme, yielding ds cDNA molecules having the poly-T sequence, having the general primer-template sequence;

(2) dividing the cDNA into N pools, wherein N is 1 to 25, by digesting the ds cDNA molecules with different restriction enzymes that produce digested cDNA molecules with cohesive ends having overhanging ssDNA sequences of a constant number of arbitrary nucleotides;

(3) ligating to the digested cDNA molecules of each pool a set of dsDNA oligonucleotide adaptors, each of which adaptors has at one of its ends a cohesive-end ssDNA adaptor sequence complementary to one of the possible overhanging ssDNA sequences of the digested cDNA, at the opposite end a specific primer-template sequence specific for the ssDNA adaptor complementary sequence, and in between the ends a constant sequence that is the same for all of the different adaptors of the set;

(4) amplifying by separate polymerase chain reactions the ligated cDNA molecules of each pool, utilizing for each separate polymerase chain reaction a primer that anneals to the cDNA poly-T sequence optionally having the cDNA general primer-template, and a primer from a set of different specific primers that anneal to the cDNA specific primer-template sequences;

(5) sorting the amplified cDNA molecules from each pool into non-redundant groups by collecting the amplification products after each separate polymerase chain reaction, each group of amplified cDNA molecules determined by the specific primer that annealed to the specific primer-template sequence and primed the polymerase chain reaction, wherein each of the restriction enzymes digests the N separate cDNA pools into 64 or 256 non-redundant sub-groups;

(6) digesting cDNA fragments in each non-redundant sub-group of the cDNA pools with different restriction enzymes, thereby obtaining restriction enzyme digested fragments;

(B) purifying the restriction enzyme digested fragments by removing the general primer-template sequence upstream from the poly-T sequence, thereby obtaining purified restriction enzyme digested fragments; and (C) ligating the purified restriction enzyme digested fragments into a plasmid vector that has a recognition sequence for a restriction enzyme and is predigested with the enzyme, thereby producing a set of ligations, wherein the set of ligations is transformed into a bacterial expression system to produce bacterial colonies of the expression system containing each of the 64×N or 256×N non-redundant subgroups of cDNA fragments, wherein N is 1 to 25.

38. The method of claim 37, wherein the expression system is a bacterium.

39. The method of claim 38, wherein the bacteria are placed in a suitable growth media.

40. The method of claim 39, wherein the growth media is bacterial growth plates.

* * * * *

SEQUENCE LISTING

<160> NUMBER OF SEQ ID NOS: 1311

<210> SEQ ID NO 1
<211> LENGTH: 63
<212> TYPE: DNA
<213> ORGANISM: Artificial Sequence
<220> FEATURE:
<223> OTHER INFORMATION: oligo (dT) primer
<221> NAME/KEY: misc_feature
<222> LOCATION: (63)..(63)
<223> OTHER INFORMATION: v can be any of the nucleotides c,g or a.

<400> SEQUENCE: 1
tgcatggcac agtactgagt ggtatcgact cgtacaggcg cgcctttttt ttttttttt        60 ttv                                                                   63

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
tgcatgggac agtactgagt                                                 20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
cacagtactg agtggtatcg                                                 20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
agtggtatcg actcgtacag                                                 20

<210> SEQ ID NO 5
<211> LENGTH: 13
<212> TYPE: DNA
<213> ORGANISM: Artificial Sequence
<220> FEATURE:
<223> OTHER INFORMATION: restriction enzyme BbvI recognition sequence
<221> NAME/KEY: misc_feature
<222> LOCATION: (1)..(13)
<223> OTHER INFORMATION: n can be any nucleotide a, c, g or t

```
<400> SEQUENCE: 5
gcagcnnnnn nnn                                              13

<210> SEQ ID NO 6
<211> LENGTH: 18
<212> TYPE: DNA
<213> ORGANISM: Artificial Sequence
<220> FEATURE:
<223> OTHER INFORMATION: restriction enzyme BbvI recognition sequence
<221> NAME/KEY: misc_feature
<222> LOCATION: (1)..(18)
<223> OTHER INFORMATION: n can be any nucleotide a, c, g or t

<400> SEQUENCE: 6
nnnnnnnnnn nnngtagg                                         18

<210> SEQ ID NO 7
<211> LENGTH: 18
<212> TYPE: DNA
<213> ORGANISM: Artificial Sequence
<220> FEATURE:
<223> OTHER INFORMATION: restriction enzyme FokI recognition sequence
<221> NAME/KEY: misc_feature
<222> LOCATION: (1)..(18)
<223> OTHER INFORMATION: n can be any nucleotide a, c, g or t

<400> SEQUENCE: 7
nnnnnnnnnn nnncatcc                                         18

<210> SEQ ID NO 8
<211> LENGTH: 49
<212> TYPE: DNA
<213> ORGANISM: Artificial Sequence
<220> FEATURE:
<223> OTHER INFORMATION: Adaptor sequence
<221> NAME/KEY: misc_feature
<222> LOCATION: (1)..(49)
<223> OTHER INFORMATION: n can be any nucleotide a, c, g or t

<400> SEQUENCE: 8
nnnngcaggt acgtcgtacc gcggccgcgt gagcttgagt cgcgtggat       49

<210> SEQ ID NO 9
<211> LENGTH: 18
<212> TYPE: DNA
<213> ORGANISM: Artificial Sequence
<220> FEATURE:
<223> OTHER INFORMATION: Adaptor sequence
<221> NAME/KEY: misc_feature
<222> LOCATION: (1)..(18)
<223> OTHER INFORMATION: n can be any nucleotide a, c, g or t
<221> NAME/KEY: misc_feature
<222> LOCATION: (1)..(18)
<223> OTHER INFORMATION: short strand of adapter sequence

<400> SEQUENCE: 9
gcggtacgac gtacctgc                                         18

<210> SEQ ID NO 10
<211> LENGTH: 18
<212> TYPE: DNA
<213> ORGANISM: Artificial Sequence
<220> FEATURE:
<223> OTHER INFORMATION: Adaptor sequence

<400> SEQUENCE: 10
gcggtacgac gtacctga                                         18
```

<210> SEQ ID NO 11
<211> LENGTH: 18
<212> TYPE: DNA
<213> ORGANISM: Artificial Sequence
<220> FEATURE:
<223> OTHER INFORMATION: Adaptor sequence

<400> SEQUENCE: 11
gcggtaccac gtacctac                                               18

<210> SEQ ID NO 12
<211> LENGTH: 40
<212> TYPE: DNA
<213> ORGANISM: Artificial Sequence
<220> FEATURE:
<223> OTHER INFORMATION: adaptor sequence general stucture
<221> NAME/KEY: misc_feature
<222> LOCATION: (1)..(48)
<223> OTHER INFORMATION: n can be any nucleotide a, c, g or t as defined
      in the specification

<400> SEQUENCE: 12
nnnngcaggt acgtcgtacc gcggccgcnn nnnnnnnn                         40

<210> SEQ ID NO 13
<211> LENGTH: 23
<212> TYPE: DNA
<213> ORGANISM: Artificial Sequence
<220> FEATURE:
<223> OTHER INFORMATION: primer set  general structure
<221> NAME/KEY: misc_feature
<222> LOCATION: (1)..(23)
<223> OTHER INFORMATION: n can be any nucleotide a, c, g or t

<400> SEQUENCE: 13
nnntccacgc gactcaagct cac                                         23

<210> SEQ ID NO 14
<211> LENGTH: 24
<212> TYPE: DNA
<213> ORGANISM: Artificial Sequence
<220> FEATURE:
<223> OTHER INFORMATION: primer set number 2 general structure
<221> NAME/KEY: misc_feature
<222> LOCATION: (1)..(24)
<223> OTHER INFORMATION: n can be any nucleotide a, c, g or t

<400> SEQUENCE: 14
nnnaacgacg cgtcgcggta ccag                                        24

<210> SEQ ID NO 15
<211> LENGTH: 25
<212> TYPE: DNA
<213> ORGANISM: Artificial Sequence
<220> FEATURE:
<223> OTHER INFORMATION: primer set general structure
<221> NAME/KEY: misc_feature
<222> LOCATION: (1)..(25)
<223> OTHER INFORMATION: n can be any nucleotide a, c, g or t

<400> SEQUENCE: 15
nnnnaacgca gtgttcgttc gacga                                       25

<210> SEQ ID NO 16
<211> LENGTH: 24
<212> TYPE: DNA
<213> ORGANISM: Artificial Sequence

```
<220> FEATURE:
<223> OTHER INFORMATION: primer

<400> SEQUENCE: 16
caccaacaga agagatgagt cctg                                              24

<210> SEQ ID NO 17
<211> LENGTH: 49
<212> TYPE: DNA
<213> ORGANISM: Artificial Sequence
<220> FEATURE:
<223> OTHER INFORMATION: sequence of adaptor Ada-ACT
<221> NAME/KEY: misc_feature
<222> LOCATION: (1)..(49)
<223> OTHER INFORMATION: n can be any nucleotide a, c, g or t

<400> SEQUENCE: 17
actngcaggt acgtcgtacc gcggccgcgt gtctcgggct aggcgtaga                   49

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
tctacgccta gcccgagaca c                                                 21

<210> SEQ ID NO 19
<211> LENGTH: 1268
<212> TYPE: DNA
<213> ORGANISM: Homo sapiens

<400> SEQUENCE: 19
gttcgacagt cagccgcatc ttcttttgcg tcgccagccg agccacatcg ctcagacacc       60
atggggaagg tgaaggtcgg agtcaacgga tttggtcgta ttgggcgcct ggtcaccagg      120
gctgctttta actctggtaa agtggatatt gttgccatca atgacccctt cattgacctc      180
aactacatgg tttacatgtt ccaatatgat tccacccatg gcaaattcca tggcaccgtc      240
aaggctgaga cgggaagct tgtcatcaat ggaaatccca tcaccatctt ccaggagcga      300
gatccctcca aaatcaagtg gggcgatgct ggcgctgagt acgtcgtgga gtccactggc      360
gtcttcacca ccatggagaa ggctgggggct catttgcagg gggagccaa agggtcatc       420 atctctgccc cctctgctga tgcccccatg ttcgtcatgg gtgtgaacca tgagaagtat      480
gacaacagcc tcaagatcat cagcaatgcc tcctgcacca ccaactgctt agcacccctg      540
gccaaggtca tccatgacaa ctttggtatc gtggaaggac tcatgaccac agtccatgcc      600
atcactgcca cccagaagac tgtggatggc ccctccggga actgtggcg tgatggccgc      660 ggggctctcc agaacatcat ccctgcctct actggcgctg ccaaggctgt gggcaaggtc      720
atccctgagc tgaacgggaa gctcactggc atggccttcc gtgtcccac tgccaacgtg      780 tcagtggtgg acctgacctg ccgtctagaa aaacctgcca aatatgatga catcaagaag      840
gtggtgaagc aggcgtcgga gggccccctc aagggcatcc tgggctacac tgagcaccag      900
gtggtctcct ctgacttcaa cagcgacacc cactcctcca cctttgacgc tggggctggc      960
attgccctca acgaccactt tgtcaagctc atttcctggt atgacaacga atttggctac     1020
agcaacaggg tggtggacct catggcccac atggcctcca aggagtaaga cccctggacc     1080
accagcccca gcaagagcac aagaggaaga gagagaccct cactgctggg gagtccctgc     1140
```

```
cacactcagt cccccaccac actgaatctc ccctcctcac agttgccatg tagacccctt    1200
gaagagggga ggggcctagg gagccgcacc ttgtcatgta ccatcaataa agtaccctgt    1260
gctcaacc                                                             1268
```

<210> SEQ ID NO 20
<211> LENGTH: 30
<212> TYPE: DNA
<213> ORGANISM: Homo sapiens

<400> SEQUENCE: 20

```
aagtgttgca aggctgccga caaggataac                                       30
```

<210> SEQ ID NO 21
<211> LENGTH: 602
<212> TYPE: DNA
<213> ORGANISM: Homo Sapiens

<400> SEQUENCE: 21

```
gcctctactg gcgctgccaa ggctgtgggc aaggtcatcc ctgagctgaa cgggaagctc      60
actggcatgg ccttccgtgt ccccactgcc aacgtgtcag tggtggacct gacctgccgt     120
ctagaaaaac ctgccaaata tgatgacatc aagaaggtgg tgaagcaggc gtcggagggc     180
cccctcaagg gcatcctggg ctacactgag caccaggtgg tctcctctga cttcaacagc     240
gacacccact cctccacctt tgacgctggg gctggcattg ccctcaacga ccactttgtc     300
aagctcattt cctggtatga caacgaattt ggctacagca cagggtggt ggacctcatg     360 gcccacatgg cctccaagga gtaagacccc tggaccacca gccccagcaa gagcacaaga     420
ggaagagaga gaccctcact gctggggagt ccctgccaca ctcagtcccc caccacactg     480
aatctcccct cctcacagtt gccatgtaga cccccttgaag aggggagggg cctagggagc     540
cgcaccttgt catgtaccat caataaagta ccctgtgctc aaccaaaaaa aaaaaaaaaa     600
aa                                                                     602
```

<210> SEQ ID NO 22
<211> LENGTH: 55
<212> TYPE: DNA
<213> ORGANISM: Artificial Sequence
<220> FEATURE:
<223> OTHER INFORMATION: adaptor
<221> NAME/KEY: misc_feature
<222> LOCATION: (1)..(55)
<223> OTHER INFORMATION: n can be any nucleotide a, c, g or t

<400> SEQUENCE: 22

```
aggccaatag gcagccgccg ctgccatgct gcaagtcgan ggagatgacc gcgac           55
```

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23

```
aggggttatc cgtcggcggc gac                                              23
```

<210> SEQ ID NO 24
<211> LENGTH: 20
<212> TYPE: DNA
<213> ORGANISM: Artificial Sequence

```
<220> FEATURE:
<223> OTHER INFORMATION: primer

<400> SEQUENCE: 24
tacagcaaca gggtggtgga                                             20

<210> SEQ ID NO 25
<211> LENGTH: 32
<212> TYPE: DNA
<213> ORGANISM: Artificial Sequence
<220> FEATURE:
<223> OTHER INFORMATION: primer
<221> NAME/KEY: modified_base
<222> LOCATION: (26)..(28)
<223> OTHER INFORMATION: i
<221> NAME/KEY: misc_feature
<222> LOCATION: (29)..(32)
<223> OTHER INFORMATION: n can be any nucleotide a, c, g or t

<400> SEQUENCE: 25
gcggccgcgg tacgacgtac ctgcnnnnnn nn                               32

<210> SEQ ID NO 26
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (21)..(24)
<223> OTHER INFORMATION: n can be any nucleotide a, c, g or t
<221> NAME/KEY: modified_base
<222> LOCATION: (18)..(20)
<223> OTHER INFORMATION: i

<400> SEQUENCE: 26
ggtacgacgt tcagctnnnn nnnn                                        24

<210> SEQ ID NO 27
<211> LENGTH: 23
<212> TYPE: DNA
<213> ORGANISM: Artificial Sequence
<220> FEATURE:
<223> OTHER INFORMATION: primer
<221> NAME/KEY: modified_base
<222> LOCATION: (18)..(20)
<223> OTHER INFORMATION: i
<221> NAME/KEY: misc_feature
<222> LOCATION: (21)..(23)
<223> OTHER INFORMATION: n can be any nucleotide a, c, g or t

<400> SEQUENCE: 27
ggtacgacgt tcagctnnnn nnn                                         23

<210> SEQ ID NO 28
<211> LENGTH: 36
<212> TYPE: DNA
<213> ORGANISM: Artificial Sequence
<220> FEATURE:
<223> OTHER INFORMATION: primer
<221> NAME/KEY: modified_base
<222> LOCATION: (29)..(31)
<223> OTHER INFORMATION: i
<221> NAME/KEY: misc_feature
<222> LOCATION: (32)..(36)
<223> OTHER INFORMATION: n can be any nucleotide a, c, g or t
<221> NAME/KEY: misc_feature
<222> LOCATION: (25)..(25)
<223> OTHER INFORMATION: n can be any nucleotide a, c, g or t

<400> SEQUENCE: 28
```

```
gcggccgcgg tacgacgtac ctgcngggnn nnnnnn                           36
```

<210> SEQ ID NO 29
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (24)..(26)
<223> OTHER INFORMATION: n can be any nucleotide a, c, g or t
<221> NAME/KEY: misc_feature
<222> LOCATION: (17)..(17)
<223> OTHER INFORMATION: n can be any nucleotide a, c, g or t
<221> NAME/KEY: modified_base
<222> LOCATION: (21)..(23)
<223> OTHER INFORMATION: i

<400> SEQUENCE: 29

```
ggtacgacgt tcagctnggg nnnnnn                                     26
```

<210> SEQ ID NO 30
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (23)..(24)
<223> OTHER INFORMATION: n can be any nucleotide a, c, g or t
<221> NAME/KEY: misc_feature
<222> LOCATION: (17)..(17)
<223> OTHER INFORMATION: n can be any nucleotide a, c, g or t
<221> NAME/KEY: modified_base
<222> LOCATION: (21)..(23)
<223> OTHER INFORMATION: i

<400> SEQUENCE: 30

```
ggtacgacgt tcagctnggg nnnnn                                      25
```

<210> SEQ ID NO 31
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(4)
<223> OTHER INFORMATION: n can be any nucleotide a, c, g or t

<400> SEQUENCE: 31

```
nnnngcaggt acgtcgtacc gcggccgcgt gagcttgagt cgcgtgga             48
```

<210> SEQ ID NO 32
<211> LENGTH: 43
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(43)
<223> OTHER INFORMATION: n can be any nucleotide a, c, g or t

<400> SEQUENCE: 32

```
nnntttnagc tgaacgtcgt acccgtcgaa cgaacacggg cgt                  43
```

<210> SEQ ID NO 33
<211> LENGTH: 14
<212> TYPE: DNA

```
<213> ORGANISM: Artificial Sequence
<220> FEATURE:
<223> OTHER INFORMATION: part of Fok I recognition sequence
<221> NAME/KEY: misc_feature
<222> LOCATION: (1)..(14)
<223> OTHER INFORMATION: n can be any nucleotide a, c, g or t

<400> SEQUENCE: 33
ggatgnnnnn nnnn                                                        14

<210> SEQ ID NO 34
<211> LENGTH: 26
<212> TYPE: DNA
<213> ORGANISM: Homo Sapiens

<400> SEQUENCE: 34
gttatccttg tcggcagcct tgcaac                                           26

<210> SEQ ID NO 35
<211> LENGTH: 32
<212> TYPE: DNA
<213> ORGANISM: Artificial Sequence
<220> FEATURE:
<223> OTHER INFORMATION: Adaptor sequence

<400> SEQUENCE: 35
ggtacgacgt tcagcagcct ctactggcgc tg                                    32

<210> SEQ ID NO 36
<211> LENGTH: 39
<212> TYPE: DNA
<213> ORGANISM: Homo sapiens

<400> SEQUENCE: 36
ccctgcctct actggcgctg ccgctcaacc aaaaaaaaa                             39

<210> SEQ ID NO 37
<211> LENGTH: 39
<212> TYPE: DNA
<213> ORGANISM: Homo sapiens

<400> SEQUENCE: 37
ccctgcctct actggcgctg ccgctcaacc aaaaaaaaa                             39

<210> SEQ ID NO 38
<211> LENGTH: 51
<212> TYPE: DNA
<213> ORGANISM: Homo sapiens

<400> SEQUENCE: 38
cgactcgtac aggcgcgcct tggttgagcg gcagcgccag tagaggcagg g               51

<210> SEQ ID NO 39
<211> LENGTH: 47
<212> TYPE: DNA
<213> ORGANISM: Homo sapiens

<400> SEQUENCE: 39
gcctctactg gcgctgccgc tcaaccaagg cgcgcctgta cgagtcg                    47

<210> SEQ ID NO 40
<211> LENGTH: 43
<212> TYPE: DNA
<213> ORGANISM: Homo sapiens
```

```
<400> SEQUENCE: 40
cgactcgtac aggcgcgcct tggttgagcg gcagcgccag tag        43

<210> SEQ ID NO 41
<211> LENGTH: 28
<212> TYPE: DNA
<213> ORGANISM: Homo sapiens

<400> SEQUENCE: 41
gcctctactg gcgctgccgc tcaaccaa                          28

<210> SEQ ID NO 42
<211> LENGTH: 28
<212> TYPE: DNA
<213> ORGANISM: Homo sapiens
<220> FEATURE:
<221> NAME/KEY: misc_feature
<222> LOCATION: (1)..(28)
<223> OTHER INFORMATION: n can be any nucleotide a,c,g or t

<400> SEQUENCE: 42
nggagatgac cgcgacggcg agttggtt                          28

<210> SEQ ID NO 43
<211> LENGTH: 27
<212> TYPE: DNA
<213> ORGANISM: Homo sapiens

<400> SEQUENCE: 43
gcctctactg gcgctgccgc caaccaa                           27

<210> SEQ ID NO 44
<211> LENGTH: 28
<212> TYPE: DNA
<213> ORGANISM: Homo sapiens
<220> FEATURE:
<221> NAME/KEY: misc_feature
<222> LOCATION: (1)..(28)
<223> OTHER INFORMATION: n can be any nucleotide a,c,g or t

<400> SEQUENCE: 44
ttggttgagc ggcagcgcca gtagaggn                          28

<210> SEQ ID NO 45
<211> LENGTH: 28
<212> TYPE: DNA
<213> ORGANISM: Homo sapiens

<400> SEQUENCE: 45
gcctctactg gcgctgccgc tcaaccaa                          28

<210> SEQ ID NO 46
<211> LENGTH: 28
<212> TYPE: DNA
<213> ORGANISM: Homo sapiens
<220> FEATURE:
<221> NAME/KEY: misc_feature
<222> LOCATION: (1)..(28)
<223> OTHER INFORMATION: n can be any nucleotide a,c,g or t

<400> SEQUENCE: 46
ttggttgagc ggcagcgcca gtagaggn                          28

<210> SEQ ID NO 47
<211> LENGTH: 27
```

```
<212> TYPE: DNA
<213> ORGANISM: Homo sapiens

<400> SEQUENCE: 47
gcctctactg gcgctgccgc tcaacca                                27

<210> SEQ ID NO 48
<211> LENGTH: 27
<212> TYPE: DNA
<213> ORGANISM: Homo sapiens
<220> FEATURE:
<221> NAME/KEY: misc_feature
<222> LOCATION: (1)..(27)
<223> OTHER INFORMATION: n can be any nucleotide a,c,g or t

<400> SEQUENCE: 48
tggttgagcg gcagcgccag tagaggn                                27

<210> SEQ ID NO 49
<211> LENGTH: 35
<212> TYPE: DNA
<213> ORGANISM: Homo sapiens

<400> SEQUENCE: 49
acctgcgcct ctactggcgc tgccgctcaa ccaaa                       35

<210> SEQ ID NO 50
<211> LENGTH: 34
<212> TYPE: DNA
<213> ORGANISM: Homo sapiens
<220> FEATURE:
<221> NAME/KEY: misc_feature
<222> LOCATION: (1)..(34)
<223> OTHER INFORMATION: n can be any nucleotide a,c,g or t

<400> SEQUENCE: 50
ttggttgagc ggcagcgcca gtagaggngc aggt                        34

<210> SEQ ID NO 51
<211> LENGTH: 24
<212> TYPE: DNA
<213> ORGANISM: Homo sapiens

<400> SEQUENCE: 51
ctactggcgc tgccgctcaa ccaa                                   24

<210> SEQ ID NO 52
<211> LENGTH: 20
<212> TYPE: DNA
<213> ORGANISM: Homo sapiens

<400> SEQUENCE: 52
ttggttgagc ggcagcgcca                                        20

<210> SEQ ID NO 53
<211> LENGTH: 30
<212> TYPE: DNA
<213> ORGANISM: Homo sapiens

<400> SEQUENCE: 53
acctgcctac tggcgctgcc gctcaaccaa                             30

<210> SEQ ID NO 54
<211> LENGTH: 30
<212> TYPE: DNA
```

<213> ORGANISM: Homo sapiens

<400> SEQUENCE: 54
ttggttgagc ggcagcgcca gtaggcaggt          30

<210> SEQ ID NO 55
<211> LENGTH: 30
<212> TYPE: DNA
<213> ORGANISM: Homo sapiens

<400> SEQUENCE: 55
acctgcctac tggcgctgcc gctcaaccaa          30

<210> SEQ ID NO 56
<211> LENGTH: 30
<212> TYPE: DNA
<213> ORGANISM: Homo sapiens

<400> SEQUENCE: 56
ttggttgagc ggcagcgcca gtaggcaggt          30

<210> SEQ ID NO 57
<211> LENGTH: 10
<212> TYPE: DNA
<213> ORGANISM: Homo sapiens

<400> SEQUENCE: 57
gctcaaccaa          10

<210> SEQ ID NO 58
<211> LENGTH: 16
<212> TYPE: DNA
<213> ORGANISM: Homo sapiens

<400> SEQUENCE: 58
ttggttgagc ggcagc          16

<210> SEQ ID NO 59
<211> LENGTH: 26
<212> TYPE: DNA
<213> ORGANISM: Homo sapiens

<400> SEQUENCE: 59
acctgctggc gctgccgctc aaccaa          26

<210> SEQ ID NO 60
<211> LENGTH: 26
<212> TYPE: DNA
<213> ORGANISM: Homo sapiens

<400> SEQUENCE: 60
tggttgagcg gcagcgccag catggt          26

<210> SEQ ID NO 61
<211> LENGTH: 26
<212> TYPE: DNA
<213> ORGANISM: Homo sapiens

<400> SEQUENCE: 61
acctgctggc gctgccgctc aaccaa          26

<210> SEQ ID NO 62
<211> LENGTH: 25

<210> SEQ ID NO 62
<211> LENGTH: 25
<212> TYPE: DNA
<213> ORGANISM: Homo sapiens

<400> SEQUENCE: 62
ttggttgagc ggcagcgcgg caggt                                    25

<210> SEQ ID NO 63
<211> LENGTH: 34
<212> TYPE: DNA
<213> ORGANISM: Homo sapiens

<400> SEQUENCE: 63
acctgcgcct ctactggcgc tgccgctcaa ccaa                          34

<210> SEQ ID NO 64
<211> LENGTH: 34
<212> TYPE: DNA
<213> ORGANISM: Homo sapiens

<400> SEQUENCE: 64
ttggttgagc ggcagcgcca gtagaggcgc aggt                          34

<210> SEQ ID NO 65
<211> LENGTH: 24
<212> TYPE: DNA
<213> ORGANISM: Homo sapiens

<400> SEQUENCE: 65
ctactggcgc tgccgctcaa ccaa                                     24

<210> SEQ ID NO 66
<211> LENGTH: 20
<212> TYPE: DNA
<213> ORGANISM: Homo sapiens

<400> SEQUENCE: 66
ttggttgagc ggcagcgcca                                          20

<210> SEQ ID NO 67
<211> LENGTH: 30
<212> TYPE: DNA
<213> ORGANISM: Homo sapiens

<400> SEQUENCE: 67
acctgcctac tggcgctgcc gctcaaccaa                               30

<210> SEQ ID NO 68
<211> LENGTH: 30
<212> TYPE: DNA
<213> ORGANISM: Homo sapiens
<220> FEATURE:
<221> NAME/KEY: misc_feature
<222> LOCATION: (1)..(30)
<223> OTHER INFORMATION: n can be any nucleotide a,c,g or t

<400> SEQUENCE: 68
ttggttgagc ggcagcgcca gtangcaggt                               30

<210> SEQ ID NO 69
<211> LENGTH: 30
<212> TYPE: DNA
<213> ORGANISM: Homo sapiens

<400> SEQUENCE: 69

```
acctgcctac tggcgctgcc gctcaaccaa                              30
```

<210> SEQ ID NO 70
<211> LENGTH: 30
<212> TYPE: DNA
<213> ORGANISM: Homo sapiens

<400> SEQUENCE: 70

```
ttggttgagc ggcagcgcca gtaggcaggt                              30
```

<210> SEQ ID NO 71
<211> LENGTH: 20
<212> TYPE: DNA
<213> ORGANISM: Homo sapiens

<400> SEQUENCE: 71

```
tggcgctgcc gctcaaccaa                                         20
```

<210> SEQ ID NO 72
<211> LENGTH: 16
<212> TYPE: DNA
<213> ORGANISM: Homo sapiens

<400> SEQUENCE: 72

```
ttggttgagc ggcagc                                             16
```

<210> SEQ ID NO 73
<211> LENGTH: 26
<212> TYPE: DNA
<213> ORGANISM: Homo sapiens

<400> SEQUENCE: 73

```
acctgctggc gctgccgctc aaccaa                                  26
```

<210> SEQ ID NO 74
<211> LENGTH: 26
<212> TYPE: DNA
<213> ORGANISM: Homo sapiens
<220> FEATURE:
<221> NAME/KEY: misc_feature
<222> LOCATION: (1)..(26)
<223> OTHER INFORMATION: n can be any nucleotide a,c,g or t

<400> SEQUENCE: 74

```
ttggttgagc ggcagcgccn gcaggt                                  26
```

<210> SEQ ID NO 75
<211> LENGTH: 26
<212> TYPE: DNA
<213> ORGANISM: Homo sapiens

<400> SEQUENCE: 75

```
acctgctggc gctgccgctc aaccaa                                  26
```

<210> SEQ ID NO 76
<211> LENGTH: 26
<212> TYPE: DNA
<213> ORGANISM: Homo sapiens

<400> SEQUENCE: 76

```
ttggttgagc ggcagcgccg gcaggt                                  26
```

<210> SEQ ID NO 77
<211> LENGTH: 40

<212> TYPE: DNA
<213> ORGANISM: Artificial Sequence
<220> FEATURE:
<223> OTHER INFORMATION: primer set general structure
<221> NAME/KEY: misc_feature
<222> LOCATION: (1)..(40)
<223> OTHER INFORMATION: n can be any nucleotide a,c,g or t

<400> SEQUENCE: 77
nnnngcaggt acgtcgtacc gcggccgcnn nnnnnnnnnn                    40

<210> SEQ ID NO 78
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(48)
<223> OTHER INFORMATION: n can be any nucleotide a,c,g or t

<400> SEQUENCE: 78
tttngcaggt acgtcgtacc gcggccgcgt gagcttgagt cgcgtgga          48

<210> SEQ ID NO 79
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 79
ttgngcaggt acgtcgtacc gcggccgccc aacgtcgcga gttagtcag         49

<210> SEQ ID NO 80
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 80
ttcngcaggt acgtcgtacc gcggccgcag gtagacgcgg tatgttcgta        50

<210> SEQ ID NO 81
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(48)
<223> OTHER INFORMATION: n can be any nucleotide a,c,g or t

<400> SEQUENCE: 81
ttangcaggt acgtcgtacc gcggccgccg gtgctagagt cgcgtgtt         48

<210> SEQ ID NO 82
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(48)
<223> OTHER INFORMATION: n can be any nucleotide a,c,g or t

<400> SEQUENCE: 82
tgtngcaggt acgtcgtacc gcggccgccg acagtaccgc gacagcta                48

<210> SEQ ID NO 83
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 83
tggngcaggt acgtcgtacc gcggccgcgc acttaactac gccgacgaag              50

<210> SEQ ID NO 84
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 84
tgcngcaggt acgtcgtacc gcggccgcgt actagcctaa ccgaggcgta              50

<210> SEQ ID NO 85
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(48)
<223> OTHER INFORMATION: n can be any nucleotide a,c,g or t

<400> SEQUENCE: 85
tgangcaggt acgtcgtacc gcggccgctc ggatcacgta cacgtgct                48

<210> SEQ ID NO 86
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 86
tctngcaggt acgtcgtacc gcggccgcgt acgtcgccta gtcgacctg               49

<210> SEQ ID NO 87
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t -continued

```
<400> SEQUENCE: 87
tcgngcaggt acgtcgtacc gcggccgcct ctcctaacgg accgactaac            50

<210> SEQ ID NO 88
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 88
tccngcaggt acgtcgtacc gcggccgccg ttccgatcta gcggtatctt            50

<210> SEQ ID NO 89
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(48)
<223> OTHER INFORMATION: n can be any nucleotide a,c,g or t

<400> SEQUENCE: 89
tcangcaggt acgtcgtacc gcggccgcgc acccgtacag gatgtgag              48

<210> SEQ ID NO 90
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(48)
<223> OTHER INFORMATION: n can be any nucleotide a,c,g or t

<400> SEQUENCE: 90
tatngcaggt acgtcgtacc gcggccgcgc aacgcgctat gctcgtag              48

<210> SEQ ID NO 91
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 91
tagngcaggt acgtcgtacc gcggccgcga ctgtggaact acgacgatcg            50

<210> SEQ ID NO 92
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 92
tacngcaggt acgtcgtacc gcggccgcag cagaccgaac cctagtcgc             49
```

<210> SEQ ID NO 93
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 93
taangcaggt acgtcgtacc gcggccgcca tacgtcgtag ggttcgcga         49

<210> SEQ ID NO 94
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 94
gttngcaggt acgtcgtacc gcggccgcct ctcatacgcg tctgcgcgt         49

<210> SEQ ID NO 95
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 95
gtgngcaggt acgtcgtacc gcggccgcga gtgtgcctta cgtcgagttc         50

<210> SEQ ID NO 96
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(48)
<223> OTHER INFORMATION: n can be any nucleotide a,c,g or t

<400> SEQUENCE: 96
gtcngcaggt acgtcgtacc gcggccgcgt cacgttgcgg ccttagtc         48

<210> SEQ ID NO 97
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 97
gtangcaggt acgtcgtacc gcggccgcga ggtacgagac ttgacacacg         50

<210> SEQ ID NO 98
<211> LENGTH: 50
<212> TYPE: DNA

<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 98
ggtngcaggt acgtcgtacc gcggccgcga ccagttgcct aacggacact           50

<210> SEQ ID NO 99
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 99
gggngcaggt acgtcgtacc gcggccgcgc aactagtctc gacctgcga            49

<210> SEQ ID NO 100
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 100
ggcngcaggt acgtcgtacc gcggccgcgt acctcgacga ccgtactgtg           50

<210> SEQ ID NO 101
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 101
ggangcaggt acgtcgtacc gcggccgcac gcgtgatagt acggagtcg            49

<210> SEQ ID NO 102
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 102
gctngcaggt acgtcgtacc gcggccgcca ctagagcggc gtcagtcta            49

<210> SEQ ID NO 103
<211> LENGTH: 47
<212> TYPE: DNA
<213> ORGANISM: Artificial Sequence
<220> FEATURE:
<223> OTHER INFORMATION: primer
<221> NAME/KEY: misc_feature

```
<222> LOCATION: (1)..(47)
<223> OTHER INFORMATION: n can be any nucleotide a,c,g or t

<400> SEQUENCE: 103
gcgngcaggt acgtcgtacc gcggccgcgc acagcgctag cacagga                    47

<210> SEQ ID NO 104
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 104
gccngcaggt acgtcgtacc gcggccgcta ccgacagtcc tctgcgtgc                  49

<210> SEQ ID NO 105
<211> LENGTH: 52
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(52)
<223> OTHER INFORMATION: n can be any nucleotide a,c,g or t

<400> SEQUENCE: 105
gcangcaggt acgtcgtacc gcggccgcct acgctacgtt gcgaagaagg ta              52

<210> SEQ ID NO 106
<211> LENGTH: 52
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(52)
<223> OTHER INFORMATION: n can be any nucleotide a,c,g or t

<400> SEQUENCE: 106
gatngcaggt acgtcgtacc gcggccgcgt ctgtcgtacc tgtcagtgac tg              52

<210> SEQ ID NO 107
<211> LENGTH: 47
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(47)
<223> OTHER INFORMATION: n can be any nucleotide a,c,g or t

<400> SEQUENCE: 107
gagngcaggt acgtcgtacc gcggccgcat cgaaccgtgc tccttgg                    47

<210> SEQ ID NO 108
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 108
```
gacngcaggt acgtcgtacc gcggccgcag gttgaggtgt acgcgatagc            50

<210> SEQ ID NO 109
<211> LENGTH: 51
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(51)
<223> OTHER INFORMATION: n can be any nucleotide a,c,g or t

<400> SEQUENCE: 109
gaangcaggt acgtcgtacc gcggccgcga cttcaacccc tgacgtacac a          51

<210> SEQ ID NO 110
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 110
cttngcaggt acgtcgtacc gcggccgcct actcgcgaga gagggctatg            50

<210> SEQ ID NO 111
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 111
ctgngcaggt acgtcgtacc gcggccgcct tgatccgtag tcgagacgg             49

<210> SEQ ID NO 112
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 112
ctcngcaggt acgtcgtacc gcggccgcgt acagacgtag cgatcgcag             49

<210> SEQ ID NO 113
<211> LENGTH: 52
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(52)
<223> OTHER INFORMATION: n can be any nucleotide a,c,g or t

<400> SEQUENCE: 113
ctangcaggt acgtcgtacc gcggccgcgt gactaacgag gtctgtaagc ta         52

<210> SEQ ID NO 114
<211> LENGTH: 51
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(51)
<223> OTHER INFORMATION: n can be any nucleotide a,c,g or t

<400> SEQUENCE: 114
cgtngcaggt acgtcgtacc gcggccgcgt ctgagagtcg actgcgctaa g    51

<210> SEQ ID NO 115
<211> LENGTH: 52
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(52)
<223> OTHER INFORMATION: n can be any nucleotide a,c,g or t

<400> SEQUENCE: 115
cggngcaggt acgtcgtacc gcggccgcct cagtaagccg gagtctagct ag   52

<210> SEQ ID NO 116
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(52)
<223> OTHER INFORMATION: n can be any nucleotide a,c,g or t

<400> SEQUENCE: 116
cgcngcaggt acgtcgtacc gcggccgccg ccctaaacgg gatcgagcga       50

<210> SEQ ID NO 117
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 117
cgangcaggt acgtcgtacc gcggccgccg tacaggctag gggttagtcg       50

<210> SEQ ID NO 118
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(48)
<223> OTHER INFORMATION: n can be any nucleotide a,c,g or t

<400> SEQUENCE: 118
cctngcaggt acgtcgtacc gcggccgccg atcgctctag tgcctacg         48

<210> SEQ ID NO 119
<211> LENGTH: 50
<212> TYPE: DNA
<213> ORGANISM: Artificial Sequence

```
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 119
ccgngcaggt acgtcgtacc gcggccgcga ctgcgattcg tgacactagt            50

<210> SEQ ID NO 120
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 120
cccngcaggt acgtcgtacc gcggccgctg cgtaatagcg actgtaccct            50

<210> SEQ ID NO 121
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(48)
<223> OTHER INFORMATION: n can be any nucleotide a,c,g or t

<400> SEQUENCE: 121
ccangcaggt acgtcgtacc gcggccgcct aggtcatccc tccggtac              48

<210> SEQ ID NO 122
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 122
catngcaggt acgtcgtacc gcggccgcga tcggactaat ccgctacgt             49

<210> SEQ ID NO 123
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 123
cagngcaggt acgtcgtacc gcggccgcga ctaccgacta gtcgtgcgac            50

<210> SEQ ID NO 124
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(48)
```

<223> OTHER INFORMATION: n can be any nucleotide a,c,g or t

<400> SEQUENCE: 124
cacngcaggt acgtcgtacc gcggccgcta gggccctaac gtagctcg          48

<210> SEQ ID NO 125
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(48)
<223> OTHER INFORMATION: n can be any nucleotide a,c,g or t

<400> SEQUENCE: 125
caangcaggt acgtcgtacc gcggccgcta cctagccctc acgggtcg          48

<210> SEQ ID NO 126
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 126
attngcaggt acgtcgtacc gcggccgcta gtgcgcggta ctaccgact          49

<210> SEQ ID NO 127
<211> LENGTH: 47
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(47)
<223> OTHER INFORMATION: n can be any nucleotide a,c,g or t

<400> SEQUENCE: 127
atgngcaggt acgtcgtacc gcggccgcag acggctatgc gtcggga          47

<210> SEQ ID NO 128
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 128
atcngcaggt acgtcgtacc gcggccgcac ctacgaacac gcgtaactcg          50

<210> SEQ ID NO 129
<211> LENGTH: 47
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(47)
<223> OTHER INFORMATION: n can be any nucleotide a,c,g or t

<400> SEQUENCE: 129
atangcaggt acgtcgtacc gcggccgcag ctacgtgggt ggcagac         47

<210> SEQ ID NO 130
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(48)
<223> OTHER INFORMATION: n can be any nucleotide a,c,g or t

<400> SEQUENCE: 130
agtngcaggt acgtcgtacc gcggccgcta ccgatacggt cgaccatc        48

<210> SEQ ID NO 131
<211> LENGTH: 51
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(51)
<223> OTHER INFORMATION: n can be any nucleotide a,c,g or t

<400> SEQUENCE: 131
aggngcaggt acgtcgtacc gcggccgcgt acgctaggta ggaactaagc g     51

<210> SEQ ID NO 132
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 132
agcngcaggt acgtcgtacc gcggccgccg gacgactagt tgctagcgtc       50

<210> SEQ ID NO 133
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(48)
<223> OTHER INFORMATION: n can be any nucleotide a,c,g or t

<400> SEQUENCE: 133
agangcaggt acgtcgtacc gcggccgcgt gaacctacgc gttgacgc         48

<210> SEQ ID NO 134
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 134
actngcaggt acgtcgtacc gcggccgcgt gtctcgggct aggcgtaga        49

<210> SEQ ID NO 135

```
<211> LENGTH: 47
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(47)
<223> OTHER INFORMATION: n can be any nucleotide a,c,g or t

<400> SEQUENCE: 135
acgngcaggt acgtcgtacc gcggccgctc cgtggtgtcc atgggag                47

<210> SEQ ID NO 136
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 136
accngcaggt acgtcgtacc gcggccgcct acgcgtaacg ctagcaggt              49

<210> SEQ ID NO 137
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 137
acangcaggt acgtcgtacc gcggccgcga agagccgtaa ggtacggct              49

<210> SEQ ID NO 138
<211> LENGTH: 50
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(50)
<223> OTHER INFORMATION: n can be any nucleotide a,c,g or t

<400> SEQUENCE: 138
aatngcaggt acgtcgtacc gcggccgcgt acgtcagcgt acgctaagtc             50

<210> SEQ ID NO 139
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 139
aagngcaggt acgtcgtacc gcggccgctc taggttccgt tgtagcgct              49

<210> SEQ ID NO 140
<211> LENGTH: 47
<212> TYPE: DNA
<213> ORGANISM: Artificial Sequence
<220> FEATURE:
```

```
<223> OTHER INFORMATION: primer
<221> NAME/KEY: misc_feature
<222> LOCATION: (1)..(47)
<223> OTHER INFORMATION: n can be any nucleotide a,c,g or t

<400> SEQUENCE: 140
aacngcaggt acgtcgtacc gcggccgcag caacgagacg acacgac          47

<210> SEQ ID NO 141
<211> LENGTH: 49
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(49)
<223> OTHER INFORMATION: n can be any nucleotide a,c,g or t

<400> SEQUENCE: 141
aaangcaggt acgtcgtacc gcggccgcgt ctagaaccca cgcacggta        49

<210> SEQ ID NO 142
<211> LENGTH: 23
<212> TYPE: DNA
<213> ORGANISM: Artificial Sequence
<220> FEATURE:
<223> OTHER INFORMATION: primer

<400> SEQUENCE: 142
ttttccacgc gactcaagct cac                                    23

<210> SEQ ID NO 143
<211> LENGTH: 24
<212> TYPE: DNA
<213> ORGANISM: Artificial Sequence
<220> FEATURE:
<223> OTHER INFORMATION: primer

<400> SEQUENCE: 143
ttgctgacta actcgcgacg ttgg                                   24

<210> SEQ ID NO 144
<211> LENGTH: 25
<212> TYPE: DNA
<213> ORGANISM: Artificial Sequence
<220> FEATURE:
<223> OTHER INFORMATION: primer

<400> SEQUENCE: 144
ttctacgaac ataccgcgtc tacct                                  25

<210> SEQ ID NO 145
<211> LENGTH: 23
<212> TYPE: DNA
<213> ORGANISM: Artificial Sequence
<220> FEATURE:
<223> OTHER INFORMATION: primer

<400> SEQUENCE: 145
ttaaacacgc gactctagca ccg                                    23

<210> SEQ ID NO 146
<211> LENGTH: 23
<212> TYPE: DNA
<213> ORGANISM: Artificial Sequence
<220> FEATURE:
<223> OTHER INFORMATION: primer
```

<400> SEQUENCE: 146
tgttagctgt cgcggtactg tcg          23

<210> SEQ ID NO 147
<211> LENGTH: 25
<212> TYPE: DNA
<213> ORGANISM: Artificial Sequence
<220> FEATURE:
<223> OTHER INFORMATION: primer

<400> SEQUENCE: 147
tggcttcgtc ggcgtagtta agtgc          25

<210> SEQ ID NO 148
<211> LENGTH: 25
<212> TYPE: DNA
<213> ORGANISM: Artificial Sequence
<220> FEATURE:
<223> OTHER INFORMATION: primer

<400> SEQUENCE: 148
tgctacgcct cggttaggct agtac          25

<210> SEQ ID NO 149
<211> LENGTH: 23
<212> TYPE: DNA
<213> ORGANISM: Artificial Sequence
<220> FEATURE:
<223> OTHER INFORMATION: primer

<400> SEQUENCE: 149
tgaagcacgt gtacgtgatc cga          23

<210> SEQ ID NO 150
<211> LENGTH: 24
<212> TYPE: DNA
<213> ORGANISM: Artificial Sequence
<220> FEATURE:
<223> OTHER INFORMATION: primer

<400> SEQUENCE: 150
tctcaggtcg actaggcgac gtac          24

<210> SEQ ID NO 151
<211> LENGTH: 25
<212> TYPE: DNA
<213> ORGANISM: Artificial Sequence
<220> FEATURE:
<223> OTHER INFORMATION: primer

<400> SEQUENCE: 151
tcggttagtc ggtccgttag gagag          25

<210> SEQ ID NO 152
<211> LENGTH: 25
<212> TYPE: DNA
<213> ORGANISM: Artificial Sequence
<220> FEATURE:
<223> OTHER INFORMATION: primer

<400> SEQUENCE: 152
tccaagatac cgctagatcg gaacg          25

<210> SEQ ID NO 153

```
<211> LENGTH: 23
<212> TYPE: DNA
<213> ORGANISM: Artificial Sequence
<220> FEATURE:
<223> OTHER INFORMATION: primer

<400> SEQUENCE: 153
tcactcacat cctgtacggg tgc                                               23

<210> SEQ ID NO 154
<211> LENGTH: 23
<212> TYPE: DNA
<213> ORGANISM: Artificial Sequence
<220> FEATURE:
<223> OTHER INFORMATION: primer

<400> SEQUENCE: 154
tatctacgag catagcgcgt tgc                                               23

<210> SEQ ID NO 155
<211> LENGTH: 25
<212> TYPE: DNA
<213> ORGANISM: Artificial Sequence
<220> FEATURE:
<223> OTHER INFORMATION: primer

<400> SEQUENCE: 155
tagcgatcgt cgtagttcca cagtc                                             25

<210> SEQ ID NO 156
<211> LENGTH: 24
<212> TYPE: DNA
<213> ORGANISM: Artificial Sequence
<220> FEATURE:
<223> OTHER INFORMATION: primer

<400> SEQUENCE: 156
tacgcgacta gggttcggtc tgct                                              24

<210> SEQ ID NO 157
<211> LENGTH: 24
<212> TYPE: DNA
<213> ORGANISM: Artificial Sequence
<220> FEATURE:
<223> OTHER INFORMATION: primer

<400> SEQUENCE: 157
taatcgcgaa ccctacgacg tatg                                              24

<210> SEQ ID NO 158
<211> LENGTH: 24
<212> TYPE: DNA
<213> ORGANISM: Artificial Sequence
<220> FEATURE:
<223> OTHER INFORMATION: primer

<400> SEQUENCE: 158
gttacgcgca gacgcgtatg agag                                              24

<210> SEQ ID NO 159
<211> LENGTH: 25
<212> TYPE: DNA
<213> ORGANISM: Artificial Sequence
<220> FEATURE:
<223> OTHER INFORMATION: primer

<400> SEQUENCE: 159
```
gtggaactcg acgtaaggca cactc                                                25

<210> SEQ ID NO 160
<211> LENGTH: 23
<212> TYPE: DNA
<213> ORGANISM: Artificial Sequence
<220> FEATURE:
<223> OTHER INFORMATION: primer

<400> SEQUENCE: 160
gtcgactaag gccgcaacgt gac                                                  23

<210> SEQ ID NO 161
<211> LENGTH: 25
<212> TYPE: DNA
<213> ORGANISM: Artificial Sequence
<220> FEATURE:
<223> OTHER INFORMATION: primer

<400> SEQUENCE: 161
gtacgtgtgt caagtctcgt acctc                                                25

<210> SEQ ID NO 162
<211> LENGTH: 25
<212> TYPE: DNA
<213> ORGANISM: Artificial Sequence
<220> FEATURE:
<223> OTHER INFORMATION: primer

<400> SEQUENCE: 162
ggtagtgtcc gttaggcaac tggtc                                                25

<210> SEQ ID NO 163
<211> LENGTH: 24
<212> TYPE: DNA
<213> ORGANISM: Artificial Sequence
<220> FEATURE:
<223> OTHER INFORMATION: primer

<400> SEQUENCE: 163
gggtcgcagg tcgagactag ttgc                                                 24

<210> SEQ ID NO 164
<211> LENGTH: 25
<212> TYPE: DNA
<213> ORGANISM: Artificial Sequence
<220> FEATURE:
<223> OTHER INFORMATION: primer

<400> SEQUENCE: 164
ggccacagta cggtcgtcga ggtac                                                25

<210> SEQ ID NO 165
<211> LENGTH: 24
<212> TYPE: DNA
<213> ORGANISM: Artificial Sequence
<220> FEATURE:
<223> OTHER INFORMATION: primer

<400> SEQUENCE: 165
ggacgactcc gtactatcac gcgt                                                 24

<210> SEQ ID NO 166
<211> LENGTH: 24
<212> TYPE: DNA

<213> ORGANISM: Artificial Sequence
<220> FEATURE:
<223> OTHER INFORMATION: primer

<400> SEQUENCE: 166
gcttagactg acgccgctct agtg                                    24

<210> SEQ ID NO 167
<211> LENGTH: 22
<212> TYPE: DNA
<213> ORGANISM: Artificial Sequence
<220> FEATURE:
<223> OTHER INFORMATION: primer

<400> SEQUENCE: 167
gcgtcctgtg ctagcgctgt gc                                      22

<210> SEQ ID NO 168
<211> LENGTH: 24
<212> TYPE: DNA
<213> ORGANISM: Artificial Sequence
<220> FEATURE:
<223> OTHER INFORMATION: primer

<400> SEQUENCE: 168
gccgcacgca gaggactgtc ggta                                    24

<210> SEQ ID NO 169
<211> LENGTH: 27
<212> TYPE: DNA
<213> ORGANISM: Artificial Sequence
<220> FEATURE:
<223> OTHER INFORMATION: primer

<400> SEQUENCE: 169
gcataccttc ttcgcaacgt agcgtag                                 27

<210> SEQ ID NO 170
<211> LENGTH: 27
<212> TYPE: DNA
<213> ORGANISM: Artificial Sequence
<220> FEATURE:
<223> OTHER INFORMATION: primer

<400> SEQUENCE: 170
gatcagtcac tgacaggtac gacagac                                 27

<210> SEQ ID NO 171
<211> LENGTH: 22
<212> TYPE: DNA
<213> ORGANISM: Artificial Sequence
<220> FEATURE:
<223> OTHER INFORMATION: primer

<400> SEQUENCE: 171
gagccaagga gcacggttcg at                                      22

<210> SEQ ID NO 172
<211> LENGTH: 25
<212> TYPE: DNA
<213> ORGANISM: Artificial Sequence
<220> FEATURE:
<223> OTHER INFORMATION: primer

<400> SEQUENCE: 172
gacgctatcg cgtacacctc aacct                                   25

<210> SEQ ID NO 173
<211> LENGTH: 26
<212> TYPE: DNA
<213> ORGANISM: Artificial Sequence
<220> FEATURE:
<223> OTHER INFORMATION: primer

<400> SEQUENCE: 173
gaatgtgtac gtcaggggtt gaagtc                                    26

<210> SEQ ID NO 174
<211> LENGTH: 25
<212> TYPE: DNA
<213> ORGANISM: Artificial Sequence
<220> FEATURE:
<223> OTHER INFORMATION: primer

<400> SEQUENCE: 174
cttcatagcc ctctctcgcg agtag                                     25

<210> SEQ ID NO 175
<211> LENGTH: 24
<212> TYPE: DNA
<213> ORGANISM: Artificial Sequence
<220> FEATURE:
<223> OTHER INFORMATION: primer

<400> SEQUENCE: 175
ctgccgtctc gactacggat caag                                      24

<210> SEQ ID NO 176
<211> LENGTH: 24
<212> TYPE: DNA
<213> ORGANISM: Artificial Sequence
<220> FEATURE:
<223> OTHER INFORMATION: primer

<400> SEQUENCE: 176
ctcctgcgat cgctacgtct gtac                                      24

<210> SEQ ID NO 177
<211> LENGTH: 27
<212> TYPE: DNA
<213> ORGANISM: Artificial Sequence
<220> FEATURE:
<223> OTHER INFORMATION: primer

<400> SEQUENCE: 177
ctatagctta cagacctcgt tagtcac                                   27

<210> SEQ ID NO 178
<211> LENGTH: 26
<212> TYPE: DNA
<213> ORGANISM: Artificial Sequence
<220> FEATURE:
<223> OTHER INFORMATION: primer

<400> SEQUENCE: 178
cgtcttagcg cagtcgactc tcagac                                    26

<210> SEQ ID NO 179
<211> LENGTH: 27
<212> TYPE: DNA
<213> ORGANISM: Artificial Sequence
<220> FEATURE:

```
<223> OTHER INFORMATION: primer

<400> SEQUENCE: 179
cggctagcta gactccggct tactgag                                27

<210> SEQ ID NO 180
<211> LENGTH: 25
<212> TYPE: DNA
<213> ORGANISM: Artificial Sequence
<220> FEATURE:
<223> OTHER INFORMATION: primer

<400> SEQUENCE: 180
cgctcgctcg atcccgttta gggcg                                  25

<210> SEQ ID NO 181
<211> LENGTH: 25
<212> TYPE: DNA
<213> ORGANISM: Artificial Sequence
<220> FEATURE:
<223> OTHER INFORMATION: primer

<400> SEQUENCE: 181
cgacgactaa ccccatgcct gtacg                                  25

<210> SEQ ID NO 182
<211> LENGTH: 23
<212> TYPE: DNA
<213> ORGANISM: Artificial Sequence
<220> FEATURE:
<223> OTHER INFORMATION: primer

<400> SEQUENCE: 182
cctcgtaggc actagagcga tcg                                    23

<210> SEQ ID NO 183
<211> LENGTH: 25
<212> TYPE: DNA
<213> ORGANISM: Artificial Sequence
<220> FEATURE:
<223> OTHER INFORMATION: primer

<400> SEQUENCE: 183
ccgactagtg tcacgaatcg cagtc                                  25

<210> SEQ ID NO 184
<211> LENGTH: 25
<212> TYPE: DNA
<213> ORGANISM: Artificial Sequence
<220> FEATURE:
<223> OTHER INFORMATION: primer

<400> SEQUENCE: 184
cccagggtac agtcgctatt acgca                                  25

<210> SEQ ID NO 185
<211> LENGTH: 23
<212> TYPE: DNA
<213> ORGANISM: Artificial Sequence
<220> FEATURE:
<223> OTHER INFORMATION: primer

<400> SEQUENCE: 185
ccagtaccgg agggatgacc tag                                    23
```

<210> SEQ ID NO 186
<211> LENGTH: 24
<212> TYPE: DNA
<213> ORGANISM: Artificial Sequence
<220> FEATURE:
<223> OTHER INFORMATION: primer

<400> SEQUENCE: 186
catacgtagc ggattagtcc gatc                                      24

<210> SEQ ID NO 187
<211> LENGTH: 25
<212> TYPE: DNA
<213> ORGANISM: Artificial Sequence
<220> FEATURE:
<223> OTHER INFORMATION: primer

<400> SEQUENCE: 187
caggtcgcac gactagtcgg tagtc                                     25

<210> SEQ ID NO 188
<211> LENGTH: 23
<212> TYPE: DNA
<213> ORGANISM: Artificial Sequence
<220> FEATURE:
<223> OTHER INFORMATION: primer

<400> SEQUENCE: 188
caccgagcta cgttagggcc cta                                       23

<210> SEQ ID NO 189
<211> LENGTH: 23
<212> TYPE: DNA
<213> ORGANISM: Artificial Sequence
<220> FEATURE:
<223> OTHER INFORMATION: primer

<400> SEQUENCE: 189
caacgacccg ttagggctag gta                                       23

<210> SEQ ID NO 190
<211> LENGTH: 24
<212> TYPE: DNA
<213> ORGANISM: Artificial Sequence
<220> FEATURE:
<223> OTHER INFORMATION: primer

<400> SEQUENCE: 190
attagtcggt agtaccgcgc acta                                      24

<210> SEQ ID NO 191
<211> LENGTH: 22
<212> TYPE: DNA
<213> ORGANISM: Artificial Sequence
<220> FEATURE:
<223> OTHER INFORMATION: primer

<400> SEQUENCE: 191
atgtcccgac gcatagccgt ct                                        22

<210> SEQ ID NO 192
<211> LENGTH: 25
<212> TYPE: DNA
<213> ORGANISM: Artificial Sequence
<220> FEATURE:
<223> OTHER INFORMATION: primer

<400> SEQUENCE: 192
atccgagtta cgcgtgttcg taggt                                      25

<210> SEQ ID NO 193
<211> LENGTH: 22
<212> TYPE: DNA
<213> ORGANISM: Artificial Sequence
<220> FEATURE:
<223> OTHER INFORMATION: primer

<400> SEQUENCE: 193
atagtctgcc acccacgtag ct                                         22

<210> SEQ ID NO 194
<211> LENGTH: 23
<212> TYPE: DNA
<213> ORGANISM: Artificial Sequence
<220> FEATURE:
<223> OTHER INFORMATION: primer

<400> SEQUENCE: 194
agtgatggtc gaccgtatcg gta                                        23

<210> SEQ ID NO 195
<211> LENGTH: 26
<212> TYPE: DNA
<213> ORGANISM: Artificial Sequence
<220> FEATURE:
<223> OTHER INFORMATION: primer

<400> SEQUENCE: 195
aggcgcttag ttcctaccta gcgtac                                     26

<210> SEQ ID NO 196
<211> LENGTH: 25
<212> TYPE: DNA
<213> ORGANISM: Artificial Sequence
<220> FEATURE:
<223> OTHER INFORMATION: primer

<400> SEQUENCE: 196
agcgacgcta gcaactagtc gtccg                                      25

<210> SEQ ID NO 197
<211> LENGTH: 23
<212> TYPE: DNA
<213> ORGANISM: Artificial Sequence
<220> FEATURE:
<223> OTHER INFORMATION: primer

<400> SEQUENCE: 197
agagcgtcaa cgcgtaggtt cac                                        23

<210> SEQ ID NO 198
<211> LENGTH: 24
<212> TYPE: DNA
<213> ORGANISM: Artificial Sequence
<220> FEATURE:
<223> OTHER INFORMATION: primer

<400> SEQUENCE: 198
acttctacgc ctagcccgag acac                                       24

<210> SEQ ID NO 199
<211> LENGTH: 22

<212> TYPE: DNA
<213> ORGANISM: Artificial Sequence
<220> FEATURE:
<223> OTHER INFORMATION: primer

<400> SEQUENCE: 199
acgctcccat ggacaccacg ga                                    22

<210> SEQ ID NO 200
<211> LENGTH: 24
<212> TYPE: DNA
<213> ORGANISM: Artificial Sequence
<220> FEATURE:
<223> OTHER INFORMATION: primer

<400> SEQUENCE: 200
accacctgct agcgttacgc gtag                                  24

<210> SEQ ID NO 201
<211> LENGTH: 24
<212> TYPE: DNA
<213> ORGANISM: Artificial Sequence
<220> FEATURE:
<223> OTHER INFORMATION: primer

<400> SEQUENCE: 201
acaagccgta ccttacggct cttc                                  24

<210> SEQ ID NO 202
<211> LENGTH: 25
<212> TYPE: DNA
<213> ORGANISM: Artificial Sequence
<220> FEATURE:
<223> OTHER INFORMATION: primer

<400> SEQUENCE: 202
aatgacttag cgtacgctga cgtac                                 25

<210> SEQ ID NO 203
<211> LENGTH: 24
<212> TYPE: DNA
<213> ORGANISM: Artificial Sequence
<220> FEATURE:
<223> OTHER INFORMATION: primer

<400> SEQUENCE: 203
aagagcgcta caacggaacc taga                                  24

<210> SEQ ID NO 204
<211> LENGTH: 22
<212> TYPE: DNA
<213> ORGANISM: Artificial Sequence
<220> FEATURE:
<223> OTHER INFORMATION: primer

<400> SEQUENCE: 204
aacgtcgtgt cgtctcgttg ct                                    22

<210> SEQ ID NO 205
<211> LENGTH: 24
<212> TYPE: DNA
<213> ORGANISM: Artificial Sequence
<220> FEATURE:
<223> OTHER INFORMATION: primer

<400> SEQUENCE: 205
aaataccgtg cgtgggttct agac        24

<210> SEQ ID NO 206
<211> LENGTH: 24
<212> TYPE: DNA
<213> ORGANISM: Artificial Sequence
<220> FEATURE:
<223> OTHER INFORMATION: primer

<400> SEQUENCE: 206
tttaacgacg cgtcgcggta ccag        24

<210> SEQ ID NO 207
<211> LENGTH: 26
<212> TYPE: DNA
<213> ORGANISM: Artificial Sequence
<220> FEATURE:
<223> OTHER INFORMATION: primer

<400> SEQUENCE: 207
ttggggctct agaactgact ccagac        26

<210> SEQ ID NO 208
<211> LENGTH: 24
<212> TYPE: DNA
<213> ORGANISM: Artificial Sequence
<220> FEATURE:
<223> OTHER INFORMATION: primer

<400> SEQUENCE: 208
ttcgtagtag cggcgactag tacc        24

<210> SEQ ID NO 209
<211> LENGTH: 25
<212> TYPE: DNA
<213> ORGANISM: Artificial Sequence
<220> FEATURE:
<223> OTHER INFORMATION: primer

<400> SEQUENCE: 209
ttaggcaggg atcgacctag ggtac        25

<210> SEQ ID NO 210
<211> LENGTH: 25
<212> TYPE: DNA
<213> ORGANISM: Artificial Sequence
<220> FEATURE:
<223> OTHER INFORMATION: primer

<400> SEQUENCE: 210
tgtagtcgct attacgcacc tagtg        25

<210> SEQ ID NO 211
<211> LENGTH: 25
<212> TYPE: DNA
<213> ORGANISM: Artificial Sequence
<220> FEATURE:
<223> OTHER INFORMATION: primer

<400> SEQUENCE: 211
tggtcacgaa tcgcaatccc gtagg        25

<210> SEQ ID NO 212
<211> LENGTH: 24
<212> TYPE: DNA
<213> ORGANISM: Artificial Sequence

```
<220> FEATURE:
<223> OTHER INFORMATION: primer

<400> SEQUENCE: 212
tgccactaga gcgacgtacc gtgc                                    24

<210> SEQ ID NO 213
<211> LENGTH: 24
<212> TYPE: DNA
<213> ORGANISM: Artificial Sequence
<220> FEATURE:
<223> OTHER INFORMATION: primer

<400> SEQUENCE: 213
tgagtgggtt ctagaccgcg tcgt                                    24

<210> SEQ ID NO 214
<211> LENGTH: 24
<212> TYPE: DNA
<213> ORGANISM: Artificial Sequence
<220> FEATURE:
<223> OTHER INFORMATION: primer

<400> SEQUENCE: 214
tctgtcgatc tttgctagcg ctac                                    24

<210> SEQ ID NO 215
<211> LENGTH: 24
<212> TYPE: DNA
<213> ORGANISM: Artificial Sequence
<220> FEATURE:
<223> OTHER INFORMATION: primer

<400> SEQUENCE: 215
tcgaacggaa cctagagact tagc                                    24

<210> SEQ ID NO 216
<211> LENGTH: 25
<212> TYPE: DNA
<213> ORGANISM: Artificial Sequence
<220> FEATURE:
<223> OTHER INFORMATION: primer

<400> SEQUENCE: 216
tccgtacgct gacgtatagc cgtac                                   25

<210> SEQ ID NO 217
<211> LENGTH: 24
<212> TYPE: DNA
<213> ORGANISM: Artificial Sequence
<220> FEATURE:
<223> OTHER INFORMATION: primer

<400> SEQUENCE: 217
tcacttacgg ctcttacctg ctag                                    24

<210> SEQ ID NO 218
<211> LENGTH: 24
<212> TYPE: DNA
<213> ORGANISM: Artificial Sequence
<220> FEATURE:
<223> OTHER INFORMATION: primer

<400> SEQUENCE: 218
tatcgttacg cgtagactcc catg                                    24
```

```
<210> SEQ ID NO 219
<211> LENGTH: 24
<212> TYPE: DNA
<213> ORGANISM: Artificial Sequence
<220> FEATURE:
<223> OTHER INFORMATION: primer

<400> SEQUENCE: 219
taggacacca cgggatctac gcct                                          24

<210> SEQ ID NO 220
<211> LENGTH: 24
<212> TYPE: DNA
<213> ORGANISM: Artificial Sequence
<220> FEATURE:
<223> OTHER INFORMATION: primer

<400> SEQUENCE: 220
tacagcccga gacacagcgt caac                                          24

<210> SEQ ID NO 221
<211> LENGTH: 24
<212> TYPE: DNA
<213> ORGANISM: Artificial Sequence
<220> FEATURE:
<223> OTHER INFORMATION: primer

<400> SEQUENCE: 221
taagcgtagg ttcacgacgc tagc                                          24

<210> SEQ ID NO 222
<211> LENGTH: 24
<212> TYPE: DNA
<213> ORGANISM: Artificial Sequence
<220> FEATURE:
<223> OTHER INFORMATION: primer

<400> SEQUENCE: 222
gttaactagt cgtccgcgct tagt                                          24

<210> SEQ ID NO 223
<211> LENGTH: 24
<212> TYPE: DNA
<213> ORGANISM: Artificial Sequence
<220> FEATURE:
<223> OTHER INFORMATION: primer

<400> SEQUENCE: 223
gtgttaccta gcgtacggat ggtc                                          24

<210> SEQ ID NO 224
<211> LENGTH: 24
<212> TYPE: DNA
<213> ORGANISM: Artificial Sequence
<220> FEATURE:
<223> OTHER INFORMATION: primer

<400> SEQUENCE: 224
gtcgaccgta tcggtagtct gcca                                          24

<210> SEQ ID NO 225
<211> LENGTH: 24
<212> TYPE: DNA
<213> ORGANISM: Artificial Sequence
<220> FEATURE:
<223> OTHER INFORMATION: primer
```

```
<400> SEQUENCE: 225
gtaccgcacg taacgtgagt tacg                                          24

<210> SEQ ID NO 226
<211> LENGTH: 24
<212> TYPE: DNA
<213> ORGANISM: Artificial Sequence
<220> FEATURE:
<223> OTHER INFORMATION: primer

<400> SEQUENCE: 226
ggtcgtgttc gtaggtccgg cgac                                          24

<210> SEQ ID NO 227
<211> LENGTH: 25
<212> TYPE: DNA
<213> ORGANISM: Artificial Sequence
<220> FEATURE:
<223> OTHER INFORMATION: primer

<400> SEQUENCE: 227
ggggcatagg ccgcctagtc ggtag                                         25

<210> SEQ ID NO 228
<211> LENGTH: 24
<212> TYPE: DNA
<213> ORGANISM: Artificial Sequence
<220> FEATURE:
<223> OTHER INFORMATION: primer

<400> SEQUENCE: 228
ggctaccgcg cactagcgac ccgt                                          24

<210> SEQ ID NO 229
<211> LENGTH: 24
<212> TYPE: DNA
<213> ORGANISM: Artificial Sequence
<220> FEATURE:
<223> OTHER INFORMATION: primer

<400> SEQUENCE: 229
ggatagggct aggtacgagc tacg                                          24

<210> SEQ ID NO 230
<211> LENGTH: 24
<212> TYPE: DNA
<213> ORGANISM: Artificial Sequence
<220> FEATURE:
<223> OTHER INFORMATION: primer

<400> SEQUENCE: 230
gctttagggc cctagtcgca cgac                                          24

<210> SEQ ID NO 231
<211> LENGTH: 24
<212> TYPE: DNA
<213> ORGANISM: Artificial Sequence
<220> FEATURE:
<223> OTHER INFORMATION: primer

<400> SEQUENCE: 231
gcgtagtcgg tagtcacccg tagc                                          24

<210> SEQ ID NO 232
```

```
<211> LENGTH: 26
<212> TYPE: DNA
<213> ORGANISM: Artificial Sequence
<220> FEATURE:
<223> OTHER INFORMATION: primer

<400> SEQUENCE: 232
gccggattag tccgatgcga ctaacc                                    26

<210> SEQ ID NO 233
<211> LENGTH: 27
<212> TYPE: DNA
<213> ORGANISM: Artificial Sequence
<220> FEATURE:
<223> OTHER INFORMATION: primer

<400> SEQUENCE: 233
gcacctagcc tgtacgtcgc tcgatcc                                   27

<210> SEQ ID NO 234
<211> LENGTH: 26
<212> TYPE: DNA
<213> ORGANISM: Artificial Sequence
<220> FEATURE:
<223> OTHER INFORMATION: primer

<400> SEQUENCE: 234
gatcgtttag ggcgtagcta gactcc                                    26

<210> SEQ ID NO 235
<211> LENGTH: 24
<212> TYPE: DNA
<213> ORGANISM: Artificial Sequence
<220> FEATURE:
<223> OTHER INFORMATION: primer

<400> SEQUENCE: 235
gagggcttac tagcttagcg agtc                                      24

<210> SEQ ID NO 236
<211> LENGTH: 25
<212> TYPE: DNA
<213> ORGANISM: Artificial Sequence
<220> FEATURE:
<223> OTHER INFORMATION: primer

<400> SEQUENCE: 236
gacgactcta gacagcttac agacc                                     25

<210> SEQ ID NO 237
<211> LENGTH: 24
<212> TYPE: DNA
<213> ORGANISM: Artificial Sequence
<220> FEATURE:
<223> OTHER INFORMATION: primer

<400> SEQUENCE: 237
gaatcgttag tcactgcgat cgct                                      24

<210> SEQ ID NO 238
<211> LENGTH: 26
<212> TYPE: DNA
<213> ORGANISM: Artificial Sequence
<220> FEATURE:
<223> OTHER INFORMATION: primer

<400> SEQUENCE: 238
```
cttacgtctg tacccgtctc gactac                      26

<210> SEQ ID NO 239
<211> LENGTH: 24
<212> TYPE: DNA
<213> ORGANISM: Artificial Sequence
<220> FEATURE:
<223> OTHER INFORMATION: primer

<400> SEQUENCE: 239
ctgggatcaa gcatagcccg tctc                        24

<210> SEQ ID NO 240
<211> LENGTH: 24
<212> TYPE: DNA
<213> ORGANISM: Artificial Sequence
<220> FEATURE:
<223> OTHER INFORMATION: primer

<400> SEQUENCE: 240
ctctcgcgag taggtgtacg tcag                        24

<210> SEQ ID NO 241
<211> LENGTH: 25
<212> TYPE: DNA
<213> ORGANISM: Artificial Sequence
<220> FEATURE:
<223> OTHER INFORMATION: primer

<400> SEQUENCE: 241
ctagggttaa gtcgctatcg cgtac                       25

<210> SEQ ID NO 242
<211> LENGTH: 24
<212> TYPE: DNA
<213> ORGANISM: Artificial Sequence
<220> FEATURE:
<223> OTHER INFORMATION: primer

<400> SEQUENCE: 242
cgtacctcaa cctccaagga gcac                        24

<210> SEQ ID NO 243
<211> LENGTH: 25
<212> TYPE: DNA
<213> ORGANISM: Artificial Sequence
<220> FEATURE:
<223> OTHER INFORMATION: primer

<400> SEQUENCE: 243
cggggcgttc gatagtcact gacag                       25

<210> SEQ ID NO 244
<211> LENGTH: 25
<212> TYPE: DNA
<213> ORGANISM: Artificial Sequence
<220> FEATURE:
<223> OTHER INFORMATION: primer

<400> SEQUENCE: 244
cgcgtacgac agactacctt cttcg                       25

<210> SEQ ID NO 245
<211> LENGTH: 26
<212> TYPE: DNA

```
<213> ORGANISM: Artificial Sequence
<220> FEATURE:
<223> OTHER INFORMATION: primer

<400> SEQUENCE: 245
cgacaacgta gcgtagcgtc acgcag                                              26

<210> SEQ ID NO 246
<211> LENGTH: 25
<212> TYPE: DNA
<213> ORGANISM: Artificial Sequence
<220> FEATURE:
<223> OTHER INFORMATION: primer

<400> SEQUENCE: 246
cataggactg tcggtatcct tgtgc                                               25

<210> SEQ ID NO 247
<211> LENGTH: 25
<212> TYPE: DNA
<213> ORGANISM: Artificial Sequence
<220> FEATURE:
<223> OTHER INFORMATION: primer

<400> SEQUENCE: 247
cagtagcgct cgtgctagac tgacg                                               25

<210> SEQ ID NO 248
<211> LENGTH: 23
<212> TYPE: DNA
<213> ORGANISM: Artificial Sequence
<220> FEATURE:
<223> OTHER INFORMATION: primer

<400> SEQUENCE: 248
cacccgctct agtgcgactc cgt                                                 23

<210> SEQ ID NO 249
<211> LENGTH: 24
<212> TYPE: DNA
<213> ORGANISM: Artificial Sequence
<220> FEATURE:
<223> OTHER INFORMATION: primer

<400> SEQUENCE: 249
caaactatca cgcgtacagt acgg                                                24

<210> SEQ ID NO 250
<211> LENGTH: 24
<212> TYPE: DNA
<213> ORGANISM: Artificial Sequence
<220> FEATURE:
<223> OTHER INFORMATION: primer

<400> SEQUENCE: 250
atttcgtcga ggtacttcgc aggt                                                24

<210> SEQ ID NO 251
<211> LENGTH: 24
<212> TYPE: DNA
<213> ORGANISM: Artificial Sequence
<220> FEATURE:
<223> OTHER INFORMATION: primer

<400> SEQUENCE: 251
atgcgagact agttgcagtt ccgt                                                24
```

<210> SEQ ID NO 252
<211> LENGTH: 24
<212> TYPE: DNA
<213> ORGANISM: Artificial Sequence
<220> FEATURE:
<223> OTHER INFORMATION: primer

<400> SEQUENCE: 252
atctaggcaa ctagtccgtg tgtc                                    24

<210> SEQ ID NO 253
<211> LENGTH: 24
<212> TYPE: DNA
<213> ORGANISM: Artificial Sequence
<220> FEATURE:
<223> OTHER INFORMATION: primer

<400> SEQUENCE: 253
ataaagttcg tacctcgact aagc                                    24

<210> SEQ ID NO 254
<211> LENGTH: 24
<212> TYPE: DNA
<213> ORGANISM: Artificial Sequence
<220> FEATURE:
<223> OTHER INFORMATION: primer

<400> SEQUENCE: 254
agtgccgcga cgtaacgaac tcga                                    24

<210> SEQ ID NO 255
<211> LENGTH: 24
<212> TYPE: DNA
<213> ORGANISM: Artificial Sequence
<220> FEATURE:
<223> OTHER INFORMATION: primer

<400> SEQUENCE: 255
aggcgtaagg catactacgc gcag                                    24

<210> SEQ ID NO 256
<211> LENGTH: 25
<212> TYPE: DNA
<213> ORGANISM: Artificial Sequence
<220> FEATURE:
<223> OTHER INFORMATION: primer

<400> SEQUENCE: 256
agcacgcgta tgagaagtcg cgaac                                   25

<210> SEQ ID NO 257
<211> LENGTH: 24
<212> TYPE: DNA
<213> ORGANISM: Artificial Sequence
<220> FEATURE:
<223> OTHER INFORMATION: primer

<400> SEQUENCE: 257
agacctacga cgtatcgcga ctag                                    24

<210> SEQ ID NO 258
<211> LENGTH: 24
<212> TYPE: DNA
<213> ORGANISM: Artificial Sequence
<220> FEATURE:

<223> OTHER INFORMATION: primer

<400> SEQUENCE: 258
actggttcgg tcgctcgatc gtcg                                    24

<210> SEQ ID NO 259
<211> LENGTH: 24
<212> TYPE: DNA
<213> ORGANISM: Artificial Sequence
<220> FEATURE:
<223> OTHER INFORMATION: primer

<400> SEQUENCE: 259
acgtagttcc aagtcgcgac gagc                                    24

<210> SEQ ID NO 260
<211> LENGTH: 24
<212> TYPE: DNA
<213> ORGANISM: Artificial Sequence
<220> FEATURE:
<223> OTHER INFORMATION: primer

<400> SEQUENCE: 260
accatagcgc gttgccctca catc                                    24

<210> SEQ ID NO 261
<211> LENGTH: 24
<212> TYPE: DNA
<213> ORGANISM: Artificial Sequence
<220> FEATURE:
<223> OTHER INFORMATION: primer

<400> SEQUENCE: 261
acactgtacg ggtgcaagat accg                                    24

<210> SEQ ID NO 262
<211> LENGTH: 24
<212> TYPE: DNA
<213> ORGANISM: Artificial Sequence
<220> FEATURE:
<223> OTHER INFORMATION: primer

<400> SEQUENCE: 262
aatctagatc ggaacggtta gtcg                                    24

<210> SEQ ID NO 263
<211> LENGTH: 24
<212> TYPE: DNA
<213> ORGANISM: Artificial Sequence
<220> FEATURE:
<223> OTHER INFORMATION: primer

<400> SEQUENCE: 263
aaggtccgtt aggagacagg tcga                                    24

<210> SEQ ID NO 264
<211> LENGTH: 24
<212> TYPE: DNA
<213> ORGANISM: Artificial Sequence
<220> FEATURE:
<223> OTHER INFORMATION: primer

<400> SEQUENCE: 264
aacctaggcg acgtaccagc acgt                                    24

```
<210> SEQ ID NO 265
<211> LENGTH: 24
<212> TYPE: DNA
<213> ORGANISM: Artificial Sequence
<220> FEATURE:
<223> OTHER INFORMATION: primer

<400> SEQUENCE: 265
aaagtacgtg atccgatacg cctc                                          24

<210> SEQ ID NO 266
<211> LENGTH: 25
<212> TYPE: DNA
<213> ORGANISM: Artificial Sequence
<220> FEATURE:
<223> OTHER INFORMATION: primer

<400> SEQUENCE: 266
ttttaacgca gtgttcgttc gacga                                         25

<210> SEQ ID NO 267
<211> LENGTH: 25
<212> TYPE: DNA
<213> ORGANISM: Artificial Sequence
<220> FEATURE:
<223> OTHER INFORMATION: primer

<400> SEQUENCE: 267
tttgtgcaga gcggaacgag acgta                                         25

<210> SEQ ID NO 268
<211> LENGTH: 25
<212> TYPE: DNA
<213> ORGANISM: Artificial Sequence
<220> FEATURE:
<223> OTHER INFORMATION: primer

<400> SEQUENCE: 268
tttcagcgca cgtcgtctag cgaag                                         25

<210> SEQ ID NO 269
<211> LENGTH: 25
<212> TYPE: DNA
<213> ORGANISM: Artificial Sequence
<220> FEATURE:
<223> OTHER INFORMATION: primer

<400> SEQUENCE: 269
tttatctgag acggagtacg agcga                                         25

<210> SEQ ID NO 270
<211> LENGTH: 25
<212> TYPE: DNA
<213> ORGANISM: Artificial Sequence
<220> FEATURE:
<223> OTHER INFORMATION: primer

<400> SEQUENCE: 270
ttgtacagtg accgttttcg cgcat                                         25

<210> SEQ ID NO 271
<211> LENGTH: 25
<212> TYPE: DNA
<213> ORGANISM: Artificial Sequence
<220> FEATURE:
<223> OTHER INFORMATION: primer
```

<400> SEQUENCE: 271
ttggactctg ggacgacgaa aagcg                                    25

<210> SEQ ID NO 272
<211> LENGTH: 25
<212> TYPE: DNA
<213> ORGANISM: Artificial Sequence
<220> FEATURE:
<223> OTHER INFORMATION: primer

<400> SEQUENCE: 272
ttgctgaccg aaccgggttt accag                                    25

<210> SEQ ID NO 273
<211> LENGTH: 25
<212> TYPE: DNA
<213> ORGANISM: Artificial Sequence
<220> FEATURE:
<223> OTHER INFORMATION: primer

<400> SEQUENCE: 273
ttgaacgaga cgtctcggac tatcg                                    25

<210> SEQ ID NO 274
<211> LENGTH: 25
<212> TYPE: DNA
<213> ORGANISM: Artificial Sequence
<220> FEATURE:
<223> OTHER INFORMATION: primer

<400> SEQUENCE: 274
ttctcaacaa cgtgccgttc gatag                                    25

<210> SEQ ID NO 275
<211> LENGTH: 25
<212> TYPE: DNA
<213> ORGANISM: Artificial Sequence
<220> FEATURE:
<223> OTHER INFORMATION: primer

<400> SEQUENCE: 275
ttcggtacca cccgaacggt cgtag                                    25

<210> SEQ ID NO 276
<211> LENGTH: 25
<212> TYPE: DNA
<213> ORGANISM: Artificial Sequence
<220> FEATURE:
<223> OTHER INFORMATION: primer

<400> SEQUENCE: 276
ttccgcacaa ccgtcgaccg tacga                                    25

<210> SEQ ID NO 277
<211> LENGTH: 25
<212> TYPE: DNA
<213> ORGANISM: Artificial Sequence
<220> FEATURE:
<223> OTHER INFORMATION: primer

<400> SEQUENCE: 277
ttcaaagccg agacgaggtc taacg                                    25

<210> SEQ ID NO 278
<211> LENGTH: 25

```
<212> TYPE: DNA
<213> ORGANISM: Artificial Sequence
<220> FEATURE:
<223> OTHER INFORMATION: primer

<400> SEQUENCE: 278
ttatatcgct gcgatcggac gttag                                    25

<210> SEQ ID NO 279
<211> LENGTH: 25
<212> TYPE: DNA
<213> ORGANISM: Artificial Sequence
<220> FEATURE:
<223> OTHER INFORMATION: primer

<400> SEQUENCE: 279
ttagaccgca gacgttccga taccg                                    25

<210> SEQ ID NO 280
<211> LENGTH: 25
<212> TYPE: DNA
<213> ORGANISM: Artificial Sequence
<220> FEATURE:
<223> OTHER INFORMATION: primer

<400> SEQUENCE: 280
ttactctacg tacgacggtt cggta                                    25

<210> SEQ ID NO 281
<211> LENGTH: 25
<212> TYPE: DNA
<213> ORGANISM: Artificial Sequence
<220> FEATURE:
<223> OTHER INFORMATION: primer

<400> SEQUENCE: 281
ttaatacacc acgtgaatcc gctag                                    25

<210> SEQ ID NO 282
<211> LENGTH: 25
<212> TYPE: DNA
<213> ORGANISM: Artificial Sequence
<220> FEATURE:
<223> OTHER INFORMATION: primer

<400> SEQUENCE: 282
tgttatcctg gacagagtcg tcgac                                    25

<210> SEQ ID NO 283
<211> LENGTH: 25
<212> TYPE: DNA
<213> ORGANISM: Artificial Sequence
<220> FEATURE:
<223> OTHER INFORMATION: primer

<400> SEQUENCE: 283
tgtgtcgtga gtcaagaacc gtcga                                    25

<210> SEQ ID NO 284
<211> LENGTH: 25
<212> TYPE: DNA
<213> ORGANISM: Artificial Sequence
<220> FEATURE:
<223> OTHER INFORMATION: primer

<400> SEQUENCE: 284
```
tgtcacagca cacgtgatcc ttacg                                                      25

<210> SEQ ID NO 285
<211> LENGTH: 26
<212> TYPE: DNA
<213> ORGANISM: Artificial Sequence
<220> FEATURE:
<223> OTHER INFORMATION: primer

<400> SEQUENCE: 285
tgtatggtac acgctcgatc cgtaag                                                     26

<210> SEQ ID NO 286
<211> LENGTH: 26
<212> TYPE: DNA
<213> ORGANISM: Artificial Sequence
<220> FEATURE:
<223> OTHER INFORMATION: primer

<400> SEQUENCE: 286
tggtctcact cgggtcgttg cgtatg                                                     26

<210> SEQ ID NO 287
<211> LENGTH: 26
<212> TYPE: DNA
<213> ORGANISM: Artificial Sequence
<220> FEATURE:
<223> OTHER INFORMATION: primer

<400> SEQUENCE: 287
tgggggatta cacacgcaag gatacg                                                     26

<210> SEQ ID NO 288
<211> LENGTH: 25
<212> TYPE: DNA
<213> ORGANISM: Artificial Sequence
<220> FEATURE:
<223> OTHER INFORMATION: primer

<400> SEQUENCE: 288
tggctggcat cgtgcttctt ccgat                                                      25

<210> SEQ ID NO 289
<211> LENGTH: 25
<212> TYPE: DNA
<213> ORGANISM: Artificial Sequence
<220> FEATURE:
<223> OTHER INFORMATION: primer

<400> SEQUENCE: 289
tggagacgtc ctcgcgagaa atcgg                                                      25

<210> SEQ ID NO 290
<211> LENGTH: 25
<212> TYPE: DNA
<213> ORGANISM: Artificial Sequence
<220> FEATURE:
<223> OTHER INFORMATION: primer

<400> SEQUENCE: 290
tgctagtatc cagcagtggg atgcg                                                      25

<210> SEQ ID NO 291
<211> LENGTH: 25
<212> TYPE: DNA
<213> ORGANISM: Artificial Sequence

```
<220> FEATURE:
<223> OTHER INFORMATION: primer

<400> SEQUENCE: 291
tgcgacgaag agcgaccgaa ccgta                                              25

<210> SEQ ID NO 292
<211> LENGTH: 25
<212> TYPE: DNA
<213> ORGANISM: Artificial Sequence
<220> FEATURE:
<223> OTHER INFORMATION: primer

<400> SEQUENCE: 292
tgccgcaact gcggttcgac gaatg                                              25

<210> SEQ ID NO 293
<211> LENGTH: 25
<212> TYPE: DNA
<213> ORGANISM: Artificial Sequence
<220> FEATURE:
<223> OTHER INFORMATION: primer

<400> SEQUENCE: 293
tgcaacgttc gcgagtcgaa attcg                                              25

<210> SEQ ID NO 294
<211> LENGTH: 25
<212> TYPE: DNA
<213> ORGANISM: Artificial Sequence
<220> FEATURE:
<223> OTHER INFORMATION: primer

<400> SEQUENCE: 294
tgataacgtg tcactgcgtc gcgtt                                              25

<210> SEQ ID NO 295
<211> LENGTH: 25
<212> TYPE: DNA
<213> ORGANISM: Artificial Sequence
<220> FEATURE:
<223> OTHER INFORMATION: primer

<400> SEQUENCE: 295
tgaggtctag acggagaagc aaagc                                              25

<210> SEQ ID NO 296
<211> LENGTH: 25
<212> TYPE: DNA
<213> ORGANISM: Artificial Sequence
<220> FEATURE:
<223> OTHER INFORMATION: primer

<400> SEQUENCE: 296
tgaccgttag cgctcgacgt tacgt                                              25

<210> SEQ ID NO 297
<211> LENGTH: 25
<212> TYPE: DNA
<213> ORGANISM: Artificial Sequence
<220> FEATURE:
<223> OTHER INFORMATION: primer

<400> SEQUENCE: 297
tgaagatcac tccgcacgtc acgta                                              25
```

<210> SEQ ID NO 298
<211> LENGTH: 25
<212> TYPE: DNA
<213> ORGANISM: Artificial Sequence
<220> FEATURE:
<223> OTHER INFORMATION: primer

<400> SEQUENCE: 298
tcttactagt taccgagcgt ctacg                                    25

<210> SEQ ID NO 299
<211> LENGTH: 25
<212> TYPE: DNA
<213> ORGANISM: Artificial Sequence
<220> FEATURE:
<223> OTHER INFORMATION: primer

<400> SEQUENCE: 299
tctgctatgc gagagacgct cgtag                                    25

<210> SEQ ID NO 300
<211> LENGTH: 25
<212> TYPE: DNA
<213> ORGANISM: Artificial Sequence
<220> FEATURE:
<223> OTHER INFORMATION: primer

<400> SEQUENCE: 300
tctcacacga acggatgcgt ttcgc                                    25

<210> SEQ ID NO 301
<211> LENGTH: 25
<212> TYPE: DNA
<213> ORGANISM: Artificial Sequence
<220> FEATURE:
<223> OTHER INFORMATION: primer

<400> SEQUENCE: 301
tctatactag cagcaacgaa gcgaa                                    25

<210> SEQ ID NO 302
<211> LENGTH: 25
<212> TYPE: DNA
<213> ORGANISM: Artificial Sequence
<220> FEATURE:
<223> OTHER INFORMATION: primer

<400> SEQUENCE: 302
tcgtctagac tccggtgtcg atcgt                                    25

<210> SEQ ID NO 303
<211> LENGTH: 25
<212> TYPE: DNA
<213> ORGANISM: Artificial Sequence
<220> FEATURE:
<223> OTHER INFORMATION: primer

<400> SEQUENCE: 303
tcggcgacta cgtcccgaca acgat                                    25

<210> SEQ ID NO 304
<211> LENGTH: 25
<212> TYPE: DNA
<213> ORGANISM: Artificial Sequence
<220> FEATURE:
<223> OTHER INFORMATION: primer

<400> SEQUENCE: 304
tcgcaactcg gaagacgatg gtcgt                                              25

<210> SEQ ID NO 305
<211> LENGTH: 25
<212> TYPE: DNA
<213> ORGANISM: Artificial Sequence
<220> FEATURE:
<223> OTHER INFORMATION: primer

<400> SEQUENCE: 305
tcgaaagtat ggacgcatcg acgac                                              25

<210> SEQ ID NO 306
<211> LENGTH: 25
<212> TYPE: DNA
<213> ORGANISM: Artificial Sequence
<220> FEATURE:
<223> OTHER INFORMATION: primer

<400> SEQUENCE: 306
tccttgaagg tcgacacgtt cggtt                                              25

<210> SEQ ID NO 307
<211> LENGTH: 25
<212> TYPE: DNA
<213> ORGANISM: Artificial Sequence
<220> FEATURE:
<223> OTHER INFORMATION: primer

<400> SEQUENCE: 307
tccgaatacc gcgcaaacgt aacca                                              25

<210> SEQ ID NO 308
<211> LENGTH: 25
<212> TYPE: DNA
<213> ORGANISM: Artificial Sequence
<220> FEATURE:
<223> OTHER INFORMATION: primer

<400> SEQUENCE: 308
tccctagaca caggaccagg gttcg                                              25

<210> SEQ ID NO 309
<211> LENGTH: 25
<212> TYPE: DNA
<213> ORGANISM: Artificial Sequence
<220> FEATURE:
<223> OTHER INFORMATION: primer

<400> SEQUENCE: 309
tccaagtact tcgtgacgag cgaac                                              25

<210> SEQ ID NO 310
<211> LENGTH: 25
<212> TYPE: DNA
<213> ORGANISM: Artificial Sequence
<220> FEATURE:
<223> OTHER INFORMATION: primer

<400> SEQUENCE: 310
tcataactag aagctgcggt ttgcg                                              25

<210> SEQ ID NO 311

```
<211> LENGTH: 25
<212> TYPE: DNA
<213> ORGANISM: Artificial Sequence
<220> FEATURE:
<223> OTHER INFORMATION: primer

<400> SEQUENCE: 311
tcagactagc tgcgaacggt cgcaa                                              25

<210> SEQ ID NO 312
<211> LENGTH: 25
<212> TYPE: DNA
<213> ORGANISM: Artificial Sequence
<220> FEATURE:
<223> OTHER INFORMATION: primer

<400> SEQUENCE: 312
tcacagcata cgcttacctg cgact                                              25

<210> SEQ ID NO 313
<211> LENGTH: 25
<212> TYPE: DNA
<213> ORGANISM: Artificial Sequence
<220> FEATURE:
<223> OTHER INFORMATION: primer

<400> SEQUENCE: 313
tcaaacgtgg agcctacgat agtcg                                              25

<210> SEQ ID NO 314
<211> LENGTH: 25
<212> TYPE: DNA
<213> ORGANISM: Artificial Sequence
<220> FEATURE:
<223> OTHER INFORMATION: primer

<400> SEQUENCE: 314
tattcctaac ctcgaatcgc tcgat                                              25

<210> SEQ ID NO 315
<211> LENGTH: 25
<212> TYPE: DNA
<213> ORGANISM: Artificial Sequence
<220> FEATURE:
<223> OTHER INFORMATION: primer

<400> SEQUENCE: 315
tatgaccacg gcgctacggt atcga                                              25

<210> SEQ ID NO 316
<211> LENGTH: 25
<212> TYPE: DNA
<213> ORGANISM: Artificial Sequence
<220> FEATURE:
<223> OTHER INFORMATION: primer

<400> SEQUENCE: 316
tatcatgccg tcgagagagt tcggt                                              25

<210> SEQ ID NO 317
<211> LENGTH: 25
<212> TYPE: DNA
<213> ORGANISM: Artificial Sequence
<220> FEATURE:
<223> OTHER INFORMATION: primer

<400> SEQUENCE: 317
```
tatatcaacc acgagtgacg atcga                    25

<210> SEQ ID NO 318
<211> LENGTH: 25
<212> TYPE: DNA
<213> ORGANISM: Artificial Sequence
<220> FEATURE:
<223> OTHER INFORMATION: primer

<400> SEQUENCE: 318
tagtactatc ctcgtcgtca gtcgc                    25

<210> SEQ ID NO 319
<211> LENGTH: 25
<212> TYPE: DNA
<213> ORGANISM: Artificial Sequence
<220> FEATURE:
<223> OTHER INFORMATION: primer

<400> SEQUENCE: 319
taggaggtta tccgtctgcc acgac                    25

<210> SEQ ID NO 320
<211> LENGTH: 25
<212> TYPE: DNA
<213> ORGANISM: Artificial Sequence
<220> FEATURE:
<223> OTHER INFORMATION: primer

<400> SEQUENCE: 320
tagctccacg actgacgaac cgcat                    25

<210> SEQ ID NO 321
<211> LENGTH: 25
<212> TYPE: DNA
<213> ORGANISM: Artificial Sequence
<220> FEATURE:
<223> OTHER INFORMATION: primer

<400> SEQUENCE: 321
tagagagcta gacggaatcg atacg                    25

<210> SEQ ID NO 322
<211> LENGTH: 25
<212> TYPE: DNA
<213> ORGANISM: Artificial Sequence
<220> FEATURE:
<223> OTHER INFORMATION: primer

<400> SEQUENCE: 322
tactaacgga gccgtcgatc ttcgt                    25

<210> SEQ ID NO 323
<211> LENGTH: 25
<212> TYPE: DNA
<213> ORGANISM: Artificial Sequence
<220> FEATURE:
<223> OTHER INFORMATION: primer

<400> SEQUENCE: 323
tacgcagtac gtggtcttcg ttcga                    25

<210> SEQ ID NO 324
<211> LENGTH: 25
<212> TYPE: DNA

<210> SEQ ID NO 325
<211> LENGTH: 25
<212> TYPE: DNA
<213> ORGANISM: Artificial Sequence
<220> FEATURE:
<223> OTHER INFORMATION: primer

<400> SEQUENCE: 324
tacccgatca ccgccgaagt cagca 25

<210> SEQ ID NO 325
<211> LENGTH: 25
<212> TYPE: DNA
<213> ORGANISM: Artificial Sequence
<220> FEATURE:
<223> OTHER INFORMATION: primer

<400> SEQUENCE: 325
tacagtcaga ctcgcgtcta cgaac 25

<210> SEQ ID NO 326
<211> LENGTH: 25
<212> TYPE: DNA
<213> ORGANISM: Artificial Sequence
<220> FEATURE:
<223> OTHER INFORMATION: primer

<400> SEQUENCE: 326
taatccattc gagtaaacgc gattg 25

<210> SEQ ID NO 327
<211> LENGTH: 25
<212> TYPE: DNA
<213> ORGANISM: Artificial Sequence
<220> FEATURE:
<223> OTHER INFORMATION: primer

<400> SEQUENCE: 327
taagatagtc gctcgttccg aatcg 25

<210> SEQ ID NO 328
<211> LENGTH: 25
<212> TYPE: DNA
<213> ORGANISM: Artificial Sequence
<220> FEATURE:
<223> OTHER INFORMATION: primer

<400> SEQUENCE: 328
taacgcctta gagccaggaa gaacg 25

<210> SEQ ID NO 329
<211> LENGTH: 25
<212> TYPE: DNA
<213> ORGANISM: Artificial Sequence
<220> FEATURE:
<223> OTHER INFORMATION: primer

<400> SEQUENCE: 329
taaaggttca cgcacgttag cgttc 25

<210> SEQ ID NO 330
<211> LENGTH: 26
<212> TYPE: DNA
<213> ORGANISM: Artificial Sequence
<220> FEATURE:
<223> OTHER INFORMATION: primer

<400> SEQUENCE: 330
gtttccaatt ccttccctgg ctcatc 26

<210> SEQ ID NO 331
<211> LENGTH: 25
<212> TYPE: DNA
<213> ORGANISM: Artificial Sequence
<220> FEATURE:
<223> OTHER INFORMATION: primer

<400> SEQUENCE: 331
gttgtctcgg tcgcctcgtc taatc                                        25

<210> SEQ ID NO 332
<211> LENGTH: 26
<212> TYPE: DNA
<213> ORGANISM: Artificial Sequence
<220> FEATURE:
<223> OTHER INFORMATION: primer

<400> SEQUENCE: 332
gttcagactc ctcagctgac ctagtc                                       26

<210> SEQ ID NO 333
<211> LENGTH: 25
<212> TYPE: DNA
<213> ORGANISM: Artificial Sequence
<220> FEATURE:
<223> OTHER INFORMATION: primer

<400> SEQUENCE: 333
gttaagtcag ctcgccactc gtagt                                        25

<210> SEQ ID NO 334
<211> LENGTH: 25
<212> TYPE: DNA
<213> ORGANISM: Artificial Sequence
<220> FEATURE:
<223> OTHER INFORMATION: primer

<400> SEQUENCE: 334
gtgtagagta ctcgagtcag taggc                                        25

<210> SEQ ID NO 335
<211> LENGTH: 25
<212> TYPE: DNA
<213> ORGANISM: Artificial Sequence
<220> FEATURE:
<223> OTHER INFORMATION: primer

<400> SEQUENCE: 335
gtggacagag gagtcgggaa caacg                                        25

<210> SEQ ID NO 336
<211> LENGTH: 25
<212> TYPE: DNA
<213> ORGANISM: Artificial Sequence
<220> FEATURE:
<223> OTHER INFORMATION: primer

<400> SEQUENCE: 336
gtgccttggg tacctgtgtc cgttg                                        25

<210> SEQ ID NO 337
<211> LENGTH: 25
<212> TYPE: DNA
<213> ORGANISM: Artificial Sequence
<220> FEATURE:

```
<223> OTHER INFORMATION: primer

<400> SEQUENCE: 337
gtgaacagta cgaagcaatc tgtga                                      25

<210> SEQ ID NO 338
<211> LENGTH: 25
<212> TYPE: DNA
<213> ORGANISM: Artificial Sequence
<220> FEATURE:
<223> OTHER INFORMATION: primer

<400> SEQUENCE: 338
gtctagctcg gagagcataa ggacg                                      25

<210> SEQ ID NO 339
<211> LENGTH: 25
<212> TYPE: DNA
<213> ORGANISM: Artificial Sequence
<220> FEATURE:
<223> OTHER INFORMATION: primer

<400> SEQUENCE: 339
gtcgtctcgg gcattactgg atagg                                      25

<210> SEQ ID NO 340
<211> LENGTH: 26
<212> TYPE: DNA
<213> ORGANISM: Artificial Sequence
<220> FEATURE:
<223> OTHER INFORMATION: primer

<400> SEQUENCE: 340
gtccccttaa cctgatctgt cccatg                                     26

<210> SEQ ID NO 341
<211> LENGTH: 25
<212> TYPE: DNA
<213> ORGANISM: Artificial Sequence
<220> FEATURE:
<223> OTHER INFORMATION: primer

<400> SEQUENCE: 341
gtcagtgcga gtccagtttg actga                                      25

<210> SEQ ID NO 342
<211> LENGTH: 24
<212> TYPE: DNA
<213> ORGANISM: Artificial Sequence
<220> FEATURE:
<223> OTHER INFORMATION: primer

<400> SEQUENCE: 342
gtatggtggc caaccacagc cttc                                       24

<210> SEQ ID NO 343
<211> LENGTH: 25
<212> TYPE: DNA
<213> ORGANISM: Artificial Sequence
<220> FEATURE:
<223> OTHER INFORMATION: primer

<400> SEQUENCE: 343
gtagtgagat gaggtgtacg actgc                                      25
```

<210> SEQ ID NO 344
<211> LENGTH: 25
<212> TYPE: DNA
<213> ORGANISM: Artificial Sequence
<220> FEATURE:
<223> OTHER INFORMATION: primer

<400> SEQUENCE: 344
gtactgtcaa tgcgccagtt gtcta                                    25

<210> SEQ ID NO 345
<211> LENGTH: 25
<212> TYPE: DNA
<213> ORGANISM: Artificial Sequence
<220> FEATURE:
<223> OTHER INFORMATION: primer

<400> SEQUENCE: 345
gtaagcacca acacctagtg gcatc                                    25

<210> SEQ ID NO 346
<211> LENGTH: 25
<212> TYPE: DNA
<213> ORGANISM: Artificial Sequence
<220> FEATURE:
<223> OTHER INFORMATION: primer

<400> SEQUENCE: 346
ggttgatctg tagagcggga ggtct                                    25

<210> SEQ ID NO 347
<211> LENGTH: 25
<212> TYPE: DNA
<213> ORGANISM: Artificial Sequence
<220> FEATURE:
<223> OTHER INFORMATION: primer

<400> SEQUENCE: 347
ggtgtggcta agggtgctgc cacgc                                    25

<210> SEQ ID NO 348
<211> LENGTH: 25
<212> TYPE: DNA
<213> ORGANISM: Artificial Sequence
<220> FEATURE:
<223> OTHER INFORMATION: primer

<400> SEQUENCE: 348
ggtcatgaga ctccagccga aacct                                    25

<210> SEQ ID NO 349
<211> LENGTH: 25
<212> TYPE: DNA
<213> ORGANISM: Artificial Sequence
<220> FEATURE:
<223> OTHER INFORMATION: primer

<400> SEQUENCE: 349
ggtaagtgta gggacgacct gcaga                                    25

<210> SEQ ID NO 350
<211> LENGTH: 25
<212> TYPE: DNA
<213> ORGANISM: Artificial Sequence
<220> FEATURE:
<223> OTHER INFORMATION: primer

<400> SEQUENCE: 350
gggtggcaac ggcatagctg ataca                                                   25

<210> SEQ ID NO 351
<211> LENGTH: 26
<212> TYPE: DNA
<213> ORGANISM: Artificial Sequence
<220> FEATURE:
<223> OTHER INFORMATION: primer

<400> SEQUENCE: 351
gggggatgct gaggtatgag gcaacg                                                  26

<210> SEQ ID NO 352
<211> LENGTH: 25
<212> TYPE: DNA
<213> ORGANISM: Artificial Sequence
<220> FEATURE:
<223> OTHER INFORMATION: primer

<400> SEQUENCE: 352
gggcacgtca tttggcctgt ctgct                                                   25

<210> SEQ ID NO 353
<211> LENGTH: 25
<212> TYPE: DNA
<213> ORGANISM: Artificial Sequence
<220> FEATURE:
<223> OTHER INFORMATION: primer

<400> SEQUENCE: 353
gggagactca cgtgctcgaa ctgct                                                   25

<210> SEQ ID NO 354
<211> LENGTH: 25
<212> TYPE: DNA
<213> ORGANISM: Artificial Sequence
<220> FEATURE:
<223> OTHER INFORMATION: primer

<400> SEQUENCE: 354
ggctagtcgg catgtggcac atctc                                                   25

<210> SEQ ID NO 355
<211> LENGTH: 25
<212> TYPE: DNA
<213> ORGANISM: Artificial Sequence
<220> FEATURE:
<223> OTHER INFORMATION: primer

<400> SEQUENCE: 355
ggcgactcgg tagacagccg ctaac                                                   25

<210> SEQ ID NO 356
<211> LENGTH: 26
<212> TYPE: DNA
<213> ORGANISM: Artificial Sequence
<220> FEATURE:
<223> OTHER INFORMATION: primer

<400> SEQUENCE: 356
ggccctggga cacggtcact attcac                                                  26

<210> SEQ ID NO 357
<211> LENGTH: 25

```
<212> TYPE: DNA
<213> ORGANISM: Artificial Sequence
<220> FEATURE:
<223> OTHER INFORMATION: primer

<400> SEQUENCE: 357
ggcaaccctt ggaacgctgt acaca                                                25

<210> SEQ ID NO 358
<211> LENGTH: 25
<212> TYPE: DNA
<213> ORGANISM: Artificial Sequence
<220> FEATURE:
<223> OTHER INFORMATION: primer

<400> SEQUENCE: 358
ggattccgga cacgtagtga gacgt                                                25

<210> SEQ ID NO 359
<211> LENGTH: 25
<212> TYPE: DNA
<213> ORGANISM: Artificial Sequence
<220> FEATURE:
<223> OTHER INFORMATION: primer

<400> SEQUENCE: 359
ggagtgcctt gcactcttac ctagc                                                25

<210> SEQ ID NO 360
<211> LENGTH: 25
<212> TYPE: DNA
<213> ORGANISM: Artificial Sequence
<220> FEATURE:
<223> OTHER INFORMATION: primer

<400> SEQUENCE: 360
ggactagcca gtatcgtgca cttgg                                                25

<210> SEQ ID NO 361
<211> LENGTH: 25
<212> TYPE: DNA
<213> ORGANISM: Artificial Sequence
<220> FEATURE:
<223> OTHER INFORMATION: primer

<400> SEQUENCE: 361
ggaaaagctt accaccctac acgaa                                                25

<210> SEQ ID NO 362
<211> LENGTH: 25
<212> TYPE: DNA
<213> ORGANISM: Artificial Sequence
<220> FEATURE:
<223> OTHER INFORMATION: primer

<400> SEQUENCE: 362
gcttaggatg atgacatggg tcgaa                                                25

<210> SEQ ID NO 363
<211> LENGTH: 25
<212> TYPE: DNA
<213> ORGANISM: Artificial Sequence
<220> FEATURE:
<223> OTHER INFORMATION: primer

<400> SEQUENCE: 363
```
gctgaacctc catgacaagt cctcc                                       25

<210> SEQ ID NO 364
<211> LENGTH: 25
<212> TYPE: DNA
<213> ORGANISM: Artificial Sequence
<220> FEATURE:
<223> OTHER INFORMATION: primer

<400> SEQUENCE: 364
gctcaacacc gtgggacaga catct                                       25

<210> SEQ ID NO 365
<211> LENGTH: 25
<212> TYPE: DNA
<213> ORGANISM: Artificial Sequence
<220> FEATURE:
<223> OTHER INFORMATION: primer

<400> SEQUENCE: 365
gctaccacgg aacatacagg gcatt                                       25

<210> SEQ ID NO 366
<211> LENGTH: 25
<212> TYPE: DNA
<213> ORGANISM: Artificial Sequence
<220> FEATURE:
<223> OTHER INFORMATION: primer

<400> SEQUENCE: 366
gcgtcatgag cgtggagcta agcat                                       25

<210> SEQ ID NO 367
<211> LENGTH: 25
<212> TYPE: DNA
<213> ORGANISM: Artificial Sequence
<220> FEATURE:
<223> OTHER INFORMATION: primer

<400> SEQUENCE: 367
gcggcatctg tcacaaggta cgagg                                       25

<210> SEQ ID NO 368
<211> LENGTH: 25
<212> TYPE: DNA
<213> ORGANISM: Artificial Sequence
<220> FEATURE:
<223> OTHER INFORMATION: primer

<400> SEQUENCE: 368
gcgcaggaga tggaacgctc gcaca                                       25

<210> SEQ ID NO 369
<211> LENGTH: 25
<212> TYPE: DNA
<213> ORGANISM: Artificial Sequence
<220> FEATURE:
<223> OTHER INFORMATION: primer

<400> SEQUENCE: 369
gcgatctgtg tcctcgacca gcatc                                       25

<210> SEQ ID NO 370
<211> LENGTH: 25
<212> TYPE: DNA
<213> ORGANISM: Artificial Sequence

```
<220> FEATURE:
<223> OTHER INFORMATION: primer

<400> SEQUENCE: 370
gcctaactcc aggtggaagc tggtt                                              25

<210> SEQ ID NO 371
<211> LENGTH: 25
<212> TYPE: DNA
<213> ORGANISM: Artificial Sequence
<220> FEATURE:
<223> OTHER INFORMATION: primer

<400> SEQUENCE: 371
gccgcagact cacatcgaac gtcac                                              25

<210> SEQ ID NO 372
<211> LENGTH: 25
<212> TYPE: DNA
<213> ORGANISM: Artificial Sequence
<220> FEATURE:
<223> OTHER INFORMATION: primer

<400> SEQUENCE: 372
gccctgtaac tccgaatggg acacc                                              25

<210> SEQ ID NO 373
<211> LENGTH: 25
<212> TYPE: DNA
<213> ORGANISM: Artificial Sequence
<220> FEATURE:
<223> OTHER INFORMATION: primer

<400> SEQUENCE: 373
gccagttgat gctctccctc acctg                                              25

<210> SEQ ID NO 374
<211> LENGTH: 25
<212> TYPE: DNA
<213> ORGANISM: Artificial Sequence
<220> FEATURE:
<223> OTHER INFORMATION: primer

<400> SEQUENCE: 374
gcatgagtct gccaacaagg tcgag                                              25

<210> SEQ ID NO 375
<211> LENGTH: 25
<212> TYPE: DNA
<213> ORGANISM: Artificial Sequence
<220> FEATURE:
<223> OTHER INFORMATION: primer

<400> SEQUENCE: 375
gcaggttgtg aggaaccgca atgca                                              25

<210> SEQ ID NO 376
<211> LENGTH: 25
<212> TYPE: DNA
<213> ORGANISM: Artificial Sequence
<220> FEATURE:
<223> OTHER INFORMATION: primer

<400> SEQUENCE: 376
gcacacctca gtgaacagct ctcag                                              25
```

<210> SEQ ID NO 377
<211> LENGTH: 25
<212> TYPE: DNA
<213> ORGANISM: Artificial Sequence
<220> FEATURE:
<223> OTHER INFORMATION: primer

<400> SEQUENCE: 377
gcaagatcca ggtcgctatc cactg                                  25

<210> SEQ ID NO 378
<211> LENGTH: 25
<212> TYPE: DNA
<213> ORGANISM: Artificial Sequence
<220> FEATURE:
<223> OTHER INFORMATION: primer

<400> SEQUENCE: 378
gattccacat gcgatctcaa atcca                                  25

<210> SEQ ID NO 379
<211> LENGTH: 25
<212> TYPE: DNA
<213> ORGANISM: Artificial Sequence
<220> FEATURE:
<223> OTHER INFORMATION: primer

<400> SEQUENCE: 379
gatgttgtcg tgacgaccta gacgc                                  25

<210> SEQ ID NO 380
<211> LENGTH: 25
<212> TYPE: DNA
<213> ORGANISM: Artificial Sequence
<220> FEATURE:
<223> OTHER INFORMATION: primer

<400> SEQUENCE: 380
gatcttgagg cgtctaatca tcggg                                  25

<210> SEQ ID NO 381
<211> LENGTH: 25
<212> TYPE: DNA
<213> ORGANISM: Artificial Sequence
<220> FEATURE:
<223> OTHER INFORMATION: primer

<400> SEQUENCE: 381
gatacgctca gcaatcgcca ctatc                                  25

<210> SEQ ID NO 382
<211> LENGTH: 25
<212> TYPE: DNA
<213> ORGANISM: Artificial Sequence
<220> FEATURE:
<223> OTHER INFORMATION: primer

<400> SEQUENCE: 382
gagtcattat cacacatgag ccgcc                                  25

<210> SEQ ID NO 383
<211> LENGTH: 25
<212> TYPE: DNA
<213> ORGANISM: Artificial Sequence
<220> FEATURE:
<223> OTHER INFORMATION: primer

<400> SEQUENCE: 383
gagggagggg caagagaaaa ccacc 25

<210> SEQ ID NO 384
<211> LENGTH: 25
<212> TYPE: DNA
<213> ORGANISM: Artificial Sequence
<220> FEATURE:
<223> OTHER INFORMATION: primer

<400> SEQUENCE: 384
gagcaagtcc agcgagctgt cttcc 25

<210> SEQ ID NO 385
<211> LENGTH: 25
<212> TYPE: DNA
<213> ORGANISM: Artificial Sequence
<220> FEATURE:
<223> OTHER INFORMATION: primer

<400> SEQUENCE: 385
gagaaggccg cttctcagta aggtc 25

<210> SEQ ID NO 386
<211> LENGTH: 25
<212> TYPE: DNA
<213> ORGANISM: Artificial Sequence
<220> FEATURE:
<223> OTHER INFORMATION: primer

<400> SEQUENCE: 386
gactgtgtac gcagagaacc ccaca 25

<210> SEQ ID NO 387
<211> LENGTH: 25
<212> TYPE: DNA
<213> ORGANISM: Artificial Sequence
<220> FEATURE:
<223> OTHER INFORMATION: primer

<400> SEQUENCE: 387
gacgggtctc ctggacaaca gttcc 25

<210> SEQ ID NO 388
<211> LENGTH: 25
<212> TYPE: DNA
<213> ORGANISM: Artificial Sequence
<220> FEATURE:
<223> OTHER INFORMATION: primer

<400> SEQUENCE: 388
gacccagttg catcactctg gcatc 25

<210> SEQ ID NO 389
<211> LENGTH: 25
<212> TYPE: DNA
<213> ORGANISM: Artificial Sequence
<220> FEATURE:
<223> OTHER INFORMATION: primer

<400> SEQUENCE: 389
gacaaagacc gaatcgcgaa atgag 25

<210> SEQ ID NO 390

```
<211> LENGTH: 25
<212> TYPE: DNA
<213> ORGANISM: Artificial Sequence
<220> FEATURE:
<223> OTHER INFORMATION: primer

<400> SEQUENCE: 390
gaatgttcag accacccggt tcaca                                              25

<210> SEQ ID NO 391
<211> LENGTH: 25
<212> TYPE: DNA
<213> ORGANISM: Artificial Sequence
<220> FEATURE:
<223> OTHER INFORMATION: primer

<400> SEQUENCE: 391
gaagtgctac agcaggatcc tctgg                                              25

<210> SEQ ID NO 392
<211> LENGTH: 25
<212> TYPE: DNA
<213> ORGANISM: Artificial Sequence
<220> FEATURE:
<223> OTHER INFORMATION: primer

<400> SEQUENCE: 392
gaacgatacc tagaccggca gcaac                                              25

<210> SEQ ID NO 393
<211> LENGTH: 26
<212> TYPE: DNA
<213> ORGANISM: Artificial Sequence
<220> FEATURE:
<223> OTHER INFORMATION: primer

<400> SEQUENCE: 393
gaaacactga gagctaggaa acccac                                             26

<210> SEQ ID NO 394
<211> LENGTH: 25
<212> TYPE: DNA
<213> ORGANISM: Artificial Sequence
<220> FEATURE:
<223> OTHER INFORMATION: primer

<400> SEQUENCE: 394
ctttgggata aatcctgatg ccgtc                                              25

<210> SEQ ID NO 395
<211> LENGTH: 25
<212> TYPE: DNA
<213> ORGANISM: Artificial Sequence
<220> FEATURE:
<223> OTHER INFORMATION: primer

<400> SEQUENCE: 395
cttgcagtct caaccttgc ctgtc                                               25

<210> SEQ ID NO 396
<211> LENGTH: 25
<212> TYPE: DNA
<213> ORGANISM: Artificial Sequence
<220> FEATURE:
<223> OTHER INFORMATION: primer

<400> SEQUENCE: 396
```
cttctcacgg agctcaccta agcac 25

<210> SEQ ID NO 397
<211> LENGTH: 25
<212> TYPE: DNA
<213> ORGANISM: Artificial Sequence
<220> FEATURE:
<223> OTHER INFORMATION: primer

<400> SEQUENCE: 397
cttagatttg gagctgacct gatgc 25

<210> SEQ ID NO 398
<211> LENGTH: 25
<212> TYPE: DNA
<213> ORGANISM: Artificial Sequence
<220> FEATURE:
<223> OTHER INFORMATION: primer

<400> SEQUENCE: 398
ctgtgatgta tctatgaaat cgagt 25

<210> SEQ ID NO 399
<211> LENGTH: 25
<212> TYPE: DNA
<213> ORGANISM: Artificial Sequence
<220> FEATURE:
<223> OTHER INFORMATION: primer

<400> SEQUENCE: 399
ctggcaaccc cgtaactccg ttcag 25

<210> SEQ ID NO 400
<211> LENGTH: 25
<212> TYPE: DNA
<213> ORGANISM: Artificial Sequence
<220> FEATURE:
<223> OTHER INFORMATION: primer

<400> SEQUENCE: 400
ctgccgtcga cttgtgcgac cttcg 25

<210> SEQ ID NO 401
<211> LENGTH: 25
<212> TYPE: DNA
<213> ORGANISM: Artificial Sequence
<220> FEATURE:
<223> OTHER INFORMATION: primer

<400> SEQUENCE: 401
ctgaaacacg cacaaccagg tcatg 25

<210> SEQ ID NO 402
<211> LENGTH: 25
<212> TYPE: DNA
<213> ORGANISM: Artificial Sequence
<220> FEATURE:
<223> OTHER INFORMATION: primer

<400> SEQUENCE: 402
ctcttcgtct ccagctactg gactc 25

<210> SEQ ID NO 403
<211> LENGTH: 25
<212> TYPE: DNA

<213> ORGANISM: Artificial Sequence
<220> FEATURE:
<223> OTHER INFORMATION: primer

<400> SEQUENCE: 403
ctcgtacgct caacacttac agacg                                    25

<210> SEQ ID NO 404
<211> LENGTH: 25
<212> TYPE: DNA
<213> ORGANISM: Artificial Sequence
<220> FEATURE:
<223> OTHER INFORMATION: primer

<400> SEQUENCE: 404
ctccgggcaa cagcacctac tatac                                    25

<210> SEQ ID NO 405
<211> LENGTH: 25
<212> TYPE: DNA
<213> ORGANISM: Artificial Sequence
<220> FEATURE:
<223> OTHER INFORMATION: primer

<400> SEQUENCE: 405
ctcacgtctg accagtcttc cactc                                    25

<210> SEQ ID NO 406
<211> LENGTH: 25
<212> TYPE: DNA
<213> ORGANISM: Artificial Sequence
<220> FEATURE:
<223> OTHER INFORMATION: primer

<400> SEQUENCE: 406
ctatgggaga ggtgttttcc agtcg                                    25

<210> SEQ ID NO 407
<211> LENGTH: 25
<212> TYPE: DNA
<213> ORGANISM: Artificial Sequence
<220> FEATURE:
<223> OTHER INFORMATION: primer

<400> SEQUENCE: 407
ctaggaccca agtagtcgtc gcgaa                                    25

<210> SEQ ID NO 408
<211> LENGTH: 25
<212> TYPE: DNA
<213> ORGANISM: Artificial Sequence
<220> FEATURE:
<223> OTHER INFORMATION: primer

<400> SEQUENCE: 408
ctaccaccat ggtgaatcag gctcc                                    25

<210> SEQ ID NO 409
<211> LENGTH: 25
<212> TYPE: DNA
<213> ORGANISM: Artificial Sequence
<220> FEATURE:
<223> OTHER INFORMATION: primer

<400> SEQUENCE: 409
ctaaacctga gtgtgggaag gtcga                                    25

<210> SEQ ID NO 410
<211> LENGTH: 25
<212> TYPE: DNA
<213> ORGANISM: Artificial Sequence
<220> FEATURE:
<223> OTHER INFORMATION: primer

<400> SEQUENCE: 410
cgtttgcgaa actgtctgtc ggaag                                    25

<210> SEQ ID NO 411
<211> LENGTH: 25
<212> TYPE: DNA
<213> ORGANISM: Artificial Sequence
<220> FEATURE:
<223> OTHER INFORMATION: primer

<400> SEQUENCE: 411
cgtggctttg gcaatcctca agcag                                    25

<210> SEQ ID NO 412
<211> LENGTH: 25
<212> TYPE: DNA
<213> ORGANISM: Artificial Sequence
<220> FEATURE:
<223> OTHER INFORMATION: primer

<400> SEQUENCE: 412
cgtctcgctc ctgactcatc gaaca                                    25

<210> SEQ ID NO 413
<211> LENGTH: 25
<212> TYPE: DNA
<213> ORGANISM: Artificial Sequence
<220> FEATURE:
<223> OTHER INFORMATION: primer

<400> SEQUENCE: 413
cgtacagagt cggtaccatc tcgac                                    25

<210> SEQ ID NO 414
<211> LENGTH: 26
<212> TYPE: DNA
<213> ORGANISM: Artificial Sequence
<220> FEATURE:
<223> OTHER INFORMATION: primer

<400> SEQUENCE: 414
cggtgcggac aaaggatatg ttgatc                                   26

<210> SEQ ID NO 415
<211> LENGTH: 26
<212> TYPE: DNA
<213> ORGANISM: Artificial Sequence
<220> FEATURE:
<223> OTHER INFORMATION: primer

<400> SEQUENCE: 415
cgggcactag gaccttttgt cggaag                                   26

<210> SEQ ID NO 416
<211> LENGTH: 25
<212> TYPE: DNA
<213> ORGANISM: Artificial Sequence
<220> FEATURE:

<223> OTHER INFORMATION: primer

<400> SEQUENCE: 416
cggctaagag cggtgctagc gtgag                               25

<210> SEQ ID NO 417
<211> LENGTH: 25
<212> TYPE: DNA
<213> ORGANISM: Artificial Sequence
<220> FEATURE:
<223> OTHER INFORMATION: primer

<400> SEQUENCE: 417
cggaggagcc tcgagattcg ttggt                               25

<210> SEQ ID NO 418
<211> LENGTH: 25
<212> TYPE: DNA
<213> ORGANISM: Artificial Sequence
<220> FEATURE:
<223> OTHER INFORMATION: primer

<400> SEQUENCE: 418
cgctgcctgg tctttcagca tggac                               25

<210> SEQ ID NO 419
<211> LENGTH: 25
<212> TYPE: DNA
<213> ORGANISM: Artificial Sequence
<220> FEATURE:
<223> OTHER INFORMATION: primer

<400> SEQUENCE: 419
cgcgcttgtc agccgaacgt ctgtc                               25

<210> SEQ ID NO 420
<211> LENGTH: 25
<212> TYPE: DNA
<213> ORGANISM: Artificial Sequence
<220> FEATURE:
<223> OTHER INFORMATION: primer

<400> SEQUENCE: 420
cgccacgctg caaggcggat aacag                               25

<210> SEQ ID NO 421
<211> LENGTH: 26
<212> TYPE: DNA
<213> ORGANISM: Artificial Sequence
<220> FEATURE:
<223> OTHER INFORMATION: primer

<400> SEQUENCE: 421
cgcacagcac atagacaggt gcctca                              26

<210> SEQ ID NO 422
<211> LENGTH: 25
<212> TYPE: DNA
<213> ORGANISM: Artificial Sequence
<220> FEATURE:
<223> OTHER INFORMATION: primer

<400> SEQUENCE: 422
cgatatcatc acgttgcacc aaggg                               25

<210> SEQ ID NO 423
<211> LENGTH: 25
<212> TYPE: DNA
<213> ORGANISM: Artificial Sequence
<220> FEATURE:
<223> OTHER INFORMATION: primer

<400> SEQUENCE: 423
cgagtccaga ggaacgtacg accct                                    25

<210> SEQ ID NO 424
<211> LENGTH: 25
<212> TYPE: DNA
<213> ORGANISM: Artificial Sequence
<220> FEATURE:
<223> OTHER INFORMATION: primer

<400> SEQUENCE: 424
cgacgaacag gagacagagc gagca                                    25

<210> SEQ ID NO 425
<211> LENGTH: 25
<212> TYPE: DNA
<213> ORGANISM: Artificial Sequence
<220> FEATURE:
<223> OTHER INFORMATION: primer

<400> SEQUENCE: 425
cgaactacgg tcagtacgac gtgga                                    25

<210> SEQ ID NO 426
<211> LENGTH: 25
<212> TYPE: DNA
<213> ORGANISM: Artificial Sequence
<220> FEATURE:
<223> OTHER INFORMATION: primer

<400> SEQUENCE: 426
ccttaaatta ttcgctggag cgctg                                    25

<210> SEQ ID NO 427
<211> LENGTH: 25
<212> TYPE: DNA
<213> ORGANISM: Artificial Sequence
<220> FEATURE:
<223> OTHER INFORMATION: primer

<400> SEQUENCE: 427
cctgcagctg cggtgtagca tacag                                    25

<210> SEQ ID NO 428
<211> LENGTH: 25
<212> TYPE: DNA
<213> ORGANISM: Artificial Sequence
<220> FEATURE:
<223> OTHER INFORMATION: primer

<400> SEQUENCE: 428
cctcactcgt aatcgttcca gacgc                                    25

<210> SEQ ID NO 429
<211> LENGTH: 25
<212> TYPE: DNA
<213> ORGANISM: Artificial Sequence
<220> FEATURE:
<223> OTHER INFORMATION: primer

```
<400> SEQUENCE: 429
cctaatacgt gttatggccg gaaag                                  25

<210> SEQ ID NO 430
<211> LENGTH: 25
<212> TYPE: DNA
<213> ORGANISM: Artificial Sequence
<220> FEATURE:
<223> OTHER INFORMATION: primer

<400> SEQUENCE: 430
ccgtgctccg aagttaggtt gggaa                                  25

<210> SEQ ID NO 431
<211> LENGTH: 25
<212> TYPE: DNA
<213> ORGANISM: Artificial Sequence
<220> FEATURE:
<223> OTHER INFORMATION: primer

<400> SEQUENCE: 431
ccgggttcac ccttgcaacg atagc                                  25

<210> SEQ ID NO 432
<211> LENGTH: 25
<212> TYPE: DNA
<213> ORGANISM: Artificial Sequence
<220> FEATURE:
<223> OTHER INFORMATION: primer

<400> SEQUENCE: 432
ccgcagggag actccctact cggat                                  25

<210> SEQ ID NO 433
<211> LENGTH: 25
<212> TYPE: DNA
<213> ORGANISM: Artificial Sequence
<220> FEATURE:
<223> OTHER INFORMATION: primer

<400> SEQUENCE: 433
ccgagagttg ccagacatgt accag                                  25

<210> SEQ ID NO 434
<211> LENGTH: 25
<212> TYPE: DNA
<213> ORGANISM: Artificial Sequence
<220> FEATURE:
<223> OTHER INFORMATION: primer

<400> SEQUENCE: 434
ccctgccagt ttcttcccac aagca                                  25

<210> SEQ ID NO 435
<211> LENGTH: 25
<212> TYPE: DNA
<213> ORGANISM: Artificial Sequence
<220> FEATURE:
<223> OTHER INFORMATION: primer

<400> SEQUENCE: 435
cccggtgaac gagtatgcga cccag                                  25

<210> SEQ ID NO 436
<211> LENGTH: 25
```

```
<212> TYPE: DNA
<213> ORGANISM: Artificial Sequence
<220> FEATURE:
<223> OTHER INFORMATION: primer

<400> SEQUENCE: 436
ccccttgcct gtattgcaac gccta                                    25

<210> SEQ ID NO 437
<211> LENGTH: 25
<212> TYPE: DNA
<213> ORGANISM: Artificial Sequence
<220> FEATURE:
<223> OTHER INFORMATION: primer

<400> SEQUENCE: 437
cccatgagct gctggaagat cagga                                    25

<210> SEQ ID NO 438
<211> LENGTH: 26
<212> TYPE: DNA
<213> ORGANISM: Artificial Sequence
<220> FEATURE:
<223> OTHER INFORMATION: primer

<400> SEQUENCE: 438
ccatagtagg ggaatacgca acatga                                   26

<210> SEQ ID NO 439
<211> LENGTH: 25
<212> TYPE: DNA
<213> ORGANISM: Artificial Sequence
<220> FEATURE:
<223> OTHER INFORMATION: primer

<400> SEQUENCE: 439
ccaggatcca cttcgaggag tgacc                                    25

<210> SEQ ID NO 440
<211> LENGTH: 25
<212> TYPE: DNA
<213> ORGANISM: Artificial Sequence
<220> FEATURE:
<223> OTHER INFORMATION: primer

<400> SEQUENCE: 440
ccacgtacca cattcgctcg acacg                                    25

<210> SEQ ID NO 441
<211> LENGTH: 25
<212> TYPE: DNA
<213> ORGANISM: Artificial Sequence
<220> FEATURE:
<223> OTHER INFORMATION: primer

<400> SEQUENCE: 441
ccaacatttc cctctcgaat tggca                                    25

<210> SEQ ID NO 442
<211> LENGTH: 25
<212> TYPE: DNA
<213> ORGANISM: Artificial Sequence
<220> FEATURE:
<223> OTHER INFORMATION: primer

<400> SEQUENCE: 442
```

-continued catttccgat gtatcgccga gatgt                                           25

<210> SEQ ID NO 443
<211> LENGTH: 25
<212> TYPE: DNA
<213> ORGANISM: Artificial Sequence
<220> FEATURE:
<223> OTHER INFORMATION: primer

<400> SEQUENCE: 443
catgaccaac tgagaaggaa ggtca                                           25

<210> SEQ ID NO 444
<211> LENGTH: 26
<212> TYPE: DNA
<213> ORGANISM: Artificial Sequence
<220> FEATURE:
<223> OTHER INFORMATION: primer

<400> SEQUENCE: 444
catccgaatc ctagtcacca gtactc                                          26

<210> SEQ ID NO 445
<211> LENGTH: 25
<212> TYPE: DNA
<213> ORGANISM: Artificial Sequence
<220> FEATURE:
<223> OTHER INFORMATION: primer

<400> SEQUENCE: 445
cataggaagg atgcactcct accga                                           25

<210> SEQ ID NO 446
<211> LENGTH: 25
<212> TYPE: DNA
<213> ORGANISM: Artificial Sequence
<220> FEATURE:
<223> OTHER INFORMATION: primer

<400> SEQUENCE: 446
cagtaatagc tccctccctc accac                                           25

<210> SEQ ID NO 447
<211> LENGTH: 25
<212> TYPE: DNA
<213> ORGANISM: Artificial Sequence
<220> FEATURE:
<223> OTHER INFORMATION: primer

<400> SEQUENCE: 447
cagggaggac catctgctac atctc                                           25

<210> SEQ ID NO 448
<211> LENGTH: 25
<212> TYPE: DNA
<213> ORGANISM: Artificial Sequence
<220> FEATURE:
<223> OTHER INFORMATION: primer

<400> SEQUENCE: 448
cagcattact tcgcgggtcc taatc                                           25

<210> SEQ ID NO 449
<211> LENGTH: 25
<212> TYPE: DNA
<213> ORGANISM: Artificial Sequence

```
<220> FEATURE:
<223> OTHER INFORMATION: primer

<400> SEQUENCE: 449
cagacagcga caacaaaagg ctatg                                    25

<210> SEQ ID NO 450
<211> LENGTH: 25
<212> TYPE: DNA
<213> ORGANISM: Artificial Sequence
<220> FEATURE:
<223> OTHER INFORMATION: primer

<400> SEQUENCE: 450
cactgcgttg acacctcatc actag                                    25

<210> SEQ ID NO 451
<211> LENGTH: 25
<212> TYPE: DNA
<213> ORGANISM: Artificial Sequence
<220> FEATURE:
<223> OTHER INFORMATION: primer

<400> SEQUENCE: 451
cacgtctacc actcaccgtc cgaac                                    25

<210> SEQ ID NO 452
<211> LENGTH: 25
<212> TYPE: DNA
<213> ORGANISM: Artificial Sequence
<220> FEATURE:
<223> OTHER INFORMATION: primer

<400> SEQUENCE: 452
caccagcatg cttctgagga agtgc                                    25

<210> SEQ ID NO 453
<211> LENGTH: 26
<212> TYPE: DNA
<213> ORGANISM: Artificial Sequence
<220> FEATURE:
<223> OTHER INFORMATION: primer

<400> SEQUENCE: 453
cacaagtcat cgtggcttgt gttaca                                   26

<210> SEQ ID NO 454
<211> LENGTH: 25
<212> TYPE: DNA
<213> ORGANISM: Artificial Sequence
<220> FEATURE:
<223> OTHER INFORMATION: primer

<400> SEQUENCE: 454
caatgacact tggctatggg tccca                                    25

<210> SEQ ID NO 455
<211> LENGTH: 25
<212> TYPE: DNA
<213> ORGANISM: Artificial Sequence
<220> FEATURE:
<223> OTHER INFORMATION: primer

<400> SEQUENCE: 455
caagcacagt acgtgagagc tccaa                                    25
```

<210> SEQ ID NO 456
<211> LENGTH: 25
<212> TYPE: DNA
<213> ORGANISM: Artificial Sequence
<220> FEATURE:
<223> OTHER INFORMATION: primer

<400> SEQUENCE: 456
caacgaagca acccaacagg accag                                          25

<210> SEQ ID NO 457
<211> LENGTH: 26
<212> TYPE: DNA
<213> ORGANISM: Artificial Sequence
<220> FEATURE:
<223> OTHER INFORMATION: primer

<400> SEQUENCE: 457
caaaagagac tcaccaggaa gcagca                                         26

<210> SEQ ID NO 458
<211> LENGTH: 25
<212> TYPE: DNA
<213> ORGANISM: Artificial Sequence
<220> FEATURE:
<223> OTHER INFORMATION: primer

<400> SEQUENCE: 458
attttgtggt acagcagaag gctga                                          25

<210> SEQ ID NO 459
<211> LENGTH: 25
<212> TYPE: DNA
<213> ORGANISM: Artificial Sequence
<220> FEATURE:
<223> OTHER INFORMATION: primer

<400> SEQUENCE: 459
attgtccaag ttcgccaaag cagga                                          25

<210> SEQ ID NO 460
<211> LENGTH: 25
<212> TYPE: DNA
<213> ORGANISM: Artificial Sequence
<220> FEATURE:
<223> OTHER INFORMATION: primer

<400> SEQUENCE: 460
attccgtgcg attctggaat gcttc                                          25

<210> SEQ ID NO 461
<211> LENGTH: 25
<212> TYPE: DNA
<213> ORGANISM: Artificial Sequence
<220> FEATURE:
<223> OTHER INFORMATION: primer

<400> SEQUENCE: 461
attaactcgg aatggtggga gagga                                          25

<210> SEQ ID NO 462
<211> LENGTH: 25
<212> TYPE: DNA
<213> ORGANISM: Artificial Sequence
<220> FEATURE:
<223> OTHER INFORMATION: primer

<400> SEQUENCE: 462
atgtagcaga ttctcgagga aacca                                              25

<210> SEQ ID NO 463
<211> LENGTH: 25
<212> TYPE: DNA
<213> ORGANISM: Artificial Sequence
<220> FEATURE:
<223> OTHER INFORMATION: primer

<400> SEQUENCE: 463
atggacctct ctggtctggt cagca                                              25

<210> SEQ ID NO 464
<211> LENGTH: 26
<212> TYPE: DNA
<213> ORGANISM: Artificial Sequence
<220> FEATURE:
<223> OTHER INFORMATION: primer

<400> SEQUENCE: 464
atgctgacaa gtggatgagt gagcag                                             26

<210> SEQ ID NO 465
<211> LENGTH: 25
<212> TYPE: DNA
<213> ORGANISM: Artificial Sequence
<220> FEATURE:
<223> OTHER INFORMATION: primer

<400> SEQUENCE: 465
atgaggattt ttcgaccgtg gtaca                                              25

<210> SEQ ID NO 466
<211> LENGTH: 25
<212> TYPE: DNA
<213> ORGANISM: Artificial Sequence
<220> FEATURE:
<223> OTHER INFORMATION: primer

<400> SEQUENCE: 466
atctgcctga gagctttact cacca                                              25

<210> SEQ ID NO 467
<211> LENGTH: 25
<212> TYPE: DNA
<213> ORGANISM: Artificial Sequence
<220> FEATURE:
<223> OTHER INFORMATION: primer

<400> SEQUENCE: 467
atcggcttag cttctgcgat ggcac                                              25

<210> SEQ ID NO 468
<211> LENGTH: 25
<212> TYPE: DNA
<213> ORGANISM: Artificial Sequence
<220> FEATURE:
<223> OTHER INFORMATION: primer

<400> SEQUENCE: 468
atcccagcag tgtcaggtag cctca                                              25

<210> SEQ ID NO 469

```
-continued

<211> LENGTH: 25
<212> TYPE: DNA
<213> ORGANISM: Artificial Sequence
<220> FEATURE:
<223> OTHER INFORMATION: primer

<400> SEQUENCE: 469
atcaagacaa gaggttctgg cacca                                               25

<210> SEQ ID NO 470
<211> LENGTH: 25
<212> TYPE: DNA
<213> ORGANISM: Artificial Sequence
<220> FEATURE:
<223> OTHER INFORMATION: primer

<400> SEQUENCE: 470
atattggtgg gtctatcaag tcgca                                               25

<210> SEQ ID NO 471
<211> LENGTH: 25
<212> TYPE: DNA
<213> ORGANISM: Artificial Sequence
<220> FEATURE:
<223> OTHER INFORMATION: primer

<400> SEQUENCE: 471
atagtgtcgt agccactgat gctac                                               25

<210> SEQ ID NO 472
<211> LENGTH: 25
<212> TYPE: DNA
<213> ORGANISM: Artificial Sequence
<220> FEATURE:
<223> OTHER INFORMATION: primer

<400> SEQUENCE: 472
atactcatcc ctggcatcga tgctc                                               25

<210> SEQ ID NO 473
<211> LENGTH: 25
<212> TYPE: DNA
<213> ORGANISM: Artificial Sequence
<220> FEATURE:
<223> OTHER INFORMATION: primer

<400> SEQUENCE: 473
ataagaggtg ccttcccaga cagag                                               25

<210> SEQ ID NO 474
<211> LENGTH: 25
<212> TYPE: DNA
<213> ORGANISM: Artificial Sequence
<220> FEATURE:
<223> OTHER INFORMATION: primer

<400> SEQUENCE: 474
agttcgtctc tggagtcgtc ctctc                                               25

<210> SEQ ID NO 475
<211> LENGTH: 25
<212> TYPE: DNA
<213> ORGANISM: Artificial Sequence
<220> FEATURE:
<223> OTHER INFORMATION: primer

<400> SEQUENCE: 475
```
agtgtggagt cacggtctat ggatg                                          25

<210> SEQ ID NO 476
<211> LENGTH: 26
<212> TYPE: DNA
<213> ORGANISM: Artificial Sequence
<220> FEATURE:
<223> OTHER INFORMATION: primer

<400> SEQUENCE: 476
agtcagtctc ctggaatgac gtggac                                         26

<210> SEQ ID NO 477
<211> LENGTH: 25
<212> TYPE: DNA
<213> ORGANISM: Artificial Sequence
<220> FEATURE:
<223> OTHER INFORMATION: primer

<400> SEQUENCE: 477
agtaccagtg tcctcaccta gatcg                                          25

<210> SEQ ID NO 478
<211> LENGTH: 25
<212> TYPE: DNA
<213> ORGANISM: Artificial Sequence
<220> FEATURE:
<223> OTHER INFORMATION: primer

<400> SEQUENCE: 478
aggtagccta cgccagttgt ccttc                                          25

<210> SEQ ID NO 479
<211> LENGTH: 26
<212> TYPE: DNA
<213> ORGANISM: Artificial Sequence
<220> FEATURE:
<223> OTHER INFORMATION: primer

<400> SEQUENCE: 479
agggccttgt agaggatacg aacgac                                         26

<210> SEQ ID NO 480
<211> LENGTH: 25
<212> TYPE: DNA
<213> ORGANISM: Artificial Sequence
<220> FEATURE:
<223> OTHER INFORMATION: primer

<400> SEQUENCE: 480
aggcaggtag cacagccagg aactc                                          25

<210> SEQ ID NO 481
<211> LENGTH: 25
<212> TYPE: DNA
<213> ORGANISM: Artificial Sequence
<220> FEATURE:
<223> OTHER INFORMATION: primer

<400> SEQUENCE: 481
aggatcgtac acgatccatc agcag                                          25

<210> SEQ ID NO 482
<211> LENGTH: 25
<212> TYPE: DNA

```
<213> ORGANISM: Artificial Sequence
<220> FEATURE:
<223> OTHER INFORMATION: primer

<400> SEQUENCE: 482
agctgaaccc tctgccttcg aacac                                              25

<210> SEQ ID NO 483
<211> LENGTH: 26
<212> TYPE: DNA
<213> ORGANISM: Artificial Sequence
<220> FEATURE:
<223> OTHER INFORMATION: primer

<400> SEQUENCE: 483
agcgctcaac ctagacccct taaacc                                             26

<210> SEQ ID NO 484
<211> LENGTH: 25
<212> TYPE: DNA
<213> ORGANISM: Artificial Sequence
<220> FEATURE:
<223> OTHER INFORMATION: primer

<400> SEQUENCE: 484
agcccttagc aacgtcccag aggag                                              25

<210> SEQ ID NO 485
<211> LENGTH: 25
<212> TYPE: DNA
<213> ORGANISM: Artificial Sequence
<220> FEATURE:
<223> OTHER INFORMATION: primer

<400> SEQUENCE: 485
agcaaggaga tcactgcgtc tgctg                                              25

<210> SEQ ID NO 486
<211> LENGTH: 25
<212> TYPE: DNA
<213> ORGANISM: Artificial Sequence
<220> FEATURE:
<223> OTHER INFORMATION: primer

<400> SEQUENCE: 486
agatccagct gctcacttca tgctc                                              25

<210> SEQ ID NO 487
<211> LENGTH: 25
<212> TYPE: DNA
<213> ORGANISM: Artificial Sequence
<220> FEATURE:
<223> OTHER INFORMATION: primer

<400> SEQUENCE: 487
agagaccagt ctctactgag gccag                                              25

<210> SEQ ID NO 488
<211> LENGTH: 25
<212> TYPE: DNA
<213> ORGANISM: Artificial Sequence
<220> FEATURE:
<223> OTHER INFORMATION: primer

<400> SEQUENCE: 488
agacctattg cactagtgcc tgcca                                              25
```

<210> SEQ ID NO 489
<211> LENGTH: 25
<212> TYPE: DNA
<213> ORGANISM: Artificial Sequence
<220> FEATURE:
<223> OTHER INFORMATION: primer

<400> SEQUENCE: 489
agaatgcgga cacgacagga tgtag         25

<210> SEQ ID NO 490
<211> LENGTH: 25
<212> TYPE: DNA
<213> ORGANISM: Artificial Sequence
<220> FEATURE:
<223> OTHER INFORMATION: primer

<400> SEQUENCE: 490
acttccagtg ctacctcaga tccgt         25

<210> SEQ ID NO 491
<211> LENGTH: 25
<212> TYPE: DNA
<213> ORGANISM: Artificial Sequence
<220> FEATURE:
<223> OTHER INFORMATION: primer

<400> SEQUENCE: 491
actggaatcg agctgaggct tctca         25

<210> SEQ ID NO 492
<211> LENGTH: 25
<212> TYPE: DNA
<213> ORGANISM: Artificial Sequence
<220> FEATURE:
<223> OTHER INFORMATION: primer

<400> SEQUENCE: 492
actccaggcg aattaacctc aaacg         25

<210> SEQ ID NO 493
<211> LENGTH: 25
<212> TYPE: DNA
<213> ORGANISM: Artificial Sequence
<220> FEATURE:
<223> OTHER INFORMATION: primer

<400> SEQUENCE: 493
actagctcgg gtatttgcag tagca         25

<210> SEQ ID NO 494
<211> LENGTH: 25
<212> TYPE: DNA
<213> ORGANISM: Artificial Sequence
<220> FEATURE:
<223> OTHER INFORMATION: primer

<400> SEQUENCE: 494
acgttgagga gttacgtgca gacga         25

<210> SEQ ID NO 495
<211> LENGTH: 25
<212> TYPE: DNA
<213> ORGANISM: Artificial Sequence
<220> FEATURE:

```
<223> OTHER INFORMATION: primer

<400> SEQUENCE: 495
acggtgacag tcgcttgaac catcc                                     25

<210> SEQ ID NO 496
<211> LENGTH: 25
<212> TYPE: DNA
<213> ORGANISM: Artificial Sequence
<220> FEATURE:
<223> OTHER INFORMATION: primer

<400> SEQUENCE: 496
acgcacagac caccagctga gagtg                                     25

<210> SEQ ID NO 497
<211> LENGTH: 25
<212> TYPE: DNA
<213> ORGANISM: Artificial Sequence
<220> FEATURE:
<223> OTHER INFORMATION: primer

<400> SEQUENCE: 497
acgagtccat tcccatcaac caagc                                     25

<210> SEQ ID NO 498
<211> LENGTH: 26
<212> TYPE: DNA
<213> ORGANISM: Artificial Sequence
<220> FEATURE:
<223> OTHER INFORMATION: primer

<400> SEQUENCE: 498
acctgtacgt ctagtcttgc ttgcag                                    26

<210> SEQ ID NO 499
<211> LENGTH: 25
<212> TYPE: DNA
<213> ORGANISM: Artificial Sequence
<220> FEATURE:
<223> OTHER INFORMATION: primer

<400> SEQUENCE: 499
accggacact tgggagcttc atgga                                     25

<210> SEQ ID NO 500
<211> LENGTH: 25
<212> TYPE: DNA
<213> ORGANISM: Artificial Sequence
<220> FEATURE:
<223> OTHER INFORMATION: primer

<400> SEQUENCE: 500 acccctgcg tttaaccaat gtgca                                      25

<210> SEQ ID NO 501
<211> LENGTH: 25
<212> TYPE: DNA
<213> ORGANISM: Artificial Sequence
<220> FEATURE:
<223> OTHER INFORMATION: primer

<400> SEQUENCE: 501
accaatctac ctgcaatgat ctgca                                     25
```

```
<210> SEQ ID NO 502
<211> LENGTH: 25
<212> TYPE: DNA
<213> ORGANISM: Artificial Sequence
<220> FEATURE:
<223> OTHER INFORMATION: primer

<400> SEQUENCE: 502
acatagaccg tcttccagtc gtgct                                              25

<210> SEQ ID NO 503
<211> LENGTH: 25
<212> TYPE: DNA
<213> ORGANISM: Artificial Sequence
<220> FEATURE:
<223> OTHER INFORMATION: primer

<400> SEQUENCE: 503
acagaccacc gatgatgttc atgct                                              25

<210> SEQ ID NO 504
<211> LENGTH: 25
<212> TYPE: DNA
<213> ORGANISM: Artificial Sequence
<220> FEATURE:
<223> OTHER INFORMATION: primer

<400> SEQUENCE: 504
acactccacc acagtccaga ctcca                                              25

<210> SEQ ID NO 505
<211> LENGTH: 25
<212> TYPE: DNA
<213> ORGANISM: Artificial Sequence
<220> FEATURE:
<223> OTHER INFORMATION: primer

<400> SEQUENCE: 505
acaagacgag tcgacgaggt gtaag                                              25

<210> SEQ ID NO 506
<211> LENGTH: 25
<212> TYPE: DNA
<213> ORGANISM: Artificial Sequence
<220> FEATURE:
<223> OTHER INFORMATION: primer

<400> SEQUENCE: 506
aattgaccta cggaagctta gccct                                              25

<210> SEQ ID NO 507
<211> LENGTH: 25
<212> TYPE: DNA
<213> ORGANISM: Artificial Sequence
<220> FEATURE:
<223> OTHER INFORMATION: primer

<400> SEQUENCE: 507
aatgacacca ccgcaactag ccaac                                              25

<210> SEQ ID NO 508
<211> LENGTH: 25
<212> TYPE: DNA
<213> ORGANISM: Artificial Sequence
<220> FEATURE:
<223> OTHER INFORMATION: primer
```

```
<400> SEQUENCE: 508
aatccgttgt gcctaagacc tgcga                                          25

<210> SEQ ID NO 509
<211> LENGTH: 25
<212> TYPE: DNA
<213> ORGANISM: Artificial Sequence
<220> FEATURE:
<223> OTHER INFORMATION: primer

<400> SEQUENCE: 509
aataggaacc agaatcggac ctgac                                          25

<210> SEQ ID NO 510
<211> LENGTH: 25
<212> TYPE: DNA
<213> ORGANISM: Artificial Sequence
<220> FEATURE:
<223> OTHER INFORMATION: primer

<400> SEQUENCE: 510
aagttggagt tgatgggtcg agctg                                          25

<210> SEQ ID NO 511
<211> LENGTH: 25
<212> TYPE: DNA
<213> ORGANISM: Artificial Sequence
<220> FEATURE:
<223> OTHER INFORMATION: primer

<400> SEQUENCE: 511
aagggacagc tatgttgccg gtagc                                          25

<210> SEQ ID NO 512
<211> LENGTH: 26
<212> TYPE: DNA
<213> ORGANISM: Artificial Sequence
<220> FEATURE:
<223> OTHER INFORMATION: primer

<400> SEQUENCE: 512
aagctcagag tggcacatac tgagga                                         26

<210> SEQ ID NO 513
<211> LENGTH: 25
<212> TYPE: DNA
<213> ORGANISM: Artificial Sequence
<220> FEATURE:
<223> OTHER INFORMATION: primer

<400> SEQUENCE: 513
aagagatggc acgtaggcaa gcaac                                          25

<210> SEQ ID NO 514
<211> LENGTH: 25
<212> TYPE: DNA
<213> ORGANISM: Artificial Sequence
<220> FEATURE:
<223> OTHER INFORMATION: primer

<400> SEQUENCE: 514
aactctctgt gcttcgggcc tagtc                                          25

<210> SEQ ID NO 515
<211> LENGTH: 25
```

```
<212> TYPE: DNA
<213> ORGANISM: Artificial Sequence
<220> FEATURE:
<223> OTHER INFORMATION: primer

<400> SEQUENCE: 515
aacgcgtatc acctgtgtcc agcaa                                    25

<210> SEQ ID NO 516
<211> LENGTH: 24
<212> TYPE: DNA
<213> ORGANISM: Artificial Sequence
<220> FEATURE:
<223> OTHER INFORMATION: primer

<400> SEQUENCE: 516
aaccctaaca acggtggcgt tcca                                     24

<210> SEQ ID NO 517
<211> LENGTH: 24
<212> TYPE: DNA
<213> ORGANISM: Artificial Sequence
<220> FEATURE:
<223> OTHER INFORMATION: primer

<400> SEQUENCE: 517
aacatgcaac ctcgatccca tacg                                     24

<210> SEQ ID NO 518
<211> LENGTH: 25
<212> TYPE: DNA
<213> ORGANISM: Artificial Sequence
<220> FEATURE:
<223> OTHER INFORMATION: primer

<400> SEQUENCE: 518
aaatgtgagg agctgatgag actga                                    25

<210> SEQ ID NO 519
<211> LENGTH: 25
<212> TYPE: DNA
<213> ORGANISM: Artificial Sequence
<220> FEATURE:
<223> OTHER INFORMATION: primer

<400> SEQUENCE: 519
aaagcgaacg gttacgtcac caagg                                    25

<210> SEQ ID NO 520
<211> LENGTH: 25
<212> TYPE: DNA
<213> ORGANISM: Artificial Sequence
<220> FEATURE:
<223> OTHER INFORMATION: primer

<400> SEQUENCE: 520
aaacacttca gttcctaggc tcgtc                                    25

<210> SEQ ID NO 521
<211> LENGTH: 25
<212> TYPE: DNA
<213> ORGANISM: Artificial Sequence
<220> FEATURE:
<223> OTHER INFORMATION: primer

<400> SEQUENCE: 521
```
aaaaaggtct ccatcacgac tccac                                              25

<210> SEQ ID NO 522
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 522
ggtacgacgt tcagctnnnn aaaa                                               24

<210> SEQ ID NO 523
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 523
ggtacgacgt tcagctnnnn aaac                                               24

<210> SEQ ID NO 524
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 524
ggtacgacgt tcagctnnnn aaag                                               24

<210> SEQ ID NO 525
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 525
ggtacgacgt tcagctnnnn aaat                                               24

<210> SEQ ID NO 526
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 526
ggtacgacgt tcagctnnnn aaca                    24

<210> SEQ ID NO 527
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 527
ggtacgacgt tcagctnnnn aacc                    24

<210> SEQ ID NO 528
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 528
ggtacgacgt tcagctnnnn aacg                    24

<210> SEQ ID NO 529
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 529
ggtacgacgt tcagctnnnn aact                    24

<210> SEQ ID NO 530
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 530
ggtacgacgt tcagctnnnn aaga                    24

<210> SEQ ID NO 531
<211> LENGTH: 24
<212> TYPE: DNA
<213> ORGANISM: Artificial Sequence
<220> FEATURE:
<223> OTHER INFORMATION: primer
<221> NAME/KEY: modified_base
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 531
ggtacgacgt tcagctnnnn aagc                                                  24

<210> SEQ ID NO 532
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 532
ggtacgacgt tcagctnnnn aagg                                                  24

<210> SEQ ID NO 533
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 533
ggtacgacgt tcagctnnnn aagt                                                  24

<210> SEQ ID NO 534
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 534
ggtacgacgt tcagctnnnn aata                                                  24

<210> SEQ ID NO 535
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 535
ggtacgacgt tcagctnnnn aatc                                                  24

<210> SEQ ID NO 536
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(23)
<223> OTHER INFORMATION: 'n' at position 17 can be any of the
      nucleotides a,c,g or t; 'n' from positions 18 to 20  is a inosine;

```
<400> SEQUENCE: 536
ggtacgacgt tcagctnnnn aat                                              23

<210> SEQ ID NO 537
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 537
ggtacgacgt tcagctnnnn aatt                                             24

<210> SEQ ID NO 538
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 538
ggtacgacgt tcagctnnnn acaa                                             24

<210> SEQ ID NO 539
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
    nucleotides a,c,g or t; 'n' from positions 18 to 20  is a inosine;

<400> SEQUENCE: 539
ggtacgacgt tcagctnnnn acac                                             24

<210> SEQ ID NO 540
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 540
ggtacgacgt tcagctnnnn acag                                             24

<210> SEQ ID NO 541
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
``` nucleotides a,c,g or t; 'n' from positions 18 to 20 is a inosine;

<400> SEQUENCE: 541
ggtacgacgt tcagctnnnn acat                                              24

<210> SEQ ID NO 542
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 542
ggtacgacgt tcagctnnnn acca                                              24

<210> SEQ ID NO 543
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 543
ggtacgacgt tcagctnnnn accc                                              24

<210> SEQ ID NO 544
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 544
ggtacgacgt tcagctnnnn accg                                              24

<210> SEQ ID NO 545
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 545
ggtacgacgt tcagctnnnn acct                                              24

<210> SEQ ID NO 546
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)

<223> OTHER INFORMATION: 'n' at position 17 can be any of the
      nucleotides a,c,g or t; 'n' from positions 18 to 20 is a inosine;

<400> SEQUENCE: 546
ggtacgacgt tcagctnnnn acga                                          24

<210> SEQ ID NO 547
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 547
ggtacgacgt tcagctnnnn acgc                                          24

<210> SEQ ID NO 548
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 548
ggtacgacgt tcagctnnnn acgg                                          24

<210> SEQ ID NO 549
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 549
ggtacgacgt tcagctnnnn acgt                                          24

<210> SEQ ID NO 550
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 550
ggtacgacgt tcagctnnnn acta                                          24

<210> SEQ ID NO 551
<211> LENGTH: 24
<212> TYPE: DNA
<213> ORGANISM: Artificial Sequence
<220> FEATURE:
<223> OTHER INFORMATION: primer
<221> NAME/KEY: misc_feature

```
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 551
ggtacgacgt tcagctnnnn actc                                              24

<210> SEQ ID NO 552
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 552
ggtacgacgt tcagctnnnn actg                                              24

<210> SEQ ID NO 553
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 553
ggtacgacgt tcagctnnnn actt                                              24

<210> SEQ ID NO 554
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 554
ggtacgacgt tcagctnnnn agaa                                              24

<210> SEQ ID NO 555
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 555
ggtacgacgt tcagctnnnn agac                                              24

<210> SEQ ID NO 556
<211> LENGTH: 24
<212> TYPE: DNA
<213> ORGANISM: Artificial Sequence
<220> FEATURE:
<223> OTHER INFORMATION: primer
```

-continued

<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 556
ggtacgacgt tcagctnnnn agag                                              24

<210> SEQ ID NO 557
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 557
ggtacgacgt tcagctnnnn agat                                              24

<210> SEQ ID NO 558
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 558
ggtacgacgt tcagctnnnn agca                                              24

<210> SEQ ID NO 559
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 559
ggtacgacgt tcagctnnnn agcc                                              24

<210> SEQ ID NO 560
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 560
ggtacgacgt tcagctnnnn agcg                                              24

<210> SEQ ID NO 561
<211> LENGTH: 24
<212> TYPE: DNA
<213> ORGANISM: Artificial Sequence
<220> FEATURE:

```
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 561
ggtacgacgt tcagctnnnn agct                                              24

<210> SEQ ID NO 562
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 562
ggtacgacgt tcagctnnnn agga                                              24

<210> SEQ ID NO 563
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 563
ggtacgacgt tcagctnnnn aggc                                              24

<210> SEQ ID NO 564
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 564
ggtacgacgt tcagctnnnn aggg                                              24

<210> SEQ ID NO 565
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 565
ggtacgacgt tcagctnnnn aggt                                              24

<210> SEQ ID NO 566
<211> LENGTH: 24
<212> TYPE: DNA
<213> ORGANISM: Artificial Sequence
```

```
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 566
ggtacgacgt tcagctnnnn agta                                              24

<210> SEQ ID NO 567
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 567
ggtacgacgt tcagctnnnn actc                                              24

<210> SEQ ID NO 568
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 568
ggtacgacgt tcagctnnnn agtg                                              24

<210> SEQ ID NO 569
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 569
ggtacgacgt tcagctnnnn agtt                                              24

<210> SEQ ID NO 570
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 570
ggtacgacgt tcagctnnnn ataa                                              24

<210> SEQ ID NO 571
<211> LENGTH: 24
<212> TYPE: DNA
```

<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 571
ggtacgacgt tcagctnnnn atac                                          24

<210> SEQ ID NO 572
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 572
ggtacgacgt tcagctnnnn atag                                          24

<210> SEQ ID NO 573
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 573
ggtacgacgt tcagctnnnn atat                                          24

<210> SEQ ID NO 574
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 574
ggtacgacgt tcagctnnnn atca                                          24

<210> SEQ ID NO 575
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 575
ggtacgacgt tcagctnnnn atcc                                          24

<210> SEQ ID NO 576
<211> LENGTH: 24

```
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 576
ggtacgacgt tcagctnnnn atcg                                              24

<210> SEQ ID NO 577
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 577
ggtacgacgt tcagctnnnn atct                                              24

<210> SEQ ID NO 578
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 578
ggtacgacgt tcagctnnnn atga                                              24

<210> SEQ ID NO 579
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 579
ggtacgacgt tcagctnnnn atgc                                              24

<210> SEQ ID NO 580
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 580
ggtacgacgt tcagctnnnn atgg                                              24

<210> SEQ ID NO 581
```

```
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 581
ggtacgacgt tcagctnnnn atgt                                              24

<210> SEQ ID NO 582
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 582
ggtacgacgt tcagctnnnn atta                                              24

<210> SEQ ID NO 583
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 583
ggtacgacgt tcagctnnnn attc                                              24

<210> SEQ ID NO 584
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 584
ggtacgacgt tcagctnnnn attg                                              24

<210> SEQ ID NO 585
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 585
ggtacgacgt tcagctnnnn attt                                              24
```

<210> SEQ ID NO 586
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 586
ggtacgacgt tcagctnnnn caaa                                              24

<210> SEQ ID NO 587
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 587
ggtacgacgt tcagctnnnn caac                                              24

<210> SEQ ID NO 588
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 588
ggtacgacgt tcagctnnnn caag                                              24

<210> SEQ ID NO 589
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 589
ggtacgacgt tcagctnnnn caat                                              24

<210> SEQ ID NO 590
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 590
ggtacgacgt tcagctnnnn caca                                              24

```
<210> SEQ ID NO 591
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 591
ggtacgacgt tcagctnnnn cacc                                        24

<210> SEQ ID NO 592
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 592
ggtacgacgt tcagctnnnn cacg                                        24

<210> SEQ ID NO 593
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 593
ggtacgacgt tcagctnnnn cact                                        24

<210> SEQ ID NO 594
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 594
ggtacgacgt tcagctnnnn caga                                        24

<210> SEQ ID NO 595
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 595
ggtacgacgt tcagctnnnn cagc                                        24
```

<210> SEQ ID NO 596
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 596
ggtacgacgt tcagctnnnn cagg                                           24

<210> SEQ ID NO 597
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 597
ggtacgacgt tcagctnnnn cagt                                           24

<210> SEQ ID NO 598
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 598
ggtacgacgt tcagctnnnn cata                                           24

<210> SEQ ID NO 599
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 599
ggtacgacgt tcagctnnnn catc                                           24

<210> SEQ ID NO 600
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 600
ggtacgacgt tcagctnnnn catg                                              24

<210> SEQ ID NO 601
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 601
ggtacgacgt tcagctnnnn catt                                              24

<210> SEQ ID NO 602
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 602
ggtacgacgt tcagctnnnn ccaa                                              24

<210> SEQ ID NO 603
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 603
ggtacgacgt tcagctnnnn ccac                                              24

<210> SEQ ID NO 604
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 604
ggtacgacgt tcagctnnnn ccag                                              24

<210> SEQ ID NO 605
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 605
ggtacgacgt tcagctnnnn ccat                                              24

<210> SEQ ID NO 606
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 606
ggtacgacgt tcagctnnnn ccca                                              24

<210> SEQ ID NO 607
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 607
ggtacgacgt tcagctnnnn cccc                                              24

<210> SEQ ID NO 608
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 608
ggtacgacgt tcagctnnnn cccg                                              24

<210> SEQ ID NO 609
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 609
ggtacgacgt tcagctnnnn ccct                                              24

<210> SEQ ID NO 610
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

```
<400> SEQUENCE: 610
ggtacgacgt tcagctnnnn ccga                                            24

<210> SEQ ID NO 611
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 611
ggtacgacgt tcagctnnnn ccgc                                            24

<210> SEQ ID NO 612
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 612
ggtacgacgt tcagctnnnn ccgg                                            24

<210> SEQ ID NO 613
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 613
ggtacgacgt tcagctnnnn ccgt                                            24

<210> SEQ ID NO 614
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 614
ggtacgacgt tcagctnnnn ccta                                            24

<210> SEQ ID NO 615
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;
```

```
<400> SEQUENCE: 615
ggtacgacgt tcagctnnnn cctc                                              24

<210> SEQ ID NO 616
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 616
ggtacgacgt tcagctnnnn cctg                                              24

<210> SEQ ID NO 617
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 617
ggtacgacgt tcagctnnnn cctt                                              24

<210> SEQ ID NO 618
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 618
ggtacgacgt tcagctnnnn cgaa                                              24

<210> SEQ ID NO 619
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 619
ggtacgacgt tcagctnnnn cgac                                              24

<210> SEQ ID NO 620
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
```

-continued nucleotides a,c,g or t; 'n' from positions 18 to 20 is a inosine;

<400> SEQUENCE: 620
ggtacgacgt tcagctnnnn cgag         24

<210> SEQ ID NO 621
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 621
ggtacgacgt tcagctnnnn cgat         24

<210> SEQ ID NO 622
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 622
ggtacgacgt tcagctnnnn cgca         24

<210> SEQ ID NO 623
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 623
ggtacgacgt tcagctnnnn cgcc         24

<210> SEQ ID NO 624
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 624
ggtacgacgt tcagctnnnn cgcg         24

<210> SEQ ID NO 625
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)

```
<223> OTHER INFORMATION: 'n' at position 17 can be any of the
      nucleotides a,c,g or t; 'n' from positions 18 to 20  is a inosine;

<400> SEQUENCE: 625
ggtacgacgt tcagctnnnn cgct                                            24

<210> SEQ ID NO 626
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 626
ggtacgacgt tcagctnnnn cgga                                            24

<210> SEQ ID NO 627
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 627
ggtacgacgt tcagctnnnn cggc                                            24

<210> SEQ ID NO 628
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 628
ggtacgacgt tcagctnnnn cggg                                            24

<210> SEQ ID NO 629
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 629
ggtacgacgt tcagctnnnn cggt                                            24

<210> SEQ ID NO 630
<211> LENGTH: 24
<212> TYPE: DNA
<213> ORGANISM: Artificial Sequence
<220> FEATURE:
<223> OTHER INFORMATION: primer
<221> NAME/KEY: misc_feature
```

```
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 630
ggtacgacgt tcagctnnnn cgta                                              24

<210> SEQ ID NO 631
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 631
ggtacgacgt tcagctnnnn cctc                                              24

<210> SEQ ID NO 632
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 632
ggtacgacgt tcagctnnnn cgtg                                              24

<210> SEQ ID NO 633
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 633
ggtacgacgt tcagctnnnn cgtt                                              24

<210> SEQ ID NO 634
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 634
ggtacgacgt tcagctnnnn ctaa                                              24

<210> SEQ ID NO 635
<211> LENGTH: 24
<212> TYPE: DNA
<213> ORGANISM: Artificial Sequence
<220> FEATURE:
<223> OTHER INFORMATION: primer
```

<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 635
ggtacgacgt tcagctnnnn ctac                                            24

<210> SEQ ID NO 636
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 636
ggtacgacgt tcagctnnnn ctag                                            24

<210> SEQ ID NO 637
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 637
ggtacgacgt tcagctnnnn ctat                                            24

<210> SEQ ID NO 638
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 638
ggtacgacgt tcagctnnnn ctca                                            24

<210> SEQ ID NO 639
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 639
ggtacgacgt tcagctnnnn ctcc                                            24

<210> SEQ ID NO 640
<211> LENGTH: 24
<212> TYPE: DNA
<213> ORGANISM: Artificial Sequence
<220> FEATURE:

```
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 640
ggtacgacgt tcagctnnnn ctcg                                              24

<210> SEQ ID NO 641
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 641
ggtacgacgt tcagctnnnn ctct                                              24

<210> SEQ ID NO 642
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 642
ggtacgacgt tcagctnnnn ctga                                              24

<210> SEQ ID NO 643
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 643
ggtacgacgt tcagctnnnn ctgc                                              24

<210> SEQ ID NO 644
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 644
ggtacgacgt tcagctnnnn ctgg                                              24

<210> SEQ ID NO 645
<211> LENGTH: 24
<212> TYPE: DNA
<213> ORGANISM: Artificial Sequence
```

```
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 645
ggtacgacgt tcagctnnnn ctgt                                       24

<210> SEQ ID NO 646
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 646
ggtacgacgt tcagctnnnn ctta                                       24

<210> SEQ ID NO 647
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 647
ggtacgacgt tcagctnnnn cttc                                       24

<210> SEQ ID NO 648
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 648
ggtacgacgt tcagctnnnn cttg                                       24

<210> SEQ ID NO 649
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 649
ggtacgacgt tcagctnnnn cttt                                       24

<210> SEQ ID NO 650
<211> LENGTH: 24
<212> TYPE: DNA
```

```
<213> ORGANISM: Artificial Sequence
<220> FEATURE:
<223> OTHER INFORMATION: primer
<221> NAME/KEY: misc_feature
<222> LOCATION: (1)..(24)
<223> OTHER INFORMATION: 'n' at position 17 can be any of the
      nucleotides a,c,g or t; 'n' from positions 18 to 20  is a inosine;

<400> SEQUENCE: 650
ggtacgacgt tcagctnnnn gaaa                                              24

<210> SEQ ID NO 651
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 651
ggtacgacgt tcagctnnnn gaac                                              24

<210> SEQ ID NO 652
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 652
ggtacgacgt tcagctnnnn gaag                                              24

<210> SEQ ID NO 653
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 653
ggtacgacgt tcagctnnnn gaat                                              24

<210> SEQ ID NO 654
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 654
ggtacgacgt tcagctnnnn gaca                                              24

<210> SEQ ID NO 655
<211> LENGTH: 24
```

<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 655
ggtacgacgt tcagctnnnn gacc                                       24

<210> SEQ ID NO 656
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 656
ggtacgacgt tcagctnnnn gacg                                       24

<210> SEQ ID NO 657
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 657
ggtacgacgt tcagctnnnn gact                                       24

<210> SEQ ID NO 658
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 658
ggtacgacgt tcagctnnnn gaga                                       24

<210> SEQ ID NO 659
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 659
ggtacgacgt tcagctnnnn gagc                                       24

<210> SEQ ID NO 660

```
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 660
ggtacgacgt tcagctnnnn gagg                                              24

<210> SEQ ID NO 661
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 661
ggtacgacgt tcagctnnnn gagt                                              24

<210> SEQ ID NO 662
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 662
ggtacgacgt tcagctnnnn gata                                              24

<210> SEQ ID NO 663
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 663
ggtacgacgt tcagctnnnn gatc                                              24

<210> SEQ ID NO 664
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 664
ggtacgacgt tcagctnnnn gatg                                              24
```

```
<210> SEQ ID NO 665
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 665
ggtacgacgt tcagctnnnn gatt                                              24

<210> SEQ ID NO 666
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 666
ggtacgacgt tcagctnnnn gcaa                                              24

<210> SEQ ID NO 667
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 667
ggtacgacgt tcagctnnnn gcac                                              24

<210> SEQ ID NO 668
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 668
ggtacgacgt tcagctnnnn gcag                                              24

<210> SEQ ID NO 669
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 669
ggtacgacgt tcagctnnnn gcat                                              24
```

<210> SEQ ID NO 670
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
     nucleotides a,c,g or t; 'n' from positions 18 to 20 is a inosine;

<400> SEQUENCE: 670
ggtacgacgt tcagctnnnn gcca                                              24

<210> SEQ ID NO 671
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
     nucleotides a,c,g or t; 'n' from positions 18 to 20 is a inosine;

<400> SEQUENCE: 671
ggtacgacgt tcagctnnnn gccc                                              24

<210> SEQ ID NO 672
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
     nucleotides a,c,g or t; 'n' from positions 18 to 20 is a inosine;

<400> SEQUENCE: 672
ggtacgacgt tcagctnnnn gccg                                              24

<210> SEQ ID NO 673
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
     nucleotides a,c,g or t; 'n' from positions 18 to 20 is a inosine;

<400> SEQUENCE: 673
ggtacgacgt tcagctnnnn gcct                                              24

<210> SEQ ID NO 674
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
     nucleotides a,c,g or t; 'n' from positions 18 to 20 is a inosine;

<400> SEQUENCE: 674
ggtacgacgt tcagctnnnn gcga                                              24

<210> SEQ ID NO 675
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 675
ggtacgacgt tcagctnnnn gcgc                                              24

<210> SEQ ID NO 676
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 676
ggtacgacgt tcagctnnnn gcgg                                              24

<210> SEQ ID NO 677
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 677
ggtacgacgt tcagctnnnn gcgt                                              24

<210> SEQ ID NO 678
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 678
ggtacgacgt tcagctnnnn gcta                                              24

<210> SEQ ID NO 679
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 679
ggtacgacgt tcagctnnnn gctc                                              24

<210> SEQ ID NO 680
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 680
ggtacgacgt tcagctnnnn gctg                                              24

<210> SEQ ID NO 681
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 681
ggtacgacgt tcagctnnnn gctt                                              24

<210> SEQ ID NO 682
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 682
ggtacgacgt tcagctnnnn ggaa                                              24

<210> SEQ ID NO 683
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 683
ggtacgacgt tcagctnnnn ggac                                              24

<210> SEQ ID NO 684
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 684
ggtacgacgt tcagctnnnn ggag                                           24

<210> SEQ ID NO 685
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 685
ggtacgacgt tcagctnnnn ggat                                           24

<210> SEQ ID NO 686
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 686
ggtacgacgt tcagctnnnn ggca                                           24

<210> SEQ ID NO 687
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 687
ggtacgacgt tcagctnnnn ggcc                                           24

<210> SEQ ID NO 688
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 688
ggtacgacgt tcagctnnnn ggcg                                           24

<210> SEQ ID NO 689
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 689
ggtacgacgt tcagctnnnn ggct                                    24

<210> SEQ ID NO 690
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 690
ggtacgacgt tcagctnnnn ggga                                    24

<210> SEQ ID NO 691
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 691
ggtacgacgt tcagctnnnn gggc                                    24

<210> SEQ ID NO 692
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 692
ggtacgacgt tcagctnnnn gggg                                    24

<210> SEQ ID NO 693
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 693
ggtacgacgt tcagctnnnn gggt                                    24

<210> SEQ ID NO 694
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 694
ggtacgacgt tcagctnnnn ggta                                          24

<210> SEQ ID NO 695
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 695
ggtacgacgt tcagctnnnn gctc                                          24

<210> SEQ ID NO 696
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 696
ggtacgacgt tcagctnnnn ggtg                                          24

<210> SEQ ID NO 697
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 697
ggtacgacgt tcagctnnnn ggtt                                          24

<210> SEQ ID NO 698
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 698
ggtacgacgt tcagctnnnn gtaa                                          24

<210> SEQ ID NO 699
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the nucleotides a,c,g or t; 'n' from positions 18 to 20 is a inosine;

<400> SEQUENCE: 699
ggtacgacgt tcagctnnnn gtac                                              24

<210> SEQ ID NO 700
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 700
ggtacgacgt tcagctnnnn gtag                                              24

<210> SEQ ID NO 701
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 701
ggtacgacgt tcagctnnnn gtat                                              24

<210> SEQ ID NO 702
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 702
ggtacgacgt tcagctnnnn gtca                                              24

<210> SEQ ID NO 703
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 703
ggtacgacgt tcagctnnnn gtcc                                              24

<210> SEQ ID NO 704
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)

<223> OTHER INFORMATION: 'n' at position 17 can be any of the
      nucleotides a,c,g or t; 'n' from positions 18 to 20  is a inosine;

<400> SEQUENCE: 704
ggtacgacgt tcagctnnnn gtcg                                             24

<210> SEQ ID NO 705
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 705
ggtacgacgt tcagctnnnn gtct                                             24

<210> SEQ ID NO 706
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 706
ggtacgacgt tcagctnnnn gtga                                             24

<210> SEQ ID NO 707
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 707
ggtacgacgt tcagctnnnn gtgc                                             24

<210> SEQ ID NO 708
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 708
ggtacgacgt tcagctnnnn gtgg                                             24

<210> SEQ ID NO 709
<211> LENGTH: 24
<212> TYPE: DNA
<213> ORGANISM: Artificial Sequence
<220> FEATURE:
<223> OTHER INFORMATION: primer
<221> NAME/KEY: misc_feature

```
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 709
ggtacgacgt tcagctnnnn gtgt                                              24

<210> SEQ ID NO 710
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 710
ggtacgacgt tcagctnnnn gtta                                              24

<210> SEQ ID NO 711
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 711
ggtacgacgt tcagctnnnn gttc                                              24

<210> SEQ ID NO 712
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 712
ggtacgacgt tcagctnnnn gttg                                              24

<210> SEQ ID NO 713
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 713
ggtacgacgt tcagctnnnn gttt                                              24

<210> SEQ ID NO 714
<211> LENGTH: 24
<212> TYPE: DNA
<213> ORGANISM: Artificial Sequence
<220> FEATURE:
<223> OTHER INFORMATION: primer
```

```
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 714
ggtacgacgt tcagctnnnn taaa                                              24

<210> SEQ ID NO 715
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 715
ggtacgacgt tcagctnnnn taac                                              24

<210> SEQ ID NO 716
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 716
ggtacgacgt tcagctnnnn taag                                              24

<210> SEQ ID NO 717
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 717
ggtacgacgt tcagctnnnn taat                                              24

<210> SEQ ID NO 718
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 718
ggtacgacgt tcagctnnnn taca                                              24

<210> SEQ ID NO 719
<211> LENGTH: 24
<212> TYPE: DNA
<213> ORGANISM: Artificial Sequence
<220> FEATURE:
```

```
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 719
ggtacgacgt tcagctnnnn tacc                                              24

<210> SEQ ID NO 720
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 720
ggtacgacgt tcagctnnnn tacg                                              24

<210> SEQ ID NO 721
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 721
ggtacgacgt tcagctnnnn tact                                              24

<210> SEQ ID NO 722
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 722
ggtacgacgt tcagctnnnn taga                                              24

<210> SEQ ID NO 723
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 723
ggtacgacgt tcagctnnnn tagc                                              24

<210> SEQ ID NO 724
<211> LENGTH: 24
<212> TYPE: DNA
<213> ORGANISM: Artificial Sequence
```

```
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 724
ggtacgacgt tcagctnnnn tagg                                            24

<210> SEQ ID NO 725
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 725
ggtacgacgt tcagctnnnn tagt                                            24

<210> SEQ ID NO 726
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 726
ggtacgacgt tcagctnnnn tata                                            24

<210> SEQ ID NO 727
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 727
ggtacgacgt tcagctnnnn tatc                                            24

<210> SEQ ID NO 728
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 728
ggtacgacgt tcagctnnnn tatg                                            24

<210> SEQ ID NO 729
<211> LENGTH: 24
<212> TYPE: DNA
```

<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 729
ggtacgacgt tcagctnnnn tatt                                          24

<210> SEQ ID NO 730
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 730
ggtacgacgt tcagctnnnn tcaa                                          24

<210> SEQ ID NO 731
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 731
ggtacgacgt tcagctnnnn tcac                                          24

<210> SEQ ID NO 732
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 732
ggtacgacgt tcagctnnnn tcag                                          24

<210> SEQ ID NO 733
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 733
ggtacgacgt tcagctnnnn tcat                                          24

<210> SEQ ID NO 734
<211> LENGTH: 24

```
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 734
ggtacgacgt tcagctnnnn tcca                                           24

<210> SEQ ID NO 735
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 735
ggtacgacgt tcagctnnnn tccc                                           24

<210> SEQ ID NO 736
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 736
ggtacgacgt tcagctnnnn tccg                                           24

<210> SEQ ID NO 737
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 737
ggtacgacgt tcagctnnnn tcct                                           24

<210> SEQ ID NO 738
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 738
ggtacgacgt tcagctnnnn tcga                                           24

<210> SEQ ID NO 739
```

```
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 739
ggtacgacgt tcagctnnnn tcgc                                           24

<210> SEQ ID NO 740
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 740
ggtacgacgt tcagctnnnn tcgg                                           24

<210> SEQ ID NO 741
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 741
ggtacgacgt tcagctnnnn tcgt                                           24

<210> SEQ ID NO 742
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 742
ggtacgacgt tcagctnnnn tcta                                           24

<210> SEQ ID NO 743
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 743
ggtacgacgt tcagctnnnn tctc                                           24
```

```
<210> SEQ ID NO 744
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 744
ggtacgacgt tcagctnnnn tctg                                              24

<210> SEQ ID NO 745
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 745
ggtacgacgt tcagctnnnn tctt                                              24

<210> SEQ ID NO 746
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 746
ggtacgacgt tcagctnnnn tgaa                                              24

<210> SEQ ID NO 747
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 747
ggtacgacgt tcagctnnnn tgac                                              24

<210> SEQ ID NO 748
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 748
ggtacgacgt tcagctnnnn tgag                                              24
```

<210> SEQ ID NO 749
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 749
ggtacgacgt tcagctnnnn tgat                                          24

<210> SEQ ID NO 750
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 750
ggtacgacgt tcagctnnnn tgca                                          24

<210> SEQ ID NO 751
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 751
ggtacgacgt tcagctnnnn tgcc                                          24

<210> SEQ ID NO 752
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 752
ggtacgacgt tcagctnnnn tgcg                                          24

<210> SEQ ID NO 753
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20 is a inosine;

<400> SEQUENCE: 753
ggtacgacgt tcagctnnnn tgct                                          24

<210> SEQ ID NO 754
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 754
ggtacgacgt tcagctnnnn tgga                                          24

<210> SEQ ID NO 755
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 755
ggtacgacgt tcagctnnnn tggc                                          24

<210> SEQ ID NO 756
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 756
ggtacgacgt tcagctnnnn tggg                                          24

<210> SEQ ID NO 757
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 757
ggtacgacgt tcagctnnnn tggt                                          24

<210> SEQ ID NO 758
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 758

```
ggtacgacgt tcagctnnnn tgta                                        24

<210> SEQ ID NO 759
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 759
ggtacgacgt tcagctnnnn tctc                                        24

<210> SEQ ID NO 760
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 760
ggtacgacgt tcagctnnnn tgtg                                        24

<210> SEQ ID NO 761
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 761
ggtacgacgt tcagctnnnn tgtt                                        24

<210> SEQ ID NO 762
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 762
ggtacgacgt tcagctnnnn ttaa                                        24

<210> SEQ ID NO 763
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 763
```

```
ggtacgacgt tcagctnnnn ttac                                              24

<210> SEQ ID NO 764
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 764
ggtacgacgt tcagctnnnn ttag                                              24

<210> SEQ ID NO 765
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 765
ggtacgacgt tcagctnnnn ttat                                              24

<210> SEQ ID NO 766
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 766
ggtacgacgt tcagctnnnn ttca                                              24

<210> SEQ ID NO 767
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 767
ggtacgacgt tcagctnnnn ttcc                                              24

<210> SEQ ID NO 768
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;
```

-continued

```
<400> SEQUENCE: 768
ggtacgacgt tcagctnnnn ttcg                                              24

<210> SEQ ID NO 769
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 769
ggtacgacgt tcagctnnnn ttct                                              24

<210> SEQ ID NO 770
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 770
ggtacgacgt tcagctnnnn ttga                                              24

<210> SEQ ID NO 771
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 771
ggtacgacgt tcagctnnnn ttgc                                              24

<210> SEQ ID NO 772
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 772
ggtacgacgt tcagctnnnn ttgg                                              24

<210> SEQ ID NO 773
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;
```

-continued

```
<400> SEQUENCE: 773
ggtacgacgt tcagctnnnn ttgt                                              24

<210> SEQ ID NO 774
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 774
ggtacgacgt tcagctnnnn ttta                                              24

<210> SEQ ID NO 775
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 775
ggtacgacgt tcagctnnnn tttc                                              24

<210> SEQ ID NO 776
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 776
ggtacgacgt tcagctnnnn tttg                                              24

<210> SEQ ID NO 777
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 777
ggtacgacgt tcagctnnnn tttt                                              24

<210> SEQ ID NO 778
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
```

```
         a,c,g or t.
<221> NAME/KEY: modified_base
<222> LOCATION: (18)..(20)
<223> OTHER INFORMATION: i

<400> SEQUENCE: 778
ggtacgacgt tcagctnnnn aaa                                           23

<210> SEQ ID NO 779
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 779
ggtacgacgt tcagctnnnn aac                                           23

<210> SEQ ID NO 780
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 780
ggtacgacgt tcagctnnnn aag                                           23

<210> SEQ ID NO 781
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (17)..(17)
<223> OTHER INFORMATION: i

<400> SEQUENCE: 781
ggtacgacgt tcagctnnnn aat                                           23

<210> SEQ ID NO 782
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
```

<223> OTHER INFORMATION: i

<400> SEQUENCE: 782
ggtacgacgt tcagctnnnn aca                                               23

<210> SEQ ID NO 783
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 783
ggtacgacgt tcagctnnnn acc                                               23

<210> SEQ ID NO 784
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 784
ggtacgacgt tcagctnnnn acg                                               23

<210> SEQ ID NO 785
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 785
ggtacgacgt tcagctnnnn act                                               23

<210> SEQ ID NO 786
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 786
ggtacgacgt tcagctnnnn aga                                               23

<210> SEQ ID NO 787
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 787
ggtacgacgt tcagctnnnn agc                                               23

<210> SEQ ID NO 788
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 788
ggtacgacgt tcagctnnnn agg                                               23

<210> SEQ ID NO 789
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 789
ggtacgacgt tcagctnnnn agt                                               23

<210> SEQ ID NO 790
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (17)..(17)
<223> OTHER INFORMATION: i

<400> SEQUENCE: 790
ggtacgacgt tcagctnnnn ata                                               23

<210> SEQ ID NO 791
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
    a,c,g or t.
<221> NAME/KEY: modified_base
<222> LOCATION: (17)..(17)
<223> OTHER INFORMATION: i

<400> SEQUENCE: 791
ggtacgacgt tcagctnnnn atc                                          23

<210> SEQ ID NO 792
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
    a,c,g or t.
<221> NAME/KEY: modified_base
<222> LOCATION: (18)..(20)
<223> OTHER INFORMATION: i

<400> SEQUENCE: 792
ggtacgacgt tcagctnnnn atg                                          23

<210> SEQ ID NO 793
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
    a,c,g or t.
<221> NAME/KEY: modified_base
<222> LOCATION: (18)..(20)
<223> OTHER INFORMATION: i

<400> SEQUENCE: 793
ggtacgacgt tcagctnnnn att                                          23

<210> SEQ ID NO 794
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
    a,c,g or t.
<221> NAME/KEY: modified_base
<222> LOCATION: (18)..(20)
<223> OTHER INFORMATION: i

<400> SEQUENCE: 794
ggtacgacgt tcagctnnnn caa                                          23

<210> SEQ ID NO 795
<211> LENGTH: 23

```
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 795
ggtacgacgt tcagctnnnn cac                                              23

<210> SEQ ID NO 796
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 796
ggtacgacgt tcagctnnnn cag                                              23

<210> SEQ ID NO 797
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 797
ggtacgacgt tcagctnnnn cat                                              23

<210> SEQ ID NO 798
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 798
ggtacgacgt tcagctnnnn cca                                              23

<210> SEQ ID NO 799
<211> LENGTH: 23
<212> TYPE: DNA
<213> ORGANISM: Artificial Sequence
<220> FEATURE:
```

```
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t
<221> NAME/KEY: modified_base
<222> LOCATION: (18)..(20)
<223> OTHER INFORMATION: i

<400> SEQUENCE: 799
ggtacgacgt tcagctnnnn ccc                                              23

<210> SEQ ID NO 800
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 800
ggtacgacgt tcagctnnnn ccg                                              23

<210> SEQ ID NO 801
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 801
ggtacgacgt tcagctnnnn cct                                              23

<210> SEQ ID NO 802
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 802
ggtacgacgt tcagctnnnn cga                                              23

<210> SEQ ID NO 803
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
```

```
<223> OTHER INFORMATION: nucleotide 'n' can be any of the nucleotides
     a,c,g or t.
<221> NAME/KEY: modified_base
<222> LOCATION: (18)..(20)
<223> OTHER INFORMATION: i

<400> SEQUENCE: 803
ggtacgacgt tcagctnnnn cgc                                              23

<210> SEQ ID NO 804
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
     a,c,g or t.
<221> NAME/KEY: modified_base
<222> LOCATION: (18)..(20)
<223> OTHER INFORMATION: i

<400> SEQUENCE: 804
ggtacgacgt tcagctnnnn cgg                                              23

<210> SEQ ID NO 805
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
     a,c,g or t.
<221> NAME/KEY: modified_base
<222> LOCATION: (18)..(20)
<223> OTHER INFORMATION: i

<400> SEQUENCE: 805
ggtacgacgt tcagctnnnn cgt                                              23

<210> SEQ ID NO 806
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
     a,c,g or t.
<221> NAME/KEY: modified_base
<222> LOCATION: (18)..(20)
<223> OTHER INFORMATION: i

<400> SEQUENCE: 806
ggtacgacgt tcagctnnnn cta                                              23

<210> SEQ ID NO 807
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
     a,c,g or t.
<221> NAME/KEY: modified_base
```

<222> LOCATION: (18)..(20)
<223> OTHER INFORMATION: i

<400> SEQUENCE: 807
ggtacgacgt tcagctnnnn ctc          23

<210> SEQ ID NO 808
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 808
ggtacgacgt tcagctnnnn ctg          23

<210> SEQ ID NO 809
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 809
ggtacgacgt tcagctnnnn ctt          23

<210> SEQ ID NO 810
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: nucleotide 'n' can be any of the nucleotides
      a,c,g or t.

<400> SEQUENCE: 810
ggtacgacgt tcagctnnnn gaa          23

<210> SEQ ID NO 811
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 811
ggtacgacgt tcagctnnnn gac                    23

<210> SEQ ID NO 812
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 812
ggtacgacgt tcagctnnnn gag                    23

<210> SEQ ID NO 813
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 813
ggtacgacgt tcagctnnnn gat                    23

<210> SEQ ID NO 814
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 814
ggtacgacgt tcagctnnnn gca                    23

<210> SEQ ID NO 815
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 815
ggtacgacgt tcagctnnnn gcc                                           23

<210> SEQ ID NO 816
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 816
ggtacgacgt tcagctnnnn gcg                                           23

<210> SEQ ID NO 817
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 817
ggtacgacgt tcagctnnnn gct                                           23

<210> SEQ ID NO 818
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 818
ggtacgacgt tcagctnnnn gga                                           23

<210> SEQ ID NO 819
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 819
ggtacgacgt tcagctnnnn ggc                                           23

<210> SEQ ID NO 820
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
    a,c,g or t.
<221> NAME/KEY: modified_base
<222> LOCATION: (18)..(20)
<223> OTHER INFORMATION: nucleotide 'n' can be any of the nucleotides
    a,c,g or t.

<400> SEQUENCE: 820
ggtacgacgt tcagctnnnn ggg                                    23

<210> SEQ ID NO 821
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
    a,c,g or t.
<221> NAME/KEY: modified_base
<222> LOCATION: (18)..(20)
<223> OTHER INFORMATION: nucleotide 'n' can be any of the nucleotides
    a,c,g or t.

<400> SEQUENCE: 821
ggtacgacgt tcagctnnnn ggt                                    23

<210> SEQ ID NO 822
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
    a,c,g or t.
<221> NAME/KEY: modified_base
<222> LOCATION: (18)..(20)
<223> OTHER INFORMATION: i

<400> SEQUENCE: 822
ggtacgacgt tcagctnnnn gta                                    23

<210> SEQ ID NO 823
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
    a,c,g or t.
<221> NAME/KEY: modified_base
<222> LOCATION: (17)..(17)
<223> OTHER INFORMATION: i

<400> SEQUENCE: 823
ggtacgacgt tcagctnnnn ctc                                    23

<210> SEQ ID NO 824

```
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 824
ggtacgacgt tcagctnnnn gtg                                            23

<210> SEQ ID NO 825
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 825
ggtacgacgt tcagctnnnn gtt                                            23

<210> SEQ ID NO 826
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 826
ggtacgacgt tcagctnnnn taa                                            23

<210> SEQ ID NO 827
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(20)
<223> OTHER INFORMATION: 'n' at position 17 can be any of the
      nucleotides a,c,g or t; 'n' from positions 18 to 20  is a inosine;

<400> SEQUENCE: 827
ggtacgacgt tcagctnnnn tac                                            23

<210> SEQ ID NO 828
<211> LENGTH: 23
<212> TYPE: DNA
<213> ORGANISM: Artificial Sequence
<220> FEATURE:
<223> OTHER INFORMATION: primer
<221> NAME/KEY: misc_feature
```

```
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 828
ggtacgacgt tcagctnnnn tag                                                23

<210> SEQ ID NO 829
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (17)..(17)
<223> OTHER INFORMATION: i

<400> SEQUENCE: 829
ggtacgacgt tcagctnnnn tat                                                23

<210> SEQ ID NO 830
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 830
ggtacgacgt tcagctnnnn tca                                                23

<210> SEQ ID NO 831
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 831
ggtacgacgt tcagctnnnn tcc                                                23

<210> SEQ ID NO 832
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
```

```
<221> NAME/KEY: modified_base
<222> LOCATION: (18)..(20)
<223> OTHER INFORMATION: i

<400> SEQUENCE: 832
ggtacgacgt tcagctnnnn tcg                                              23

<210> SEQ ID NO 833
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 833
ggtacgacgt tcagctnnnn tct                                              23

<210> SEQ ID NO 834
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 834
ggtacgacgt tcagctnnnn tga                                              23

<210> SEQ ID NO 835
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 835
ggtacgacgt tcagctnnnn tgc                                              23

<210> SEQ ID NO 836
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i
```

<400> SEQUENCE: 836
ggtacgacgt tcagctnnnn tgg                    23

<210> SEQ ID NO 837
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 837
ggtacgacgt tcagctnnnn tgt                    23

<210> SEQ ID NO 838
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 838
ggtacgacgt tcagctnnnn tta                    23

<210> SEQ ID NO 839
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 839
ggtacgacgt tcagctnnnn ttc                    23

<210> SEQ ID NO 840
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 840

```
ggtacgacgt tcagctnnnn ttg                                        23

<210> SEQ ID NO 841
<211> LENGTH: 23
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(17)
<223> OTHER INFORMATION: nucleotide 'n' can be any of the nucleotides
      a,c,g or t.
<221> NAME/KEY: modified_base
<222> LOCATION: (18)..(20)
<223> OTHER INFORMATION: i

<400> SEQUENCE: 841
ggtacgacgt tcagctnnnn ttt                                        23

<210> SEQ ID NO 842
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 842
ggtacgacgt tcagctnggg nnnaaa                                     26

<210> SEQ ID NO 843
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 843
ggtacgacgt tcagctnggg nnnaac                                     26

<210> SEQ ID NO 844
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 844
ggtacgacgt tcagctnggg nnnaag                                     26

<210> SEQ ID NO 845
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
``` nucleotides a,c,g or t; 'n' from positions 21 to 23 is a inosine;

<400> SEQUENCE: 845
ggtacgacgt tcagctnggg nnnaat                                              26

<210> SEQ ID NO 846
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23 is a inosine;

<400> SEQUENCE: 846
ggtacgacgt tcagctnggg nnnaca                                              26

<210> SEQ ID NO 847
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23 is a inosine;

<400> SEQUENCE: 847
ggtacgacgt tcagctnggg nnnacc                                              26

<210> SEQ ID NO 848
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23 is a inosine;

<400> SEQUENCE: 848
ggtacgacgt tcagctnggg nnnacg                                              26

<210> SEQ ID NO 849
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23 is a inosine;

<400> SEQUENCE: 849
ggtacgacgt tcagctnggg nnnact                                              26

<210> SEQ ID NO 850
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)

<223> OTHER INFORMATION: 'n' at position 17 can be any of the
      nucleotides a,c,g or t; 'n' from positions 21 to 23  is a inosine;

<400> SEQUENCE: 850
ggtacgacgt tcagctnggg nnnaga                                    26

<210> SEQ ID NO 851
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 851
ggtacgacgt tcagctnggg nnnagc                                    26

<210> SEQ ID NO 852
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 852
ggtacgacgt tcagctnggg nnnagg                                    26

<210> SEQ ID NO 853
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 853
ggtacgacgt tcagctnggg nnnagt                                    26

<210> SEQ ID NO 854
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 854
ggtacgacgt tcagctnggg nnnata                                    26

<210> SEQ ID NO 855
<211> LENGTH: 26
<212> TYPE: DNA
<213> ORGANISM: Artificial Sequence
<220> FEATURE:
<223> OTHER INFORMATION: primer
<221> NAME/KEY: misc_feature

```
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 855
ggtacgacgt tcagctnggg nnnatc                                              26

<210> SEQ ID NO 856
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 856
ggtacgacgt tcagctnggg nnnatg                                              26

<210> SEQ ID NO 857
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 857
ggtacgacgt tcagctnggg nnnatt                                              26

<210> SEQ ID NO 858
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 858
ggtacgacgt tcagctnggg nnncaa                                              26

<210> SEQ ID NO 859
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 859
ggtacgacgt tcagctnggg nnncac                                              26

<210> SEQ ID NO 860
<211> LENGTH: 26
<212> TYPE: DNA
<213> ORGANISM: Artificial Sequence
<220> FEATURE:
<223> OTHER INFORMATION: primer
```

```
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 860
ggtacgacgt tcagctnggg nnncag                                              26

<210> SEQ ID NO 861
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 861
ggtacgacgt tcagctnggg nnncat                                              26

<210> SEQ ID NO 862
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 862
ggtacgacgt tcagctnggg nnncca                                              26

<210> SEQ ID NO 863
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 863
ggtacgacgt tcagctnggg nnnccc                                              26

<210> SEQ ID NO 864
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 864
ggtacgacgt tcagctnggg nnnccg                                              26

<210> SEQ ID NO 865
<211> LENGTH: 26
<212> TYPE: DNA
<213> ORGANISM: Artificial Sequence
<220> FEATURE:
```

```
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 865
ggtacgacgt tcagctnggg nnncct                                              26

<210> SEQ ID NO 866
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 866
ggtacgacgt tcagctnggg nnncga                                              26

<210> SEQ ID NO 867
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 867
ggtacgacgt tcagctnggg nnncgc                                              26

<210> SEQ ID NO 868
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 868
ggtacgacgt tcagctnggg nnncgg                                              26

<210> SEQ ID NO 869
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 869
ggtacgacgt tcagctnggg nnncgt                                              26

<210> SEQ ID NO 870
<211> LENGTH: 26
<212> TYPE: DNA
<213> ORGANISM: Artificial Sequence
```

<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 870
ggtacgacgt tcagctnggg nnncta                                      26

<210> SEQ ID NO 871
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 871
ggtacgacgt tcagctnggg nnnctc                                      26

<210> SEQ ID NO 872
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 872
ggtacgacgt tcagctnggg nnnctg                                      26

<210> SEQ ID NO 873
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 873
ggtacgacgt tcagctnggg nnnctt                                      26

<210> SEQ ID NO 874
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 874
ggtacgacgt tcagctnggg nnngaa                                      26

<210> SEQ ID NO 875
<211> LENGTH: 26
<212> TYPE: DNA

```
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 875
ggtacgacgt tcagctnggg nnngac                                        26

<210> SEQ ID NO 876
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 876
ggtacgacgt tcagctnggg nnngag                                        26

<210> SEQ ID NO 877
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 877
ggtacgacgt tcagctnggg nnngat                                        26

<210> SEQ ID NO 878
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 878
ggtacgacgt tcagctnggg nnngca                                        26

<210> SEQ ID NO 879
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 879
ggtacgacgt tcagctnggg nnngcc                                        26

<210> SEQ ID NO 880
<211> LENGTH: 26
```

```
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 880
ggtacgacgt tcagctnggg nnngcg                                      26

<210> SEQ ID NO 881
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 881
ggtacgacgt tcagctnggg nnngct                                      26

<210> SEQ ID NO 882
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 882
ggtacgacgt tcagctnggg nnngga                                      26

<210> SEQ ID NO 883
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 883
ggtacgacgt tcagctnggg nnnggc                                      26

<210> SEQ ID NO 884
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 884
ggtacgacgt tcagctnggg nnnggg                                      26

<210> SEQ ID NO 885
```

```
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 885
ggtacgacgt tcagctnggg nnnggt                                          26

<210> SEQ ID NO 886
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 886
ggtacgacgt tcagctnggg nnngta                                          26

<210> SEQ ID NO 887
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 887
ggtacgacgt tcagctnggg nnnctc                                          26

<210> SEQ ID NO 888
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 888
ggtacgacgt tcagctnggg nnngtg                                          26

<210> SEQ ID NO 889
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 889
ggtacgacgt tcagctnggg nnngtt                                          26
```

```
<210> SEQ ID NO 890
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 890
ggtacgacgt tcagctnggg nnntaa                                              26

<210> SEQ ID NO 891
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 891
ggtacgacgt tcagctnggg nnntac                                              26

<210> SEQ ID NO 892
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 892
ggtacgacgt tcagctnggg nnntag                                              26

<210> SEQ ID NO 893
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 893
ggtacgacgt tcagctnggg nnntat                                              26

<210> SEQ ID NO 894
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 894
ggtacgacgt tcagctnggg nnntca                                              26
```

<210> SEQ ID NO 895
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 895
ggtacgacgt tcagctnggg nnntcc                                        26

<210> SEQ ID NO 896
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 896
ggtacgacgt tcagctnggg nnntcg                                        26

<210> SEQ ID NO 897
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 897
ggtacgacgt tcagctnggg nnntct                                        26

<210> SEQ ID NO 898
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 898
ggtacgacgt tcagctnggg nnntga                                        26

<210> SEQ ID NO 899
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 899
ggtacgacgt tcagctnggg nnntgc                                        26

<210> SEQ ID NO 900
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 900
ggtacgacgt tcagctnggg nnntgg                                           26

<210> SEQ ID NO 901
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 901
ggtacgacgt tcagctnggg nnntgt                                           26

<210> SEQ ID NO 902
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 902
ggtacgacgt tcagctnggg nnntta                                           26

<210> SEQ ID NO 903
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 903
ggtacgacgt tcagctnggg nnnttc                                           26

<210> SEQ ID NO 904
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 904
ggtacgacgt tcagctnggg nnnttg                          26

<210> SEQ ID NO 905
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 905
ggtacgacgt tcagctnggg nnnttt                          26

<210> SEQ ID NO 906
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 906
ggtacgacgt tcagctnggg nnnaa                           25

<210> SEQ ID NO 907
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 907
ggtacgacgt tcagctnggg nnnac                           25

<210> SEQ ID NO 908
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 908
ggtacgacgt tcagctnggg nnnag                           25

<210> SEQ ID NO 909
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 909
ggtacgacgt tcagctnggg nnnat                                          25

<210> SEQ ID NO 910
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 910
ggtacgacgt tcagctnggg nnnca                                          25

<210> SEQ ID NO 911
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 911
ggtacgacgt tcagctnggg nnncc                                          25

<210> SEQ ID NO 912
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 912
ggtacgacgt tcagctnggg nnncg                                          25

<210> SEQ ID NO 913
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 913
ggtacgacgt tcagctnggg nnnct                                          25

<210> SEQ ID NO 914
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

```
<400> SEQUENCE: 914
ggtacgacgt tcagctnggg nnnga                                    25

<210> SEQ ID NO 915
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 915
ggtacgacgt tcagctnggg nnngc                                    25

<210> SEQ ID NO 916
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 916
ggtacgacgt tcagctnggg nnngg                                    25

<210> SEQ ID NO 917
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 917
ggtacgacgt tcagctnggg nnngt                                    25

<210> SEQ ID NO 918
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 918
ggtacgacgt tcagctnggg nnnta                                    25

<210> SEQ ID NO 919
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;
```

<400> SEQUENCE: 919
ggtacgacgt tcagctnggg nnntc                                    25

<210> SEQ ID NO 920
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 920
ggtacgacgt tcagctnggg nnntg                                    25

<210> SEQ ID NO 921
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (17)..(23)
<223> OTHER INFORMATION: 'n' at position 17 can be any of the
      nucleotides a,c,g or t; 'n' from positions 21 to 23  is a inosine;

<400> SEQUENCE: 921
ggtacgacgt tcagctnggg nnntt                                    25

<210> SEQ ID NO 922
<211> LENGTH: 49
<212> TYPE: DNA
<213> ORGANISM: Artificial Sequence
<220> FEATURE:
<223> OTHER INFORMATION: Adaptor

<400> SEQUENCE: 922
ttttgcaggt acgtcgtacc gcggccgctc gtcgaacgaa cactgcgtt          49

<210> SEQ ID NO 923
<211> LENGTH: 49
<212> TYPE: DNA
<213> ORGANISM: Artificial Sequence
<220> FEATURE:
<223> OTHER INFORMATION: Adaptor

<400> SEQUENCE: 923
tttggcaggt acgtcgtacc gcggccgcta cgtctcgttc cgctctgca          49

<210> SEQ ID NO 924
<211> LENGTH: 49
<212> TYPE: DNA
<213> ORGANISM: Artificial Sequence
<220> FEATURE:
<223> OTHER INFORMATION: Adaptor

<400> SEQUENCE: 924
tttcgcaggt acgtcgtacc gcggccgcct tcgctagacg acgtgcgct          49

<210> SEQ ID NO 925
<211> LENGTH: 49
<212> TYPE: DNA
<213> ORGANISM: Artificial Sequence
<220> FEATURE:

<223> OTHER INFORMATION: Adaptor

<400> SEQUENCE: 925
tttagcaggt acgtcgtacc gcggccgctc gctcgtactc cgtctcaga        49

<210> SEQ ID NO 926
<211> LENGTH: 49
<212> TYPE: DNA
<213> ORGANISM: Artificial Sequence
<220> FEATURE:
<223> OTHER INFORMATION: Adaptor

<400> SEQUENCE: 926
ttgtgcaggt acgtcgtacc gcggccgcat gcgcgaaaac ggtcactgt        49

<210> SEQ ID NO 927
<211> LENGTH: 49
<212> TYPE: DNA
<213> ORGANISM: Artificial Sequence
<220> FEATURE:
<223> OTHER INFORMATION: Adaptor

<400> SEQUENCE: 927
ttgggcaggt acgtcgtacc gcggccgccg cttttcgtcg tcccagagt        49

<210> SEQ ID NO 928
<211> LENGTH: 49
<212> TYPE: DNA
<213> ORGANISM: Artificial Sequence
<220> FEATURE:
<223> OTHER INFORMATION: Adaptor

<400> SEQUENCE: 928
ttgcgcaggt acgtcgtacc gcggccgcct ggtaaacccg gttcggtca        49

<210> SEQ ID NO 929
<211> LENGTH: 49
<212> TYPE: DNA
<213> ORGANISM: Artificial Sequence
<220> FEATURE:
<223> OTHER INFORMATION: Adaptor

<400> SEQUENCE: 929
ttgagcaggt acgtcgtacc gcggccgccg atagtccgag acgtctcgt        49

<210> SEQ ID NO 930
<211> LENGTH: 49
<212> TYPE: DNA
<213> ORGANISM: Artificial Sequence
<220> FEATURE:
<223> OTHER INFORMATION: Adaptor

<400> SEQUENCE: 930
ttctgcaggt acgtcgtacc gcggccgcct atcgaacggc acgttgttg        49

<210> SEQ ID NO 931
<211> LENGTH: 49
<212> TYPE: DNA
<213> ORGANISM: Artificial Sequence
<220> FEATURE:
<223> OTHER INFORMATION: Adaptor

<400> SEQUENCE: 931
ttcggcaggt acgtcgtacc gcggccgcct acgaccgttc gggtggtac        49

<210> SEQ ID NO 932
<211> LENGTH: 49
<212> TYPE: DNA
<213> ORGANISM: Artificial Sequence
<220> FEATURE:
<223> OTHER INFORMATION: Adaptor

<400> SEQUENCE: 932
ttccgcaggt acgtcgtacc gcggccgctc gtacggtcga cggttgtgc            49

<210> SEQ ID NO 933
<211> LENGTH: 49
<212> TYPE: DNA
<213> ORGANISM: Artificial Sequence
<220> FEATURE:
<223> OTHER INFORMATION: Adaptor

<400> SEQUENCE: 933
ttcagcaggt acgtcgtacc gcggccgccg ttagacctcg tctcggctt            49

<210> SEQ ID NO 934
<211> LENGTH: 49
<212> TYPE: DNA
<213> ORGANISM: Artificial Sequence
<220> FEATURE:
<223> OTHER INFORMATION: Adaptor

<400> SEQUENCE: 934
ttatgcaggt acgtcgtacc gcggccgcct aacgtccgat cgcagcgat            49

<210> SEQ ID NO 935
<211> LENGTH: 49
<212> TYPE: DNA
<213> ORGANISM: Artificial Sequence
<220> FEATURE:
<223> OTHER INFORMATION: Adaptor

<400> SEQUENCE: 935
ttaggcaggt acgtcgtacc gcggccgccg gtatcggaac gtctgcggt            49

<210> SEQ ID NO 936
<211> LENGTH: 49
<212> TYPE: DNA
<213> ORGANISM: Artificial Sequence
<220> FEATURE:
<223> OTHER INFORMATION: Adaptor

<400> SEQUENCE: 936
ttacgcaggt acgtcgtacc gcggccgcta ccgaaccgtc gtacgtaga            49

<210> SEQ ID NO 937
<211> LENGTH: 49
<212> TYPE: DNA
<213> ORGANISM: Artificial Sequence
<220> FEATURE:
<223> OTHER INFORMATION: Adaptor

<400> SEQUENCE: 937
ttaagcaggt acgtcgtacc gcggccgcct agcggattca cgtggtgta            49

<210> SEQ ID NO 938
<211> LENGTH: 49
<212> TYPE: DNA
<213> ORGANISM: Artificial Sequence
<220> FEATURE:
<223> OTHER INFORMATION: Adaptor -continued

<400> SEQUENCE: 938
tgttgcaggt acgtcgtacc gcggccgcgt cgacgactct gtccaggat          49

<210> SEQ ID NO 939
<211> LENGTH: 49
<212> TYPE: DNA
<213> ORGANISM: Artificial Sequence
<220> FEATURE:
<223> OTHER INFORMATION: Adaptor

<400> SEQUENCE: 939
tgtggcaggt acgtcgtacc gcggccgctc gacggttctt gactcacga          49

<210> SEQ ID NO 940
<211> LENGTH: 49
<212> TYPE: DNA
<213> ORGANISM: Artificial Sequence
<220> FEATURE:
<223> OTHER INFORMATION: Adaptor

<400> SEQUENCE: 940
tgtcgcaggt acgtcgtacc gcggccgccg taaggatcac gtgtgctgt          49

<210> SEQ ID NO 941
<211> LENGTH: 50
<212> TYPE: DNA
<213> ORGANISM: Artificial Sequence
<220> FEATURE:
<223> OTHER INFORMATION: Adaptor

<400> SEQUENCE: 941
tgtagcaggt acgtcgtacc gcggccgcct tacggatcga gcgtgtacca         50

<210> SEQ ID NO 942
<211> LENGTH: 50
<212> TYPE: DNA
<213> ORGANISM: Artificial Sequence
<220> FEATURE:
<223> OTHER INFORMATION: Adaptor

<400> SEQUENCE: 942
tggtgcaggt acgtcgtacc gcggccgcca tacgcaacga cccgagtgag         50

<210> SEQ ID NO 943
<211> LENGTH: 50
<212> TYPE: DNA
<213> ORGANISM: Artificial Sequence
<220> FEATURE:
<223> OTHER INFORMATION: Adaptor

<400> SEQUENCE: 943
tggggcaggt acgtcgtacc gcggccgccg tatccttgcg tgtgtaatcc         50

<210> SEQ ID NO 944
<211> LENGTH: 49
<212> TYPE: DNA
<213> ORGANISM: Artificial Sequence
<220> FEATURE:
<223> OTHER INFORMATION: Adaptor

<400> SEQUENCE: 944
tggcgcaggt acgtcgtacc gcggccgcat cggaagaagc acgatgcca          49

<210> SEQ ID NO 945
<211> LENGTH: 49

```
<212> TYPE: DNA
<213> ORGANISM: Artificial Sequence
<220> FEATURE:
<223> OTHER INFORMATION: Adaptor

<400> SEQUENCE: 945
tggagcaggt acgtcgtacc gcggccgccc gatttctcgc gaggacgtc          49

<210> SEQ ID NO 946
<211> LENGTH: 49
<212> TYPE: DNA
<213> ORGANISM: Artificial Sequence
<220> FEATURE:
<223> OTHER INFORMATION: Adaptor

<400> SEQUENCE: 946
tgctgcaggt acgtcgtacc gcggccgccg catcccactg ctggatact          49

<210> SEQ ID NO 947
<211> LENGTH: 49
<212> TYPE: DNA
<213> ORGANISM: Artificial Sequence
<220> FEATURE:
<223> OTHER INFORMATION: Adaptor

<400> SEQUENCE: 947
tgcggcaggt acgtcgtacc gcggccgcta cggttcggtc gctcttcgt          49

<210> SEQ ID NO 948
<211> LENGTH: 49
<212> TYPE: DNA
<213> ORGANISM: Artificial Sequence
<220> FEATURE:
<223> OTHER INFORMATION: Adaptor

<400> SEQUENCE: 948
tgccgcaggt acgtcgtacc gcggccgcca ttcgtcgaac cgcagttgc          49

<210> SEQ ID NO 949
<211> LENGTH: 49
<212> TYPE: DNA
<213> ORGANISM: Artificial Sequence
<220> FEATURE:
<223> OTHER INFORMATION: Adaptor

<400> SEQUENCE: 949
tgcagcaggt acgtcgtacc gcggccgccg aatttcgact cgcgaacgt          49

<210> SEQ ID NO 950
<211> LENGTH: 49
<212> TYPE: DNA
<213> ORGANISM: Artificial Sequence
<220> FEATURE:
<223> OTHER INFORMATION: Adaptor

<400> SEQUENCE: 950
tgatgcaggt acgtcgtacc gcggccgcaa cgcgacgcag tgacacgtt          49

<210> SEQ ID NO 951
<211> LENGTH: 49
<212> TYPE: DNA
<213> ORGANISM: Artificial Sequence
<220> FEATURE:
<223> OTHER INFORMATION: Adaptor

<400> SEQUENCE: 951
```

```
tgaggcaggt acgtcgtacc gcggccgcgc tttgcttctc cgtctagac        49
```

<210> SEQ ID NO 952
<211> LENGTH: 49
<212> TYPE: DNA
<213> ORGANISM: Artificial Sequence
<220> FEATURE:
<223> OTHER INFORMATION: Adaptor

<400> SEQUENCE: 952

```
tgacgcaggt acgtcgtacc gcggccgcac gtaacgtcga gcgctaacg        49
```

<210> SEQ ID NO 953
<211> LENGTH: 49
<212> TYPE: DNA
<213> ORGANISM: Artificial Sequence
<220> FEATURE:
<223> OTHER INFORMATION: Adaptor

<400> SEQUENCE: 953

```
tgaagcaggt acgtcgtacc gcggccgcta cgtgacgtgc ggagtgatc        49
```

<210> SEQ ID NO 954
<211> LENGTH: 49
<212> TYPE: DNA
<213> ORGANISM: Artificial Sequence
<220> FEATURE:
<223> OTHER INFORMATION: Adaptor

<400> SEQUENCE: 954

```
tcttgcaggt acgtcgtacc gcggccgccg tagacgctcg gtaactagt        49
```

<210> SEQ ID NO 955
<211> LENGTH: 49
<212> TYPE: DNA
<213> ORGANISM: Artificial Sequence
<220> FEATURE:
<223> OTHER INFORMATION: Adaptor

<400> SEQUENCE: 955

```
tctggcaggt acgtcgtacc gcggccgcct acgagcgtct ctcgcatag        49
```

<210> SEQ ID NO 956
<211> LENGTH: 49
<212> TYPE: DNA
<213> ORGANISM: Artificial Sequence
<220> FEATURE:
<223> OTHER INFORMATION: Adaptor

<400> SEQUENCE: 956

```
tctcgcaggt acgtcgtacc gcggccgcgc gaaacgcatc cgttcgtgt        49
```

<210> SEQ ID NO 957
<211> LENGTH: 49
<212> TYPE: DNA
<213> ORGANISM: Artificial Sequence
<220> FEATURE:
<223> OTHER INFORMATION: Adaptor

<400> SEQUENCE: 957

```
tctagcaggt acgtcgtacc gcggccgctt cgcttcgttg ctgctagta        49
```

<210> SEQ ID NO 958
<211> LENGTH: 49
<212> TYPE: DNA
<213> ORGANISM: Artificial Sequence

```
<220> FEATURE:
<223> OTHER INFORMATION: Adaptor

<400> SEQUENCE: 958
tcgtgcaggt acgtcgtacc gcggccgcac gatcgacacc ggagtctag        49

<210> SEQ ID NO 959
<211> LENGTH: 49
<212> TYPE: DNA
<213> ORGANISM: Artificial Sequence
<220> FEATURE:
<223> OTHER INFORMATION: Adaptor

<400> SEQUENCE: 959
tcgggcaggt acgtcgtacc gcggccgcat cgttgtcggg acgtagtcg        49

<210> SEQ ID NO 960
<211> LENGTH: 49
<212> TYPE: DNA
<213> ORGANISM: Artificial Sequence
<220> FEATURE:
<223> OTHER INFORMATION: Adaptor

<400> SEQUENCE: 960
tcgcgcaggt acgtcgtacc gcggccgcac gaccatcgtc ttccgagtt        49

<210> SEQ ID NO 961
<211> LENGTH: 49
<212> TYPE: DNA
<213> ORGANISM: Artificial Sequence
<220> FEATURE:
<223> OTHER INFORMATION: Adaptor

<400> SEQUENCE: 961
tcgagcaggt acgtcgtacc gcggccgcgt cgtcgatgcg tccatactt        49

<210> SEQ ID NO 962
<211> LENGTH: 49
<212> TYPE: DNA
<213> ORGANISM: Artificial Sequence
<220> FEATURE:
<223> OTHER INFORMATION: Adaptor

<400> SEQUENCE: 962
tcctgcaggt acgtcgtacc gcggccgcaa ccgaacgtgt cgaccttca        49

<210> SEQ ID NO 963
<211> LENGTH: 49
<212> TYPE: DNA
<213> ORGANISM: Artificial Sequence
<220> FEATURE:
<223> OTHER INFORMATION: Adaptor

<400> SEQUENCE: 963
tccggcaggt acgtcgtacc gcggccgctg gttacgtttg cgcggtatt        49

<210> SEQ ID NO 964
<211> LENGTH: 49
<212> TYPE: DNA
<213> ORGANISM: Artificial Sequence
<220> FEATURE:
<223> OTHER INFORMATION: Adaptor

<400> SEQUENCE: 964
tcccgcaggt acgtcgtacc gcggccgccg aaccctggtc ctgtgtcta        49
```

<210> SEQ ID NO 965
<211> LENGTH: 49
<212> TYPE: DNA
<213> ORGANISM: Artificial Sequence
<220> FEATURE:
<223> OTHER INFORMATION: Adaptor

<400> SEQUENCE: 965
tccagcaggt acgtcgtacc gcggccgcgt tcgctcgtca cgaagtact        49

<210> SEQ ID NO 966
<211> LENGTH: 49
<212> TYPE: DNA
<213> ORGANISM: Artificial Sequence
<220> FEATURE:
<223> OTHER INFORMATION: Adaptor

<400> SEQUENCE: 966
tcatgcaggt acgtcgtacc gcggccgccg caaaccgcag cttctagtt        49

<210> SEQ ID NO 967
<211> LENGTH: 49
<212> TYPE: DNA
<213> ORGANISM: Artificial Sequence
<220> FEATURE:
<223> OTHER INFORMATION: Adaptor

<400> SEQUENCE: 967
tcaggcaggt acgtcgtacc gcggccgctt gcgaccgttc gcagctagt        49

<210> SEQ ID NO 968
<211> LENGTH: 49
<212> TYPE: DNA
<213> ORGANISM: Artificial Sequence
<220> FEATURE:
<223> OTHER INFORMATION: Adaptor

<400> SEQUENCE: 968
tcacgcaggt acgtcgtacc gcggccgcag tcgcaggtaa gcgtatgct        49

<210> SEQ ID NO 969
<211> LENGTH: 49
<212> TYPE: DNA
<213> ORGANISM: Artificial Sequence
<220> FEATURE:
<223> OTHER INFORMATION: Adaptor

<400> SEQUENCE: 969
tcaagcaggt acgtcgtacc gcggccgccg actatcgtag gctccacgt        49

<210> SEQ ID NO 970
<211> LENGTH: 49
<212> TYPE: DNA
<213> ORGANISM: Artificial Sequence
<220> FEATURE:
<223> OTHER INFORMATION: Adaptor

<400> SEQUENCE: 970
tattgcaggt acgtcgtacc gcggccgcat cgagcgattc gaggttagg        49

<210> SEQ ID NO 971
<211> LENGTH: 49
<212> TYPE: DNA
<213> ORGANISM: Artificial Sequence
<220> FEATURE:
<223> OTHER INFORMATION: Adaptor

<400> SEQUENCE: 971
tatggcaggt acgtcgtacc gcggccgctc gataccgtag cgccgtggt        49

<210> SEQ ID NO 972
<211> LENGTH: 49
<212> TYPE: DNA
<213> ORGANISM: Artificial Sequence
<220> FEATURE:
<223> OTHER INFORMATION: Adaptor

<400> SEQUENCE: 972
tatcgcaggt acgtcgtacc gcggccgcac cgaactctct cgacggcat        49

<210> SEQ ID NO 973
<211> LENGTH: 49
<212> TYPE: DNA
<213> ORGANISM: Artificial Sequence
<220> FEATURE:
<223> OTHER INFORMATION: Adaptor

<400> SEQUENCE: 973
tatagcaggt acgtcgtacc gcggccgctc gatcgtcact cgtggttga        49

<210> SEQ ID NO 974
<211> LENGTH: 49
<212> TYPE: DNA
<213> ORGANISM: Artificial Sequence
<220> FEATURE:
<223> OTHER INFORMATION: Adaptor

<400> SEQUENCE: 974
tagtgcaggt acgtcgtacc gcggccgcgc gactgacgac gaggatagt        49

<210> SEQ ID NO 975
<211> LENGTH: 49
<212> TYPE: DNA
<213> ORGANISM: Artificial Sequence
<220> FEATURE:
<223> OTHER INFORMATION: Adaptor

<400> SEQUENCE: 975
tagggcaggt acgtcgtacc gcggccgcgt cgtggcagac ggataacct        49

<210> SEQ ID NO 976
<211> LENGTH: 49
<212> TYPE: DNA
<213> ORGANISM: Artificial Sequence
<220> FEATURE:
<223> OTHER INFORMATION: Adaptor

<400> SEQUENCE: 976
tagcgcaggt acgtcgtacc gcggccgcat gcggttcgtc agtcgtgga        49

<210> SEQ ID NO 977
<211> LENGTH: 49
<212> TYPE: DNA
<213> ORGANISM: Artificial Sequence
<220> FEATURE:
<223> OTHER INFORMATION: Adaptor

<400> SEQUENCE: 977
tagagcaggt acgtcgtacc gcggccgccg tatcgattcc gtctagctc        49

<210> SEQ ID NO 978

```
<211> LENGTH: 49
<212> TYPE: DNA
<213> ORGANISM: Artificial Sequence
<220> FEATURE:
<223> OTHER INFORMATION: Adaptor

<400> SEQUENCE: 978
tactgcaggt acgtcgtacc gcggccgcac gaagatcgac ggctccgtt          49

<210> SEQ ID NO 979
<211> LENGTH: 49
<212> TYPE: DNA
<213> ORGANISM: Artificial Sequence
<220> FEATURE:
<223> OTHER INFORMATION: Adaptor

<400> SEQUENCE: 979
tacggcaggt acgtcgtacc gcggccgctc gaacgaagac cacgtactg          49

<210> SEQ ID NO 980
<211> LENGTH: 49
<212> TYPE: DNA
<213> ORGANISM: Artificial Sequence
<220> FEATURE:
<223> OTHER INFORMATION: Adaptor

<400> SEQUENCE: 980
taccgcaggt acgtcgtacc gcggccgctg ctgacttcgg cggtgatcg          49

<210> SEQ ID NO 981
<211> LENGTH: 49
<212> TYPE: DNA
<213> ORGANISM: Artificial Sequence
<220> FEATURE:
<223> OTHER INFORMATION: Adaptor

<400> SEQUENCE: 981
tacagcaggt acgtcgtacc gcggccgcgt tcgtagacgc gagtctgac          49

<210> SEQ ID NO 982
<211> LENGTH: 49
<212> TYPE: DNA
<213> ORGANISM: Artificial Sequence
<220> FEATURE:
<223> OTHER INFORMATION: Adaptor

<400> SEQUENCE: 982
taatgcaggt acgtcgtacc gcggccgcca atcgcgttta ctcgaatgg          49

<210> SEQ ID NO 983
<211> LENGTH: 49
<212> TYPE: DNA
<213> ORGANISM: Artificial Sequence
<220> FEATURE:
<223> OTHER INFORMATION: Adaptor

<400> SEQUENCE: 983
taaggcaggt acgtcgtacc gcggccgccg attcggaacg agcgactat          49

<210> SEQ ID NO 984
<211> LENGTH: 49
<212> TYPE: DNA
<213> ORGANISM: Artificial Sequence
<220> FEATURE:
<223> OTHER INFORMATION: Adaptor

<400> SEQUENCE: 984
```
taacgcaggt acgtcgtacc gcggccgccg ttcttcctgg ctctaaggc    49

<210> SEQ ID NO 985
<211> LENGTH: 49
<212> TYPE: DNA
<213> ORGANISM: Artificial Sequence
<220> FEATURE:
<223> OTHER INFORMATION: Adaptor

<400> SEQUENCE: 985
taaagcaggt acgtcgtacc gcggccgcga acgctaacgt gcgtgaacc    49

<210> SEQ ID NO 986
<211> LENGTH: 50
<212> TYPE: DNA
<213> ORGANISM: Artificial Sequence
<220> FEATURE:
<223> OTHER INFORMATION: Adaptor

<400> SEQUENCE: 986
gtgggcaggt acgtcgtacc gcggccgcga tgagccaggg aaggaattgg    50

<210> SEQ ID NO 987
<211> LENGTH: 49
<212> TYPE: DNA
<213> ORGANISM: Artificial Sequence
<220> FEATURE:
<223> OTHER INFORMATION: Adaptor

<400> SEQUENCE: 987
gttggcaggt acgtcgtacc gcggccgcga ttagacgagg cgaccgaga    49

<210> SEQ ID NO 988
<211> LENGTH: 50
<212> TYPE: DNA
<213> ORGANISM: Artificial Sequence
<220> FEATURE:
<223> OTHER INFORMATION: Adaptor

<400> SEQUENCE: 988
gttcgcaggt acgtcgtacc gcggccgcga ctaggtcagc tgaggagtct    50

<210> SEQ ID NO 989
<211> LENGTH: 49
<212> TYPE: DNA
<213> ORGANISM: Artificial Sequence
<220> FEATURE:
<223> OTHER INFORMATION: Adaptor

<400> SEQUENCE: 989
gttagcaggt acgtcgtacc gcggccgcac tacgagtggc gagctgact    49

<210> SEQ ID NO 990
<211> LENGTH: 49
<212> TYPE: DNA
<213> ORGANISM: Artificial Sequence
<220> FEATURE:
<223> OTHER INFORMATION: Adaptor

<400> SEQUENCE: 990
gtgtgcaggt acgtcgtacc gcggccgcgc ctactgactc gagtactct    49

<210> SEQ ID NO 991
<211> LENGTH: 49
<212> TYPE: DNA

<213> ORGANISM: Artificial Sequence
<220> FEATURE:
<223> OTHER INFORMATION: Adaptor

<400> SEQUENCE: 991
gtgggcaggt acgtcgtacc gcggccgccg ttgttcccga ctcctctgt                49

<210> SEQ ID NO 992
<211> LENGTH: 49
<212> TYPE: DNA
<213> ORGANISM: Artificial Sequence
<220> FEATURE:
<223> OTHER INFORMATION: Adaptor

<400> SEQUENCE: 992
gtgcgcaggt acgtcgtacc gcggccgcca acggacacag gtacccaag                49

<210> SEQ ID NO 993
<211> LENGTH: 49
<212> TYPE: DNA
<213> ORGANISM: Artificial Sequence
<220> FEATURE:
<223> OTHER INFORMATION: Adaptor

<400> SEQUENCE: 993
gtgagcaggt acgtcgtacc gcggccgctc acagattgct tcgtactgt                49

<210> SEQ ID NO 994
<211> LENGTH: 49
<212> TYPE: DNA
<213> ORGANISM: Artificial Sequence
<220> FEATURE:
<223> OTHER INFORMATION: Adaptor

<400> SEQUENCE: 994
gtctgcaggt acgtcgtacc gcggccgccg tccttatgct ctccgagct                49

<210> SEQ ID NO 995
<211> LENGTH: 49
<212> TYPE: DNA
<213> ORGANISM: Artificial Sequence
<220> FEATURE:
<223> OTHER INFORMATION: Adaptor

<400> SEQUENCE: 995
gtcggcaggt acgtcgtacc gcggccgccc tatccagtaa tgcccgaga                49

<210> SEQ ID NO 996
<211> LENGTH: 50
<212> TYPE: DNA
<213> ORGANISM: Artificial Sequence
<220> FEATURE:
<223> OTHER INFORMATION: Adaptor

<400> SEQUENCE: 996
gtccgcaggt acgtcgtacc gcggccgcca tgggacagat caggttaagg                50

<210> SEQ ID NO 997
<211> LENGTH: 49
<212> TYPE: DNA
<213> ORGANISM: Artificial Sequence
<220> FEATURE:
<223> OTHER INFORMATION: Adaptor

<400> SEQUENCE: 997
gtcagcaggt acgtcgtacc gcggccgctc agtcaaactg gactcgcac                49

<210> SEQ ID NO 998
<211> LENGTH: 48
<212> TYPE: DNA
<213> ORGANISM: Artificial Sequence
<220> FEATURE:
<223> OTHER INFORMATION: Adaptor

<400> SEQUENCE: 998
gtatgcaggt acgtcgtacc gcggccgcga aggctgtggt tggccacc           48

<210> SEQ ID NO 999
<211> LENGTH: 49
<212> TYPE: DNA
<213> ORGANISM: Artificial Sequence
<220> FEATURE:
<223> OTHER INFORMATION: Adaptor

<400> SEQUENCE: 999
gtaggcaggt acgtcgtacc gcggccgcgc agtcgtacac ctcatctca          49

<210> SEQ ID NO 1000
<211> LENGTH: 49
<212> TYPE: DNA
<213> ORGANISM: Artificial Sequence
<220> FEATURE:
<223> OTHER INFORMATION: Adaptor

<400> SEQUENCE: 1000
gtacgcaggt acgtcgtacc gcggccgcta gacaactggc gcattgaca          49

<210> SEQ ID NO 1001
<211> LENGTH: 49
<212> TYPE: DNA
<213> ORGANISM: Artificial Sequence
<220> FEATURE:
<223> OTHER INFORMATION: Adaptor

<400> SEQUENCE: 1001
gtaagcaggt acgtcgtacc gcggccgcga tgccactagg tgttggtgc          49

<210> SEQ ID NO 1002
<211> LENGTH: 49
<212> TYPE: DNA
<213> ORGANISM: Artificial Sequence
<220> FEATURE:
<223> OTHER INFORMATION: Adaptor

<400> SEQUENCE: 1002
ggttgcaggt acgtcgtacc gcggccgcag acctcccgct ctacagatc          49

<210> SEQ ID NO 1003
<211> LENGTH: 49
<212> TYPE: DNA
<213> ORGANISM: Artificial Sequence
<220> FEATURE:
<223> OTHER INFORMATION: Adaptor

<400> SEQUENCE: 1003
ggtggcaggt acgtcgtacc gcggccgcgc gtggcagcac ccttagcca          49

<210> SEQ ID NO 1004
<211> LENGTH: 49
<212> TYPE: DNA
<213> ORGANISM: Artificial Sequence
<220> FEATURE:

<223> OTHER INFORMATION: Adaptor

<400> SEQUENCE: 1004
ggtcgcaggt acgtcgtacc gcggccgcag gtttcggctg gagtctcat    49

<210> SEQ ID NO 1005
<211> LENGTH: 49
<212> TYPE: DNA
<213> ORGANISM: Artificial Sequence
<220> FEATURE:
<223> OTHER INFORMATION: Adaptor

<400> SEQUENCE: 1005
ggtagcaggt acgtcgtacc gcggccgctc tgcaggtcgt ccctacact    49

<210> SEQ ID NO 1006
<211> LENGTH: 49
<212> TYPE: DNA
<213> ORGANISM: Artificial Sequence
<220> FEATURE:
<223> OTHER INFORMATION: Adaptor

<400> SEQUENCE: 1006
gggtgcaggt acgtcgtacc gcggccgctg tatcagctat gccgttgcc    49

<210> SEQ ID NO 1007
<211> LENGTH: 50
<212> TYPE: DNA
<213> ORGANISM: Artificial Sequence
<220> FEATURE:
<223> OTHER INFORMATION: Adaptor

<400> SEQUENCE: 1007
gggggcaggt acgtcgtacc gcggccgccg ttgcctcata cctcagcatc    50

<210> SEQ ID NO 1008
<211> LENGTH: 49
<212> TYPE: DNA
<213> ORGANISM: Artificial Sequence
<220> FEATURE:
<223> OTHER INFORMATION: Adaptor

<400> SEQUENCE: 1008
gggcgcaggt acgtcgtacc gcggccgcag cagacaggcc aaatgacgt    49

<210> SEQ ID NO 1009
<211> LENGTH: 49
<212> TYPE: DNA
<213> ORGANISM: Artificial Sequence
<220> FEATURE:
<223> OTHER INFORMATION: Adaptor

<400> SEQUENCE: 1009
gggagcaggt acgtcgtacc gcggccgcag cagttcgagc acgtgagtc    49

<210> SEQ ID NO 1010
<211> LENGTH: 49
<212> TYPE: DNA
<213> ORGANISM: Artificial Sequence
<220> FEATURE:
<223> OTHER INFORMATION: Adaptor

<400> SEQUENCE: 1010
ggctgcaggt acgtcgtacc gcggccgcga gatgtgccac atgccgact    49

<210> SEQ ID NO 1011
<211> LENGTH: 49
<212> TYPE: DNA
<213> ORGANISM: Artificial Sequence
<220> FEATURE:
<223> OTHER INFORMATION: Adaptor

<400> SEQUENCE: 1011
ggcggcaggt acgtcgtacc gcggccgcgt tagcggctgt ctaccgagt            49

<210> SEQ ID NO 1012
<211> LENGTH: 50
<212> TYPE: DNA
<213> ORGANISM: Artificial Sequence
<220> FEATURE:
<223> OTHER INFORMATION: Adaptor

<400> SEQUENCE: 1012
ggccgcaggt acgtcgtacc gcggccgcgt gaatagtgac cgtgtcccag           50

<210> SEQ ID NO 1013
<211> LENGTH: 49
<212> TYPE: DNA
<213> ORGANISM: Artificial Sequence
<220> FEATURE:
<223> OTHER INFORMATION: Adaptor

<400> SEQUENCE: 1013
ggcagcaggt acgtcgtacc gcggccgctg tgtacagcgt tccaagggt            49

<210> SEQ ID NO 1014
<211> LENGTH: 49
<212> TYPE: DNA
<213> ORGANISM: Artificial Sequence
<220> FEATURE:
<223> OTHER INFORMATION: Adaptor

<400> SEQUENCE: 1014
ggatgcaggt acgtcgtacc gcggccgcac gtctcactac gtgtccgga            49

<210> SEQ ID NO 1015
<211> LENGTH: 49
<212> TYPE: DNA
<213> ORGANISM: Artificial Sequence
<220> FEATURE:
<223> OTHER INFORMATION: Adaptor

<400> SEQUENCE: 1015
ggaggcaggt acgtcgtacc gcggccgcgc taggtaagag tgcaaggca            49

<210> SEQ ID NO 1016
<211> LENGTH: 49
<212> TYPE: DNA
<213> ORGANISM: Artificial Sequence
<220> FEATURE:
<223> OTHER INFORMATION: Adaptor

<400> SEQUENCE: 1016
ggacgcaggt acgtcgtacc gcggccgccc aagtgcacga tactggcta            49

<210> SEQ ID NO 1017
<211> LENGTH: 49
<212> TYPE: DNA
<213> ORGANISM: Artificial Sequence
<220> FEATURE:
<223> OTHER INFORMATION: Adaptor

<400> SEQUENCE: 1017
ggaagcaggt acgtcgtacc gcggccgctt cgtgtagggt ggtaagctt            49

<210> SEQ ID NO 1018
<211> LENGTH: 49
<212> TYPE: DNA
<213> ORGANISM: Artificial Sequence
<220> FEATURE:
<223> OTHER INFORMATION: Adaptor

<400> SEQUENCE: 1018
gcttgcaggt acgtcgtacc gcggccgctt cgacccatgt catcatcct            49

<210> SEQ ID NO 1019
<211> LENGTH: 49
<212> TYPE: DNA
<213> ORGANISM: Artificial Sequence
<220> FEATURE:
<223> OTHER INFORMATION: Adaptor

<400> SEQUENCE: 1019
gctggcaggt acgtcgtacc gcggccgcgg aggacttgtc atggaggtt            49

<210> SEQ ID NO 1020
<211> LENGTH: 49
<212> TYPE: DNA
<213> ORGANISM: Artificial Sequence
<220> FEATURE:
<223> OTHER INFORMATION: Adaptor

<400> SEQUENCE: 1020
gctcgcaggt acgtcgtacc gcggccgcag atgtctgtcc cacggtgtt            49

<210> SEQ ID NO 1021
<211> LENGTH: 49
<212> TYPE: DNA
<213> ORGANISM: Artificial Sequence
<220> FEATURE:
<223> OTHER INFORMATION: Adaptor

<400> SEQUENCE: 1021
gctagcaggt acgtcgtacc gcggccgcaa tgccctgtat gttccgtgg            49

<210> SEQ ID NO 1022
<211> LENGTH: 49
<212> TYPE: DNA
<213> ORGANISM: Artificial Sequence
<220> FEATURE:
<223> OTHER INFORMATION: Adaptor

<400> SEQUENCE: 1022
gcgtgcaggt acgtcgtacc gcggccgcat gcttagctcc acgctcatg            49

<210> SEQ ID NO 1023
<211> LENGTH: 49
<212> TYPE: DNA
<213> ORGANISM: Artificial Sequence
<220> FEATURE:
<223> OTHER INFORMATION: Adaptor

<400> SEQUENCE: 1023
gcgggcaggt acgtcgtacc gcggccgccc tcgtaccttg tgacagatg            49

<210> SEQ ID NO 1024
<211> LENGTH: 49

```
<212> TYPE: DNA
<213> ORGANISM: Artificial Sequence
<220> FEATURE:
<223> OTHER INFORMATION: Adaptor

<400> SEQUENCE: 1024
gcgcgcaggt acgtcgtacc gcggccgctg tgcgagcgtt ccatctcct          49

<210> SEQ ID NO 1025
<211> LENGTH: 49
<212> TYPE: DNA
<213> ORGANISM: Artificial Sequence
<220> FEATURE:
<223> OTHER INFORMATION: Adaptor

<400> SEQUENCE: 1025
gcgagcaggt acgtcgtacc gcggccgcga tgctggtcga ggacacaga          49

<210> SEQ ID NO 1026
<211> LENGTH: 49
<212> TYPE: DNA
<213> ORGANISM: Artificial Sequence
<220> FEATURE:
<223> OTHER INFORMATION: Adaptor

<400> SEQUENCE: 1026
gcctgcaggt acgtcgtacc gcggccgcaa ccagcttcca cctggagtt          49

<210> SEQ ID NO 1027
<211> LENGTH: 49
<212> TYPE: DNA
<213> ORGANISM: Artificial Sequence
<220> FEATURE:
<223> OTHER INFORMATION: Adaptor

<400> SEQUENCE: 1027
gccggcaggt acgtcgtacc gcggccgcgt gacgttcgat gtgagtctg          49

<210> SEQ ID NO 1028
<211> LENGTH: 49
<212> TYPE: DNA
<213> ORGANISM: Artificial Sequence
<220> FEATURE:
<223> OTHER INFORMATION: Adaptor

<400> SEQUENCE: 1028
gcccgcaggt acgtcgtacc gcggccgcgg tgtcccattc ggagttaca          49

<210> SEQ ID NO 1029
<211> LENGTH: 49
<212> TYPE: DNA
<213> ORGANISM: Artificial Sequence
<220> FEATURE:
<223> OTHER INFORMATION: Adaptor

<400> SEQUENCE: 1029
gccagcaggt acgtcgtacc gcggccgcca ggtgagggag agcatcaac          49

<210> SEQ ID NO 1030
<211> LENGTH: 49
<212> TYPE: DNA
<213> ORGANISM: Artificial Sequence
<220> FEATURE:
<223> OTHER INFORMATION: Adaptor

<400> SEQUENCE: 1030
```

-continued gcatgcaggt acgtcgtacc gcggccgcct cgaccttgtt ggcagactc    49

<210> SEQ ID NO 1031
<211> LENGTH: 49
<212> TYPE: DNA
<213> ORGANISM: Artificial Sequence
<220> FEATURE:
<223> OTHER INFORMATION: Adaptor

<400> SEQUENCE: 1031
gcaggcaggt acgtcgtacc gcggccgctg cattgcggtt cctcacaac    49

<210> SEQ ID NO 1032
<211> LENGTH: 49
<212> TYPE: DNA
<213> ORGANISM: Artificial Sequence
<220> FEATURE:
<223> OTHER INFORMATION: Adaptor

<400> SEQUENCE: 1032
gcacgcaggt acgtcgtacc gcggccgcct gagagctgtt cactgaggt    49

<210> SEQ ID NO 1033
<211> LENGTH: 49
<212> TYPE: DNA
<213> ORGANISM: Artificial Sequence
<220> FEATURE:
<223> OTHER INFORMATION: Adaptor

<400> SEQUENCE: 1033
gcaagcaggt acgtcgtacc gcggccgcca gtggatagcg acctggatc    49

<210> SEQ ID NO 1034
<211> LENGTH: 49
<212> TYPE: DNA
<213> ORGANISM: Artificial Sequence
<220> FEATURE:
<223> OTHER INFORMATION: Adaptor

<400> SEQUENCE: 1034
gattgcaggt acgtcgtacc gcggccgctg gatttgagat cgcatgtgg    49

<210> SEQ ID NO 1035
<211> LENGTH: 49
<212> TYPE: DNA
<213> ORGANISM: Artificial Sequence
<220> FEATURE:
<223> OTHER INFORMATION: Adaptor

<400> SEQUENCE: 1035
gatcgcaggt acgtcgtacc gcggccgcgc gtctaggtcg tcacgacaa    49

<210> SEQ ID NO 1036
<211> LENGTH: 49
<212> TYPE: DNA
<213> ORGANISM: Artificial Sequence
<220> FEATURE:
<223> OTHER INFORMATION: Adaptor

<400> SEQUENCE: 1036
gatcgcaggt acgtcgtacc gcggccgccc cgatgattag acgcctcaa    49

<210> SEQ ID NO 1037
<211> LENGTH: 49
<212> TYPE: DNA
<213> ORGANISM: Artificial Sequence

```
<220> FEATURE:
<223> OTHER INFORMATION: Adaptor

<400> SEQUENCE: 1037
gatagcaggt acgtcgtacc gcggccgcga tagtggcgat tgctgagcg          49

<210> SEQ ID NO 1038
<211> LENGTH: 49
<212> TYPE: DNA
<213> ORGANISM: Artificial Sequence
<220> FEATURE:
<223> OTHER INFORMATION: Adaptor

<400> SEQUENCE: 1038
gagtgcaggt acgtcgtacc gcggccgcgg cggctcatgt gtgataatg          49

<210> SEQ ID NO 1039
<211> LENGTH: 49
<212> TYPE: DNA
<213> ORGANISM: Artificial Sequence
<220> FEATURE:
<223> OTHER INFORMATION: Adaptor

<400> SEQUENCE: 1039
gagggcaggt acgtcgtacc gcggccgcgg tggttttctc ttgcccctc          49

<210> SEQ ID NO 1040
<211> LENGTH: 49
<212> TYPE: DNA
<213> ORGANISM: Artificial Sequence
<220> FEATURE:
<223> OTHER INFORMATION: Adaptor

<400> SEQUENCE: 1040
gagcgcaggt acgtcgtacc gcggccgcgg aagacagctc gctggactt          49

<210> SEQ ID NO 1041
<211> LENGTH: 49
<212> TYPE: DNA
<213> ORGANISM: Artificial Sequence
<220> FEATURE:
<223> OTHER INFORMATION: Adaptor

<400> SEQUENCE: 1041
gagagcaggt acgtcgtacc gcggccgcga ccttactgag aagcggcct          49

<210> SEQ ID NO 1042
<211> LENGTH: 49
<212> TYPE: DNA
<213> ORGANISM: Artificial Sequence
<220> FEATURE:
<223> OTHER INFORMATION: Adaptor

<400> SEQUENCE: 1042
gactgcaggt acgtcgtacc gcggccgctg tggggttctc tgcgtacac          49

<210> SEQ ID NO 1043
<211> LENGTH: 49
<212> TYPE: DNA
<213> ORGANISM: Artificial Sequence
<220> FEATURE:
<223> OTHER INFORMATION: Adaptor

<400> SEQUENCE: 1043
gacggcaggt acgtcgtacc gcggccgcgg aactgttgtc caggagacc          49
```

<210> SEQ ID NO 1044
<211> LENGTH: 49
<212> TYPE: DNA
<213> ORGANISM: Artificial Sequence
<220> FEATURE:
<223> OTHER INFORMATION: Adaptor

<400> SEQUENCE: 1044
gaccgcaggt acgtcgtacc gcggccgcga tgccagagtg atgcaactg                 49

<210> SEQ ID NO 1045
<211> LENGTH: 49
<212> TYPE: DNA
<213> ORGANISM: Artificial Sequence
<220> FEATURE:
<223> OTHER INFORMATION: Adaptor

<400> SEQUENCE: 1045
gacagcaggt acgtcgtacc gcggccgcct catttcgcga ttcggtctt                 49

<210> SEQ ID NO 1046
<211> LENGTH: 49
<212> TYPE: DNA
<213> ORGANISM: Artificial Sequence
<220> FEATURE:
<223> OTHER INFORMATION: Adaptor

<400> SEQUENCE: 1046
gaatgcaggt acgtcgtacc gcggccgctg tgaaccgggt ggtctgaac                 49

<210> SEQ ID NO 1047
<211> LENGTH: 49
<212> TYPE: DNA
<213> ORGANISM: Artificial Sequence
<220> FEATURE:
<223> OTHER INFORMATION: Adaptor

<400> SEQUENCE: 1047
gaaggcaggt acgtcgtacc gcggccgccc agaggatcct gctgtagca                 49

<210> SEQ ID NO 1048
<211> LENGTH: 49
<212> TYPE: DNA
<213> ORGANISM: Artificial Sequence
<220> FEATURE:
<223> OTHER INFORMATION: Adaptor

<400> SEQUENCE: 1048
gaacgcaggt acgtcgtacc gcggccgcgt tgctgccggt ctaggtatc                 49

<210> SEQ ID NO 1049
<211> LENGTH: 50
<212> TYPE: DNA
<213> ORGANISM: Artificial Sequence
<220> FEATURE:
<223> OTHER INFORMATION: Adaptor

<400> SEQUENCE: 1049
gaaagcaggt acgtcgtacc gcggccgcgt gggtttccta gctctcagtg                 50

<210> SEQ ID NO 1050
<211> LENGTH: 49
<212> TYPE: DNA
<213> ORGANISM: Artificial Sequence
<220> FEATURE:
<223> OTHER INFORMATION: Adaptor

<400> SEQUENCE: 1050
ctttgcaggt acgtcgtacc gcggccgcga cggcatcagg atttatccc            49

<210> SEQ ID NO 1051
<211> LENGTH: 49
<212> TYPE: DNA
<213> ORGANISM: Artificial Sequence
<220> FEATURE:
<223> OTHER INFORMATION: Adaptor

<400> SEQUENCE: 1051
cttggcaggt acgtcgtacc gcggccgcga caggcaaggg ttgagactg            49

<210> SEQ ID NO 1052
<211> LENGTH: 49
<212> TYPE: DNA
<213> ORGANISM: Artificial Sequence
<220> FEATURE:
<223> OTHER INFORMATION: Adaptor

<400> SEQUENCE: 1052
cttcgcaggt acgtcgtacc gcggccgcgt gcttaggtga gctccgtga            49

<210> SEQ ID NO 1053
<211> LENGTH: 49
<212> TYPE: DNA
<213> ORGANISM: Artificial Sequence
<220> FEATURE:
<223> OTHER INFORMATION: Adaptor

<400> SEQUENCE: 1053
cttagcaggt acgtcgtacc gcggccgcgc atcaggtcag ctccaaatc            49

<210> SEQ ID NO 1054
<211> LENGTH: 49
<212> TYPE: DNA
<213> ORGANISM: Artificial Sequence
<220> FEATURE:
<223> OTHER INFORMATION: Adaptor

<400> SEQUENCE: 1054
ctgtgcaggt acgtcgtacc gcggccgcac tcgatttcat agatacatc            49

<210> SEQ ID NO 1055
<211> LENGTH: 49
<212> TYPE: DNA
<213> ORGANISM: Artificial Sequence
<220> FEATURE:
<223> OTHER INFORMATION: Adaptor

<400> SEQUENCE: 1055
ctgggcaggt acgtcgtacc gcggccgcct gaacggagtt acggggttg            49

<210> SEQ ID NO 1056
<211> LENGTH: 49
<212> TYPE: DNA
<213> ORGANISM: Artificial Sequence
<220> FEATURE:
<223> OTHER INFORMATION: Adaptor

<400> SEQUENCE: 1056
ctgcgcaggt acgtcgtacc gcggccgccg aaggtcgcac aagtcgacg            49

<210> SEQ ID NO 1057

```
<211> LENGTH: 49
<212> TYPE: DNA
<213> ORGANISM: Artificial Sequence
<220> FEATURE:
<223> OTHER INFORMATION: Adaptor

<400> SEQUENCE: 1057
ctgagcaggt acgtcgtacc gcggccgcca tgacctggtt gtgcgtgtt           49

<210> SEQ ID NO 1058
<211> LENGTH: 49
<212> TYPE: DNA
<213> ORGANISM: Artificial Sequence
<220> FEATURE:
<223> OTHER INFORMATION: Adaptor

<400> SEQUENCE: 1058
ctctgcaggt acgtcgtacc gcggccgcga gtccagtagc tggagacga           49

<210> SEQ ID NO 1059
<211> LENGTH: 49
<212> TYPE: DNA
<213> ORGANISM: Artificial Sequence
<220> FEATURE:
<223> OTHER INFORMATION: Adaptor

<400> SEQUENCE: 1059
ctcggcaggt acgtcgtacc gcggccgccg tctgtaagtg ttgagcgta           49

<210> SEQ ID NO 1060
<211> LENGTH: 49
<212> TYPE: DNA
<213> ORGANISM: Artificial Sequence
<220> FEATURE:
<223> OTHER INFORMATION: Adaptor

<400> SEQUENCE: 1060
ctccgcaggt acgtcgtacc gcggccgcgt atagtaggtg ctgttgccc           49

<210> SEQ ID NO 1061
<211> LENGTH: 49
<212> TYPE: DNA
<213> ORGANISM: Artificial Sequence
<220> FEATURE:
<223> OTHER INFORMATION: Adaptor

<400> SEQUENCE: 1061
ctcagcaggt acgtcgtacc gcggccgcga gtggaagact ggtcagacg           49

<210> SEQ ID NO 1062
<211> LENGTH: 49
<212> TYPE: DNA
<213> ORGANISM: Artificial Sequence
<220> FEATURE:
<223> OTHER INFORMATION: Adaptor

<400> SEQUENCE: 1062
ctatgcaggt acgtcgtacc gcggccgccg actggaaaac acctctccc           49

<210> SEQ ID NO 1063
<211> LENGTH: 49
<212> TYPE: DNA
<213> ORGANISM: Artificial Sequence
<220> FEATURE:
<223> OTHER INFORMATION: Adaptor

<400> SEQUENCE: 1063
```
ctaggcaggt acgtcgtacc gcggccgctt cgcgacgact acttgggtc            49

<210> SEQ ID NO 1064
<211> LENGTH: 49
<212> TYPE: DNA
<213> ORGANISM: Artificial Sequence
<220> FEATURE:
<223> OTHER INFORMATION: Adaptor

<400> SEQUENCE: 1064
ctacgcaggt acgtcgtacc gcggccgcgg agcctgattc accatggtg            49

<210> SEQ ID NO 1065
<211> LENGTH: 49
<212> TYPE: DNA
<213> ORGANISM: Artificial Sequence
<220> FEATURE:
<223> OTHER INFORMATION: Adaptor

<400> SEQUENCE: 1065
ctaagcaggt acgtcgtacc gcggccgctc gaccttccca cactcaggt            49

<210> SEQ ID NO 1066
<211> LENGTH: 49
<212> TYPE: DNA
<213> ORGANISM: Artificial Sequence
<220> FEATURE:
<223> OTHER INFORMATION: Adaptor

<400> SEQUENCE: 1066
cgttgcaggt acgtcgtacc gcggccgcct tccgacagac agtttcgca            49

<210> SEQ ID NO 1067
<211> LENGTH: 49
<212> TYPE: DNA
<213> ORGANISM: Artificial Sequence
<220> FEATURE:
<223> OTHER INFORMATION: Adaptor

<400> SEQUENCE: 1067
cgtggcaggt acgtcgtacc gcggccgcct gcttgaggat tgccaaagc            49

<210> SEQ ID NO 1068
<211> LENGTH: 49
<212> TYPE: DNA
<213> ORGANISM: Artificial Sequence
<220> FEATURE:
<223> OTHER INFORMATION: Adaptor

<400> SEQUENCE: 1068
cgtcgcaggt acgtcgtacc gcggccgctg ttcgatgagt caggagcga            49

<210> SEQ ID NO 1069
<211> LENGTH: 49
<212> TYPE: DNA
<213> ORGANISM: Artificial Sequence
<220> FEATURE:
<223> OTHER INFORMATION: Adaptor

<400> SEQUENCE: 1069
cgtagcaggt acgtcgtacc gcggccgcgt cgagatggta ccgactctg            49

<210> SEQ ID NO 1070
<211> LENGTH: 50
<212> TYPE: DNA

<213> ORGANISM: Artificial Sequence
<220> FEATURE:
<223> OTHER INFORMATION: Adaptor

<400> SEQUENCE: 1070
cggtgcaggt acgtcgtacc gcggccgcga tcaacatatc ctttgtccgc        50

<210> SEQ ID NO 1071
<211> LENGTH: 50
<212> TYPE: DNA
<213> ORGANISM: Artificial Sequence
<220> FEATURE:
<223> OTHER INFORMATION: Adaptor

<400> SEQUENCE: 1071
cggggcaggt acgtcgtacc gcggccgcct tccgacaaaa ggtcctagtg        50

<210> SEQ ID NO 1072
<211> LENGTH: 49
<212> TYPE: DNA
<213> ORGANISM: Artificial Sequence
<220> FEATURE:
<223> OTHER INFORMATION: Adaptor

<400> SEQUENCE: 1072
cggcgcaggt acgtcgtacc gcggccgcct cacgctagca ccgctctta        49

<210> SEQ ID NO 1073
<211> LENGTH: 49
<212> TYPE: DNA
<213> ORGANISM: Artificial Sequence
<220> FEATURE:
<223> OTHER INFORMATION: Adaptor

<400> SEQUENCE: 1073
cggagcaggt acgtcgtacc gcggccgcac caacgaatct cgaggctcc        49

<210> SEQ ID NO 1074
<211> LENGTH: 49
<212> TYPE: DNA
<213> ORGANISM: Artificial Sequence
<220> FEATURE:
<223> OTHER INFORMATION: Adaptor

<400> SEQUENCE: 1074
cgctgcaggt acgtcgtacc gcggccgcgt ccatgctgaa agaccaggc        49

<210> SEQ ID NO 1075
<211> LENGTH: 49
<212> TYPE: DNA
<213> ORGANISM: Artificial Sequence
<220> FEATURE:
<223> OTHER INFORMATION: Adaptor

<400> SEQUENCE: 1075
cgcggcaggt acgtcgtacc gcggccgcga cagacgttcg gctgacaag        49

<210> SEQ ID NO 1076
<211> LENGTH: 49
<212> TYPE: DNA
<213> ORGANISM: Artificial Sequence
<220> FEATURE:
<223> OTHER INFORMATION: Adaptor

<400> SEQUENCE: 1076
cgccgcaggt acgtcgtacc gcggccgcct gttatccgcc ttgcagcgt        49

<210> SEQ ID NO 1077
<211> LENGTH: 50
<212> TYPE: DNA
<213> ORGANISM: Artificial Sequence
<220> FEATURE:
<223> OTHER INFORMATION: Adaptor

<400> SEQUENCE: 1077
cgcagcaggt acgtcgtacc gcggccgctg aggcacctgt ctatgtgctg     50

<210> SEQ ID NO 1078
<211> LENGTH: 49
<212> TYPE: DNA
<213> ORGANISM: Artificial Sequence
<220> FEATURE:
<223> OTHER INFORMATION: Adaptor

<400> SEQUENCE: 1078
cgatgcaggt acgtcgtacc gcggccgccc cttggtgcaa cgtgatgat      49

<210> SEQ ID NO 1079
<211> LENGTH: 49
<212> TYPE: DNA
<213> ORGANISM: Artificial Sequence
<220> FEATURE:
<223> OTHER INFORMATION: Adaptor

<400> SEQUENCE: 1079
cgaggcaggt acgtcgtacc gcggccgcag ggtcgtacgt tcctctgga      49

<210> SEQ ID NO 1080
<211> LENGTH: 49
<212> TYPE: DNA
<213> ORGANISM: Artificial Sequence
<220> FEATURE:
<223> OTHER INFORMATION: Adaptor

<400> SEQUENCE: 1080
cgacgcaggt acgtcgtacc gcggccgctg ctcgctctgt ctcctgttc      49

<210> SEQ ID NO 1081
<211> LENGTH: 49
<212> TYPE: DNA
<213> ORGANISM: Artificial Sequence
<220> FEATURE:
<223> OTHER INFORMATION: Adaptor

<400> SEQUENCE: 1081
cgaagcaggt acgtcgtacc gcggccgctc cacgtcgtac tgaccgtag      49

<210> SEQ ID NO 1082
<211> LENGTH: 49
<212> TYPE: DNA
<213> ORGANISM: Artificial Sequence
<220> FEATURE:
<223> OTHER INFORMATION: Adaptor

<400> SEQUENCE: 1082
ccttgcaggt acgtcgtacc gcggccgcca gcgctccagc gaataattt      49

<210> SEQ ID NO 1083
<211> LENGTH: 49
<212> TYPE: DNA
<213> ORGANISM: Artificial Sequence
<220> FEATURE:

-continued

<223> OTHER INFORMATION: Adaptor

<400> SEQUENCE: 1083
cctggcaggt acgtcgtacc gcggccgcct gtatgctaca ccgcagctg        49

<210> SEQ ID NO 1084
<211> LENGTH: 49
<212> TYPE: DNA
<213> ORGANISM: Artificial Sequence
<220> FEATURE:
<223> OTHER INFORMATION: Adaptor

<400> SEQUENCE: 1084
cctcgcaggt acgtcgtacc gcggccgcgc gtctggaacg attacgagt        49

<210> SEQ ID NO 1085
<211> LENGTH: 49
<212> TYPE: DNA
<213> ORGANISM: Artificial Sequence
<220> FEATURE:
<223> OTHER INFORMATION: Adaptor

<400> SEQUENCE: 1085
cctagcaggt acgtcgtacc gcggccgcct ttccggccat aacacgtat        49

<210> SEQ ID NO 1086
<211> LENGTH: 49
<212> TYPE: DNA
<213> ORGANISM: Artificial Sequence
<220> FEATURE:
<223> OTHER INFORMATION: Adaptor

<400> SEQUENCE: 1086
ccgtgcaggt acgtcgtacc gcggccgctt cccaacctaa cttcggagc        49

<210> SEQ ID NO 1087
<211> LENGTH: 49
<212> TYPE: DNA
<213> ORGANISM: Artificial Sequence
<220> FEATURE:
<223> OTHER INFORMATION: Adaptor

<400> SEQUENCE: 1087
ccgggcaggt acgtcgtacc gcggccgcgc tatcgttgca agggtgaac        49

<210> SEQ ID NO 1088
<211> LENGTH: 49
<212> TYPE: DNA
<213> ORGANISM: Artificial Sequence
<220> FEATURE:
<223> OTHER INFORMATION: Adaptor

<400> SEQUENCE: 1088
ccgcgcaggt acgtcgtacc gcggccgcat ccgagtaggg agtctccct        49

<210> SEQ ID NO 1089
<211> LENGTH: 49
<212> TYPE: DNA
<213> ORGANISM: Artificial Sequence
<220> FEATURE:
<223> OTHER INFORMATION: Adaptor

<400> SEQUENCE: 1089
ccgagcaggt acgtcgtacc gcggccgcct ggtacatgtc tggcaactc        49

<210> SEQ ID NO 1090
<211> LENGTH: 49
<212> TYPE: DNA
<213> ORGANISM: Artificial Sequence
<220> FEATURE:
<223> OTHER INFORMATION: Adaptor

<400> SEQUENCE: 1090
ccctgcaggt acgtcgtacc gcggccgctg cttgtgggaa gaaactggc        49

<210> SEQ ID NO 1091
<211> LENGTH: 49
<212> TYPE: DNA
<213> ORGANISM: Artificial Sequence
<220> FEATURE:
<223> OTHER INFORMATION: Adaptor

<400> SEQUENCE: 1091
cccggcaggt acgtcgtacc gcggccgcct gggtcgcata ctcgttcac        49

<210> SEQ ID NO 1092
<211> LENGTH: 49
<212> TYPE: DNA
<213> ORGANISM: Artificial Sequence
<220> FEATURE:
<223> OTHER INFORMATION: Adaptor

<400> SEQUENCE: 1092
ccccgcaggt acgtcgtacc gcggccgcta ggcgttgcaa tacaggcaa        49

<210> SEQ ID NO 1093
<211> LENGTH: 49
<212> TYPE: DNA
<213> ORGANISM: Artificial Sequence
<220> FEATURE:
<223> OTHER INFORMATION: Adaptor

<400> SEQUENCE: 1093
cccagcaggt acgtcgtacc gcggccgctc ctgatcttcc agcagctca        49

<210> SEQ ID NO 1094
<211> LENGTH: 50
<212> TYPE: DNA
<213> ORGANISM: Artificial Sequence
<220> FEATURE:
<223> OTHER INFORMATION: Adaptor

<400> SEQUENCE: 1094
ccatgcaggt acgtcgtacc gcggccgctc atgttgcgta ttcccctact        50

<210> SEQ ID NO 1095
<211> LENGTH: 49
<212> TYPE: DNA
<213> ORGANISM: Artificial Sequence
<220> FEATURE:
<223> OTHER INFORMATION: Adaptor

<400> SEQUENCE: 1095
ccaggcaggt acgtcgtacc gcggccgcgg tcactcctcg aagtggatc        49

<210> SEQ ID NO 1096
<211> LENGTH: 49
<212> TYPE: DNA
<213> ORGANISM: Artificial Sequence
<220> FEATURE:
<223> OTHER INFORMATION: Adaptor -continued

```
<400> SEQUENCE: 1096
ccacgcaggt acgtcgtacc gcggccgccg tgtcgagcga atgtggtac        49

<210> SEQ ID NO 1097
<211> LENGTH: 49
<212> TYPE: DNA
<213> ORGANISM: Artificial Sequence
<220> FEATURE:
<223> OTHER INFORMATION: Adaptor

<400> SEQUENCE: 1097
ccaagcaggt acgtcgtacc gcggccgctg ccaattcgag agggaaatg        49

<210> SEQ ID NO 1098
<211> LENGTH: 49
<212> TYPE: DNA
<213> ORGANISM: Artificial Sequence
<220> FEATURE:
<223> OTHER INFORMATION: Adaptor

<400> SEQUENCE: 1098
cattgcaggt acgtcgtacc gcggccgcac atctcggcga tacatcgga        49

<210> SEQ ID NO 1099
<211> LENGTH: 49
<212> TYPE: DNA
<213> ORGANISM: Artificial Sequence
<220> FEATURE:
<223> OTHER INFORMATION: Adaptor

<400> SEQUENCE: 1099
catggcaggt acgtcgtacc gcggccgctg accttccttc tcagttggt        49

<210> SEQ ID NO 1100
<211> LENGTH: 50
<212> TYPE: DNA
<213> ORGANISM: Artificial Sequence
<220> FEATURE:
<223> OTHER INFORMATION: Adaptor

<400> SEQUENCE: 1100
catcgcaggt acgtcgtacc gcggccgcga gtactggtga ctaggattcg        50

<210> SEQ ID NO 1101
<211> LENGTH: 49
<212> TYPE: DNA
<213> ORGANISM: Artificial Sequence
<220> FEATURE:
<223> OTHER INFORMATION: Adaptor

<400> SEQUENCE: 1101
catagcaggt acgtcgtacc gcggccgctc ggtaggagtg catccttcc        49

<210> SEQ ID NO 1102
<211> LENGTH: 49
<212> TYPE: DNA
<213> ORGANISM: Artificial Sequence
<220> FEATURE:
<223> OTHER INFORMATION: Adaptor

<400> SEQUENCE: 1102
cagtgcaggt acgtcgtacc gcggccgcgt ggtgagggag ggagctatt        49

<210> SEQ ID NO 1103
<211> LENGTH: 49
```

-continued

<212> TYPE: DNA
<213> ORGANISM: Artificial Sequence
<220> FEATURE:
<223> OTHER INFORMATION: Adaptor

<400> SEQUENCE: 1103
cagggcaggt acgtcgtacc gcggccgcga gatgtagcag atggtcctc         49

<210> SEQ ID NO 1104
<211> LENGTH: 49
<212> TYPE: DNA
<213> ORGANISM: Artificial Sequence
<220> FEATURE:
<223> OTHER INFORMATION: Adaptor

<400> SEQUENCE: 1104
cagcgcaggt acgtcgtacc gcggccgcga ttaggacccg cgaagtaat         49

<210> SEQ ID NO 1105
<211> LENGTH: 49
<212> TYPE: DNA
<213> ORGANISM: Artificial Sequence
<220> FEATURE:
<223> OTHER INFORMATION: Adaptor

<400> SEQUENCE: 1105
cagagcaggt acgtcgtacc gcggccgcca tagccttttg ttgtcgctg         49

<210> SEQ ID NO 1106
<211> LENGTH: 49
<212> TYPE: DNA
<213> ORGANISM: Artificial Sequence
<220> FEATURE:
<223> OTHER INFORMATION: Adaptor

<400> SEQUENCE: 1106
cactgcaggt acgtcgtacc gcggccgcct agtgatgagg tgtcaacgc         49

<210> SEQ ID NO 1107
<211> LENGTH: 49
<212> TYPE: DNA
<213> ORGANISM: Artificial Sequence
<220> FEATURE:
<223> OTHER INFORMATION: Adaptor

<400> SEQUENCE: 1107
cacggcaggt acgtcgtacc gcggccgcgt tcggacggtg agtggtaga         49

<210> SEQ ID NO 1108
<211> LENGTH: 49
<212> TYPE: DNA
<213> ORGANISM: Artificial Sequence
<220> FEATURE:
<223> OTHER INFORMATION: Adaptor

<400> SEQUENCE: 1108
caccgcaggt acgtcgtacc gcggccgcgc acttcctcag aagcatgct         49

<210> SEQ ID NO 1109
<211> LENGTH: 50
<212> TYPE: DNA
<213> ORGANISM: Artificial Sequence
<220> FEATURE:
<223> OTHER INFORMATION: Adaptor

<400> SEQUENCE: 1109
cacagcaggt acgtcgtacc gcggccgctg taacacaagc cacgatgact          50

<210> SEQ ID NO 1110
<211> LENGTH: 49
<212> TYPE: DNA
<213> ORGANISM: Artificial Sequence
<220> FEATURE:
<223> OTHER INFORMATION: Adaptor

<400> SEQUENCE: 1110
caatgcaggt acgtcgtacc gcggccgctg ggacccatag ccaagtgtc           49

<210> SEQ ID NO 1111
<211> LENGTH: 49
<212> TYPE: DNA
<213> ORGANISM: Artificial Sequence
<220> FEATURE:
<223> OTHER INFORMATION: Adaptor

<400> SEQUENCE: 1111
caaggcaggt acgtcgtacc gcggccgctt ggagctctca cgtactgtg           49

<210> SEQ ID NO 1112
<211> LENGTH: 49
<212> TYPE: DNA
<213> ORGANISM: Artificial Sequence
<220> FEATURE:
<223> OTHER INFORMATION: Adaptor

<400> SEQUENCE: 1112
caacgcaggt acgtcgtacc gcggccgcct ggtcctgttg ggttgcttc           49

<210> SEQ ID NO 1113
<211> LENGTH: 50
<212> TYPE: DNA
<213> ORGANISM: Artificial Sequence
<220> FEATURE:
<223> OTHER INFORMATION: Adaptor

<400> SEQUENCE: 1113
caaagcaggt acgtcgtacc gcggccgctg ctgcttcctg gtgagtctct          50

<210> SEQ ID NO 1114
<211> LENGTH: 49
<212> TYPE: DNA
<213> ORGANISM: Artificial Sequence
<220> FEATURE:
<223> OTHER INFORMATION: Adaptor

<400> SEQUENCE: 1114
atttgcaggt acgtcgtacc gcggccgctc agccttctgc tgtaccaca           49

<210> SEQ ID NO 1115
<211> LENGTH: 49
<212> TYPE: DNA
<213> ORGANISM: Artificial Sequence
<220> FEATURE:
<223> OTHER INFORMATION: Adaptor

<400> SEQUENCE: 1115
attggcaggt acgtcgtacc gcggccgctc ctgctttggc gaacttgga           49

<210> SEQ ID NO 1116
<211> LENGTH: 49
<212> TYPE: DNA
<213> ORGANISM: Artificial Sequence

```
<220> FEATURE:
<223> OTHER INFORMATION: Adaptor

<400> SEQUENCE: 1116
attcgcaggt acgtcgtacc gcggccgcga agcattccag aatcgcacg          49

<210> SEQ ID NO 1117
<211> LENGTH: 49
<212> TYPE: DNA
<213> ORGANISM: Artificial Sequence
<220> FEATURE:
<223> OTHER INFORMATION: Adaptor

<400> SEQUENCE: 1117
attagcaggt acgtcgtacc gcggccgctc ctctcccacc attccgagt          49

<210> SEQ ID NO 1118
<211> LENGTH: 49
<212> TYPE: DNA
<213> ORGANISM: Artificial Sequence
<220> FEATURE:
<223> OTHER INFORMATION: Adaptor

<400> SEQUENCE: 1118
atgtgcaggt acgtcgtacc gcggccgctg gtttcctcga gaatctgct          49

<210> SEQ ID NO 1119
<211> LENGTH: 49
<212> TYPE: DNA
<213> ORGANISM: Artificial Sequence
<220> FEATURE:
<223> OTHER INFORMATION: Adaptor

<400> SEQUENCE: 1119
atgggcaggt acgtcgtacc gcggccgctg ctgaccagac cagagaggt          49

<210> SEQ ID NO 1120
<211> LENGTH: 50
<212> TYPE: DNA
<213> ORGANISM: Artificial Sequence
<220> FEATURE:
<223> OTHER INFORMATION: Adaptor

<400> SEQUENCE: 1120
atgcgcaggt acgtcgtacc gcggccgcct gctcactcat ccacttgtca         50

<210> SEQ ID NO 1121
<211> LENGTH: 49
<212> TYPE: DNA
<213> ORGANISM: Artificial Sequence
<220> FEATURE:
<223> OTHER INFORMATION: Adaptor

<400> SEQUENCE: 1121
atgagcaggt acgtcgtacc gcggccgctg taccacggtc gaaaaatcc          49

<210> SEQ ID NO 1122
<211> LENGTH: 49
<212> TYPE: DNA
<213> ORGANISM: Artificial Sequence
<220> FEATURE:
<223> OTHER INFORMATION: Adaptor

<400> SEQUENCE: 1122
atctgcaggt acgtcgtacc gcggccgctg gtgagtaaag ctctcaggc          49
```

<210> SEQ ID NO 1123
<211> LENGTH: 49
<212> TYPE: DNA
<213> ORGANISM: Artificial Sequence
<220> FEATURE:
<223> OTHER INFORMATION: Adaptor

<400> SEQUENCE: 1123
atcggcaggt acgtcgtacc gcggccgcgt gccatcgcag aagctaagc        49

<210> SEQ ID NO 1124
<211> LENGTH: 49
<212> TYPE: DNA
<213> ORGANISM: Artificial Sequence
<220> FEATURE:
<223> OTHER INFORMATION: Adaptor

<400> SEQUENCE: 1124
atccgcaggt acgtcgtacc gcggccgctg aggctacctg acactgctg        49

<210> SEQ ID NO 1125
<211> LENGTH: 49
<212> TYPE: DNA
<213> ORGANISM: Artificial Sequence
<220> FEATURE:
<223> OTHER INFORMATION: Adaptor

<400> SEQUENCE: 1125
atcagcaggt acgtcgtacc gcggccgctg gtgccagaac ctcttgtct        49

<210> SEQ ID NO 1126
<211> LENGTH: 49
<212> TYPE: DNA
<213> ORGANISM: Artificial Sequence
<220> FEATURE:
<223> OTHER INFORMATION: Adaptor

<400> SEQUENCE: 1126
atatgcaggt acgtcgtacc gcggccgctg cgacttgata gacccacca        49

<210> SEQ ID NO 1127
<211> LENGTH: 49
<212> TYPE: DNA
<213> ORGANISM: Artificial Sequence
<220> FEATURE:
<223> OTHER INFORMATION: Adaptor

<400> SEQUENCE: 1127
ataggcaggt acgtcgtacc gcggccgcgt agcatcagtg gctacgaca        49

<210> SEQ ID NO 1128
<211> LENGTH: 49
<212> TYPE: DNA
<213> ORGANISM: Artificial Sequence
<220> FEATURE:
<223> OTHER INFORMATION: Adaptor

<400> SEQUENCE: 1128
atacgcaggt acgtcgtacc gcggccgcga gcatcgatgc cagggatga        49

<210> SEQ ID NO 1129
<211> LENGTH: 49
<212> TYPE: DNA
<213> ORGANISM: Artificial Sequence
<220> FEATURE:
<223> OTHER INFORMATION: Adaptor

```
<400> SEQUENCE: 1129
ataagcaggt acgtcgtacc gcggccgcct ctgtctggga aggcacctc          49

<210> SEQ ID NO 1130
<211> LENGTH: 49
<212> TYPE: DNA
<213> ORGANISM: Artificial Sequence
<220> FEATURE:
<223> OTHER INFORMATION: Adaptor

<400> SEQUENCE: 1130
agttgcaggt acgtcgtacc gcggccgcga gaggacgact ccagagacg          49

<210> SEQ ID NO 1131
<211> LENGTH: 49
<212> TYPE: DNA
<213> ORGANISM: Artificial Sequence
<220> FEATURE:
<223> OTHER INFORMATION: Adaptor

<400> SEQUENCE: 1131
agtggcaggt acgtcgtacc gcggccgcca tccatagacc gtgactcca          49

<210> SEQ ID NO 1132
<211> LENGTH: 50
<212> TYPE: DNA
<213> ORGANISM: Artificial Sequence
<220> FEATURE:
<223> OTHER INFORMATION: Adaptor

<400> SEQUENCE: 1132
agtcgcaggt acgtcgtacc gcggccgcgt ccacgtcatt ccaggagact         50

<210> SEQ ID NO 1133
<211> LENGTH: 49
<212> TYPE: DNA
<213> ORGANISM: Artificial Sequence
<220> FEATURE:
<223> OTHER INFORMATION: Adaptor

<400> SEQUENCE: 1133
agtagcaggt acgtcgtacc gcggccgccg atctaggtga ggacactgg          49

<210> SEQ ID NO 1134
<211> LENGTH: 49
<212> TYPE: DNA
<213> ORGANISM: Artificial Sequence
<220> FEATURE:
<223> OTHER INFORMATION: Adaptor

<400> SEQUENCE: 1134
aggtgcaggt acgtcgtacc gcggccgcga aggacaactg gcgtaggct          49

<210> SEQ ID NO 1135
<211> LENGTH: 50
<212> TYPE: DNA
<213> ORGANISM: Artificial Sequence
<220> FEATURE:
<223> OTHER INFORMATION: Adaptor

<400> SEQUENCE: 1135
aggggcaggt acgtcgtacc gcggccgcgt cgttcgtatc ctctacaagg         50

<210> SEQ ID NO 1136
```

-continued

<210> SEQ ID NO 1136
<211> LENGTH: 49
<212> TYPE: DNA
<213> ORGANISM: Artificial Sequence
<220> FEATURE:
<223> OTHER INFORMATION: Adaptor

<400> SEQUENCE: 1136
aggcgcaggt acgtcgtacc gcggccgcga gttcctggct gtgctacct          49

<210> SEQ ID NO 1137
<211> LENGTH: 49
<212> TYPE: DNA
<213> ORGANISM: Artificial Sequence
<220> FEATURE:
<223> OTHER INFORMATION: Adaptor

<400> SEQUENCE: 1137
aggagcaggt acgtcgtacc gcggccgcct gctgatggat cgtgtacga          49

<210> SEQ ID NO 1138
<211> LENGTH: 49
<212> TYPE: DNA
<213> ORGANISM: Artificial Sequence
<220> FEATURE:
<223> OTHER INFORMATION: Adaptor

<400> SEQUENCE: 1138
agctgcaggt acgtcgtacc gcggccgcgt gttcgaaggc agagggttc          49

<210> SEQ ID NO 1139
<211> LENGTH: 50
<212> TYPE: DNA
<213> ORGANISM: Artificial Sequence
<220> FEATURE:
<223> OTHER INFORMATION: Adaptor

<400> SEQUENCE: 1139
agcggcaggt acgtcgtacc gcggccgcgg tttaaggggt ctaggttgag          50

<210> SEQ ID NO 1140
<211> LENGTH: 49
<212> TYPE: DNA
<213> ORGANISM: Artificial Sequence
<220> FEATURE:
<223> OTHER INFORMATION: Adaptor

<400> SEQUENCE: 1140
agccgcaggt acgtcgtacc gcggccgcct cctctgggac gttgctaag          49

<210> SEQ ID NO 1141
<211> LENGTH: 49
<212> TYPE: DNA
<213> ORGANISM: Artificial Sequence
<220> FEATURE:
<223> OTHER INFORMATION: Adaptor

<400> SEQUENCE: 1141
agcagcaggt acgtcgtacc gcggccgcca gcagacgcag tgatctcct          49

<210> SEQ ID NO 1142
<211> LENGTH: 49
<212> TYPE: DNA
<213> ORGANISM: Artificial Sequence
<220> FEATURE:
<223> OTHER INFORMATION: Adaptor

<400> SEQUENCE: 1142

```
agatgcaggt acgtcgtacc gcggccgcga gcatgaagtg agcagctgg       49
```

<210> SEQ ID NO 1143
<211> LENGTH: 49
<212> TYPE: DNA
<213> ORGANISM: Artificial Sequence
<220> FEATURE:
<223> OTHER INFORMATION: Adaptor

<400> SEQUENCE: 1143

```
agaggcaggt acgtcgtacc gcggccgcct ggcctcagta gagactggt       49
```

<210> SEQ ID NO 1144
<211> LENGTH: 49
<212> TYPE: DNA
<213> ORGANISM: Artificial Sequence
<220> FEATURE:
<223> OTHER INFORMATION: Adaptor

<400> SEQUENCE: 1144

```
agacgcaggt acgtcgtacc gcggccgctg gcaggcacta gtgcaatag       49
```

<210> SEQ ID NO 1145
<211> LENGTH: 49
<212> TYPE: DNA
<213> ORGANISM: Artificial Sequence
<220> FEATURE:
<223> OTHER INFORMATION: Adaptor

<400> SEQUENCE: 1145

```
agaagcaggt acgtcgtacc gcggccgcct acatcctgtc gtgtccgca       49
```

<210> SEQ ID NO 1146
<211> LENGTH: 49
<212> TYPE: DNA
<213> ORGANISM: Artificial Sequence
<220> FEATURE:
<223> OTHER INFORMATION: Adaptor

<400> SEQUENCE: 1146

```
acttgcaggt acgtcgtacc gcggccgcac ggatctgagg tagcactgg       49
```

<210> SEQ ID NO 1147
<211> LENGTH: 49
<212> TYPE: DNA
<213> ORGANISM: Artificial Sequence
<220> FEATURE:
<223> OTHER INFORMATION: Adaptor

<400> SEQUENCE: 1147

```
actggcaggt acgtcgtacc gcggccgctg agaagcctca gctcgattc       49
```

<210> SEQ ID NO 1148
<211> LENGTH: 49
<212> TYPE: DNA
<213> ORGANISM: Artificial Sequence
<220> FEATURE:
<223> OTHER INFORMATION: Adaptor

<400> SEQUENCE: 1148

```
actcgcaggt acgtcgtacc gcggccgccg tttgaggtta attcgcctg       49
```

<210> SEQ ID NO 1149
<211> LENGTH: 49
<212> TYPE: DNA

-continued

<213> ORGANISM: Artificial Sequence
<220> FEATURE:
<223> OTHER INFORMATION: Adaptor

<400> SEQUENCE: 1149
actagcaggt acgtcgtacc gcggccgctg ctactgcaaa tacccgagc         49

<210> SEQ ID NO 1150
<211> LENGTH: 49
<212> TYPE: DNA
<213> ORGANISM: Artificial Sequence
<220> FEATURE:
<223> OTHER INFORMATION: Adaptor

<400> SEQUENCE: 1150
acgtgcaggt acgtcgtacc gcggccgctc gtctgcacgt aactcctca         49

<210> SEQ ID NO 1151
<211> LENGTH: 49
<212> TYPE: DNA
<213> ORGANISM: Artificial Sequence
<220> FEATURE:
<223> OTHER INFORMATION: Adaptor

<400> SEQUENCE: 1151
acgggcaggt acgtcgtacc gcggccgcgg atggttcaag cgactgtca         49

<210> SEQ ID NO 1152
<211> LENGTH: 49
<212> TYPE: DNA
<213> ORGANISM: Artificial Sequence
<220> FEATURE:
<223> OTHER INFORMATION: Adaptor

<400> SEQUENCE: 1152
acgcgcaggt acgtcgtacc gcggccgcca ctctcagctg gtggtctgt         49

<210> SEQ ID NO 1153
<211> LENGTH: 49
<212> TYPE: DNA
<213> ORGANISM: Artificial Sequence
<220> FEATURE:
<223> OTHER INFORMATION: Adaptor

<400> SEQUENCE: 1153
acgagcaggt acgtcgtacc gcggccgcgc ttggttgatg ggaatggac         49

<210> SEQ ID NO 1154
<211> LENGTH: 50
<212> TYPE: DNA
<213> ORGANISM: Artificial Sequence
<220> FEATURE:
<223> OTHER INFORMATION: Adaptor

<400> SEQUENCE: 1154
acctgcaggt acgtcgtacc gcggccgcct gcaagcaaga ctagacgtac         50

<210> SEQ ID NO 1155
<211> LENGTH: 49
<212> TYPE: DNA
<213> ORGANISM: Artificial Sequence
<220> FEATURE:
<223> OTHER INFORMATION: Adaptor

<400> SEQUENCE: 1155
accggcaggt acgtcgtacc gcggccgctc catgaagctc ccaagtgtc         49

<210> SEQ ID NO 1156
<211> LENGTH: 49
<212> TYPE: DNA
<213> ORGANISM: Artificial Sequence
<220> FEATURE:
<223> OTHER INFORMATION: Adaptor

<400> SEQUENCE: 1156
acccgcaggt acgtcgtacc gcggccgctg cacattggtt aaacgcagg                49

<210> SEQ ID NO 1157
<211> LENGTH: 49
<212> TYPE: DNA
<213> ORGANISM: Artificial Sequence
<220> FEATURE:
<223> OTHER INFORMATION: Adaptor

<400> SEQUENCE: 1157
accagcaggt acgtcgtacc gcggccgctg cagatcattg caggtagat                49

<210> SEQ ID NO 1158
<211> LENGTH: 49
<212> TYPE: DNA
<213> ORGANISM: Artificial Sequence
<220> FEATURE:
<223> OTHER INFORMATION: Adaptor

<400> SEQUENCE: 1158
acatgcaggt acgtcgtacc gcggccgcag cacgactgga agacggtct                49

<210> SEQ ID NO 1159
<211> LENGTH: 49
<212> TYPE: DNA
<213> ORGANISM: Artificial Sequence
<220> FEATURE:
<223> OTHER INFORMATION: Adaptor

<400> SEQUENCE: 1159
acaggcaggt acgtcgtacc gcggccgcag catgaacatc atcggtggt                49

<210> SEQ ID NO 1160
<211> LENGTH: 49
<212> TYPE: DNA
<213> ORGANISM: Artificial Sequence
<220> FEATURE:
<223> OTHER INFORMATION: Adaptor

<400> SEQUENCE: 1160
acacgcaggt acgtcgtacc gcggccgctg gagtctggac tgtggtgga                49

<210> SEQ ID NO 1161
<211> LENGTH: 49
<212> TYPE: DNA
<213> ORGANISM: Artificial Sequence
<220> FEATURE:
<223> OTHER INFORMATION: Adaptor

<400> SEQUENCE: 1161
acaagcaggt acgtcgtacc gcggccgcct tacacctcgt cgactcgtc                49

<210> SEQ ID NO 1162
<211> LENGTH: 49
<212> TYPE: DNA
<213> ORGANISM: Artificial Sequence
<220> FEATURE:

<223> OTHER INFORMATION: Adaptor

<400> SEQUENCE: 1162
aattgcaggt acgtcgtacc gcggccgcag ggctaagctt ccgtaggtc         49

<210> SEQ ID NO 1163
<211> LENGTH: 49
<212> TYPE: DNA
<213> ORGANISM: Artificial Sequence
<220> FEATURE:
<223> OTHER INFORMATION: Adaptor

<400> SEQUENCE: 1163
aatggcaggt acgtcgtacc gcggccgcgt tggctagttg cggtggtgt         49

<210> SEQ ID NO 1164
<211> LENGTH: 49
<212> TYPE: DNA
<213> ORGANISM: Artificial Sequence
<220> FEATURE:
<223> OTHER INFORMATION: Adaptor

<400> SEQUENCE: 1164
aatcgcaggt acgtcgtacc gcggccgctc gcaggtctta ggcacaacg         49

<210> SEQ ID NO 1165
<211> LENGTH: 49
<212> TYPE: DNA
<213> ORGANISM: Artificial Sequence
<220> FEATURE:
<223> OTHER INFORMATION: Adaptor

<400> SEQUENCE: 1165
aatagcaggt acgtcgtacc gcggccgcgt caggtccgat tctggttcc         49

<210> SEQ ID NO 1166
<211> LENGTH: 49
<212> TYPE: DNA
<213> ORGANISM: Artificial Sequence
<220> FEATURE:
<223> OTHER INFORMATION: Adaptor

<400> SEQUENCE: 1166
aagtgcaggt acgtcgtacc gcggccgcca gctcgaccca tcaactcca         49

<210> SEQ ID NO 1167
<211> LENGTH: 49
<212> TYPE: DNA
<213> ORGANISM: Artificial Sequence
<220> FEATURE:
<223> OTHER INFORMATION: Adaptor

<400> SEQUENCE: 1167
aagggcaggt acgtcgtacc gcggccgcgc taccggcaac atagctgtc         49

<210> SEQ ID NO 1168
<211> LENGTH: 54
<212> TYPE: DNA
<213> ORGANISM: Artificial Sequence
<220> FEATURE:
<223> OTHER INFORMATION: Adaptor

<400> SEQUENCE: 1168
aagcaagcgc aggtacgtcg taccgcggcc gctcctcagt atgtgccact ctga         54

<210> SEQ ID NO 1169
<211> LENGTH: 49
<212> TYPE: DNA
<213> ORGANISM: Artificial Sequence
<220> FEATURE:
<223> OTHER INFORMATION: Adaptor

<400> SEQUENCE: 1169
aagagcaggt acgtcgtacc gcggccgcgt tgcttgccta cgtgccatc        49

<210> SEQ ID NO 1170
<211> LENGTH: 49
<212> TYPE: DNA
<213> ORGANISM: Artificial Sequence
<220> FEATURE:
<223> OTHER INFORMATION: Adaptor

<400> SEQUENCE: 1170
aactgcaggt acgtcgtacc gcggccgcga ctaggcccga agcacagag        49

<210> SEQ ID NO 1171
<211> LENGTH: 49
<212> TYPE: DNA
<213> ORGANISM: Artificial Sequence
<220> FEATURE:
<223> OTHER INFORMATION: Adaptor

<400> SEQUENCE: 1171
aacggcaggt acgtcgtacc gcggccgctt gctggacaca ggtgatacg        49

<210> SEQ ID NO 1172
<211> LENGTH: 48
<212> TYPE: DNA
<213> ORGANISM: Artificial Sequence
<220> FEATURE:
<223> OTHER INFORMATION: Adaptor

<400> SEQUENCE: 1172
aaccgcaggt acgtcgtacc gcggccgctg gaacgccacc gttgttag        48

<210> SEQ ID NO 1173
<211> LENGTH: 48
<212> TYPE: DNA
<213> ORGANISM: Artificial Sequence
<220> FEATURE:
<223> OTHER INFORMATION: Adaptor

<400> SEQUENCE: 1173
aacagcaggt acgtcgtacc gcggccgccg tatgggatcg aggttgca        48

<210> SEQ ID NO 1174
<211> LENGTH: 49
<212> TYPE: DNA
<213> ORGANISM: Artificial Sequence
<220> FEATURE:
<223> OTHER INFORMATION: Adaptor

<400> SEQUENCE: 1174
aaatgcaggt acgtcgtacc gcggccgctc agtctcatca gctcctcac        49

<210> SEQ ID NO 1175
<211> LENGTH: 49
<212> TYPE: DNA
<213> ORGANISM: Artificial Sequence
<220> FEATURE:
<223> OTHER INFORMATION: Adaptor

<400> SEQUENCE: 1175
aaaggcaggt acgtcgtacc gcggccgccc ttggtgacgt aaccgttcg    49

<210> SEQ ID NO 1176
<211> LENGTH: 49
<212> TYPE: DNA
<213> ORGANISM: Artificial Sequence
<220> FEATURE:
<223> OTHER INFORMATION: Adaptor

<400> SEQUENCE: 1176
aaacgcaggt acgtcgtacc gcggccgcga cgagcctagg aactgaagt    49

<210> SEQ ID NO 1177
<211> LENGTH: 49
<212> TYPE: DNA
<213> ORGANISM: Artificial Sequence
<220> FEATURE:
<223> OTHER INFORMATION: Adaptor

<400> SEQUENCE: 1177
aaaagcaggt acgtcgtacc gcggccgcgt ggagtcgtga tggagacct    49

<210> SEQ ID NO 1178
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1178
tttnagctga acgtcgtacc cgtcgaacga acacgggcgt    40

<210> SEQ ID NO 1179
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1179
ttgnagctga acgtcgtacc tacgctcgtt ccgctctgcg    40

<210> SEQ ID NO 1180
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1180
ttcnagctga acgtcgtacc cgcgagacga cgtgcgcggc    40

<210> SEQ ID NO 1181
<211> LENGTH: 40

```
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1181
ttanagctga acgtcgtacc tcgcgtcgtc cccgtcgcag                              40

<210> SEQ ID NO 1182
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1182
tgtnagctga acgtcgtacc acgcgcgaaa acgggcaccg                              40

<210> SEQ ID NO 1183
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1183
tggnagctga acgtcgtacc cgcgttttcg ccgtccgaga                              40

<210> SEQ ID NO 1184
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1184
tgcnagctga acgtcgtacc cgtaccggac gccgacgcca                              40

<210> SEQ ID NO 1185
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1185
tganagctga acgtcgtacc cgatagtccg agacgtctcg                              40

<210> SEQ ID NO 1186
```

```
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1186
tctnagctga acgtcgtacc tatcgaacgg cacgttggcg                              40

<210> SEQ ID NO 1187
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1187
tcgnagctga acgtcgtacc tacgaccgtt cgggtggtac                              40

<210> SEQ ID NO 1188
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1188
tccnagctga acgtcgtacc tcgtacggtc gacggccgtg                              40

<210> SEQ ID NO 1189
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1189
tcanagctga acgtcgtacc cgttagaccg cgtctcggct                              40

<210> SEQ ID NO 1190
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1190
tatnagctga acgtcgtacc taacgtccga tcgggcagcg                              40
```

```
<210> SEQ ID NO 1191
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1191
tagnagctga acgtcgtacc cggtatcgga acgccgccgc                            40

<210> SEQ ID NO 1192
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1192
tacnagctga acgtcgtacc taccgatccg tcggccggag                            40

<210> SEQ ID NO 1193
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1193
taanagctga acgtcgtacc tagcgcggat tcacgcggtg                            40

<210> SEQ ID NO 1194
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1194
gttnagctga acgtcgtacc gtcgacgacc cccgacacgg                            40

<210> SEQ ID NO 1195
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1195
gtgnagctga acgtcgtacc tcgacggtcg cgtgactccg                            40
```

```
<210> SEQ ID NO 1196
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1196
gtcnagctga acgtcgtacc cgtaacgatc acgtgcgctg                              40

<210> SEQ ID NO 1197
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1197
gtanagctga acgtcgtacc ttacggatcg agcgggtacc                              40

<210> SEQ ID NO 1198
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1198
ggtnagctga acgtcgtacc atacgcaacg acccgagccg                              40

<210> SEQ ID NO 1199
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1199
gggnagctga acgtcgtacc cgtatcgttg cgtgtgtaac                              40

<210> SEQ ID NO 1200
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1200
ggcnagctga acgtcgtacc atcggccgaa gcacggcgcc                              40
```

<210> SEQ ID NO 1201
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1201
gganagctga acgtcgtacc ccgatttcgg gcgagggcgc                          40

<210> SEQ ID NO 1202
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1202
gctnagctga acgtcgtacc ccgtaccgac tgcgggatac                          40

<210> SEQ ID NO 1203
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1203
gcgnagctga acgtcgtacc tacgggtcgg tcgctcctcg                          40

<210> SEQ ID NO 1204
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1204
gccnagctga acgtcgtacc attcgtcgaa ccgcagttac                          40

<210> SEQ ID NO 1205
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1205
gcanagctga acgtcgtacc cgaatttcga ctcgcgcccg                40

<210> SEQ ID NO 1206
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1206
gatnagctga acgtcgtacc aacgcgacgc agcgacacgc                40

<210> SEQ ID NO 1207
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1207
gagnagctga acgtcgtacc gcgttgcgtc tccgctagac                40

<210> SEQ ID NO 1208
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1208
gacnagctga acgtcgtacc acgtaacgtc gagcgctaac                40

<210> SEQ ID NO 1209
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1209
gaanagctga acgtcgtacc tacgtgacgt gcggagtatc                40

<210> SEQ ID NO 1210
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1210
cttnagctga acgtcgtacc cgtagacgct cggcaactag                                 40

<210> SEQ ID NO 1211
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
 a,c,g or t;

<400> SEQUENCE: 1211
ctgnagctga acgtcgtacc ctacgagcgt cgctcgcata                                 40

<210> SEQ ID NO 1212
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1212
ctcnagctga acgtcgtacc gcgaaacgca tccgggcgtg                                 40

<210> SEQ ID NO 1213
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1213
ctanagctga acgtcgtacc ttcgctgcgt tgccgctagt                                 40

<210> SEQ ID NO 1214
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1214
cgtnagctga acgtcgtacc acgatcgaca ccggagtcta                                 40

<210> SEQ ID NO 1215
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

```
<400> SEQUENCE: 1215
cggnagctga acgtcgtacc atcgttgtcg ggacgtagtc                         40

<210> SEQ ID NO 1216
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1216
cgcnagctga acgtcgtacc acgaccatcg tcgcccgagg                         40

<210> SEQ ID NO 1217
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1217
cganagctga acgtcgtacc gtcgtcgatg cgtccatacc                         40

<210> SEQ ID NO 1218
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1218
cctnagctga acgtcgtacc aaccgaacgt ggcgaccggc                         40

<210> SEQ ID NO 1219
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1219
ccgnagctga acgtcgtacc cggttacgtt tgcgcggtat                         40

<210> SEQ ID NO 1220
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;
```

<400> SEQUENCE: 1220
cccnagctga acgtcgtacc cgaacccgcg tcgtggccgg                        40

<210> SEQ ID NO 1221
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1221
ccanagctga acgtcgtacc gttcgcgcgg cacgaagtac                        40

<210> SEQ ID NO 1222
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1222
catnagctga acgtcgtacc cgcaaaccgg cgcttctagc                        40

<210> SEQ ID NO 1223
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1223
cagnagctga acgtcgtacc ttgcgaccgg gcgcagctag                        40

<210> SEQ ID NO 1224
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1224
cacnagctga acgtcgtacc agtcgccggt aagcgtatgc                        40

<210> SEQ ID NO 1225
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides a,c,g or t;

<400> SEQUENCE: 1225
caanagctga acgtcgtacc cgactatcgc gcgctccacg                                40

<210> SEQ ID NO 1226
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1226
attnagctga acgtcgtacc atcgagcgat tcgaggttag                                40

<210> SEQ ID NO 1227
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1227
atgnagctga acgtcgtacc tcgataccgt agcgccgtgg                                40

<210> SEQ ID NO 1228
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1228
atcnagctga acgtcgtacc accgaacggt ctcgacggcc                                40

<210> SEQ ID NO 1229
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1229
atanagctga acgtcgtacc tcggtcgtca ctcgtggtta                                40

<210> SEQ ID NO 1230
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)

<223> OTHER INFORMATION: 'n' at position 4 can be any of the nucleotides
      a,c,g or t;

<400> SEQUENCE: 1230
agtnagctga acgtcgtacc gcgactgacg acgaggatag                              40

<210> SEQ ID NO 1231
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1231
aggnagctga acgtcgtacc gtcgccgccg acggataacc                              40

<210> SEQ ID NO 1232
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1232
agcnagctga acgtcgtacc atgcgcggcg tccgtcggga                              40

<210> SEQ ID NO 1233
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1233
aganagctga acgtcgtacc cgcatcgcgc gccgtctatc                              40

<210> SEQ ID NO 1234
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1234
actnagctga acgtcgtacc acgaagcgcg acggctcccg                              40

<210> SEQ ID NO 1235
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature

```
<222> LOCATION: (4)..(4)
<223> OTHER INFORMATION: 'n' at position 4 can be any of the nucleotides
      a,c,g or t;

<400> SEQUENCE: 1235
acgnagctga acgtcgtacc tcgcacgaag accgcgtact                              40

<210> SEQ ID NO 1236
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1236
accnagctga acgtcgtacc tgcgacttcg gcggtggccg                              40

<210> SEQ ID NO 1237
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1237
acanagctga acgtcgtacc ttcgtaaacg cgagtctaac                              40

<210> SEQ ID NO 1238
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1238
aatnagctga acgtcgtacc aatcgcgttt actcgggcgg                              40

<210> SEQ ID NO 1239
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1239
aagnagctga acgtcgtacc cgattcggaa cgagcgacta                              40

<210> SEQ ID NO 1240
<211> LENGTH: 40
<212> TYPE: DNA
<213> ORGANISM: Artificial Sequence
<220> FEATURE:
<223> OTHER INFORMATION: Adaptor
```

```
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1240
aacnagctga acgtcgtacc cgttcttccg gctcgcgggc                              40

<210> SEQ ID NO 1241
<211> LENGTH: 40
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1241
aaanagctga acgtcgtacc gaacgcgcac gtgcgtaacc                              40

<210> SEQ ID NO 1242
<211> LENGTH: 16
<212> TYPE: DNA
<213> ORGANISM: Artificial Sequence
<220> FEATURE:
<223> OTHER INFORMATION: helper oligonucleotide
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1242
ggtacgacgt tcagct                                                       16

<210> SEQ ID NO 1243
<211> LENGTH: 16
<212> TYPE: DNA
<213> ORGANISM: Artificial Sequence
<220> FEATURE:
<223> OTHER INFORMATION: helper oligonucleotide
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1243
ggtacgacgt tcagca                                                       16

<210> SEQ ID NO 1244
<211> LENGTH: 16
<212> TYPE: DNA
<213> ORGANISM: Artificial Sequence
<220> FEATURE:
<223> OTHER INFORMATION: helper oligonucleotide
<221> NAME/KEY: misc_feature
<222> LOCATION: (4)..(4)
<223> OTHER INFORMATION: 'n' at position 4 can be any of the nucleotides
      a,c,g or t;

<400> SEQUENCE: 1244
ggtacgacgt tcagat                                                       16

<210> SEQ ID NO 1245
<211> LENGTH: 48
<212> TYPE: DNA
<213> ORGANISM: Artificial Sequence
<220> FEATURE:
```

```
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1245
tttngcaggt acgtcgtacc gcggccgcgt gagcttgagt cgcgtgga            48

<210> SEQ ID NO 1246
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1246
ttgngcaggt acgtcgtacc gcggccgccc aacgtcgcga gttagtcag            49

<210> SEQ ID NO 1247
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1247
ttcngcaggt acgtcgtacc gcggccgcag gtagacgcgg tatgttcgta           50

<210> SEQ ID NO 1248
<211> LENGTH: 48
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1248
ttangcaggt acgtcgtacc gcggccgccg gtgctagagt cgcgtgtt             48

<210> SEQ ID NO 1249
<211> LENGTH: 48
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1249
tgtngcaggt acgtcgtacc gcggccgccg acagtaccgc gacagcta             48

<210> SEQ ID NO 1250
<211> LENGTH: 50
<212> TYPE: DNA
<213> ORGANISM: Artificial Sequence
```

```
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1250
tggngcaggt acgtcgtacc gcggccgcgc acttaactac gccgacgaag              50

<210> SEQ ID NO 1251
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1251
tgcngcaggt acgtcgtacc gcggccgcgt actagcctaa ccgaggcgta              50

<210> SEQ ID NO 1252
<211> LENGTH: 48
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1252
tgangcaggt acgtcgtacc gcggccgctc ggatcacgta cacgtgct                48

<210> SEQ ID NO 1253
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1253
tctngcaggt acgtcgtacc gcggccgcgt acgtcgccta gtcgacctg               49

<210> SEQ ID NO 1254
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1254
tcgngcaggt acgtcgtacc gcggccgcct ctcctaacgg accgactaac              50

<210> SEQ ID NO 1255
<211> LENGTH: 50
<212> TYPE: DNA
```

<210> SEQ ID NO 1255
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or t

<400> SEQUENCE: 1255
tccngcaggt acgtcgtacc gcggccgccg ttccgatcta gcggtatctt        50

<210> SEQ ID NO 1256
<211> LENGTH: 48
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or t

<400> SEQUENCE: 1256
tcangcaggt acgtcgtacc gcggccgcgc acccgtacag gatgtgag          48

<210> SEQ ID NO 1257
<211> LENGTH: 48
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or t

<400> SEQUENCE: 1257
tatngcaggt acgtcgtacc gcggccgcgc aacgcgctat gctcgtag          48

<210> SEQ ID NO 1258
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or t

<400> SEQUENCE: 1258
tagngcaggt acgtcgtacc gcggccgcga ctgtggaact acgacgatcg        50

<210> SEQ ID NO 1259
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or t

<400> SEQUENCE: 1259
tacngcaggt acgtcgtacc gcggccgcag cagaccgaac cctagtcgc         49

<210> SEQ ID NO 1260
<211> LENGTH: 49

```
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1260
taangcaggt acgtcgtacc gcggccgcca tacgtcgtag ggttcgcga            49

<210> SEQ ID NO 1261
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1261
gttngcaggt acgtcgtacc gcggccgcct ctcatacgcg tctgcgcgt            49

<210> SEQ ID NO 1262
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1262
gtgngcaggt acgtcgtacc gcggccgcga gtgtgcctta cgtcgagttc           50

<210> SEQ ID NO 1263
<211> LENGTH: 98
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1263
gtcngcaggt acgtcgtacc gcggccgcgt cacgttgcgg ccttagtcgt angcaggtac    60
gtcgtaccgc ggccgcgagg tacgagactt gacacacg                           98

<210> SEQ ID NO 1264
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: n can be any nucleotide a,c,g or t

<400> SEQUENCE: 1264
gtangcaggt acgtcgtacc gcggccgcga ggtacgagac ttgacacacg           50
```

<210> SEQ ID NO 1265
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1265
ggtngcaggt acgtcgtacc gcggccgcga ccagttgcct aacggacact            50

<210> SEQ ID NO 1266
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1266
gggngcaggt acgtcgtacc gcggccgcgc aactagtctc gacctgcga             49

<210> SEQ ID NO 1267
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1267
ggcngcaggt acgtcgtacc gcggccgcgt acctcgacga ccgtactgtg            50

<210> SEQ ID NO 1268
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1268
ggangcaggt acgtcgtacc gcggccgcac gcgtgatagt acggagtcg             49

<210> SEQ ID NO 1269
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1269
gctngcaggt acgtcgtacc gcggccgcca ctagagcggc gtcagtcta             49

<210> SEQ ID NO 1270
<211> LENGTH: 47
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1270
gcgngcaggt acgtcgtacc gcggccgcgc acagcgctag cacagga                47

<210> SEQ ID NO 1271
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1271
gccngcaggt acgtcgtacc gcggccgcta ccgacagtcc tctgcgtgc              49

<210> SEQ ID NO 1272
<211> LENGTH: 52
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1272
gcangcaggt acgtcgtacc gcggccgcct acgctacgtt gcgaagaagg ta          52

<210> SEQ ID NO 1273
<211> LENGTH: 52
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1273
gatngcaggt acgtcgtacc gcggccgcgt ctgtcgtacc tgtcagtgac tg          52

<210> SEQ ID NO 1274
<211> LENGTH: 47
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1274
gagngcaggt acgtcgtacc gcggccgcat cgaaccgtgc tccttgg                47

<210> SEQ ID NO 1275
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or t

<400> SEQUENCE: 1275
gacngcaggt acgtcgtacc gcggccgcag gttgaggtgt acgcgatagc                50

<210> SEQ ID NO 1276
<211> LENGTH: 51
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or t

<400> SEQUENCE: 1276
gaangcaggt acgtcgtacc gcggccgcga cttcaacccc tgacgtacac a              51

<210> SEQ ID NO 1277
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or t

<400> SEQUENCE: 1277
cttngcaggt acgtcgtacc gcggccgcct actcgcgaga gagggctatg                50

<210> SEQ ID NO 1278
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or t

<400> SEQUENCE: 1278
ctgngcaggt acgtcgtacc gcggccgcct tgatccgtag tcgagacgg                 49

<210> SEQ ID NO 1279
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or t

<400> SEQUENCE: 1279
ctcngcaggt acgtcgtacc gcggccgcgt acagacgtag cgatcgcag                49

<210> SEQ ID NO 1280
<211> LENGTH: 52
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1280
ctangcaggt acgtcgtacc gcggccgcgt gactaacgag gtctgtaagc ta            52

<210> SEQ ID NO 1281
<211> LENGTH: 51
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1281
cgtngcaggt acgtcgtacc gcggccgcgt ctgagagtcg actgcgctaa g             51

<210> SEQ ID NO 1282
<211> LENGTH: 52
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1282
cggngcaggt acgtcgtacc gcggccgcct cagtaagccg gagtctagct ag            52

<210> SEQ ID NO 1283
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1283
cgcngcaggt acgtcgtacc gcggccgccg ccctaaacgg gatcgagcga              50

<210> SEQ ID NO 1284
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1284

```
cgangcaggt acgtcgtacc gcggccgccg tacaggctag gggttagtcg          50
```

<210> SEQ ID NO 1285
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1285

```
catngcaggt acgtcgtacc gcggccgcga tcggactaat ccgctacgt           49
```

<210> SEQ ID NO 1286
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1286

```
cagngcaggt acgtcgtacc gcggccgcga ctaccgacta gtcgtgcgac          50
```

<210> SEQ ID NO 1287
<211> LENGTH: 48
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1287

```
cacngcaggt acgtcgtacc gcggccgcta gggccctaac gtagctcg            48
```

<210> SEQ ID NO 1288
<211> LENGTH: 48
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1288

```
caangcaggt acgtcgtacc gcggccgcta cctagccta acgggtcg             48
```

<210> SEQ ID NO 1289
<211> LENGTH: 48
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

```
<400> SEQUENCE: 1289
cctngcaggt acgtcgtacc gcggccgccg atcgctctag tgcctacg                48

<210> SEQ ID NO 1290
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1290
ccgngcaggt acgtcgtacc gcggccgcga ctgcgattcg tgacactagt                50

<210> SEQ ID NO 1291
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or t

<400> SEQUENCE: 1291
cccngcaggt acgtcgtacc gcggccgctg cgtaatagcg actgtaccct                50

<210> SEQ ID NO 1292
<211> LENGTH: 48
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1292
ccangcaggt acgtcgtacc gcggccgcct aggtcatccc tccggtac                48

<210> SEQ ID NO 1293
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1293
attngcaggt acgtcgtacc gcggccgcta gtgcgcggta ctaccgact                49

<210> SEQ ID NO 1294
<211> LENGTH: 47
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t
```

<400> SEQUENCE: 1294
atgngcaggt acgtcgtacc gcggccgcag acggctatgc gtcggga        47

<210> SEQ ID NO 1295
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1295
atcngcaggt acgtcgtacc gcggccgcac ctacgaacac gcgtaactcg        50

<210> SEQ ID NO 1296
<211> LENGTH: 47
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1296
atangcaggt acgtcgtacc gcggccgcag ctacgtgggt ggcagac        47

<210> SEQ ID NO 1297
<211> LENGTH: 48
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1297
agtngcaggt acgtcgtacc gcggccgcta ccgatacggt cgaccatc        48

<210> SEQ ID NO 1298
<211> LENGTH: 51
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1298
aggngcaggt acgtcgtacc gcggccgcgt acgctaggta ggaactaagc g        51

<210> SEQ ID NO 1299
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1299
agcngcaggt acgtcgtacc gcggccgccg gacgactagt tgctagcgtc    50

<210> SEQ ID NO 1300
<211> LENGTH: 48
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1300
agangcaggt acgtcgtacc gcggccgcgt gaacctacgc gttgacgc    48

<210> SEQ ID NO 1301
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1301
actngcaggt acgtcgtacc gcggccgcgt gtctcgggct aggcgtaga    49

<210> SEQ ID NO 1302
<211> LENGTH: 47
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1302
acgngcaggt acgtcgtacc gcggccgctc cgtggtgtcc atgggag    47

<210> SEQ ID NO 1303
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1303
accngcaggt acgtcgtacc gcggccgcct acgcgtaacg ctagcaggt    49

<210> SEQ ID NO 1304
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or t

<400> SEQUENCE: 1304
acangcaggt acgtcgtacc gcggccgcga agagccgtaa ggtacggct                49

<210> SEQ ID NO 1305
<211> LENGTH: 50
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1305
aatngcaggt acgtcgtacc gcggccgcgt acgtcagcgt acgctaagtc                50

<210> SEQ ID NO 1306
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1306
aagngcaggt acgtcgtacc gcggccgctc taggttccgt tgtagcgct                 49

<210> SEQ ID NO 1307
<211> LENGTH: 47
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1307
aacngcaggt acgtcgtacc gcggccgcag caacgagacg acacgac                   47

<210> SEQ ID NO 1308
<211> LENGTH: 49
<212> TYPE: DNA
<213> ORGANISM: Artificial Sequence
<220> FEATURE:
<223> OTHER INFORMATION: Adaptor
<221> NAME/KEY: misc_feature
<222> LOCATION: (4)..(4)
<223> OTHER INFORMATION: 'n' can be any one of the nucleotides a,c,g or
      t

<400> SEQUENCE: 1308
aaangcaggt acgtcgtacc gcggccgcgt ctagaaccca cgcacggta                 49

<210> SEQ ID NO 1309
<211> LENGTH: 16
<212> TYPE: DNA
<213> ORGANISM: Artificial Sequence
<220> FEATURE:
<223> OTHER INFORMATION: helper oligonucleotide

<400> SEQUENCE: 1309

```
ggtacgacgt acctga                                                          16

<210> SEQ ID NO 1310
<211> LENGTH: 16
<212> TYPE: DNA
<213> ORGANISM: Artificial Sequence
<220> FEATURE:
<223> OTHER INFORMATION: helper oligonucleotide

<400> SEQUENCE: 1310
ggtacgacgt acctgc                                                          16

<210> SEQ ID NO 1311
<211> LENGTH: 16
<212> TYPE: DNA
<213> ORGANISM: Artificial Sequence
<220> FEATURE:
<223> OTHER INFORMATION: helper oligonucleotide

<400> SEQUENCE: 1311
ggtacgacgt acctac                                                          16
```